(12) United States Patent
Costanzo et al.

(10) Patent No.: US 8,158,792 B2
(45) Date of Patent: Apr. 17, 2012

(54) SPIROPIPERIDINES FOR USE AS TRYPTASE INHIBITORS

(75) Inventors: Michael J. Costanzo, Ivyland, PA (US); Stephen C. Yabut, Perkasie, PA (US); Brett Tounge, Blue Bell, PA (US); Bruce E. Maryanoff, Forest Grove, PA (US); Han-Cheng Zhang, Lansdale, PA (US)

(73) Assignee: Janssen Pharmaceutica N.V. (BE)

( * ) Notice: Subject to any disclaimer, the term of this patent is extended or adjusted under 35 U.S.C. 154(b) by 443 days.

(21) Appl. No.: 12/313,289

(22) Filed: Nov. 19, 2008

(65) Prior Publication Data
US 2009/0163527 A1  Jun. 25, 2009

Related U.S. Application Data

(60) Provisional application No. 61/003,970, filed on Nov. 21, 2007.

(51) Int. Cl.
C07D 491/107 (2006.01)
A61K 31/438 (2006.01)

(52) U.S. Cl. .......................................... 546/17; 514/278
(58) Field of Classification Search .................... 546/17; 514/278
See application file for complete search history.

(56) References Cited

U.S. PATENT DOCUMENTS

| 7,067,525 B2 | 6/2006 | Yu et al. |
| 2006/0183904 A1 | 8/2006 | Guo et al. |

FOREIGN PATENT DOCUMENTS

| WO | WO0006153 A1 * | 2/2000 |
| WO | WO 01/90101 A1 | 11/2001 |
| WO | WO 2004/060884 A1 | 7/2004 |
| WO | WO 2005/058897 A1 | 6/2005 |
| WO | WO 2005/095385 A1 | 10/2005 |
| WO | WO 2005/097780 | 10/2005 |

OTHER PUBLICATIONS

Bohm, Hans-Joachim et. al. "Scaffold hopping" Drug Discovery Today: Technologies 2004, 1( 3), 217-224.*
Gervais, Christian et. al. "Potential psychotropic drugs. XIII. New butyrophenones related to haloperidol" European Journal of Medicinal Chemistry, 1980, 15(1), 71-6 (abstract only).*
International Search Report, dated Jan. 9, 2009.
Walls et al, "Human mast cell tryptase: a stimulus of microvascular leakage and mast cell activation," Eur. Journal of Pharmacology, 1997, pp. 89-97, vol. 328, Elsevier Science B.V.
Bode et al, "Human β-tryptase is a ring-like eteramer with active sites facing a central pore," Nature, 1998, pp. 306-311, vol. 392, MacMillan Publishers, Ltd.
Schwartz et al, "Cloning and Cahracterization of Complementary DNA for Human Tryptase," J. Clin. Invest., 1989, pp. 1188-1195, vol. 84, The American Society for Clinical Investigation, Inc.
Rice et al, "Inhibitors of Tryptase for the Treatment of Mast Cell-Mediated Diseases," Current Pharmaceutical Design, 1998, pp. 381-396, vol. 4, Bentham Science Publishers, B.V.
Kalenderian et al, "Elevated Histamine and Tryptase Levels in Smokers' Bronchoalveolar Lavage Fluid," Chest, 1988, pp. 119-123, vol. 94.
Drazen et al, "Peptidase Modulation of Vasoactive Intestinal Peptide Pulmonary Relaxation in Tracheal Superfused Guinea Pig Lungs," J. Clin Invest., 1993, pp. 235-243, vol. 91, The American Society for Clinical Investigation, Inc.
Zhang et al, "Mast cell tryptase and asthma," Mediators of Inflammation, 1997, pp. 311-317, vol. 6, Rapid Science Publishers.
Walls et al, "Potent Induction of a Neutrophil and Eosinophil-Rich Infiltrate in Vivo by Human Mast Cell Tryptase: Selective Enhancement of Eosinophil Recruitment by Histamine," Journal of Immunol., 1997, pp. 6216-6225, vol. 159, The American Assoc. of Immunologists.
Abraham et al , "Inhaled Tryptase Causes Bronchoconstriciton in Sheep Via Histamine Release," Amer. J of Respir. and Crit. Care Med., 1996, pp. 649-654, vol. 154.
Stone et al, "Identification of potential activators of proteinase-activated receptor-2," FEBS Letters, 1997, pp. 267-269, vol. 417, Federation of European Biochemical Societies.
Marone et al, "Stem cell Factor in Mast Cells and Increased Mast Cell Density in Idiopathic and Ischemic Cardiomyopathy," Circulation, 1998, pp. 971-978, vol. 97, American Heart Association.
Tanaka et al, "Tryptase Inhibitors Block Allergen-induced Airway and Inflammatory Responses in Allergic Sheep," Am. J. Respir. Crit. Care Med., 1995, pp. 2076-2083, vol. 152.
Barnes et al, "Inhaled Glucocorticoids for Asthma," The New England Journal of Medicine, 1995, pp. 868-875, vol. 332.

* cited by examiner

Primary Examiner — David K O Dell
(74) Attorney, Agent, or Firm — Yuriy P. Stercho

(57) ABSTRACT

The present invention is directed to a compound of Formula (I):

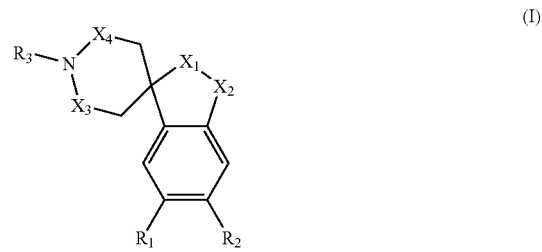

or a form thereof, wherein $X_1$, $X_2$, $X_3$, $X_4$, $R_1$, $R_2$ and $R_3$ are as defined herein, useful as tryptase inhibitors.

8 Claims, 4 Drawing Sheets

SPIROPIPERIDINES FOR USE AS TRYPTASE INHIBITORS

CROSS REFERENCE TO RELATED APPLICATIONS

This application claims benefit of priority from U.S. provisional application Ser. No. 61/003,970, filed on Nov. 21, 2007.

FIELD OF THE INVENTION

The present invention relates to certain spiropiperidine tryptase inhibitor compounds, methods for preparing compounds, compositions, intermediates and derivatives thereof and methods for treating a tryptase mediated disorder.

BACKGROUND OF THE INVENTION

Mast cells are a key cellular component of the inflammatory response and when activated, secrete numerous proinflammatory mediators, including histamine, arachidonic acid derivatives, and some serine proteases. Among these mast cell serine proteases are the unique carboxypeptidases, chymase and tryptase (Walls et al. *Eur. J. Pharmacol.* 1997, 328, 89-97). Active tryptase is a structurally unique trypsin-like serine protease which exists as a tetramer that is stabilized by heparin proteoglycans which are stored and secreted with the enzyme (Bode et al. *Nature* 1998, 392, 306-311). With the exception of neutrophil lactoferrin and possibly secretory leukocyte proteinase inhibitor, tryptase is generally not affected by endogenous serine protease inhibitors such as $\alpha$2-macroglobin, $\alpha$2-proteinase inhibitor, aprotinin, and antithrombin. It is postulated that in vivo tryptase activity may be regulated by the dissociation of the active tryptase tetramer into inactive monomers via the removal of heparin.

Tryptase is secreted exclusively by mast cells and comprises up to 25% of the total protein of the mast cell (Schwartz et al., *J. Clin. Invest* 1989, 84, 1188-1195). Consequently, mast cell-derived tryptase is secreted in high concentrations at sites of tissue injury. Activated mast cells in atherosclerotic/restenotic plaque have been implicated in plaque rupture and stenosis and are also manifested in inflamed tissues of the gastrointestinal tract. Elevated tryptase levels have been detected in bronchoalveolar lavage fluid (asthma), tears (conjunctivitis), blister fluids (dermatitis), blood (anaphylaxis), cerebrospinal fluid (multiple sclerosis), synovial fluid (rheumatoid arthritis) (Rice et al. *Curr. Pharm. Design,* 1998, 4, 381-396). Elevated levels of tryptase have also been found in diseased arteries (atherosclerotic, restenotic) relative to normal arteries. Some cigarette smokers have elevated bronchooalveolar lavage fluid tryptase levels relative to nonsmokers, providing support for the hypothesis that mast cell proteases may contribute to lung destruction in smoker's emphysema (Kalenderian et al. *Chest* 1998, 94, 119-123).

The potent bronchodilating neuropeptides, vasoactive intestinal peptide (VIP) and peptide histidine methionine (PHM) are readily cleaved by tryptase in vitro whereas substance P, a potent bronchoconstricting peptide, is not (Drazen et al. *J. Clin. Invest* 1993, 91, 235-243). Tryptase has demonstrated the ability to generate bradykinin, which is known to induce bronchoconstriction in asthmatics (Zhang et al. *Mediators of Inflammation.* 1997, 6, 311-317). The ability of tryptase to stimulate inflammatory eosinophils and neutrophil chemotaxis in vitro and in vivo is well known (Walls et al. *J. Immunol.* 1997, 159, 6216-6225). Inhaled tryptase has been shown to cause bronchoconstriction in sheep through the release of histamine (Abraham et al. *Amer. J. of Respir. and Crit. Care Med.* 1996, 154, 649-654). The ability of tryptase to directly stimulate mast cell degranulation in vitro and in animal models suggests that there may be a tryptase mediated amplification mechanism of the allergic inflammatory response (Walls et al. *Eur. J. Pharmacol.* 1997, 328, 89-97).

Currently, only trypsin and tryptase are known to activate the protease-activated receptor 2 (PAR-2), a cell surface G-protein-coupled receptor. The activation of PAR-2 is primarily associated with the induction of mitogenic response indicating that tryptase may have a role in pathological conditions associated with tissue hyperplasia, including the airway hyperplasia found in chronic asthmatics (Stone et al. *FEBS Letters* 1997, 417, 267-269). Tryptase also has multiple effects on fibroblasts and there is in vitro evidence to suggest that tryptase may involved in the early stages of fibrotic diseases, such as fibrotic lung disease, schieroderma, atherosclerosis, and cardiomyopathic disorders (Marone et al. *Circulation* 1998, 97, 971-978). Hence, an inhibitor of tryptase could provide a novel therapeutic approach for the prevention and treatment of a variety of inflammatory diseases, such as vascular injury (atherosclerosis, restenosis), arthritis, inflammatory bowel disease, Crohn's disease, dermatitis, urticaria, bullous pemphigoid, psoriasis, schleroderma, fibrosis, conjunctivitis, allergic rhinitis, and particularly asthma.

Asthma is the most common chronic disease in developed countries. A complex disease involving multiple biochemical mediators for both its acute and chronic manifestations, asthma is frequently characterized by the progressive development of hyperresponsiveness of the trachea and bronchi to both immunospecific allergens as well as generalized chemical or physical stimuli. The hyperresponsiveness of asthmatic bronchiolar tissue is postulated to result from chronic inflammation reactions, which irritate and damage the epithelium lining the airway wall and promote pathological thickening of the underlying tissue. Bronchial biopsy studies have indicated that even patients with mild asthma have features of inflammation in the airway wall. Mast cells have long been implicated in the pathogenesis of asthma, particularly in the acute response immediately after the exposure to allergen (Zhang et al. *Mediators of Inflammation* 1997, 6, 311-317).

The therapeutic strategy of employing tryptase inhibitors as a treatment for asthma in humans has been recently validated by the selective tryptase inhibitor, APC-366 (Tanaka et al. *Am. J. Respir. Crit. Care Med.* 1995, 152, 2076-2083). A recent Phase IIa study was conducted with 16 mild asthmatics who were dosed with either placebo or a nebulized dry powder formulation of APC-366 (Rice et al. *Curr. Pharm. Design,* 1998, 4, 381-396). Compared with placebo, the same subjects had a statistically significant improvement for the late airway response (33%; $\rho$=0.012) and a mean maximum decrease of forced expiratory volume in one second (21%; $\rho$=0.007) for late airway hyperresponsiveness. These positive results demonstrate that tryptase inhibition is a promising approach for the treatment of asthma in humans.

Currently, the most effective therapy for chronic asthma involves treatment with glucocorticoids (Barnes *New Engl. J. Med.,* 1995, 332, 868-875). However, glucocorticoid administration also generates a litany of local and systemic side-effects. Because of the limitations of glucocorticoids, there is an unmet medical need for improved asthma therapy. In contrast to drugs, such as steroids, that elicit multiple actions, tryptase inhibitors may elicit fewer side-effects through the selective inhibition of a specific inflammatory mediator (tryptase) that is exclusive to mast cells. Hence, tryptase inhibitors may offer similar efficacy in the treatment of asthma as the glucocorticoids without the same undesirable systemic side-effects.

International application WO 2005/058897 describes spiroindoline derivatives having insecticidal properties.

International application WO 2001/090101 describes arylmethylamine derivatives for use as tryptase inhibitors.

International application WO 2004/060884 describes (5-phenylethynyl-furan-2-yl)carbonyl substituted piperidinyl benzylamine compounds for use as mast cell tryptase inhibitors.

International application WO 2005/095385 describes a process for preparing (5-phenylethynyl-furan-2-yl)carbonyl substituted piperidinyl benzylamine compounds for use as tryptase inhibitors.

International application WO 2005/097780 describes (3-methyl-4-bromo-5-propoxy-thien-2-yl)carbonyl substituted piperidinyl benzylamine compounds for use as mast cell tryptase inhibitors.

SUMMARY OF THE INVENTION

The present invention is directed to a compound of Formula (I):

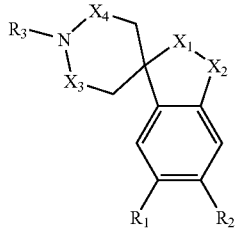

or a form thereof, wherein $X_1$, $X_2$, $X_3$, $X_4$, $R_1$, $R_2$ and $R_3$ are as defined herein, useful as tryptase inhibitors.

Illustrative of the invention is a pharmaceutical composition comprising a pharmaceutically acceptable carrier and a compound of Formula (I). Also illustrative of the invention is a process for making a pharmaceutical composition comprising mixing a compound of Formula (I) and a pharmaceutically acceptable carrier.

The present invention is further directed to methods for treating or ameliorating a tryptase-mediated disorder. In particular, the method of the present invention is directed to treating or ameliorating a tryptase-mediated disorder including, but not limited to, inflammatory diseases associated with the respiratory tract, such as asthma and allergic rhinitis, as well as other immunomediated inflammatory disorders, such as rheumatoid arthritis, conjunctivitis, psoriasis, inflammatory bowel disease, and various vascular or dermatological conditions.

Accordingly, it is an object of the present invention to provide compounds that are tryptase inhibitors useful for treating tryptase mediated disorders. It is another object of the invention to provide a process for preparing such spiro compounds, compositions, intermediates and derivatives thereof.

It is a further object of the invention to provide a method for treating a tryptase mediated inflammatory, vascular or dermatological condition in a subject in need thereof comprising administering to the subject an effective amount of a compound of Formula (I), wherein the inflammatory, vascular or dermatological condition is selected from, but not limited to, inflammatory diseases associated with the respiratory tract, such as asthma and allergic rhinitis, as well as other immunomediated inflammatory disorders, such as rheumatoid arthritis, rheumatoid spondylitis, osteoarthritis, gouty arthritis, peptic ulcers, ocular and vernal conjunctivitis, psoriasis, inflammatory bowel disease, Crohn's disease, chronic obstructive pulmonary disease, urticaria, bullous pemphiguoid, scleroderma, fibrosis, dermatitis, psoriasis, pruritis, angioedema, eczematous dermatitis, anaphylaxis, hyperproliferative skin disease, inflammatory skin conditions, hepatic cirrhosis, glomerulonephritis, nephritis, vascular inflammation, atherosclerosis or restenosis.

Also included in the invention is the use of any of the compounds described above for the preparation of a medicament for treating a tryptase mediated inflammatory, vascular or dermatological condition in a subject in need thereof.

DETAILED DESCRIPTION OF THE INVENTION

Figure 1:
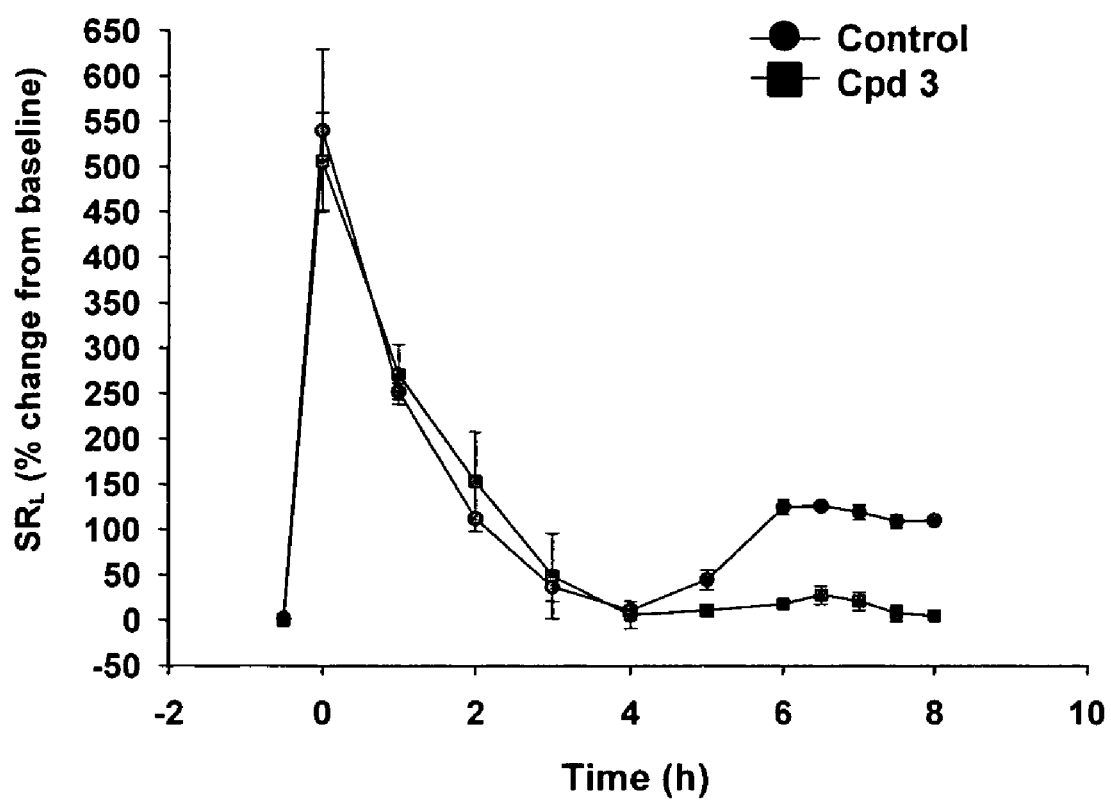
FIG. 1 shows changes in specific airway resistance in early phase response to antigen challenge.

The present invention is directed to a compound of Formula (I):

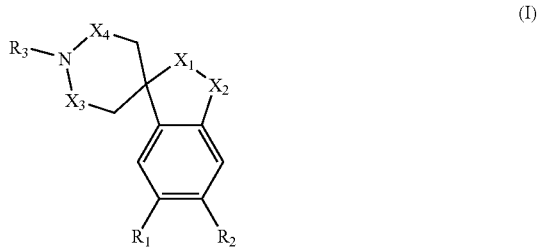

or a form thereof, wherein $X_1$ and $X_2$, respectively, are selected from the group consisting of —$CH_2$— and —$CH_2$—, —$CH_2$— and —O—, —O— and —$CH_2$—, —$CH_2$— and —$N(R_4)$—, —$N(R_4)$— and —$CH_2$—, —$CH_2$— and —S—, —S— and —$CH_2$—, —$CH_2$— and —S(O)—, —S(O)— and —$CH_2$—, —$CH_2$— and —$SO_2$—, —$SO_2$— and —$CH_2$—, —$CH_2$— and —C(O)— and —$CH_2$—, —$CH_2$— and —C(O)—, —C(O)— and —$N(R_4)$—, —$N(R_4)$— and —C(O)—, —C(O)— and —S— and —S— and —C(O)—;

$X_3$ and $X_4$, respectively, are selected from the group consisting of —$CH_2$— and —$CH_2$—, —$CH_2$— and —C(O)— and —C(O)— and —$CH_2$—;

$R_1$ is selected from the group consisting of amino$C_{1-4}$alkyl, $(C_{1-4}$alkyl)amino$C_{1-4}$alkyl, $(C_{1-4}$alkyl)$_2$-amino$C_{1-4}$alkyl, $(C_{1-4}$alkyl)$_3$-amino$C_{1-4}$alkyl, formylamino$C_{1-4}$alkyl, arylcarbonylamino$C_{1-4}$alkyl, aminosulfonylamino$C_{1-4}$alkyl, aryl$C_{1-4}$alkylamino$C_{1-4}$alkyl, $C_{3-14}$cycloalkylcarbonylamino$C_{1-4}$alkyl, $C_{3-14}$cycloalkyl$C_{1-4}$alkenylcarbonylamino$C_{1-4}$alkyl, aryl$C_{1-4}$alkylcarbonylamino$C_{1-4}$alkyl, aryl$C_{2-4}$alkenylcarbonylamino$C_{1-4}$alkyl, aryl$C_{2-4}$alkynylcarbonylamino$C_{1-4}$alkyl, arylsulfonylamino$C_{1-4}$alkyl, heterocyclylcarbonylamino$C_{1-4}$alkyl, heterocyclyl$C_{1-4}$alkylcarbonylamino$C_{1-4}$alkyl, heterocyclyl$C_{1-4}$alkenylcarbonylamino$C_{1-4}$alkyl, heteroarylcarbonylamino$C_{1-4}$alkyl, heteroaryl$C_{2-4}$alkenylcarbonylamino$C_{1-4}$alkyl, aminoimino, hydroxyaminoimino, ($C_{1-4}$alkyl)aminoimino, ($C_{1-4}$alkyl)$_2$-aminoimino and aminoaminoimino, wherein each instance of aryl is optionally substituted with one or two halogen substituents;

$R_2$ is absent or is one halogen substituent;

$R^3$ is hydrogen or is selected from the group consisting of $R^5$-aryl$C_{1-4}$alkyl, carbonyl and sulfonyl, wherein carbonyl and sulfonyl are each substituted with a substituent selected from the group consisting of $R^5$-aryl, $R^5$-aryl$C_{1-4}$alkyl, $R^5$-aryl$C_{1-4}$alkylamino, ($R^5$-aryl)$_{1-2}C_{1-4}$ alkyl, $R^5$-aryl$C_{2-4}$alkenyl, $R^5$-aryl$C_{2-4}$alkynyl, $R^6$—$C_{3-14}$cycloalkyl, $R^6$—$C_{3-14}$cycloalkyl$C_{1-4}$alkyl, $R^6$—$C_{3-14}$cycloalkyl$C_{1-4}$alkenyl, $R^7$-heterocyclyl, $R^7$-heterocyclyl$C_{1-4}$alkyl, $R^7$-heterocyclyl$C_{1-4}$alkenyl, $R^8$-heteroaryl and $R^8$-heteroaryl$C_{2-4}$alkenyl, wherein each instance of $C_{2-4}$alkenyl is optionally substituted with one substituent selected from the group consisting of halogen, cyano, $C_{1-4}$alkylcarbonylamino and aryl;

$R^5$ is one optional substituent selected from the group consisting of $R^{5a}$-aryl, $R^{5a}$-aryl$C_{1-4}$alkyl, $R^{5a}$-aryl$C_{1-4}$alkoxy, $R^{5a}$-aryloxy, $R^{5a}$-arylcarbonyl $R^{5a}$-arylsulfonylamino, $R^{5b}$-heteroaryl, $R^{5b}$-heteroaryl$C_{1-4}$alkyl, $R^{5b}$-heteroaryl$C_{1-4}$alkylcarbonylamino, $R^{5b}$-heteroarylthio, $R^{5b}$-heteroaryl-($R^{5b}$)-heteroaryl, $R^{5b}$-heterocyclyl and $C_{3-14}$cycloalkyl, and one or two optional substituents each selected from the group consisting of halogen, hydroxy, cyano, nitro, $C_{1-4}$alkyl, $C_{2-4}$alkenyl, $C_{2-4}$alkynyl, halo$C_{1-4}$alkyl, hydroxy$C_{1-4}$alkyl, $C_{1-4}$alkoxy, $C_{1-4}$alkoxy$C_{1-4}$alkyl, $C_{1-4}$alkoxy$C_{1-4}$alkoxy, halo$C_{1-4}$alkoxy, $C_{1-4}$alkylthio, halo$C_{1-4}$alkylthio, $C_{1-4}$alkylcarbonyl, $C_{1-4}$alkoxycarbonyl, aminothiocarbonylamino, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl, ($C_{1-4}$alkyl)$_2$-amino$C_{1-4}$alkyl, aminocarbonyl, $C_{1-4}$alkylsulfonyl, aminosulfonyl, ($C_{1-4}$alkyl)aminosulfonyl and ($C_{1-4}$alkyl)$_2$-aminosulfonyl;

$R^{5a}$ is one, two or three optional substituents each selected from the group consisting of halogen, hydroxy, cyano, nitro, $C_{1-4}$alkyl, halo$C_{1-4}$alkyl, hydroxy$C_{1-4}$alkyl, $C_{1-4}$alkoxy, halo$C_{1-4}$alkoxy, $C_{1-4}$alkylthio, halo$C_{1-4}$alkylthio, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl and ($C_{1-4}$alkyl)$_2$-amino$C_{1-4}$alkyl;

$R^{5b}$ is one, two or three optional substituents each selected from the group consisting of halogen, hydroxy, cyano, nitro, $C_{1-4}$alkyl, halo$C_{1-4}$alkyl, hydroxy$C_{1-4}$alkyl, $C_{1-4}$alkoxy, halo$C_{1-4}$alkoxy, $C_{1-4}$alkylthio, halo$C_{1-4}$alkylthio, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl and ($C_{1-4}$alkyl)$_2$-amino$C_{1-4}$alkyl;

$R^6$ is one or two optional substituents each selected from the group consisting of $C_{1-4}$alkyl, oxo and aryl;

$R^7$ is an optional substituent on one, two or three carbon atoms each selected from the group consisting of halogen, $C_{1-4}$alkyl, $C_{1-4}$alkoxy, $C_{1-4}$alkylthio, aryl$C_{1-4}$alkylthio, oxo and aryl, and two optional substituents on one carbon atom each selected from the group consisting of $C_{1-4}$alkyl and halogen, and one or two optional oxo substituents on a sulfur atom, when said sulfur atom is present;

$R^8$ is an optional substituent on one carbon atom or an available nitrogen atom selected from the group consisting of $R^{8a}$-aryl, $R^{8a}$-aryl$C_{1-4}$alkyl, $R^{8a}$-aryl$C_{2-4}$alkenyl, $R^{8a}$-aryl$C_{2-4}$alkynyl, $R^{8a}$-aryloxy, $R^{8a}$-aryloxy$C_{1-4}$alkyl, $R^{8a}$-arylthio, $R^{8a}$-aryl$C_{1-4}$alkylthio, $R^{8a}$-aryl$C_{1-4}$alkylthio$C_{1-4}$alkyl, $R^{8a}$-arylsulfonyl, $R^{8b}$-heteroaryl, $R^{8b}$-heteroaryl$C_{1-4}$ alkyl, $R^{8b}$-heteroarylthio$C_{1-4}$alkyl, $R^{8b}$-heteroarylcarbonylamino$C_{1-4}$alkyl and $R^{8c}$-heterocyclyl$C_{1-4}$alkyl, and an optional $C_{1-4}$alkyl substituent on an available nitrogen atom, and an optional substituent on one, two or three carbon atoms each selected from the group consisting of halogen, cyano, $C_{1-4}$alkyl, halo$C_{1-4}$alkyl, hydroxy$C_{1-4}$alkyl, $C_{1-4}$alkoxy, halo$C_{1-4}$alkoxy, formyl, $C_{1-4}$alkylcarbonyl, $C_{1-4}$alkoxycarbonyl, $C_{1-4}$alkylthio and $C_{1-4}$alkylsulfonyl;

$R^{8a}$ is one, two or three optional substituents each selected from the group consisting of halogen, hydroxy, cyano, nitro, $C_{1-4}$alkyl, $C_{2-4}$alkenyl, $C_{2-4}$alkynyl, halo$C_{1-4}$alkyl, hydroxy$C_{1-4}$alkyl, $C_{1-4}$alkoxy, halo$C_{1-4}$alkoxy, $C_{1-4}$alkylthio, halo$C_{1-4}$alkylthio, $C_{1-4}$alkylcarbonyl, $C_{1-4}$alkoxycarbonyl, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl and ($C_{1-4}$alkyl)$_2$-amino$C_{1-4}$alkyl;

$R^{8b}$ is one, two or three optional substituents each selected from the group consisting of halogen, hydroxy, cyano, nitro, $C_{1-4}$alkyl, $C_{2-4}$alkenyl, $C_{2-4}$alkynyl, halo$C_{1-4}$alkyl, hydroxy$C_{1-4}$alkyl, $C_{1-4}$alkoxy, halo$C_{1-4}$alkoxy, $C_{1-4}$alkylthio, halo$C_{1-4}$alkylthio, $C_{1-4}$alkylcarbonyl, $C_{1-4}$alkoxycarbonyl, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl and ($C_{1-4}$alkyl)$_2$-amino$C_{1-4}$alkyl;

$R_4$ is one substituent selected from the group consisting of hydrogen, $C_{1-4}$alkyl, carboxy$C_{1-4}$alkyl, $C_{1-4}$alkylcarbonyl, $C_{1-4}$alkoxycarbonyl, $C_{1-4}$alkoxycarbonyl$C_{1-4}$alkyl, $C_{1-4}$alkoxycarbonyl$C_{1-4}$alkylcarbonyl, $C_{1-4}$alkoxycarbonylcarbonyl, aminocarbonyl, $R^9$-aryl$C_{1-4}$alkyl, $R^9$-arylcarbonyl, hydroxysulfonyl, aminosulfonyl, $C_{1-4}$alkylsulfonyl, hydroxysulfonyl$C_{1-4}$alkylcarbonyl, $C_{1-4}$alkylsulfonyl$C_{1-4}$alkylcarbonyl, $C_{1-4}$alkylsulfonyl$C_{1-4}$ alkylsulfonyl, $C_{1-4}$alkoxycarbonyl$C_{1-4}$alkylsulfonyl, $R^9$-arylsulfonyl, P[(O)(OH)$_2$]-$C_{1-4}$alkyl, $R^{10}$-heterocyclylcarbonyl, $R^{10}$-heterocyclylsulfonyl, $R^{11}$-heteroarylcarbonyl, $R^{11}$-heteroaryl$C_{1-4}$alkylcarbonyl and $R^{11}$-heteroarylsulfonyl, wherein $C_{1-4}$alkoxycarbonyl$C_{1-4}$alkylcarbonyl is optionally substituted on $C_{1-4}$alkyl with ($C_{1-4}$alkyl)aminoamino;

$R^9$ is one or two optional substituents each selected from the group consisting of halogen, hydroxy, cyano, nitro, $C_{1-4}$alkyl, $C_{2-4}$alkenyl, $C_{2-4}$alkynyl, halo$C_{1-4}$alkyl, hydroxy$C_{1-4}$alkyl, $C_{1-4}$alkoxy, carboxy, $C_{1-4}$alkoxy$C_{1-4}$ alkyl, $C_{1-4}$alkoxy$C_{1-4}$alkoxy, halo$C_{1-4}$alkoxy, $C_{1-4}$alkylthio, halo$C_{1-4}$alkylthio, $C_{1-4}$alkylcarbonyl, $C_{1-4}$alkoxycarbonyl, aminothiocarbonylamino, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl, ($C_{1-4}$alkyl)$_2$-amino$C_{1-4}$alkyl, aminocarbonyl, $C_{1-4}$alkylsulfonyl, aminosulfonyl, ($C_{1-4}$alkyl)aminosulfonyl and ($C_{1-4}$alkyl)$_2$-aminosulfonyl;

$R^{10}$ is an optional substituent on one, two or three carbon atoms each selected from the group consisting of halogen, $C_{1-4}$alkyl, $C_{1-4}$alkoxy, $C_{1-4}$alkylthio, ($C_{1-4}$alkyl)aminoamino and oxo, and two optional substituents on one carbon atom each selected from the group consisting of $C_{1-4}$alkyl and halogen, and one or two optional oxo substituents on a sulfur atom, when said sulfur atom is present; and $R^{11}$ is an optional $C_{1-4}$alkyl substituent on an available nitrogen atom, and an optional substituent on one, two or three carbon atoms each selected from the group consisting of halogen, cyano, $C_{1-4}$alkyl, $C_{1-4}$alkoxy, halo$C_{1-4}$alkoxy, carboxy, formyl, $C_{1-4}$alkylcarbonyl, $C_{1-4}$alkoxycarbonyl and $C_{1-4}$alkylthio.

An example of a compound of Formula (I) includes compounds or a form thereof, wherein $X_1$ and $X_2$, respectively, are selected from the group consisting of —$CH_2$— and —$CH_2$—, —$CH_2$— and —O—, —O— and —$CH_2$—, —$CH_2$— and —N($R_4$)—, —N($R_4$)— and —$CH_2$—, —$CH_2$— and —S—, —S— and —$CH_2$—, —$CH_2$— and —S(O)—, —S(O)— and —$CH_2$—, —$CH_2$— and —$SO_2$—, —$SO_2$— and —$CH_2$—, —$CH_2$— and —C(O)— and —$CH_2$—, —$CH_2$— and —C(O)—, —C(O)— and —N($R_4$)—, —N($R_4$)— and —C(O)—, —C(O)— and —S— and —S— and —C(O)—;

$X_3$ and $X_4$, respectively, are selected from the group consisting of —$CH_2$— and —$CH_2$—, —$CH_2$— and —C(O)— and —C(O)— and —$CH_2$—;

$R_1$ is selected from the group consisting of amino$C_{1-4}$alkyl, ($C_{1-4}$alkyl)amino$C_{1-4}$alkyl, ($C_{1-4}$alkyl)$_2$-amino$C_{1-4}$alkyl, ($C_{1-4}$alkyl)$_3$-amino$C_{1-4}$alkyl, formylamino$C_{1-4}$alkyl, phenylcarbonylamino$C_{1-4}$alkyl, aminosulfonylamino$C_{1-4}$alkyl, aryl$C_{1-4}$alkylamino$C_{1-4}$alkyl, $C_{3-14}$cycloalkylcarbonylamino$C_{1-4}$alkyl, $C_{3-14}$cycloalkyl$C_{1-4}$ alkenylcarbonylamino$C_{1-4}$alkyl, aryl$C_{1-4}$alkylcarbonylamino$C_{1-4}$alkyl, aryl$C_{2-4}$alkenylcarbonylamino$C_{1-4}$alkyl, aryl$C_{2-4}$alkynylcarbonylamino$C_{1-4}$alkyl, arylsulfonylamino$C_{1-4}$alkyl, heterocyclylcarbonylamino$C_{1-4}$alkyl, heterocyclyl$C_{1-4}$alkylcarbonylamino$C_{1-4}$alkyl, heterocyclyl$C_{1-4}$alkenylcarbonylamino$C_{1-4}$alkyl, heteroarylcarbonylamino$C_{1-4}$alkyl, heteroaryl$C_{2-4}$alkenylcarbonylamino$C_{1-4}$alkyl, aminoimino, hydroxyaminoimino, ($C_{1-4}$alkyl)aminoimino, ($C_{1-4}$alkyl)$_2$-aminoimino and aminoaminoimino, wherein each instance of phenyl is optionally substituted with one or two halogen substituents;

$R_2$ is absent or is one halogen substituent;

$R^3$ is hydrogen or is selected from the group consisting of $R^5$-phenyl$C_{1-4}$alkyl, carbonyl and sulfonyl, wherein carbonyl and sulfonyl are each substituted with a substituent selected from the group consisting of $R^5$-phenyl, $R^5$-naphthalenyl, $R^5$-phenyl-$C_{1-4}$alkyl, $R^5$-naphthalenyl-$C_{1-4}$alkyl, $R^6$-fluorenyl-$C_{1-4}$alkyl, $R^5$-phenyl-$C_{1-4}$alkylamino, ($R^5$-phenyl)$_{1-2}C_{1-4}$alkyl, $R^5$-phenyl-$C_{2-4}$alkenyl, $R^5$-naphthalenyl-$C_{2-4}$alkenyl, $R^5$-phenyl$C_{2-4}$alkynyl, $R^6$-cyclopropyl, $R^6$-indanyl, $R^6$-1H-indenyl, $R^6$-9H-fluorenyl, $R^6$—$C_{3-14}$cycloalkyl$C_{1-4}$alkyl, $R^6$-9H-fluorenyl-$C_{1-4}$alkenyl, $R^7$-benzo[1,3]dioxolyl, $R^7$-4,5-dihydro-benzo[c]thiophenyl, $R^7$-4,5,6,7-tetrahydro-benzo[c]thiophenyl, $R^7$-4,5,6,7-tetrahydro-benzo[b]thiophenyl, $R^7$-chromenyl, $R^7$-9H-xanthenyl, $R^7$-9H-thioxanthenyl, $R^7$-5,6-dihydro-4H-cyclopenta[b]thiophenyl, $R^7$-4,5,6,7-tetrahydro-benzofuranyl, $R^7$-5,6,7,8-tetrahydro-4H-cyclohepta[b]thiophenyl, $R^7$-spiro[cyclohexane-1,6'-5,7-dihydro-4H-benzo[b]thiophene], $R^7$-benzo[1,3]dioxolyl-$C_{1-4}$alkyl, $R^7$-benzo[1,3]dioxolyl-$C_{1-4}$alkenyl, $R^7$-3H-isobenzofuranyl-$C_{1-4}$alkenyl, $R^8$-furanyl, $R^8$-thienyl, $R^8$-thiazolyl, $R^8$-[1,2,3]thiadiazolyl, $R^8$-pyridinyl, $R^8$-1H-indolyl, $R^8$-benzo[b]furanyl, $R^8$-benzo[b]thiophenyl, $R^8$-benzo[c]thiophenyl, $R^8$-1H-benzoimidazolyl, $R^8$-benzothiazolyl, $R^8$-thieno[3,2-b]thiophenyl, $R^8$-thieno[2,3-b]thiophenyl, $R^8$-naphtho[2,1-b]thiophenyl, $R^8$-1H-thieno[2,3-c]pyrazolyl, $R^8$-imidazo[1,2-a]pyridinyl, $R^8$-1H-imidazolyl-$C_{2-4}$alkenyl, $R^8$-furanyl-$C_{2-4}$alkenyl, $R^8$-thienyl-$C_{2-4}$alkenyl and $R^8$-pyridinyl-$C_{2-4}$alkenyl, wherein each instance of $C_{2-4}$alkenyl is optionally substituted with one substituent selected from the group consisting of halogen, cyano, $C_{1-4}$alkylcarbonylamino and aryl;

$R^5$ is one optional substituent selected from the group consisting of $R^{5a}$-phenyl, $R^{5a}$-phenyl$C_{1-4}$alkyl, $R^{5a}$-phenyl$C_{1-4}$ alkoxy, $R^{5a}$-phenoxy, $R^{5a}$-phenylcarbonyl, $R^{5a}$-phenylsulfonylamino, $R^{5b}$-heteroaryl, $R^{5b}$-1H-benzoimidazolyl-$C_{1-4}$alkyl, $R^{5b}$-1H-benzoimidazolyl-$C_{1-4}$ alkylcarbonylamino, $R^{5b}$-thienyl-$C_{1-4}$ alkylcarbonylamino, $R^{5b}$-pyrimidinylthio, $R^{5b}$-benzoxazolyl-($R^{5b}$)-pyrazolyl, $R^{5b}$-thienyl-($R^{5b}$)-[1,2,4]oxadiazolyl, $R^{5b}$-benzo[1,3]dioxolyl and cyclohexyl, and one or two optional substituents each selected from the group consisting of halogen, hydroxy, cyano, nitro, $C_{1-4}$alkyl, $C_{2-4}$alkenyl, $C_{2-4}$alkynyl, halo$C_{1-4}$alkyl, hydroxy$C_{1-4}$alkyl, $C_{1-4}$alkoxy, $C_{1-4}$alkoxy$C_{1-4}$alkyl, $C_{1-4}$alkoxy$C_{1-4}$alkoxy, halo$C_{1-4}$alkoxy, $C_{1-4}$alkylthio, halo$C_{1-4}$alkylthio, $C_{1-4}$alkylcarbonyl, $C_{1-4}$alkoxycarbonyl, aminothiocarbonylamino, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl, ($C_{1-4}$alkyl)$_2$-amino$C_{1-4}$alkyl, aminocarbonyl, $C_{1-4}$alkylsulfonyl, aminosulfonyl, ($C_{1-4}$alkyl)aminosulfonyl and ($C_{1-4}$alkyl)$_2$-aminosulfonyl;

$R^{5a}$ is one, two or three optional substituents each selected from the group consisting of halogen, hydroxy, cyano, nitro, $C_{1-4}$alkyl, halo$C_{1-4}$alkyl, hydroxy$C_{1-4}$alkyl, $C_{1-4}$alkoxy, halo$C_{1-4}$alkoxy, $C_{1-4}$alkylthio, halo$C_{1-4}$alkylthio, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl and ($C_{1-4}$alkyl)$_2$-amino$C_{1-4}$alkyl;

$R^{5b}$ is one, two or three optional substituents each selected from the group consisting of halogen, hydroxy, cyano, nitro, $C_{1-4}$alkyl, halo$C_{1-4}$alkyl, hydroxy$C_{1-4}$alkyl, $C_{1-4}$alkoxy, halo$C_{1-4}$alkoxy, $C_{1-4}$alkylthio, halo$C_{1-4}$alkylthio, amino, ($C_{1-4}$alkyl)amino, ($C_{1-4}$alkyl)$_2$-amino, amino$C_{1-4}$alkyl, ($C_{1-4}$alkyl)amino$C_{1-4}$alkyl and ($C_{1-4}$alkyl)$_2$-amino$C_{1-4}$alkyl;

$R^6$ is one or two optional substituents each selected from the group consisting of $C_{1-4}$alkyl, oxo and phenyl;

$R^7$ is an optional substituent on one, two or three carbon atoms each selected from the group consisting of halogen, $C_{1-4}$alkyl, $C_{1-4}$alkoxy, $C_{1-4}$alkylthio, phenyl$C_{1-4}$alkylthio, oxo and phenyl, and two optional substituents on one carbon atom each selected from the group consisting of $C_{1-4}$alkyl and halogen, and one or two optional oxo substituents on a sulfur atom, when said sulfur atom is present;

$R^8$ is an optional substituent on one carbon atom or an available nitrogen atom selected from the group consisting of $R^{8a}$-phenyl, $R^{8a}$-phenyl$C_{1-4}$alkyl, $R^{8a}$-phenyl$C_{2-4}$alkenyl, $R^{8a}$-phenyl$C_{2-4}$alkynyl, $R^{8a}$-naphthalenyl$C_{2-4}$alkynyl, $R^{8a}$-phenoxy, $R^{8a}$-phenoxy$C_{1-4}$alkyl, $R^{8a}$-phenylthio, $R^{8a}$-phenyl$C_{1-4}$alkylthio, $R^{8a}$-phenyl$C_{1-4}$alkylthio$C_{1-4}$ alkyl, $R^{8a}$-phenylsulfonyl, $R^{8b}$-pyridinyl, $R^{8b}$-pyrazolyl, $R^{8b}$ thienyl, $R^{8b}$ thiazolyl $R^{8b}$-pyrazolyl$C_{1-4}$alkyl, $R^{8b}$-pyrimidinylthio$C_{1-4}$alkyl, $R^{8b}$-furanylcarbonylamino$C_{1-4}$ alkyl and $R^{8c}$-morpholinyl$C_{1-4}$alkyl, and an optional $C_{1-4}$alkyl substituent on an available nitrogen atom, and an optional substituent on one, two or three carbon atoms each selected from the group consisting of halogen, cyano, $C_{1-4}$alkyl, halo$C_{1-4}$alkyl, hydroxy$C_{1-4}$alkyl, $C_{1-4}$alkoxy, halo$C_{1-4}$alkoxy, formyl, $C_{1-4}$alkylcarbonyl, $C_{1-4}$alkoxycarbonyl, $C_{1-4}$alkylthio and $C_{1-4}$alkylsulfonyl;

$R^{8a}$ is one, two or three optional substituents each selected from the group consisting of halogen, hydroxy, cyano, nitro, $C_{1-4}$alkyl, $C_{2-4}$alkenyl, $C_{2-4}$alkynyl, halo$C_{1-4}$alkyl, hydroxyC$_{1-4}$alkyl, C$_{1-4}$alkoxy, haloC$_{1-4}$alkoxy, C$_{1-4}$alkylthio, haloC$_{1-4}$alkylthio, C$_{1-4}$alkylcarbonyl, C$_{1-4}$alkoxycarbonyl, amino, (C$_{1-4}$alkyl)amino, (C$_{1-4}$alkyl)$_2$-amino, aminoC$_{1-4}$alkyl, (C$_{1-4}$alkyl)aminoC$_{1-4}$alkyl and (C$_{1-4}$alkyl)$_2$-aminoC$_{1-4}$alkyl;

R$^{8b}$ is one, two or three optional substituents each selected from the group consisting of halogen, hydroxy, cyano, nitro, C$_{1-4}$alkyl, C$_{2-4}$alkenyl, C$_{2-4}$alkynyl, haloC$_{1-4}$alkyl, hydroxyC$_{1-4}$alkyl, C$_{1-4}$alkoxy, haloC$_{1-4}$alkoxy, C$_{1-4}$alkylthio, haloC$_{1-4}$alkylthio, C$_{1-4}$alkylcarbonyl, C$_{1-4}$alkoxycarbonyl, amino, (C$_{1-4}$alkyl)amino, (C$_{1-4}$alkyl)$_2$-amino, aminoC$_{1-4}$alkyl, (C$_{1-4}$alkyl)aminoC$_{1-4}$alkyl and (C$_{1-4}$alkyl)$_2$-aminoC$_{1-4}$alkyl;

R$_4$ is one substituent selected from the group consisting of hydrogen, C$_{1-4}$alkyl, carboxyC$_{1-4}$alkyl, C$_{1-4}$alkylcarbonyl, C$_{1-4}$alkoxycarbonyl, C$_{1-4}$alkoxycarbonylC$_{1-4}$alkyl, C$_{1-4}$alkoxycarbonylC$_{1-4}$alkylcarbonyl, C$_{1-4}$alkoxycarbonylcarbonyl, aminocarbonyl, R$^9$-phenyl-C$_{1-4}$alkyl, R$^9$-phenyl-carbonyl, hydroxysulfonyl, aminosulfonyl, C$_{1-4}$alkylsulfonyl, hydroxysulfonylC$_{1-4}$alkylcarbonyl, C$_4$alkylsulfonylC$_{1-4}$alkylcarbonyl, C$_{1-4}$alkylsulfonylC$_{1-4}$alkylsulfonyl, C$_{1-4}$alkoxycarbonylC$_{1-4}$alkylsulfonyl, R$^9$-phenyl-sulfonyl, P[(O)(OH)$_2$]-C$_{1-4}$alkyl, R$^{10}$-tetrahydrothienyl-sulfonyl, R$^{11}$-1H-tetrazolyl-carbonyl, R$^{11}$-1H-tetrazolyl-C$_{1-4}$alkylcarbonyl, R$^{11}$-1H-imidazolyl-sulfonyl, R$^{11}$-furanyl-sulfonyl and R$^{11}$-thienyl-sulfonyl, wherein C$_{1-4}$alkoxycarbonylC$_{1-4}$alkylcarbonyl is optionally substituted on C$_{1-4}$alkyl with (C$_{1-4}$alkyl)aminoamino;

R$^9$ is one or two optional substituents each selected from the group consisting of halogen, hydroxy, cyano, nitro, C$_{1-4}$alkyl, C$_{2-4}$alkenyl, C$_{2-4}$alkynyl, haloC$_{1-4}$alkyl, hydroxyC$_{1-4}$alkyl, C$_{1-4}$alkoxy, carboxy, C$_{1-4}$alkoxyC$_{1-4}$alkyl, C$_{1-4}$alkoxyC$_{1-4}$alkoxy, haloC$_{1-4}$alkoxy, C$_{1-4}$alkylthio, haloC$_{1-4}$alkylthio, C$_{1-4}$alkylcarbonyl, C$_{1-4}$alkoxycarbonyl, aminothiocarbonylamino, amino, (C$_{1-4}$alkyl)amino, (C$_{1-4}$alkyl)$_2$-amino, aminoC$_{1-4}$alkyl, (C$_{1-4}$alkyl)aminoC$_{1-4}$alkyl, (C$_{1-4}$alkyl)$_2$-aminoC$_{1-4}$alkyl, aminocarbonyl, C$_{1-4}$alkylsulfonyl, aminosulfonyl, (C$_{1-4}$alkyl)aminosulfonyl and (C$_{1-4}$alkyl)$_2$-aminosulfonyl;

R$^{10}$ is an optional substituent on one, two or three carbon atoms each selected from the group consisting of halogen, C$_{1-4}$alkyl, C$_{1-4}$alkoxy, C$_{1-4}$alkylthio, (C$_{1-4}$alkyl)aminoamino and oxo, two optional substituents on one carbon atom each selected from the group consisting of C$_{1-4}$alkyl and halogen, and one or two optional oxo substituents on a sulfur atom, when said sulfur atom is present;

R$^{11}$ is an optional C$_{1-4}$alkyl substituent on an available nitrogen atom, and an optional substituent on one, two or three carbon atoms each selected from the group consisting of halogen, cyano, C$_{1-4}$alkyl, C$_{1-4}$alkoxy, haloC$_{1-4}$alkoxy, carboxy, formyl, C$_{1-4}$alkylcarbonyl, C$_{1-4}$alkoxycarbonyl and C$_{1-4}$alkylthio.

An example of a compound of Formula (I) includes compounds or a form thereof, wherein X$_1$ and X$_2$, respectively, are selected from the group consisting of —CH$_2$— and —CH$_2$—, —CH$_2$— and —O—, —CH$_2$— and —N(R$_4$)—, —CH$_2$— and —S—, —C(O)— and —N(R$_4$)— and —N(R$_4$)— and —C(O)—;

X$_3$ and X$_4$, respectively, are —CH$_2$— and —CH$_2$—;

R$_1$ is selected from the group consisting of aminoC$_{1-4}$alkyl, (C$_{1-4}$alkyl)aminoC$_{1-4}$alkyl, formylaminoC$_{1-4}$alkyl, arylcarbonylaminoC$_{1-4}$alkyl, aminoimino, hydroxyaminoimino, (C$_{1-4}$alkyl)aminoimino, (C$_{1-4}$alkyl)$_2$-aminoimino and aminoaminoimino, wherein each instance of aryl is optionally substituted with one or two halogen substituents;

R$_2$ is absent or is one halogen substituent;

R$^3$ is hydrogen or is selected from the group consisting of R$^5$-arylC$_{1-4}$alkyl, carbonyl and sulfonyl, wherein carbonyl and sulfonyl are each substituted with a substituent selected from the group consisting of R$^5$-aryl, R$^5$-arylC$_{1-4}$alkyl, R$^5$-arylC$_{1-4}$alkylamino, (R$^5$-aryl)$_{1-2}$C$_{1-4}$alkyl, R$^5$-arylC$_{2-4}$alkenyl, R$^5$-arylC$_{2-4}$alkynyl, R$^6$—C$_{3-14}$cycloalkyl, R$^6$—C$_{3-14}$cycloalkylC$_{1-4}$alkyl, R$^6$—C$_{3-14}$cycloalkylC$_{1-4}$alkenyl, R$^7$-heterocyclyl, R$^7$-heterocyclylC$_{1-4}$alkyl, R$^7$-heterocyclylC$_{1-4}$alkenyl, R$^8$-heteroaryl and R$^8$-heteroarylC$_{2-4}$alkenyl, wherein each instance of C$_{2-4}$alkenyl is optionally substituted with one substituent selected from the group consisting of halogen, cyano, C$_{1-4}$alkylcarbonylamino and aryl;

R$^5$ is one optional substituent selected from the group consisting of R$^{5a}$-aryl, R$^{5a}$-arylC$_{1-4}$alkyl, R$^{5a}$-arylC$_{1-4}$alkoxy, R$^{5a}$-aryloxy R$^{5a}$-arylcarbonyl R$^{5a}$-arylsulfonylamino, R$^{5b}$-heteroaryl, R$^{5b}$-heteroarylC$_{1-4}$alkyl, R$^{5b}$-heteroarylC$_{1-4}$alkylcarbonylamino, R$^{5b}$-heteroarylthio, R$^{5b}$-heteroaryl-(R$^{5b}$)-heteroaryl, R$^{5b}$-heterocyclyl and C$_{3-14}$cycloalkyl, and one or two optional substituents each selected from the group consisting of halogen, hydroxy, cyano, nitro, C$_{1-4}$alkyl, C$_{2-4}$alkenyl, haloC$_{1-4}$alkyl, C$_{1-4}$alkoxy, C$_{1-4}$alkoxyC$_{1-4}$alkoxy, haloC$_{1-4}$alkoxy, C$_{1-4}$alkylthio, haloC$_{1-4}$alkylthio, C$_{1-4}$alkylcarbonyl, C$_{1-4}$alkoxycarbonyl, aminothiocarbonylamino, (C$_{1-4}$alkyl)$_2$-amino, aminocarbonyl, C$_{1-4}$alkylsulfonyl and aminosulfonyl;

R$^{5a}$ is one or two optional substituents each selected from the group consisting of halogen, C$_{1-4}$alkyl, haloC$_{1-4}$alkyl and C$_{1-4}$alkoxy;

R$^{5b}$ is one or two optional halogen substituents;

R$^6$ is one optional substituent selected from the group consisting of C$_{1-4}$alkyl, oxo and aryl;

R$^7$ is an optional substituent on one, two or three carbon atoms each selected from the group consisting of halogen, C$_{1-4}$alkyl, C$_{1-4}$alkoxy, C$_{1-4}$alkylthio, arylC$_{1-4}$alkylthio, oxo and aryl, and two optional C$_{1-4}$alkyl substituents on one carbon atom, and two oxo substituents on a sulfur atom, when said sulfur atom is present;

R$^8$ is an optional substituent on one carbon atom or an available nitrogen atom selected from the group consisting of R$^{8a}$-aryl, R$^{8a}$-arylC$_{1-4}$alkyl, R$^{8a}$-arylC$_{2-4}$alkenyl, R$^{8a}$-arylC$_{2-4}$alkynyl, R$^{8a}$-aryloxy, R$^{8a}$-aryloxyC$_{1-4}$alkyl, R$^{8a}$-arylthio, R$^{8a}$-arylC$_{1-4}$alkylthio, R$^{8a}$-arylC$_{1-4}$alkylthioC$_{1-4}$alkyl, R$^{8a}$-arylsulfonyl, R$^{8b}$-heteroaryl, R$^{8b}$-heteroarylC$_{1-4}$ alkyl, R$^{8b}$-heteroarylthioC$_{1-4}$alkyl, R$^{8b}$-heteroarylcarbonylaminoC$_{1-4}$alkyl and R$^{8c}$-heterocyclylC$_{1-4}$alkyl, and an optional C$_{1-4}$alkyl substituent on an available nitrogen atom, and an optional substituent on one, two or three carbon atoms each selected from the group consisting of halogen, cyano, C$_{1-4}$alkyl, haloC$_{1-4}$alkyl, hydroxyC$_{1-4}$alkyl, C$_{1-4}$alkoxy, formyl, C$_{1-4}$alkoxycarbonyl, C$_{1-4}$alkylthio and C$_{1-4}$alkylsulfonyl;

R$^{8a}$ is one or two optional substituents each selected from the group consisting of halogen, C$_{1-4}$alkyl, C$_{2-4}$alkenyl, haloC$_{1-4}$alkyl and C$_{1-4}$alkoxy;

R$^{8b}$ is one, two or three optional substituents each selected from the group consisting of halogen, C$_{1-4}$alkyl and haloC$_{1-4}$alkyl;

R$_4$ is one substituent selected from the group consisting of hydrogen, C$_{1-4}$alkyl, carboxyC$_{1-4}$alkyl, C$_{1-4}$alkylcarbonyl, $C_{1-4}$alkoxycarbonyl, $C_{1-4}$alkoxycarbonyl$C_{1-4}$alkyl, $C_{1-4}$alkoxycarbonyl$C_{1-4}$alkylcarbonyl, $C_{1-4}$alkoxycarbonylcarbonyl, aminocarbonyl, $R^9$-arylcarbonyl, hydroxysulfonyl, aminosulfonyl, $C_{1-4}$alkylsulfonyl, hydroxysulfonyl$C_{1-4}$alkylcarbonyl, $C_{1-4}$alkylsulfonyl$C_{1-4}$alkylcarbonyl, $C_{1-4}$alkylsulfonyl$C_{1-4}$alkylsulfonyl, $C_{1-4}$alkoxycarbonyl$C_{1-4}$alkylsulfonyl, $R^9$-arylsulfonyl, P[(O)(OH)$_2$]-$C_{1-4}$alkyl, $R^{10}$-heterocyclylcarbonyl, $R^{10}$-heterocyclylsulfonyl, $R^{11}$-heteroarylcarbonyl, $R^{11}$-heteroaryl$C_{1-4}$alkylcarbonyl and $R^{11}$-heteroarylsulfonyl, wherein $C_{1-4}$alkoxycarbonyl$C_{1-4}$alkylcarbonyl is optionally substituted on $C_{1-4}$alkyl with ($C_{1-4}$alkyl)aminoamino;

$R^9$ is one or two optional substituents each selected from the group consisting of $C_{1-4}$alkoxy, carboxy and $C_{1-4}$alkoxycarbonyl;

$R^{10}$ is an optional ($C_{1-4}$alkyl)aminoamino substituent on one carbon atom, and two oxo substituents on a sulfur atom, when said sulfur atom is present; and $R^{11}$ is an optional $C_{1-4}$alkyl substituent on an available nitrogen atom, and an optional substituent on one carbon atom selected from the group consisting of carboxy and $C_{1-4}$alkoxycarbonyl.

An example of a compound of Formula (I) includes compounds or a form thereof, wherein $X_1$ and $X_2$, respectively, are selected from the group consisting of —CH$_2$— and —CH$_2$—, —CH$_2$— and —O—, —CH$_2$— and —N(R$_4$)—, —CH$_2$— and —S—, —C(O)— and —N(R$_4$)— and —N(R$_4$)— and —C(O)—;

$X_3$ and $X_4$, respectively, are —CH$_2$— and —CH$_2$—;

$R_1$ is selected from the group consisting of amino$C_{1-4}$alkyl, ($C_{1-4}$alkyl)amino$C_{1-4}$alkyl, formylamino$C_{1-4}$alkyl, phenylcarbonylamino$C_{1-4}$alkyl, aminoimino, hydroxyaminoimino, ($C_{1-4}$alkyl)aminoimino, ($C_{1-4}$alkyl)$_2$-aminoimino and aminoaminoimino, wherein each instance of phenyl is optionally substituted with one or two halogen substituents;

$R_2$ is absent or is one halogen substituent;

$R^3$ is hydrogen or is selected from the group consisting of $R^5$-phenyl$C_{1-4}$alkyl, carbonyl and sulfonyl, wherein carbonyl and sulfonyl are each substituted with a substituent selected from the group consisting of $R^5$-phenyl, $R^5$-naphthalenyl, $R^5$-phenyl-$C_{1-4}$alkyl, $R^5$-naphthalenyl-$C_{1-4}$alkyl, $R^6$-fluorenyl-$C_{1-4}$alkyl, $R^5$-phenyl-$C_{1-4}$alkylamino, ($R^5$-phenyl)$_{1-2}$$C_{1-4}$alkyl, $R^5$-phenyl-$C_{2-4}$alkenyl, $R^5$-naphthalenyl-$C_{2-4}$alkenyl, $R^5$-phenyl$C_{2-4}$alkynyl, $R^6$-cyclopropyl, $R^6$-indanyl, $R^6$-1H-indenyl, $R^6$-9H-fluorenyl, $R^6$—$C_{3-14}$cycloalkyl$C_{1-4}$alkyl, $R^6$-9H-fluorenyl-$C_{1-4}$alkenyl, $R^7$-benzo[1,3]dioxolyl, $R^7$-4,5-dihydro-benzo[c]thiophenyl, $R^7$-4,5,6,7-tetrahydro-benzo[c]thiophenyl, $R^7$-4,5,6,7-tetrahydro-benzo[b]thiophenyl, $R^7$-chromenyl, $R^7$-9H-xanthenyl, $R^7$-9H-thioxanthenyl, $R^7$-5,6-dihydro-4H-cyclopenta[b]thiophenyl, $R^7$-4,5,6,7-tetrahydro-benzofuranyl, $R^7$-5,6,7,8-tetrahydro-4H-cyclohepta[b]thiophenyl, $R^7$-spiro[cyclohexane-1,6'-5,7-dihydro-4H-benzo[b]thiophene], $R^7$-benzo[1,3]dioxolyl-$C_{1-4}$alkyl, $R^7$-benzo[1,3]dioxolyl-$C_{1-4}$alkenyl, $R^7$-3H-isobenzofuranyl-$C_{1-4}$alkenyl, $R^8$-furanyl, $R^8$-thienyl, $R^8$-thiazolyl, $R^8$-[1,2,3]thiadiazolyl, $R^8$-pyridinyl, $R^8$-1H-indolyl, $R^8$-benzo[b]furanyl, $R^8$-benzo[b]thiophenyl, $R^8$-benzo[c]thiophenyl, $R^8$-1H-benzoimidazolyl, $R^8$-benzothiazolyl, $R^8$-thieno[3,2-b]thiophenyl, $R^8$-thieno[2,3-b]thiophenyl, $R^8$-naphtho[2,1-b]thiophenyl, $R^8$-1H-thieno[2,3-c]pyrazolyl, $R^8$-imidazo[1,2-a]pyridinyl, $R^8$-1H-imidazolyl-$C_{2-4}$alkenyl, $R^8$-furanyl-$C_{2-4}$alkenyl, $R^8$-thienyl-$C_{2-4}$alkenyl and $R^8$-pyridinyl-$C_{2-4}$alkenyl, wherein each instance of $C_{2-4}$alkenyl is optionally substituted with one substituent selected from the group consisting of halogen, cyano, $C_{1-4}$alkylcarbonylamino and aryl;

$R^5$ is one optional substituent selected from the group consisting of $R^{5a}$-phenyl, $R^{5a}$-phenyl$C_{1-4}$alkyl, $R^{5a}$-phenyl$C_{1-4}$ alkoxy, $R^{5a}$-phenoxy, $R^{5a}$-phenylcarbonyl, $R^{5a}$-phenylsulfonylamino, $R^{5b}$-1H-benzoimidazolyl-$C_{1-4}$alkyl, $R^{5b}$-1H-benzoimidazolyl-$C_{1-4}$alkylcarbonylamino, $R^{5b}$-thienyl-$C_{1-4}$alkylcarbonylamino, $R^{5b}$-pyrimidinylthio, $R^{5b}$-benzoxazolyl-($R^{5b}$)-pyrazolyl, $R^{5b}$-thienyl-($R^{5b}$)-[1,2,4]oxadiazolyl, $R^{5b}$-benzo[1,3]dioxolyl and cyclohexyl, and one or two optional substituents each selected from the group consisting of halogen, hydroxy, cyano, nitro, $C_{1-4}$alkyl, $C_{2-4}$alkenyl, halo$C_{1-4}$alkyl, $C_{1-4}$alkoxy, $C_{1-4}$alkoxy$C_{1-4}$alkoxy, halo$C_{1-4}$alkoxy, $C_{1-4}$alkylthio, halo$C_{1-4}$alkylthio, $C_{1-4}$alkylcarbonyl, $C_{1-4}$alkoxycarbonyl, aminothiocarbonylamino, ($C_{1-4}$alkyl)$_2$-amino, aminocarbonyl, $C_{1-4}$alkylsulfonyl and aminosulfonyl;

$R^{5a}$ is one or two optional substituents each selected from the group consisting of halogen, $C_{1-4}$alkyl, halo$C_{1-4}$alkyl and $C_{1-4}$alkoxy;

$R^{5b}$ is one or two optional halogen substituents;

$R^6$ is one optional substituent selected from the group consisting of $C_{1-4}$alkyl, oxo and phenyl;

$R^7$ is an optional substituent on one, two or three carbon atoms each selected from the group consisting of halogen, $C_{1-4}$alkyl, $C_{1-4}$alkoxy, $C_{1-4}$alkylthio, aryl$C_{1-4}$alkylthio, oxo and phenyl, and two optional $C_{1-4}$alkyl substituents on one carbon atom, and two optional oxo substituents on a sulfur atom, when said sulfur atom is present;

$R^8$ is an optional substituent on one carbon atom or an available nitrogen atom selected from the group consisting of $R^{8a}$-phenyl, $R^{8a}$-phenyl$C_{1-4}$alkyl, $R^{8a}$-phenyl$C_{2-4}$alkenyl, $R^{8a}$-phenyl$C_{2-4}$alkynyl, $R^{8a}$-naphthalenyl$C_{2-4}$alkynyl, $R^{8a}$-phenoxy, $R^{8a}$-phenoxy$C_{1-4}$alkyl, $R^{8a}$-phenylthio, $R^{8a}$-aryl$C_{1-4}$alkylthio, $R^{8a}$-phenyl$C_{1-4}$alkylthio$C_{1-4}$alkyl, $R^{8a}$-phenylsulfonyl, $R^{8b}$-pyridinyl, $R^{8b}$-pyrazolyl, $R^{8b}$-thienyl, $R^{8b}$-thiazolyl, $R^{8b}$-pyrazolyl$C_{1-4}$alkyl, $R^{8b}$-pyrimidinylthio$C_{1-4}$alkyl, $R^{8b}$-furanylcarbonylamino$C_{1-4}$alkyl and $R^{8c}$-morpholinyl$C_{1-4}$alkyl, and an optional $C_{1-4}$alkyl substituent on an available nitrogen atom, and an optional substituent on one, two or three carbon atoms each selected from the group consisting of halogen, cyano, $C_{1-4}$alkyl, halo$C_{1-4}$alkyl, hydroxy$C_{1-4}$alkyl, $C_{1-4}$alkoxy, formyl, $C_{1-4}$alkoxycarbonyl, $C_{1-4}$alkylthio and $C_{1-4}$alkylsulfonyl;

$R^{8a}$ is one or two optional substituents each selected from the group consisting of halogen, $C_{1-4}$alkyl, $C_{2-4}$alkenyl, halo$C_{1-4}$alkyl and $C_{1-4}$alkoxy;

$R^{8b}$ is one, two or three optional substituents each selected from the group consisting of halogen, $C_{1-4}$alkyl and halo$C_{1-4}$alkyl;

$R_4$ is one substituent selected from the group consisting of hydrogen, $C_{1-4}$alkyl, carboxy$C_{1-4}$alkyl, $C_{1-4}$alkylcarbonyl, $C_{1-4}$alkoxycarbonyl, $C_{1-4}$alkoxycarbonyl$C_{1-4}$alkyl, $C_{1-4}$alkoxycarbonyl$C_{1-4}$alkylcarbonyl, $C_{1-4}$alkoxycarbonylcarbonyl, aminocarbonyl, $R^9$-phenyl-$C_{1-4}$alkyl, $R^9$-phenyl-carbonyl, hydroxysulfonyl, aminosulfonyl, $C_{1-4}$alkylsulfonyl, hydroxysulfonyl$C_{1-4}$alkylcarbonyl, $C_{1-4}$alkylsulfonyl$C_{1-4}$alkylcarbonyl, $C_{1-4}$alkylsulfonyl$C_{1-4}$ alkylsulfonyl, $C_{1-4}$alkoxycarbonyl$C_{1-4}$alkylsulfonyl, $R^9$-phenyl-sulfonyl, P[(O)(OH)$_2$]-$C_{1-4}$alkyl, $R^{10}$-heterocyclylcarbonyl, $R^{10}$-tetrahydrothienyl-sulfonyl, $R^{11}$-1H-tetrazolyl-carbonyl, $R^{11}$-1H-tetrazolyl-$C_{1-4}$ alkylcarbonyl and $R^{11}$—H-imidazolyl-sulfonyl, $R^{11}$-furanyl-sulfonyl, $R^{11}$-thienyl-sulfonyl,
wherein $C_{1-4}$alkoxycarbonyl$C_{1-4}$alkylcarbonyl is optionally substituted on $C_{1-4}$alkyl with ($C_{1-4}$alkyl)aminoamino;
$R^9$ is one or two optional substituents each selected from the group consisting of $C_{1-4}$alkoxy, carboxy and $C_{1-4}$alkoxycarbonyl;
$R^{10}$ is an optional ($C_{1-4}$alkyl)aminoamino substituent on one carbon atom, and
two oxo substituents on a sulfur atom, when said sulfur atom is present; and
$R^{11}$ is an optional $C_{1-4}$alkyl substituent on an available nitrogen atom, and
an optional substituent on one carbon atom selected from the group consisting of carboxy and $C_{1-4}$alkoxycarbonyl.

An example of a compound of Formula (I) includes compounds or a form thereof, wherein
$X_1$ and $X_2$, respectively, are selected from the group consisting of —$CH_2$— and —$CH_2$—, —$CH_2$— and —O—, —$CH_2$— and —N($R_4$)— and —N($R_4$)— and —C(O)—;
$X_3$ and $X_4$, respectively, are —$CH_2$— and —$CH_2$—;
$R_1$ is selected from the group consisting of amino$C_{1-4}$alkyl and aminoimino,
$R_2$ is absent;
$R^3$ is carbonyl substituted with a substituent selected from the group consisting of $R^5$-aryl, $R^7$-heterocyclyl and $R^8$-heteroaryl;
$R^5$ is heteroaryl-heteroaryl, and
an optional aminocarbonyl substituent;
$R^7$ is an optional substituent on one or two carbon atoms each selected from the group consisting of $C_{1-4}$alkylthio, aryl$C_{1-4}$alkylthio and oxo;
$R^8$ is an optional substituent on one carbon atom selected from the group consisting of $R^{8a}$-aryl, $R^{8a}$-aryl$C_{2-4}$alkynyl and $R^{8a}$-aryl$C_{1-4}$alkylthio, and
an optional substituent on one, two or three carbon atoms each selected from the group consisting of halogen, $C_{1-4}$alkyl, $C_{1-4}$alkoxy and $C_{1-4}$alkylthio;
$R^{8a}$ is one or two optional substituents each selected from the group consisting of halogen and $C_{1-4}$alkyl;
$R_4$ is one substituent selected from the group consisting of hydrogen, aminosulfonyl, $C_{1-4}$alkylsulfonyl and arylsulfonyl.

An example of a compound of Formula (I) includes compounds or a form thereof, wherein
$X_1$ and $X_2$, respectively, are selected from the group consisting of —$CH_2$— and —$CH_2$—, —$CH_2$— and —O—, —$CH_2$— and —N($R_4$)— and —N($R_4$)— and —C(O)—;
$X_3$ and $X_4$, respectively, are —$CH_2$— and —$CH_2$—;
$R_1$ is selected from the group consisting of amino$C_{1-4}$alkyl and aminoimino,
$R_2$ is absent;
$R^3$ is carbonyl substituted with a substituent selected from the group consisting of $R^5$-phenyl, $R^7$-4,5-dihydro-benzo[c]thiophenyl, $R^7$-4,5,6,7-tetrahydro-benzo[c]thiophenyl, $R^8$-furanyl, $R^8$-thienyl, $R^8$-pyridinyl and $R^8$-benzo[c]thiophenyl;
$R^5$ is thienyl-[1,2,4]oxadiazolyl, and
an optional aminocarbonyl substituent;
$R^7$ is an optional substituent on one or two carbon atoms each selected from the group consisting of $C_{1-4}$alkylthio, phenyl$C_{1-4}$alkylthio and oxo;
$R^8$ is an optional substituent on one carbon atom selected from the group consisting of $R^{8a}$-phenyl, $R^{8a}$-phenyl$C_{2-4}$alkynyl and $R^{8a}$-phenyl$C_{1-4}$alkylthio, and an optional substituent on one, two or three carbon atoms each selected from the group consisting of halogen, $C_{1-4}$alkyl, $C_{1-4}$alkoxy and $C_{1-4}$alkylthio;
$R^{8a}$ is one or two optional substituents each selected from the group consisting of halogen and $C_{1-4}$alkyl;
$R_4$ is one substituent selected from the group consisting of hydrogen, aminosulfonyl, $C_{1-4}$alkylsulfonyl and arylsulfonyl.

An example of a compound of Formula (I) includes compounds or a form thereof, wherein
$X_1$ and $X_2$, respectively, are selected from the group consisting of —$CH_2$— and —$CH_2$—, —$CH_2$— and —O—, —$CH_2$— and —N($R_4$)— and —N($R_4$)— and —C(O)—;
$X_3$ and $X_4$, respectively, are —$CH_2$— and —$CH_2$—;
$R_1$ is selected from the group consisting of aminomethyl and aminoimino,
$R_2$ is absent;
$R^3$ is carbonyl substituted with a substituent selected from the group consisting of $R^5$-phenyl, $R^7$-4,5-dihydro-benzo[c]thiophenyl, $R^7$-4,5,6,7-tetrahydro-benzo[c]thiophenyl, $R^8$-furanyl, $R^8$-thienyl, $R^8$-pyridinyl and $R^8$-benzo[c]thiophenyl;
$R^5$ is thienyl-[1,2,4]oxadiazolyl, and
an optional aminocarbonyl substituent;
$R^7$ is an optional substituent on one or two carbon atoms each selected from the group consisting of methylthio, butylthio, phenylmethylthio and oxo;
$R^8$ is an optional substituent on one carbon atom selected from the group consisting of $R^{8a}$-phenyl, $R^{8a}$-phenylethynyl and $R^{8a}$-phenylmethylthio, and
an optional substituent on one, two or three carbon atoms each selected from the group consisting of bromo, methyl, methoxy, propoxy and methylthio;
$R^{8a}$ is one or two optional substituents each selected from the group consisting of chloro, fluoro and methyl; and
$R_4$ is one substituent selected from the group consisting of hydrogen, aminosulfonyl, methylsulfonyl and phenylsulfonyl.

An example of a compound of Formula (I) includes compounds or a form thereof, wherein
$X_1$ and $X_2$, respectively, are selected from the group consisting of —$CH_2$— and —$CH_2$—, —$CH_2$— and —O—, —$CH_2$— and —N($R_4$)— and —N($R_4$)— and —C(O)—;
$X_3$ and $X_4$, respectively, are —$CH_2$— and —$CH_2$—;
$R_1$ is selected from the group consisting of aminomethyl and aminoimino;
$R_2$ is absent;
$R^3$ is selected from the group consisting of (5-phenylethynyl-furan-2-yl)carbonyl, [5-(2-fluoro-phenylethynyl)-furan-2-yl]carbonyl, [5-(2-chloro-phenylethynyl)-furan-2-yl]carbonyl, [4-phenylethynyl-pyridin-2-yl]carbonyl, [5-(2-methyl-phenylethynyl)-furan-2-yl]carbonyl, [5-(4-methyl-phenylethynyl)-furan-2-yl]carbonyl, [5-(2,5-dimethyl-phenylethynyl)-furan-2-yl]carbonyl, (3-benzylthio-4-oxo-5,6,7-trihydro-4H-benzo[c]thien-1-yl)carbonyl, (3-butylthio-4-oxo-5,6,7-trihydro-4H-benzo[c]thien-1-yl)carbonyl, (3-methylthio-5,6,7-trihydro-4H-benzo[c]thien-1-yl)carbonyl, (3-methylthio-7-hydro-6H-benzo[c]thien-1-yl)carbonyl, (3-methylthio-benzo[c]thien-1-yl)carbonyl, (3-methylthio-4-methoxy-benzo[c]thien-1-yl)carbonyl, (3-benzylthio-benzo[c]thien-1-yl)carbonyl, (3-benzylthio-7-hydro-6H-benzo[c]thien-1-yl)carbonyl, (3-thien-2-yl-[1,2,4]oxadiazol-5-yl)carbonyl, [3-(3-thien-2-yl-[1,2,4]oxadiazol-5-yl)-5-aminocarbonyl-phenyl]carbonyl and (3-methyl-4-bromo-5-propoxy-thien-2-yl)carbonyl; and $R_4$ is one substituent selected from the group consisting of hydrogen, aminosulfonyl, methylsulfonyl and phenylsulfonyl.
An example of a compound of Formula (I) includes compounds or a form thereof selected from the group consisting of:
Cpd 1
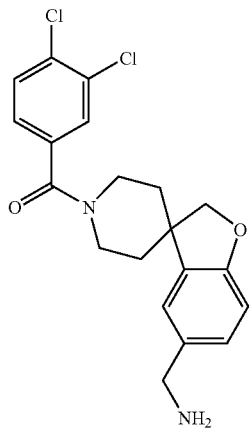
Cpd 2
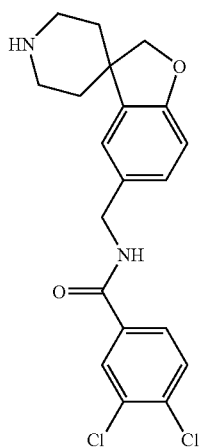
Cpd 3
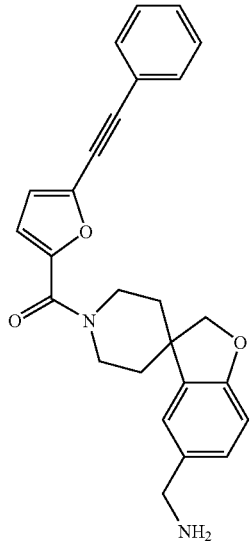
Cpd 4
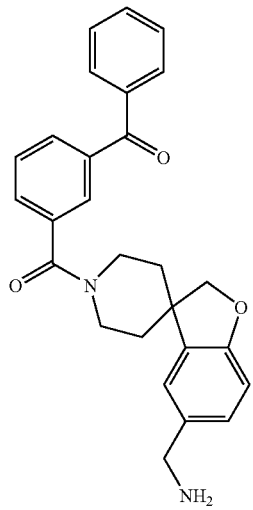
Cpd 5
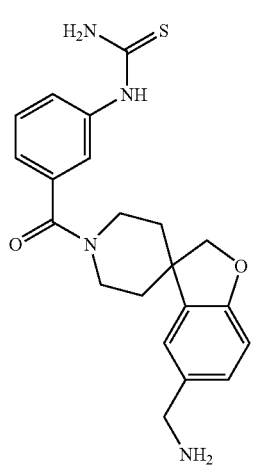
Cpd 6
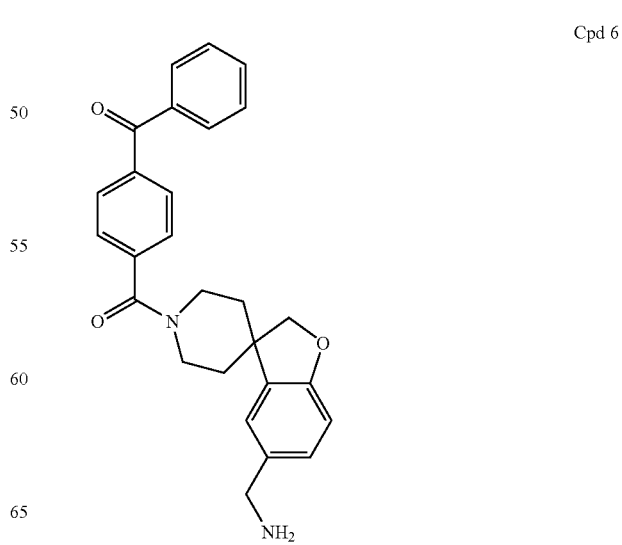

Cpd 7
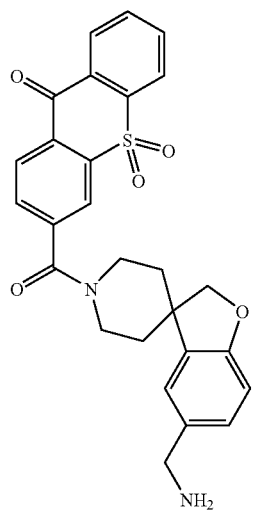
Cpd 8
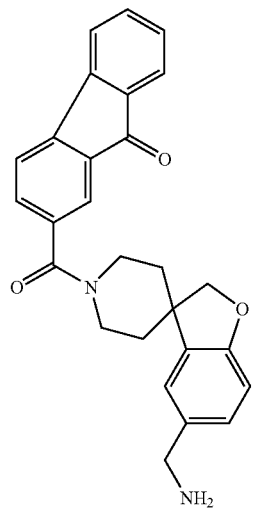
Cpd 9
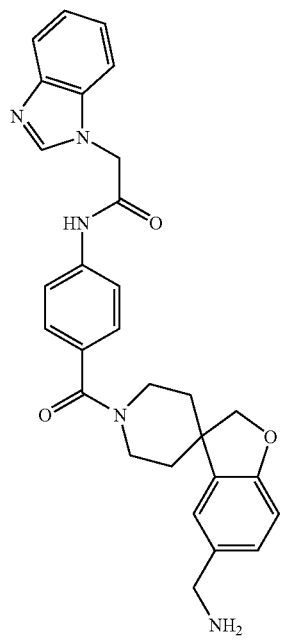
Cpd 10
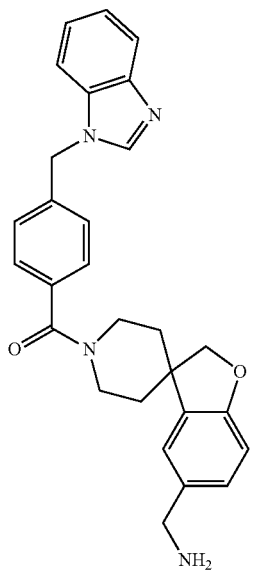
Cpd 11
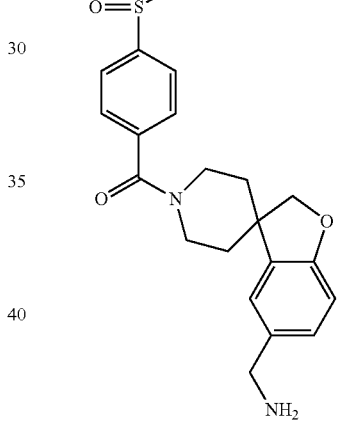
Cpd 12
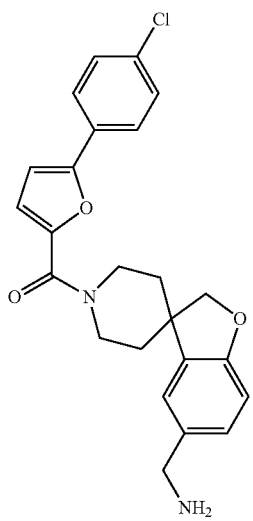

-continued
Cpd 13
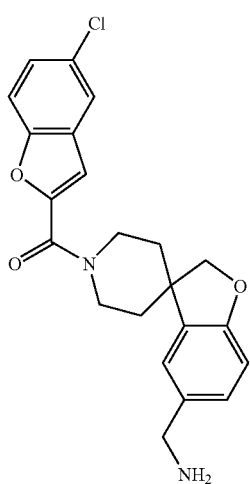
Cpd 16
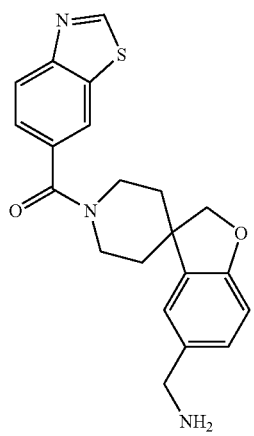
Cpd 14
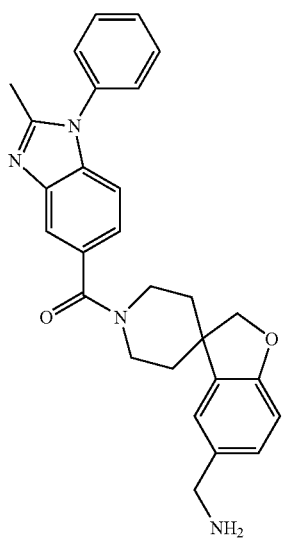
Cpd 17
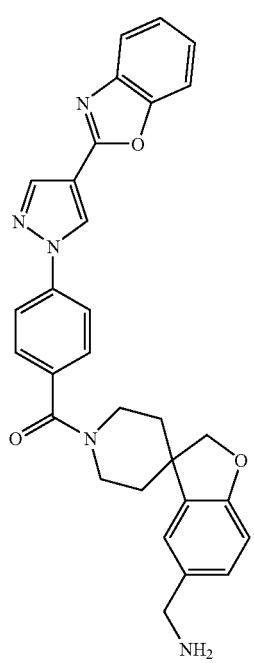
Cpd 15
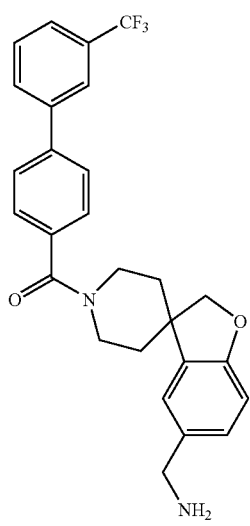
Cpd 18
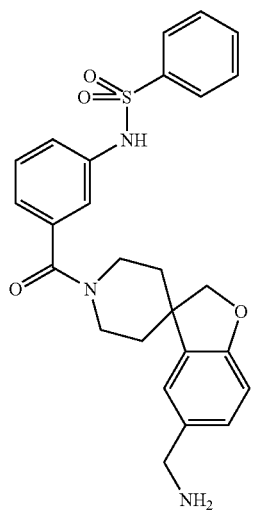

Cpd 19
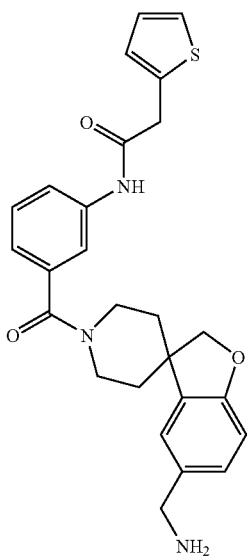
Cpd 20
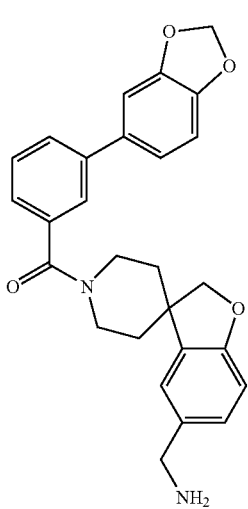
Cpd 21
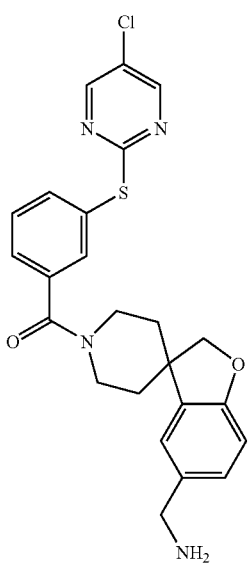
Cpd 22
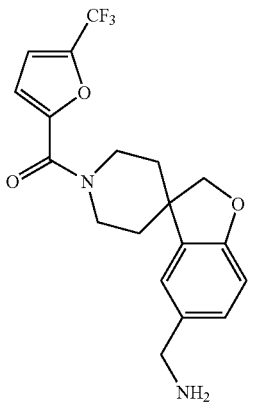
Cpd 23
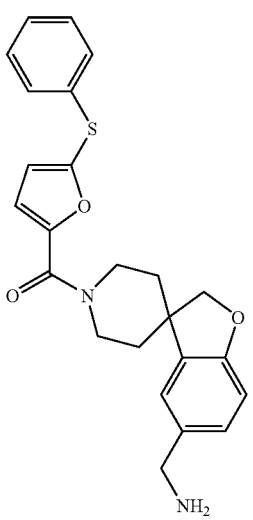
Cpd 24
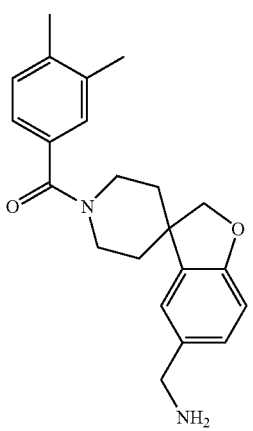

-continued
Cpd 25
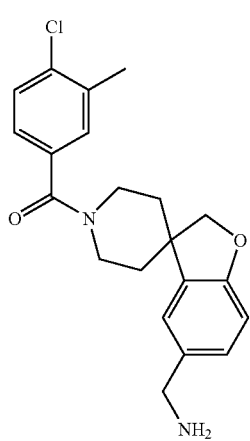
Cpd 26
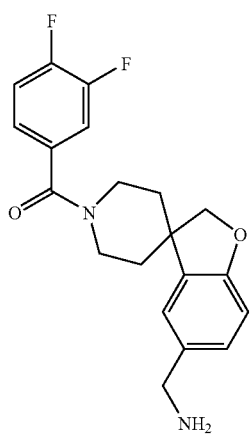
Cpd 27
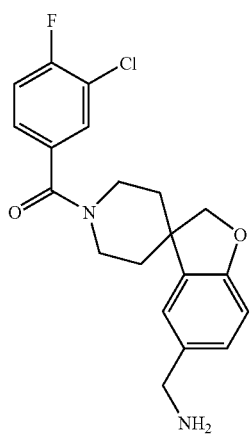
-continued
Cpd 28
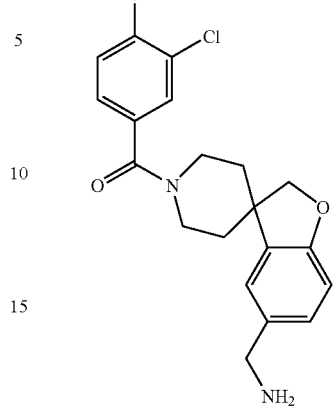
Cpd 29
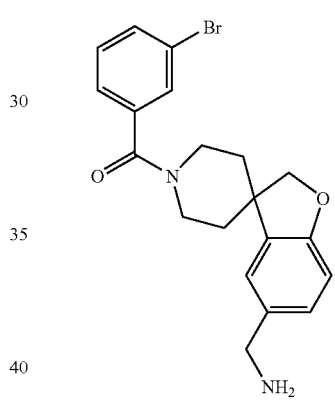
Cpd 30
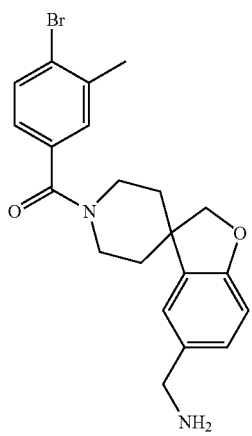

Cpd 31
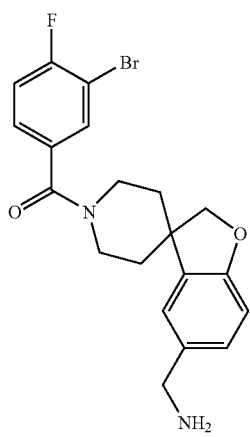
Cpd 34
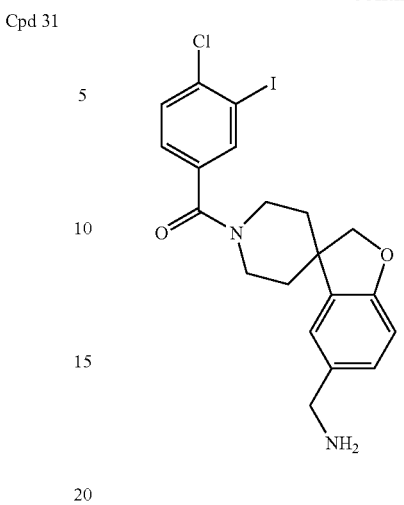
Cpd 32
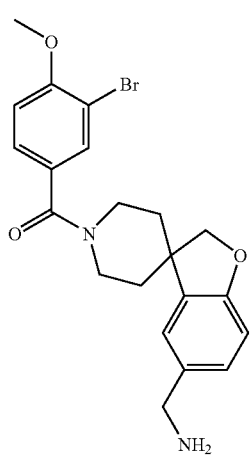
Cpd 35
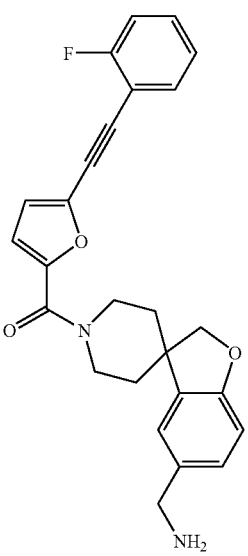
Cpd 33
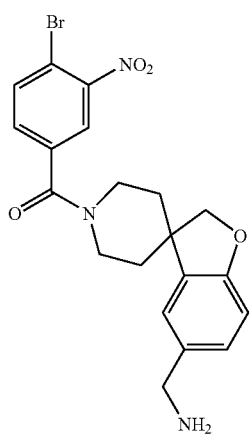
Cpd 36
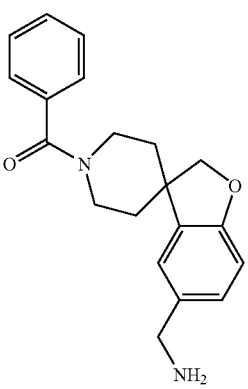

Cpd 37
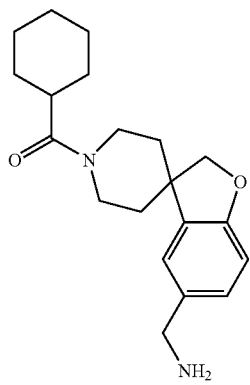
Cpd 38
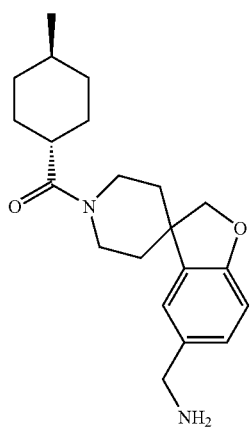
Cpd 39
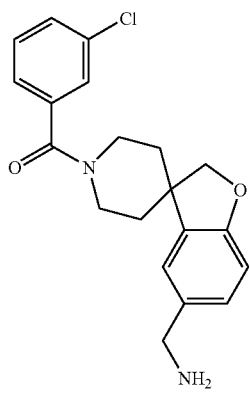
Cpd 40
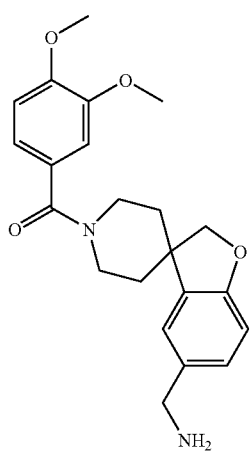
Cpd 41
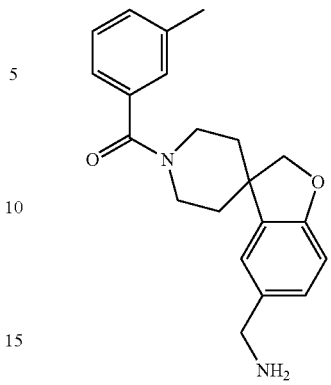
Cpd 42
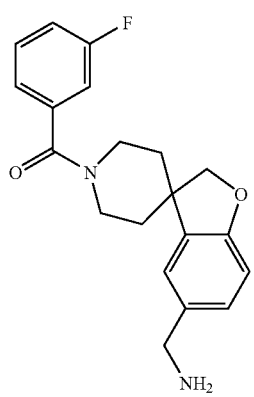
Cpd 43
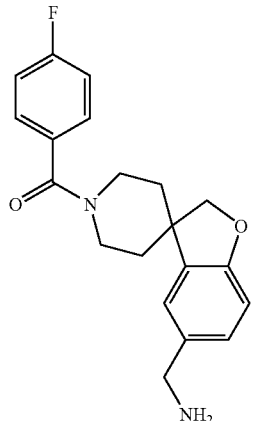
Cpd 44
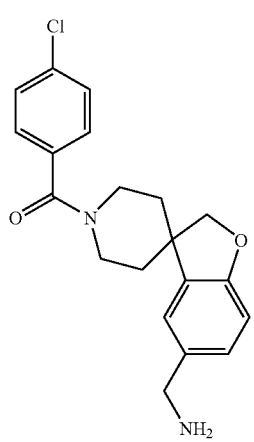

Cpd 45
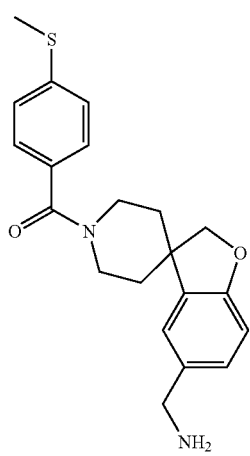
Cpd 46
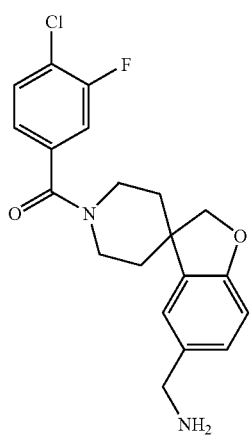
Cpd 47
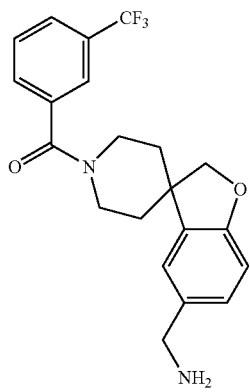
Cpd 48
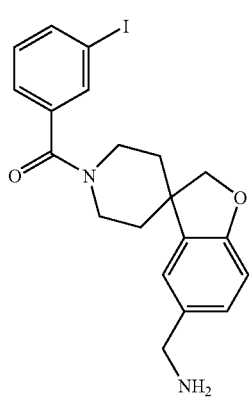
Cpd 49
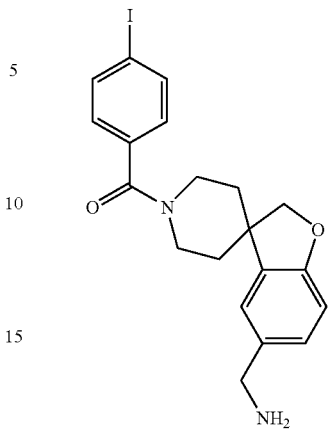
Cpd 50
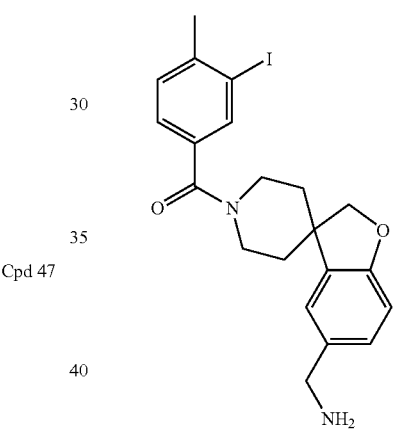
Cpd 51
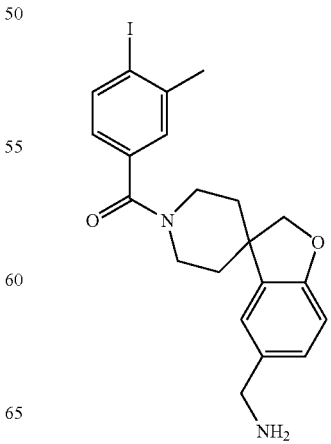

Cpd 52
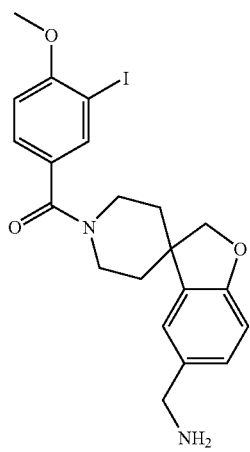
Cpd 53
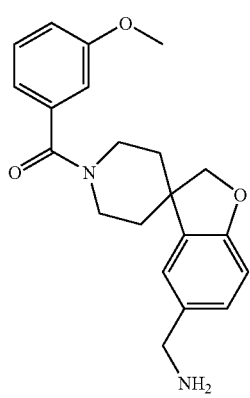
Cpd 54
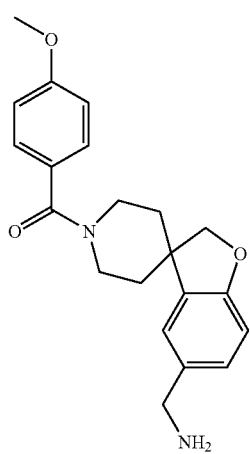
Cpd 55
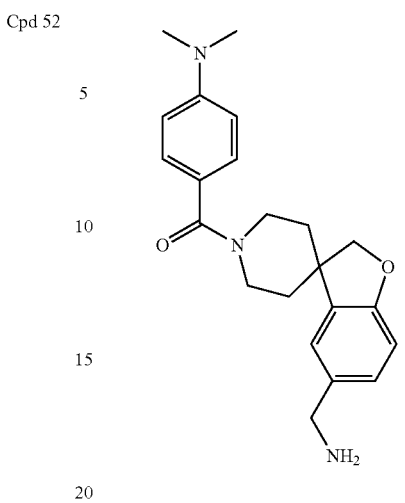
Cpd 56
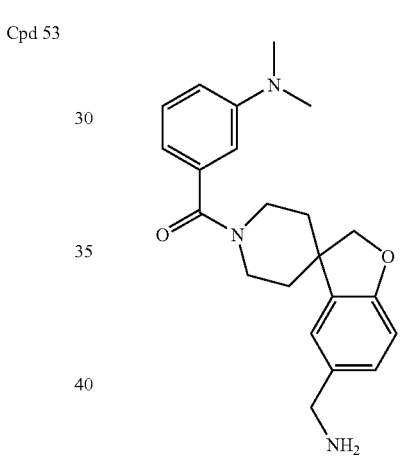
Cpd 57
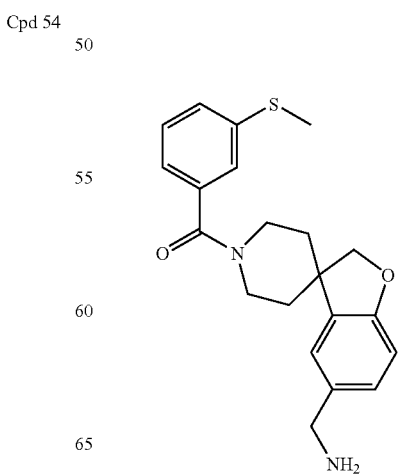

Cpd 58
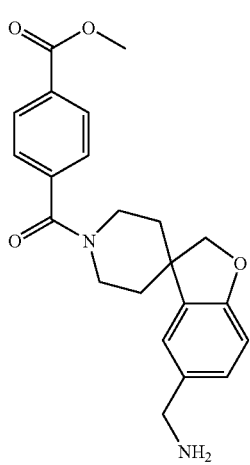
Cpd 61
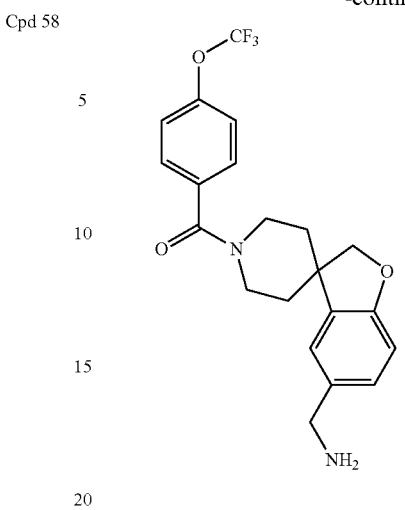
Cpd 59
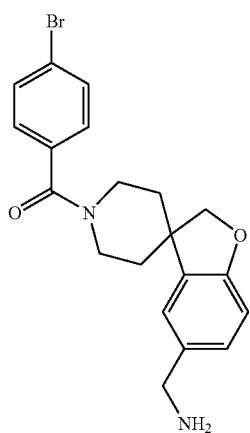
Cpd 62
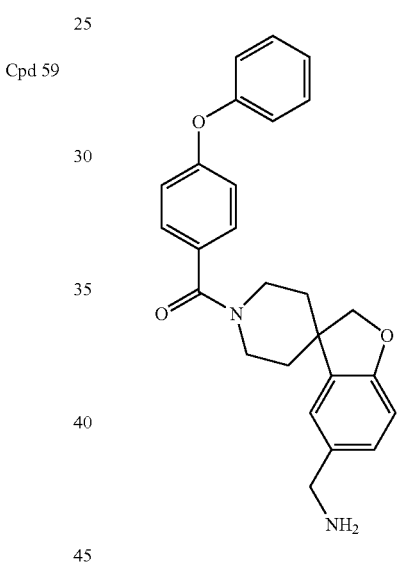
Cpd 60
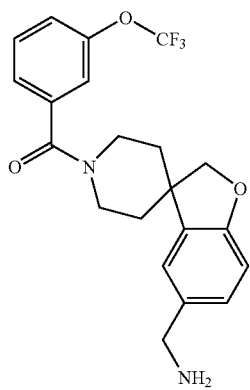
Cpd 63
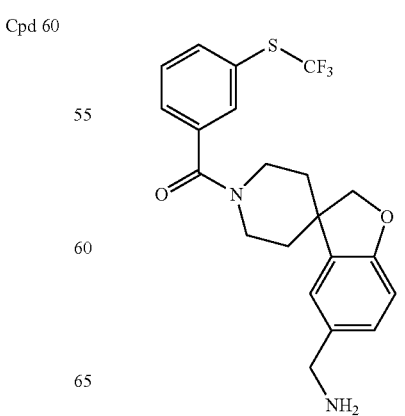

Cpd 64
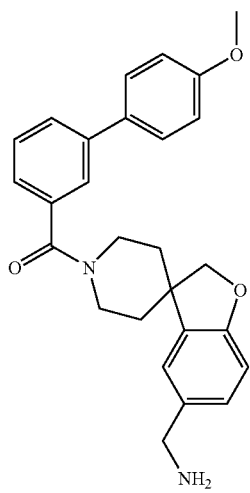
Cpd 65
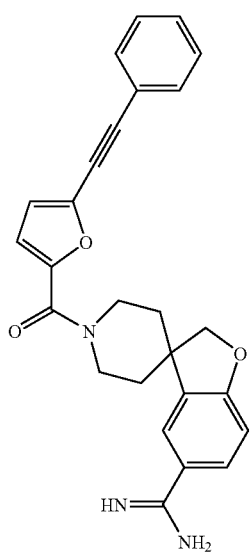
Cpd 66
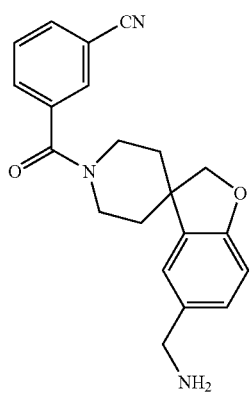
Cpd 67
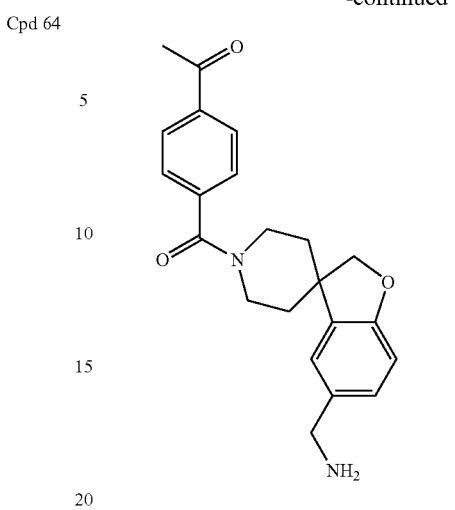
Cpd 68
Cpd 69
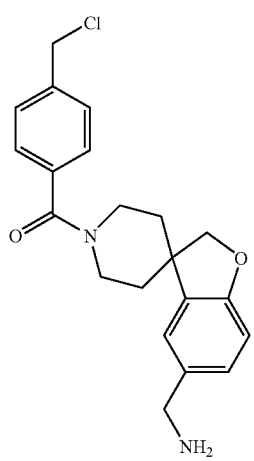

Cpd 70
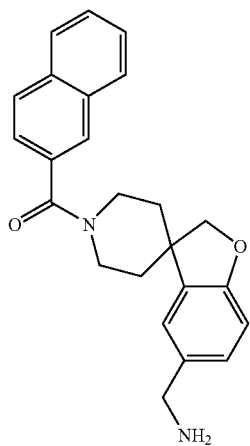
Cpd 73
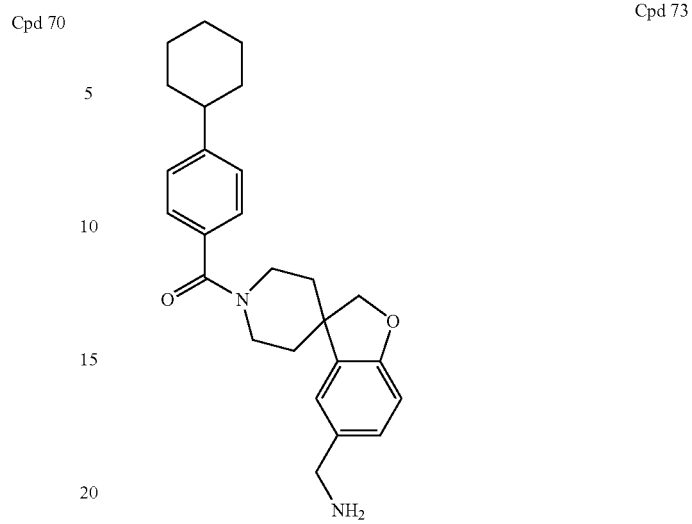
Cpd 71
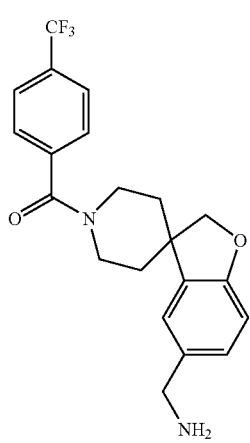
Cpd 74
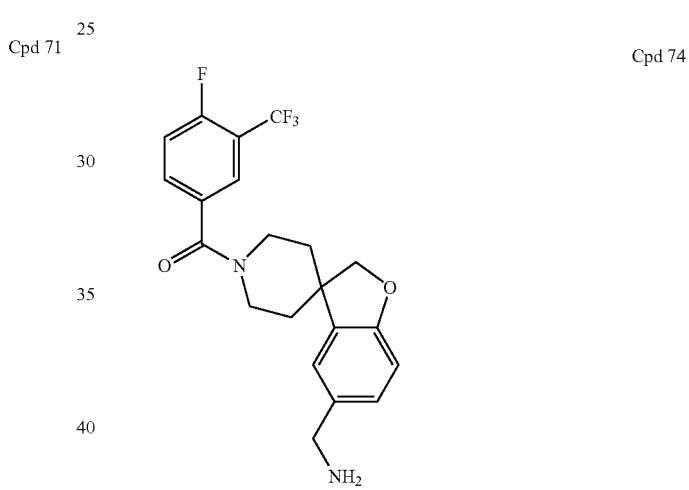
Cpd 72
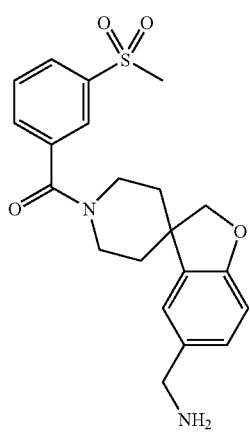
Cpd 75
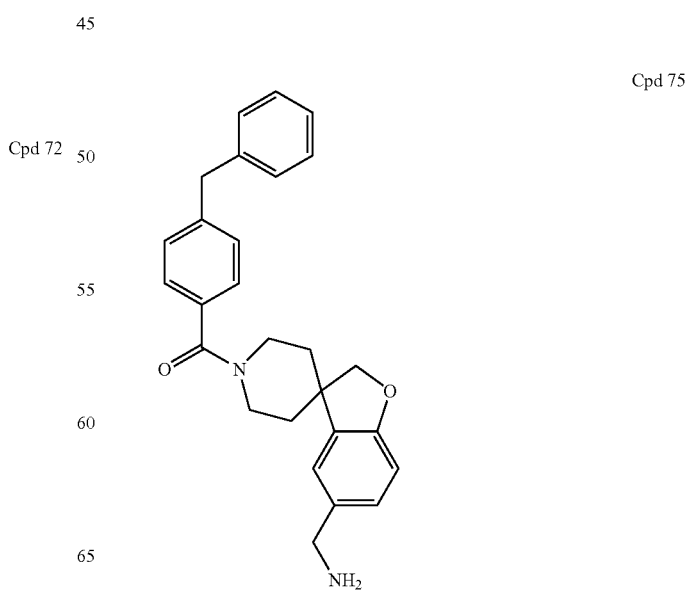

Cpd 76
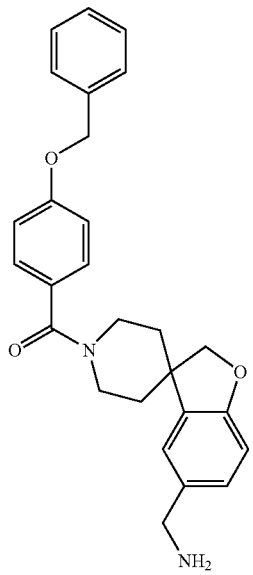
Cpd 77
Cpd 78
Cpd 79
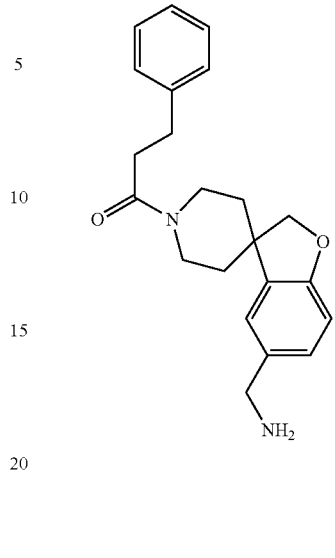
Cpd 80
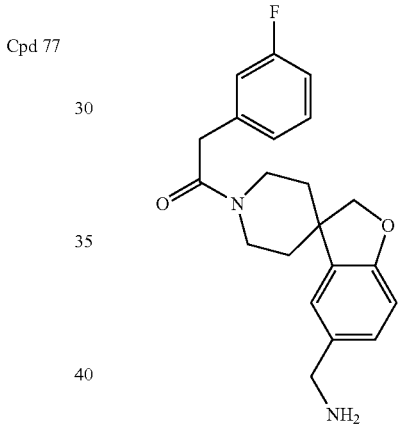
Cpd 81
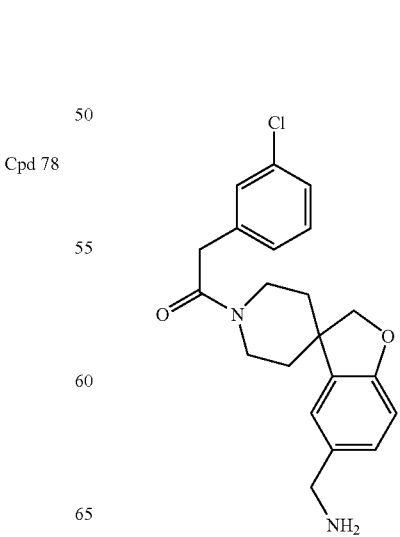

Cpd 82
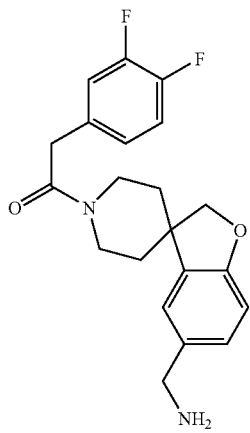
Cpd 83
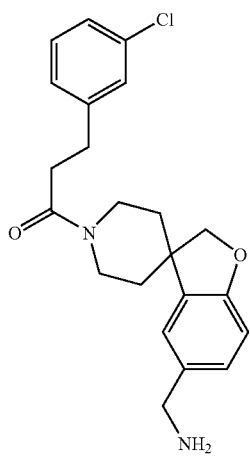
Cpd 84
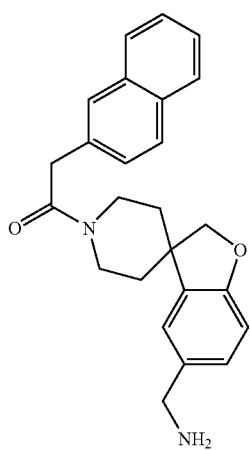
Cpd 85
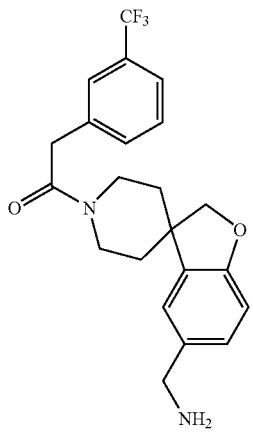
Cpd 86
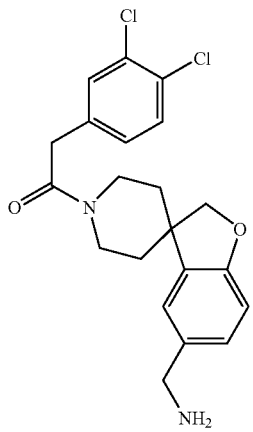
Cpd 87
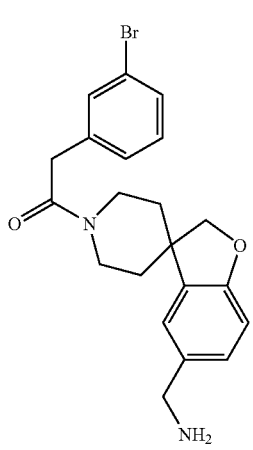

Cpd 88
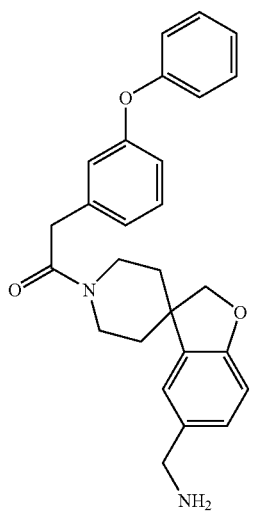
Cpd 89
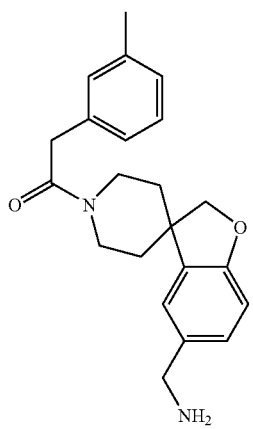
Cpd 90
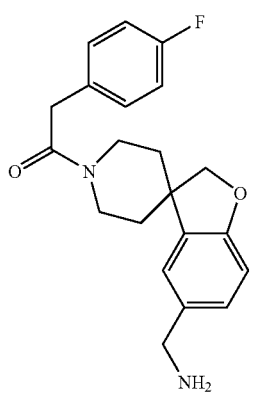
Cpd 91
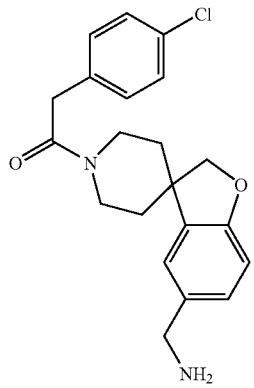
Cpd 92
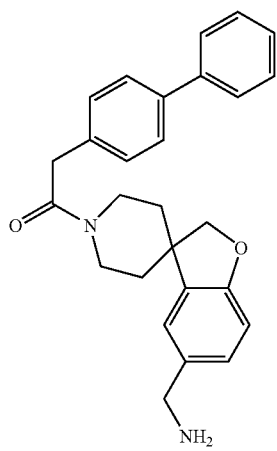
Cpd 93
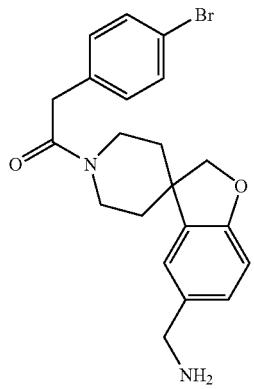
Cpd 94
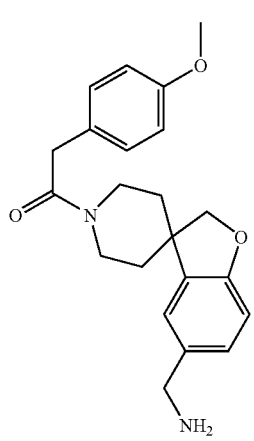

Cpd 95
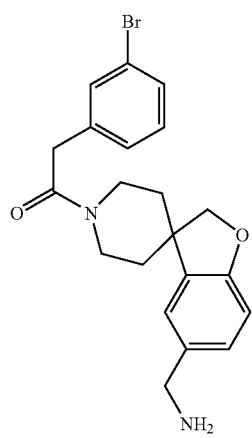
Cpd 98
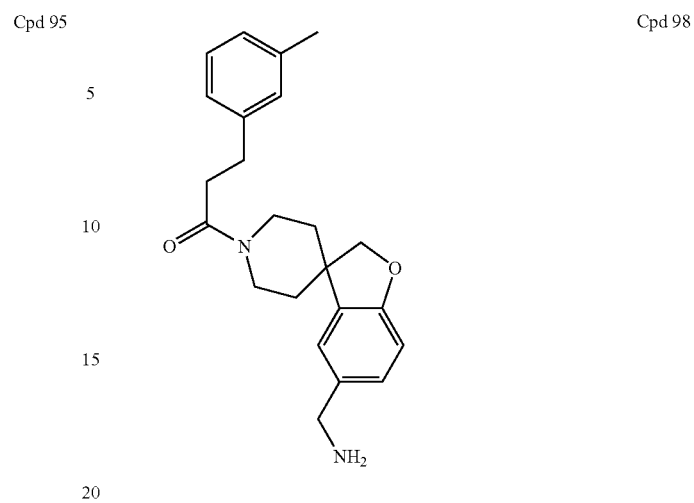
Cpd 96
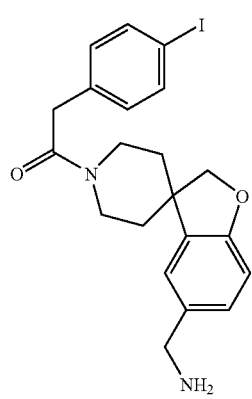
Cpd 99
Cpd 97
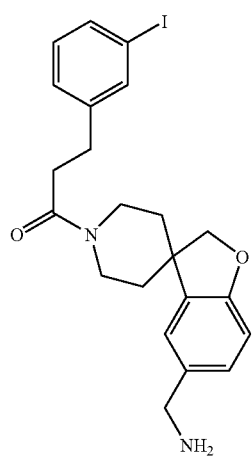
Cpd 100
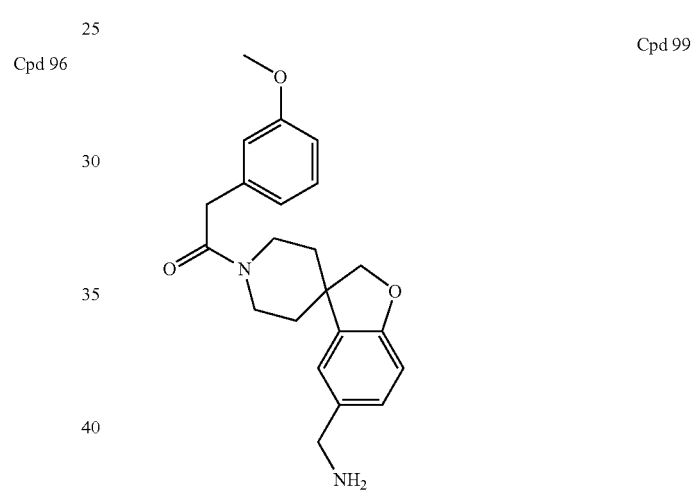
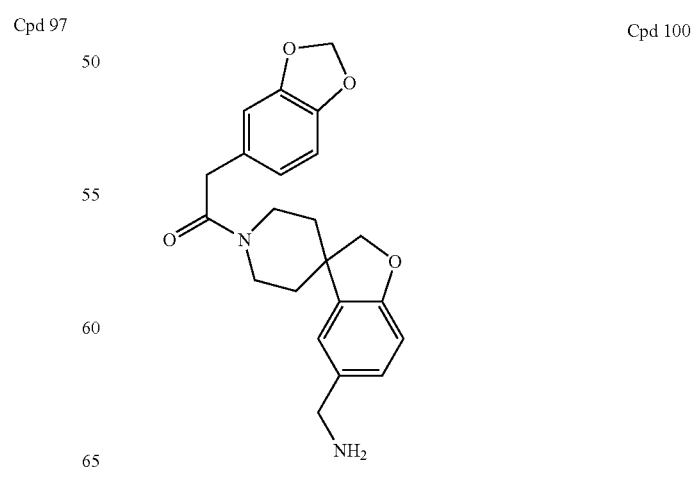

Cpd 101
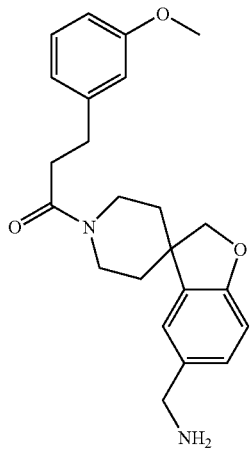
Cpd 102
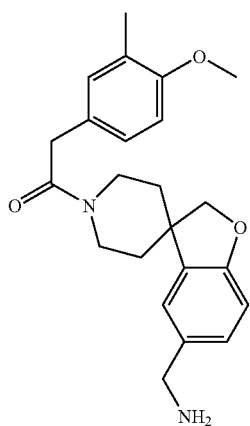
Cpd 103
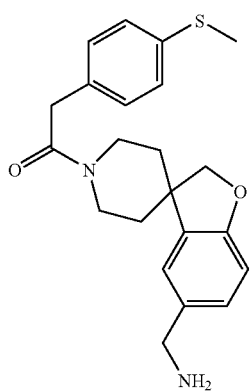
Cpd 104
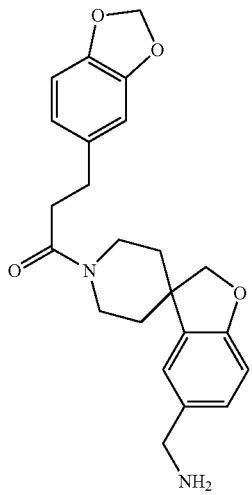
Cpd 105
Cpd 106

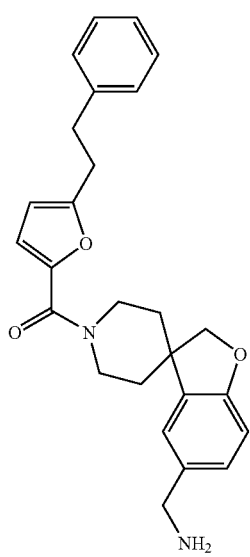
Cpd 107
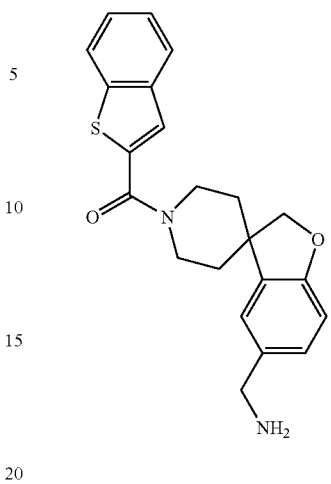
Cpd 110
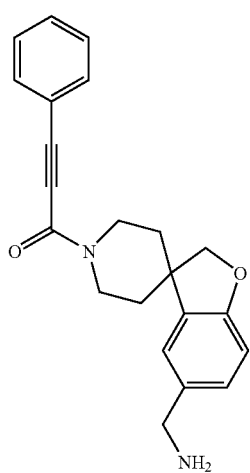
Cpd 108
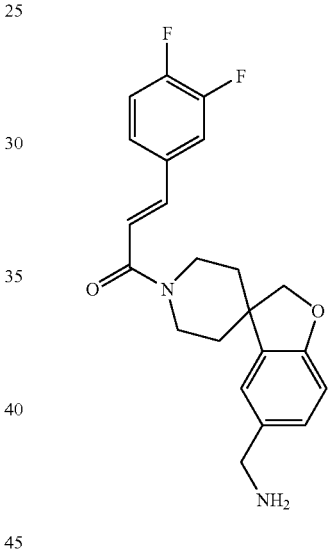
Cpd 111
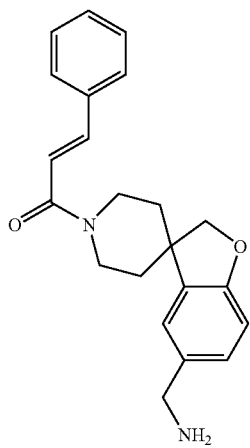
Cpd 109
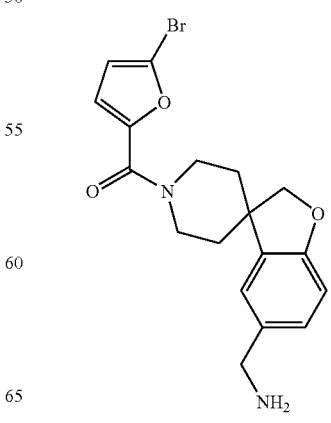
Cpd 112

Cpd 113
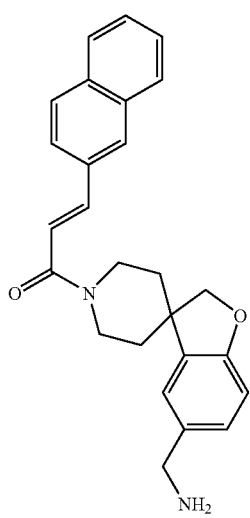
Cpd 114
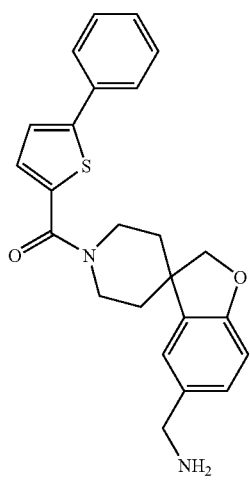
Cpd 115
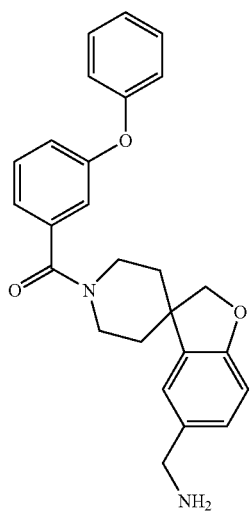
Cpd 116
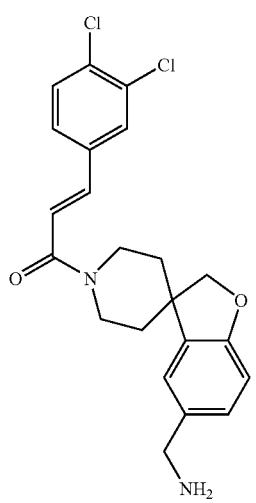
Cpd 117
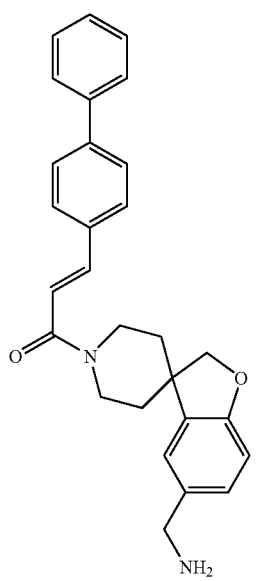
Cpd 118
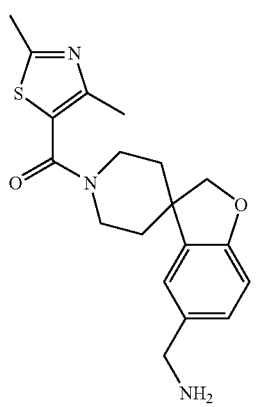

Cpd 119
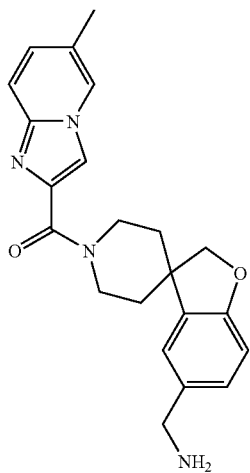
Cpd 120
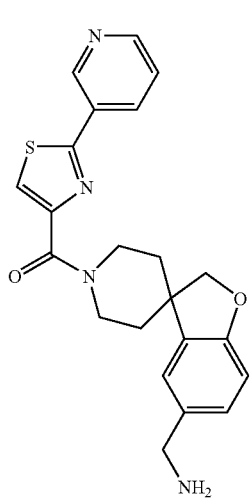
Cpd 121
Cpd 122
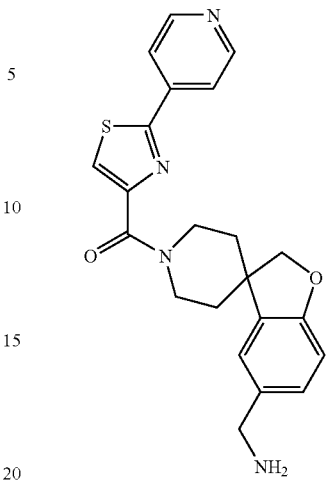
Cpd 123
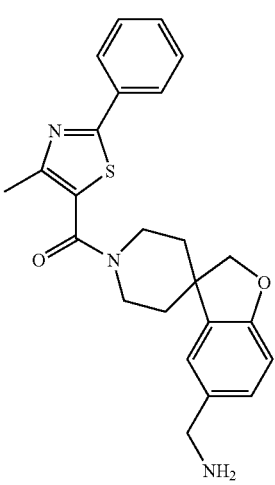
Cpd 124
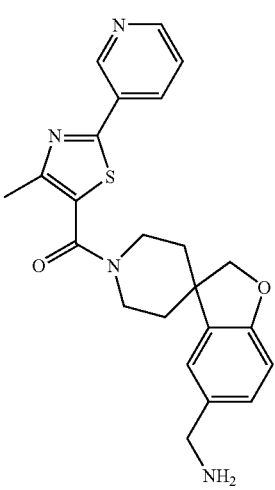

Cpd 125
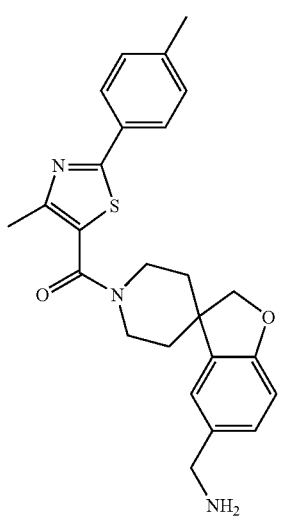
Cpd 128
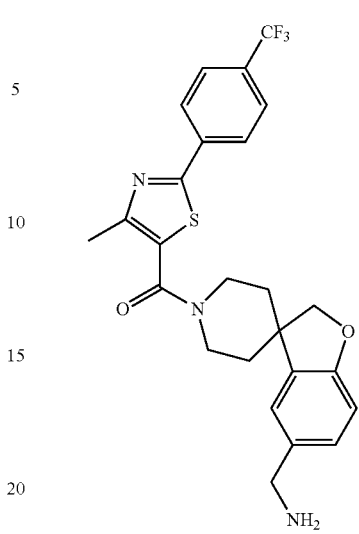
Cpd 126
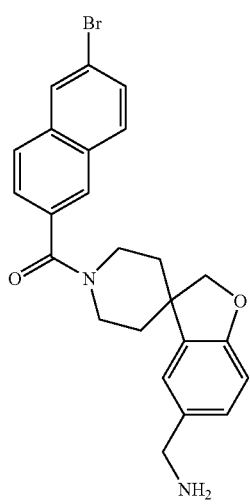
Cpd 129
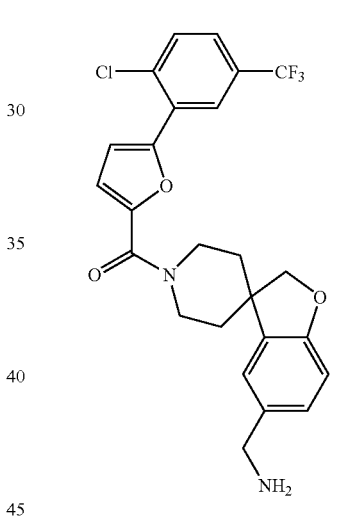
Cpd 127
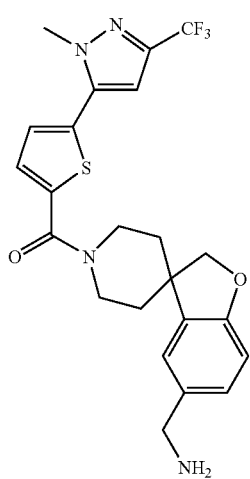
Cpd 130
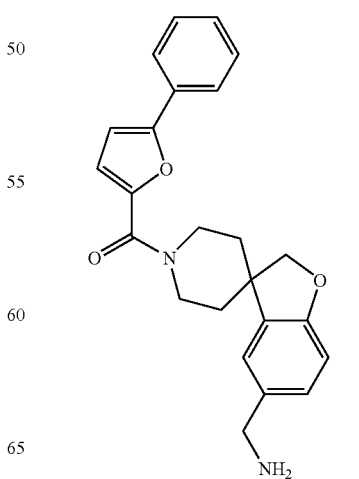

-continued
Cpd 131
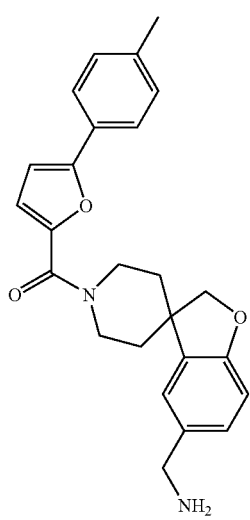
Cpd 132
Cpd 133
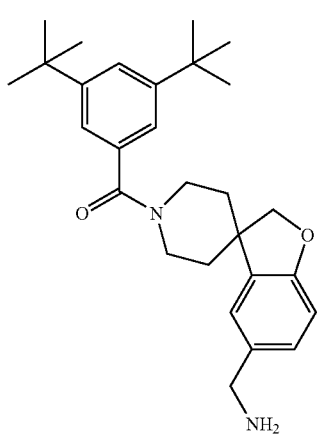
-continued
Cpd 134
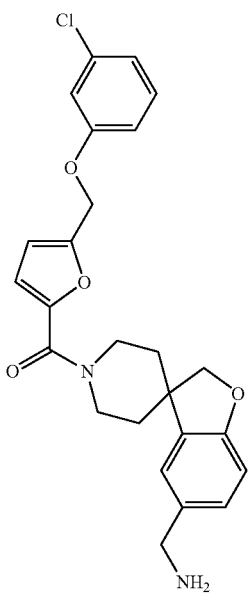
Cpd 135
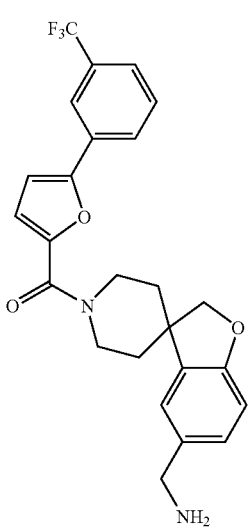
Cpd 136
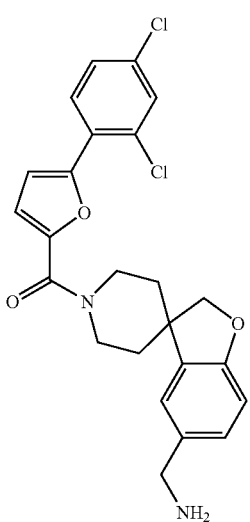

Cpd 137
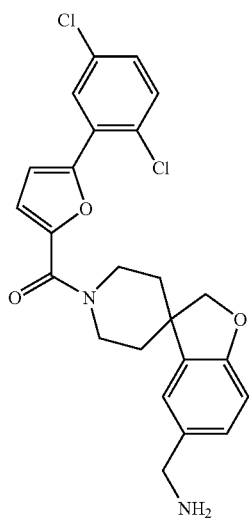
Cpd 138
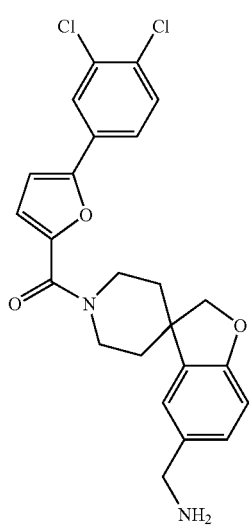
Cpd 139
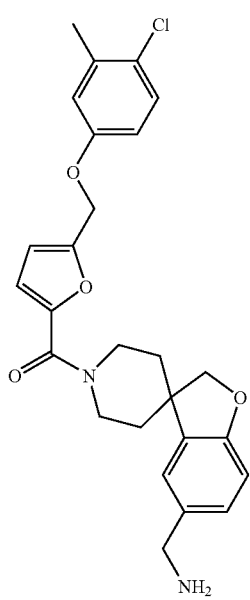
Cpd 140
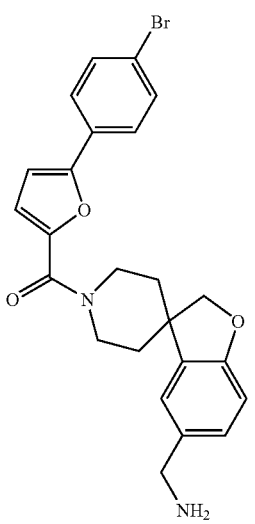
Cpd 141
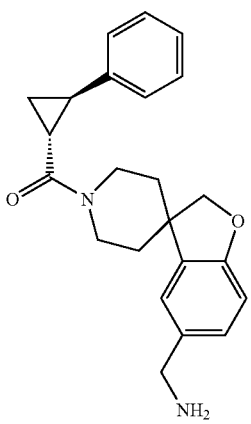
Cpd 142
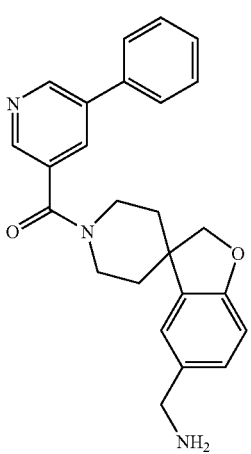

-continued
Cpd 143
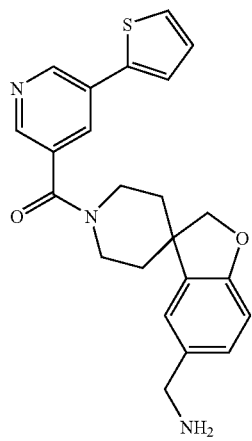
Cpd 144
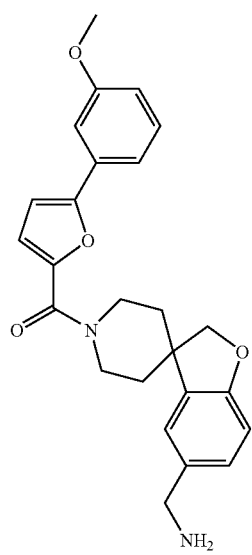
Cpd 145
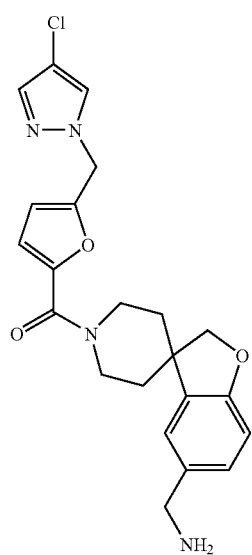
-continued
Cpd 146
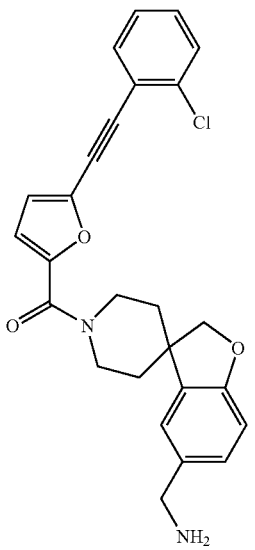
Cpd 147
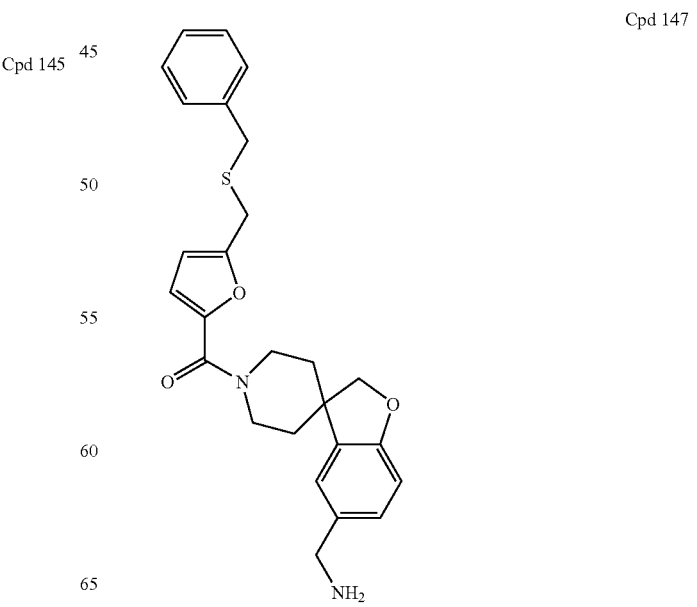

Cpd 148
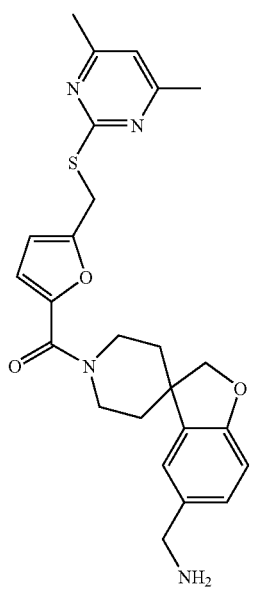
Cpd 150
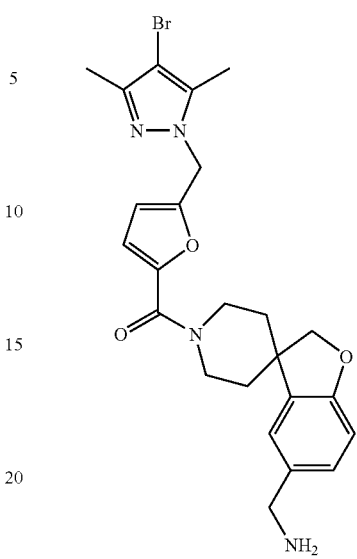
Cpd 151
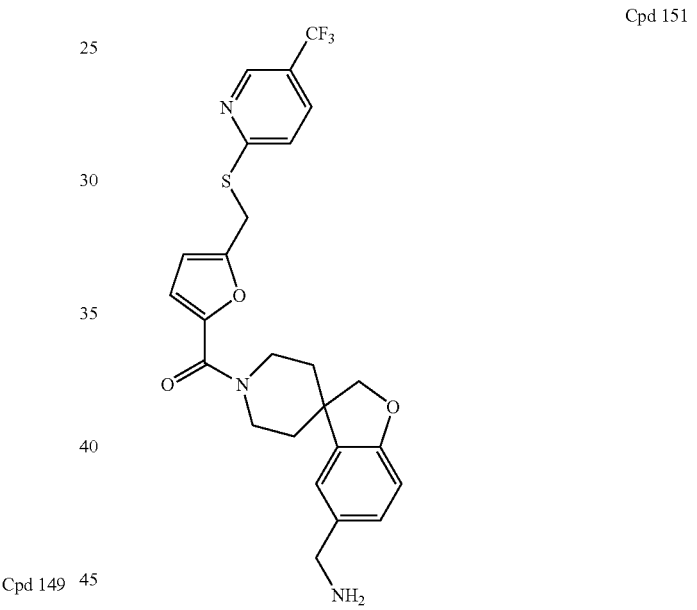
Cpd 149
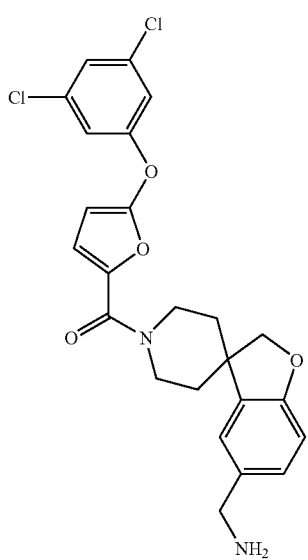
Cpd 152
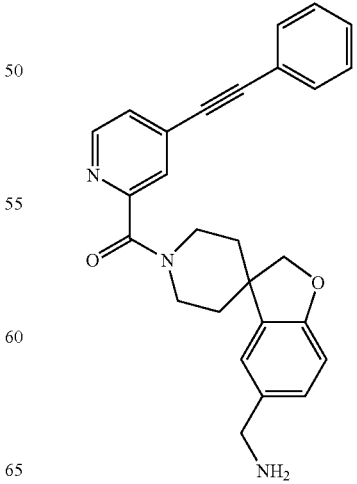

Cpd 153
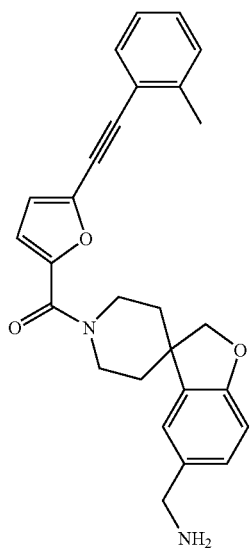
Cpd 154
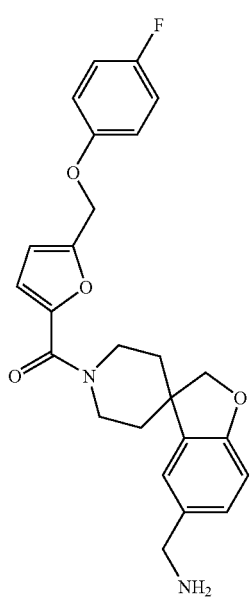
Cpd 155
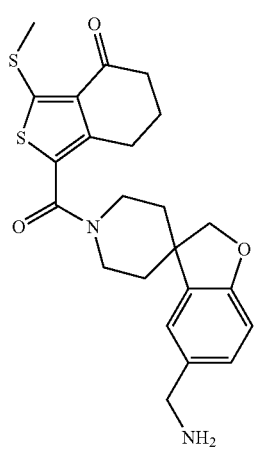
Cpd 156
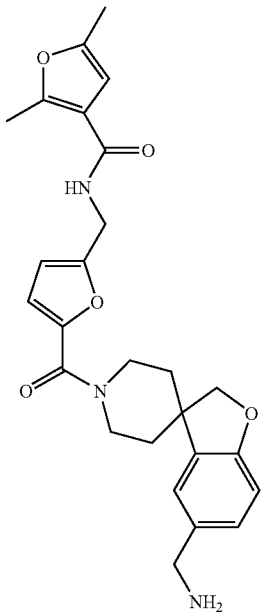
Cpd 157
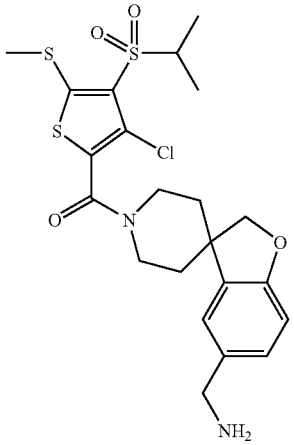
Cpd 158
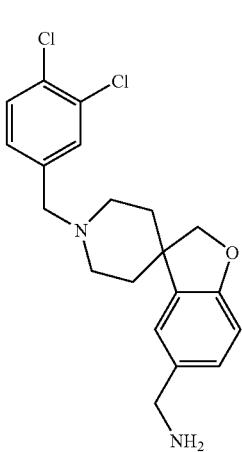

Cpd 159
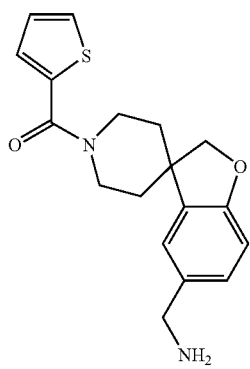
Cpd 162
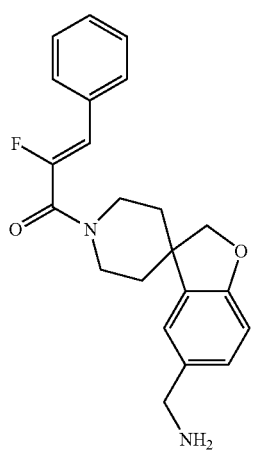
Cpd 160
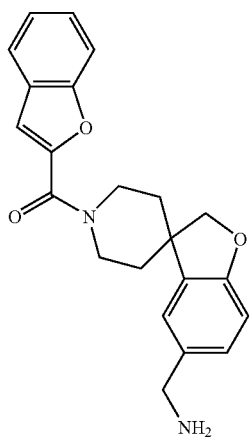
Cpd 163
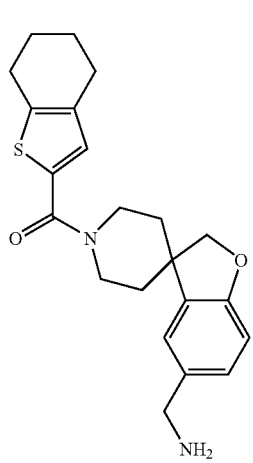
Cpd 161
Cpd 164
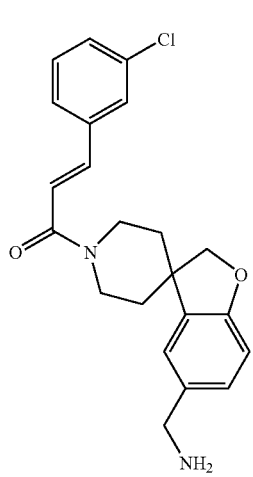

Cpd 165
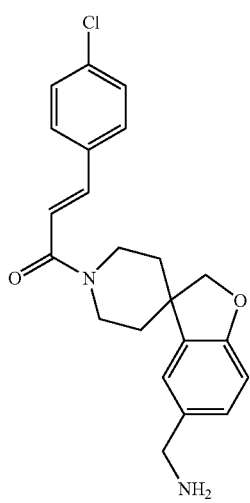
Cpd 166
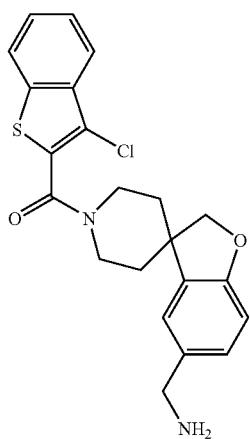
Cpd 167
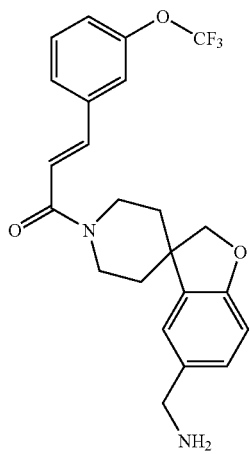
Cpd 168
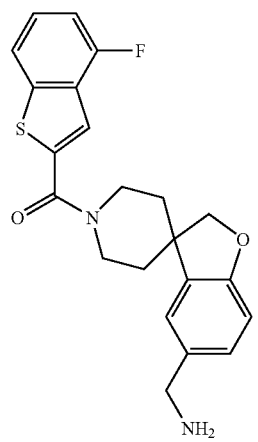
Cpd 169
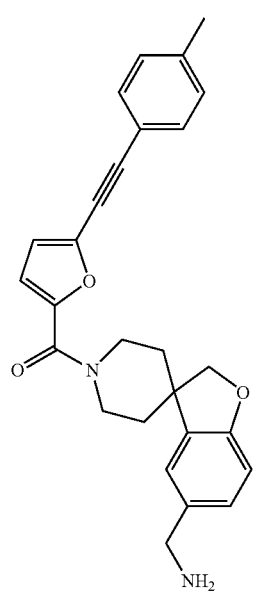
Cpd 170

-continued
Cpd 171
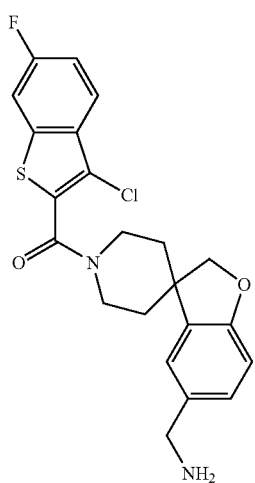
Cpd 172
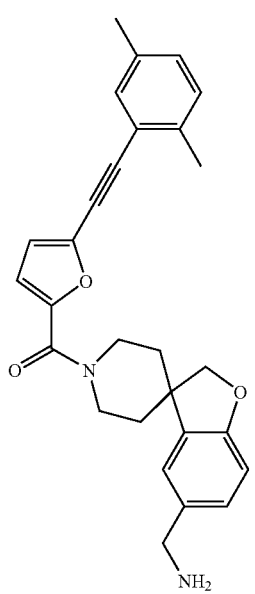
Cpd 173
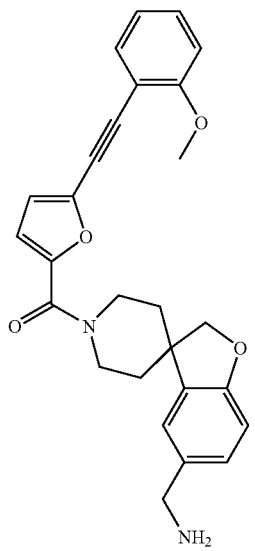
-continued
Cpd 174
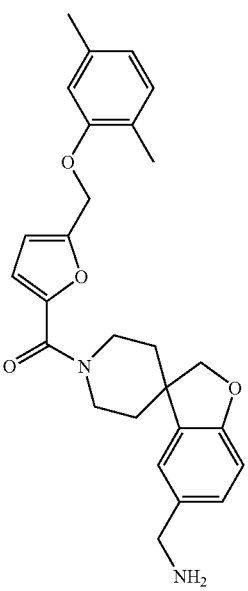
Cpd 175
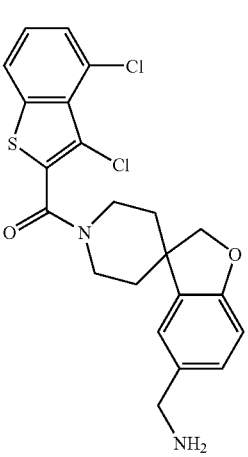
Cpd 176
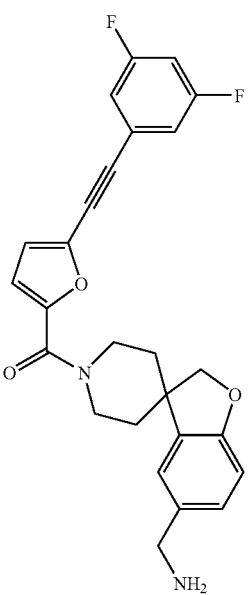

-continued
Cpd 177
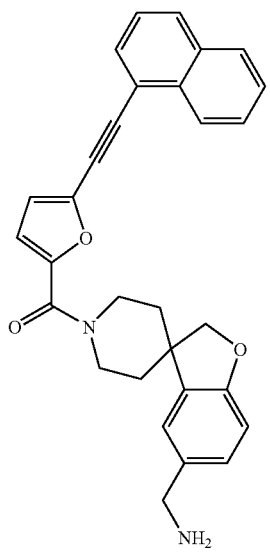
Cpd 178
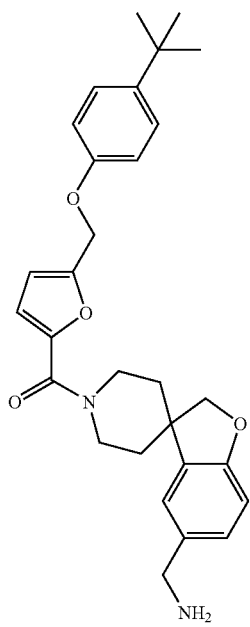
Cpd 179
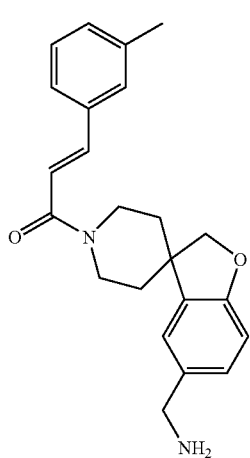
-continued
Cpd 180
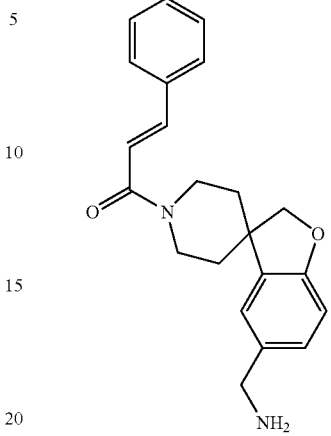
Cpd 181
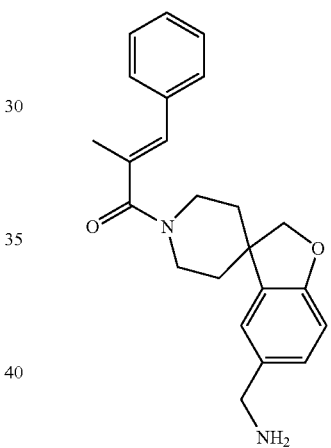
Cpd 182
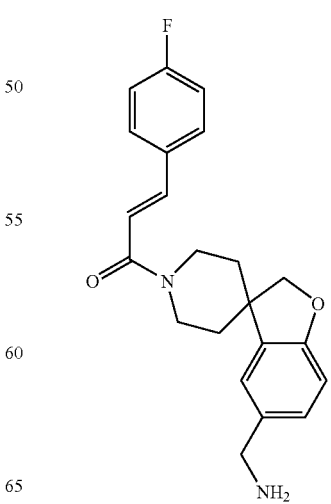

Cpd 183
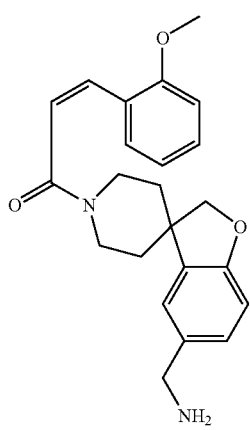
Cpd 186
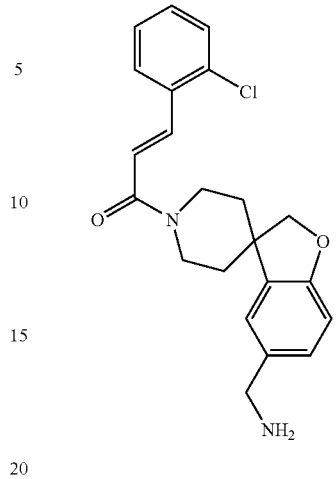
Cpd 184
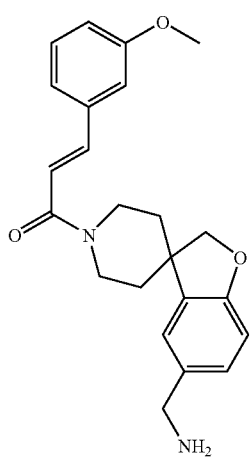
Cpd 187
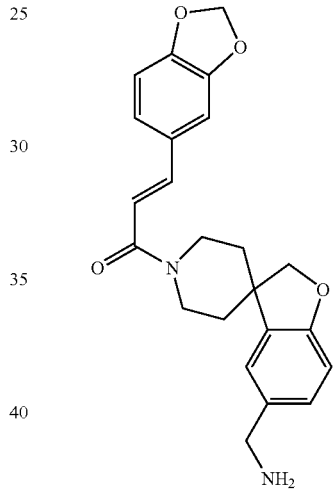
Cpd 185
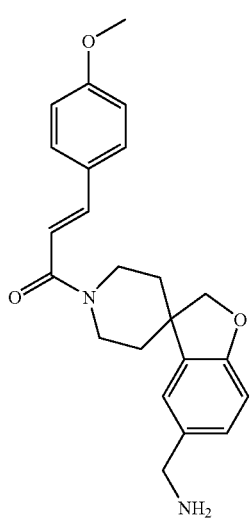
Cpd 188
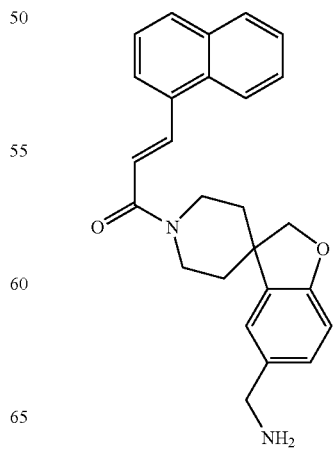

-continued
Cpd 189
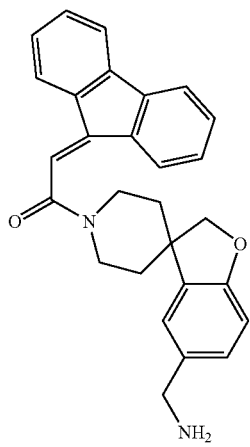
Cpd 192
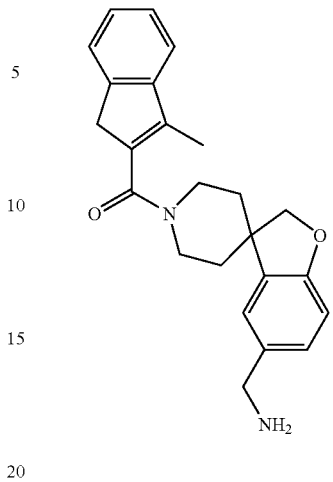
Cpd 190
Cpd 193
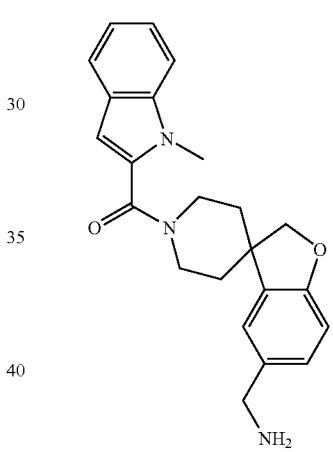
Cpd 191
Cpd 194
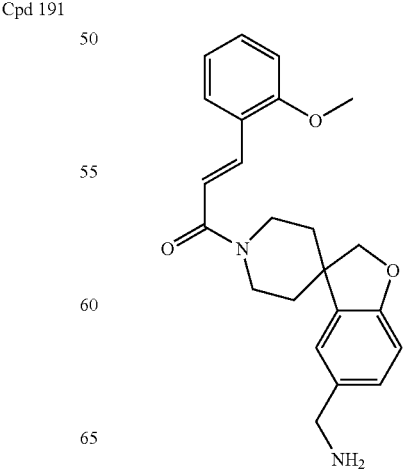

Cpd 195
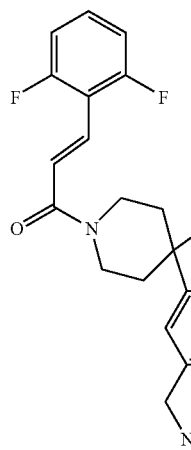
Cpd 196
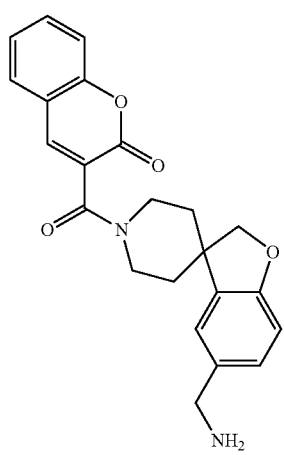
Cpd 197
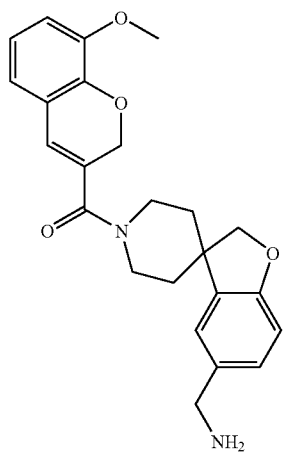
Cpd 198
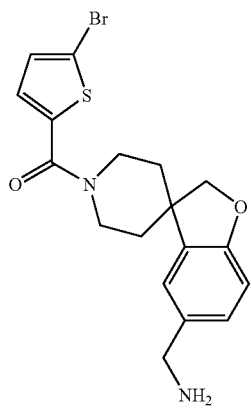
Cpd 199
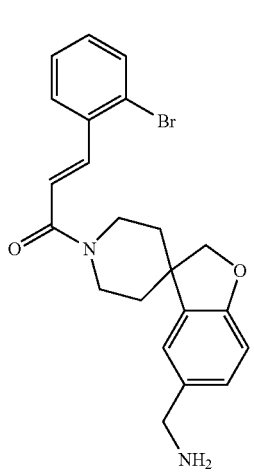
Cpd 200
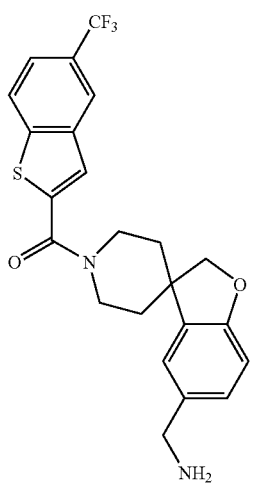

Cpd 201
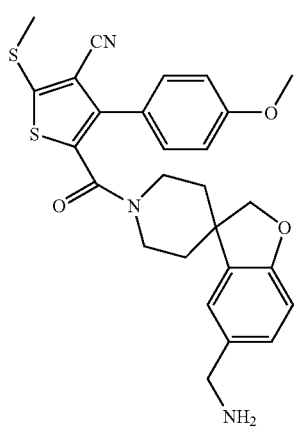
Cpd 202
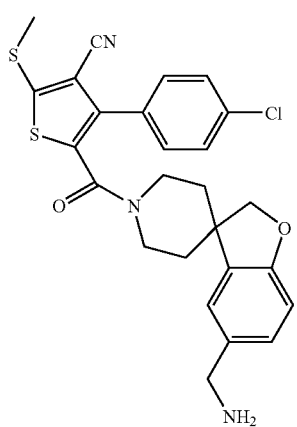
Cpd 203
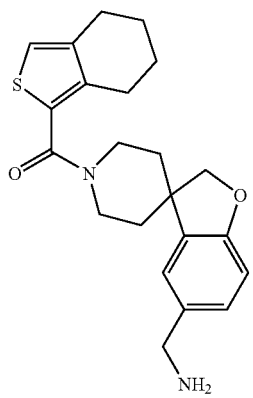
Cpd 204
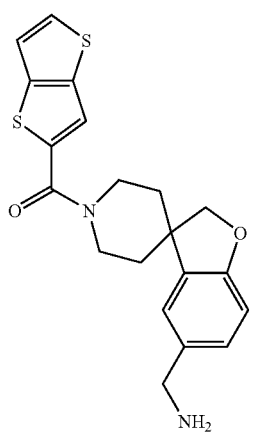
Cpd 205
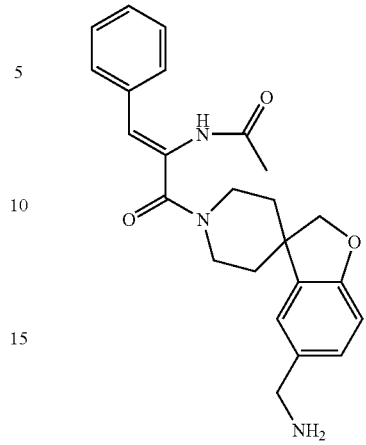
Cpd 206
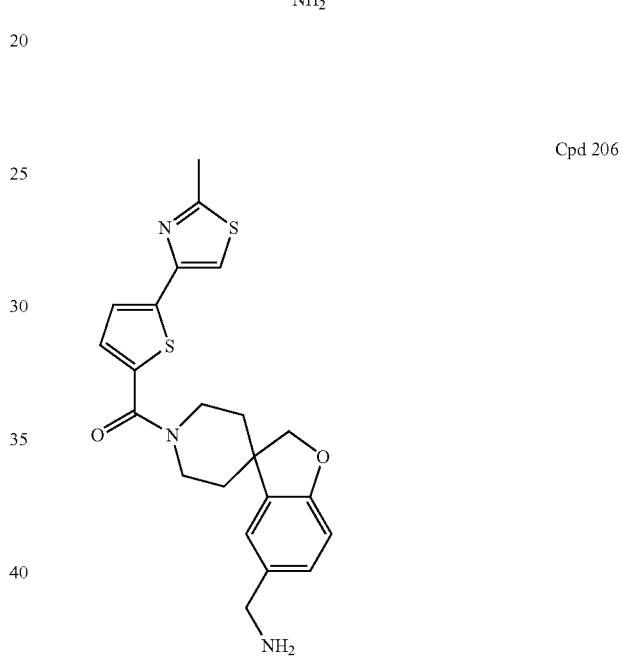
Cpd 207
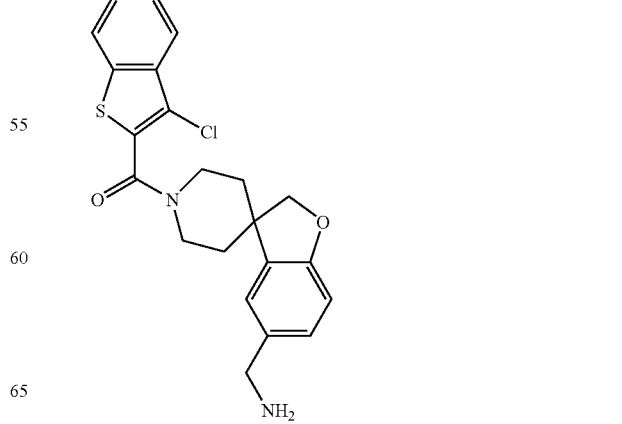

Cpd 208
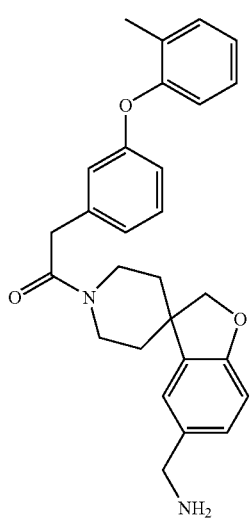
Cpd 211
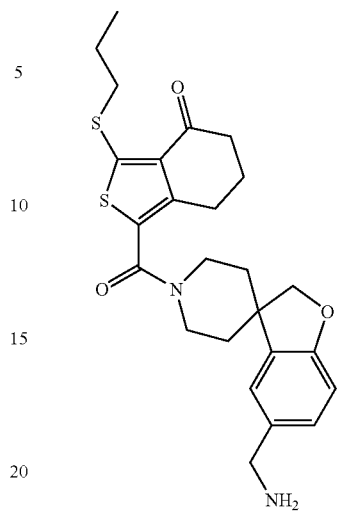
Cpd 209
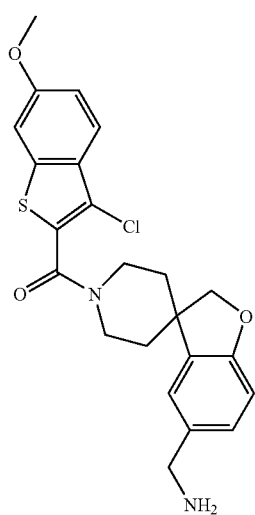
Cpd 210
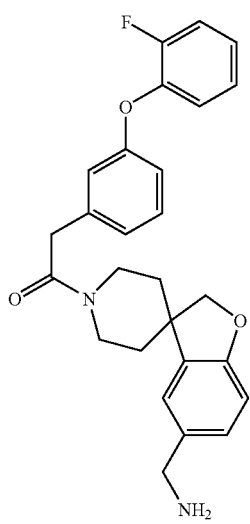
Cpd 212
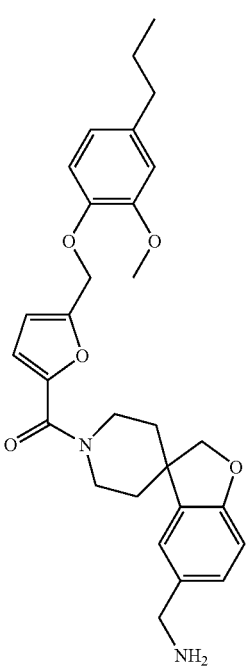

Cpd 213
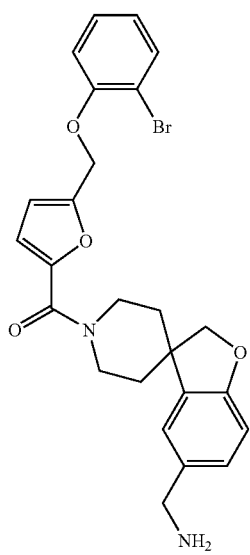
Cpd 214
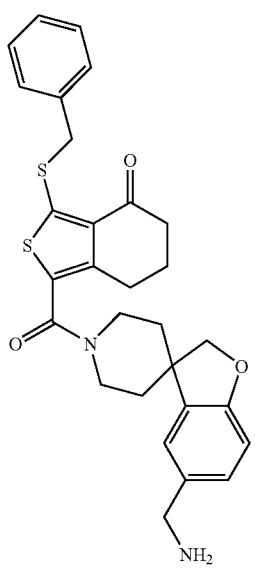
Cpd 215
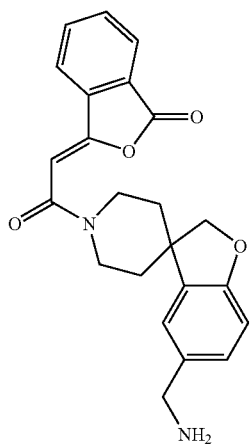
Cpd 216
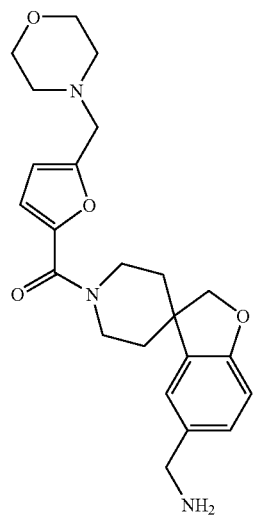
Cpd 217
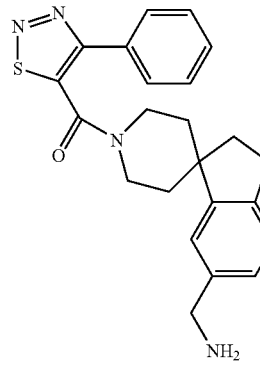
Cpd 218
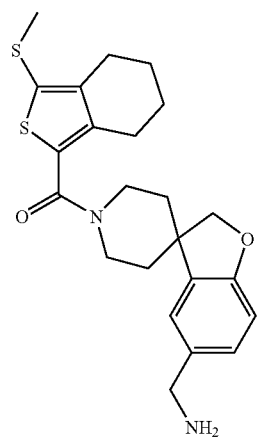

-continued
Cpd 219
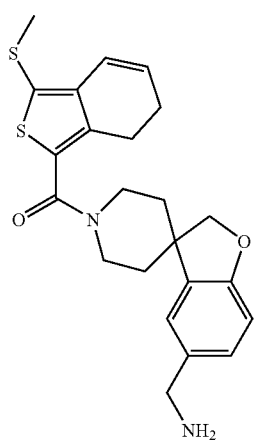
Cpd 220
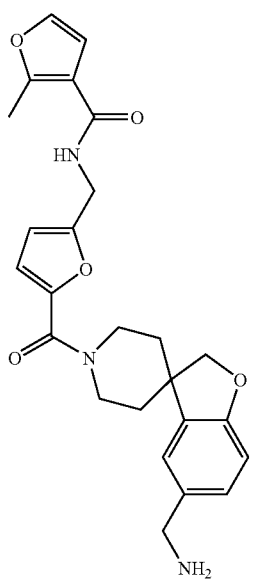
Cpd 221
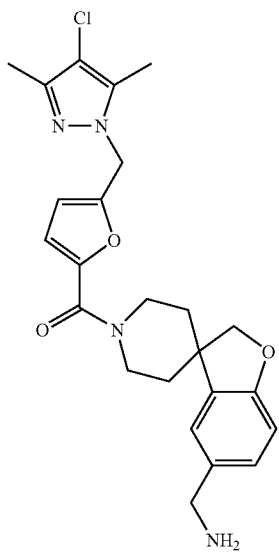
-continued
Cpd 222
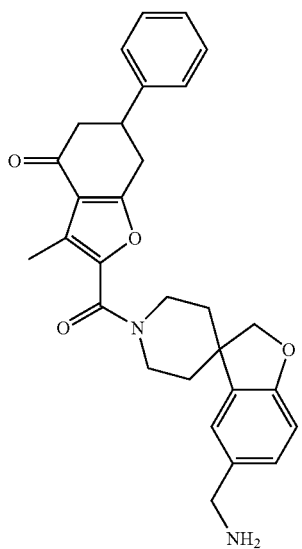
Cpd 223
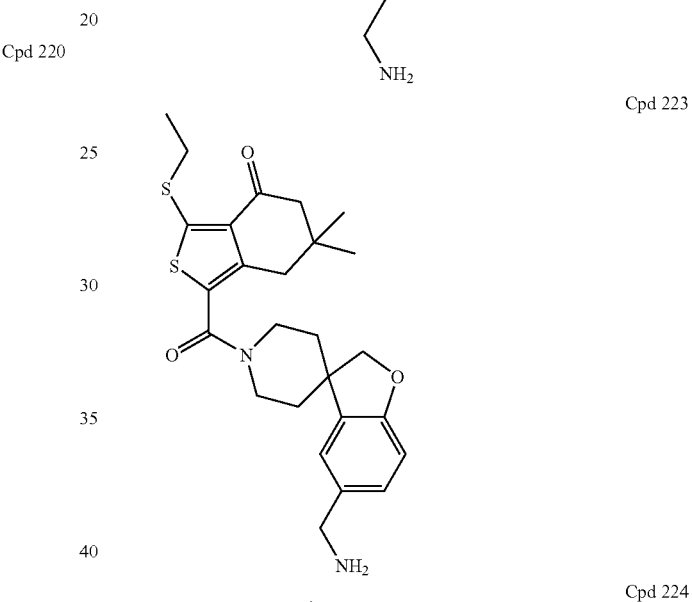
Cpd 224
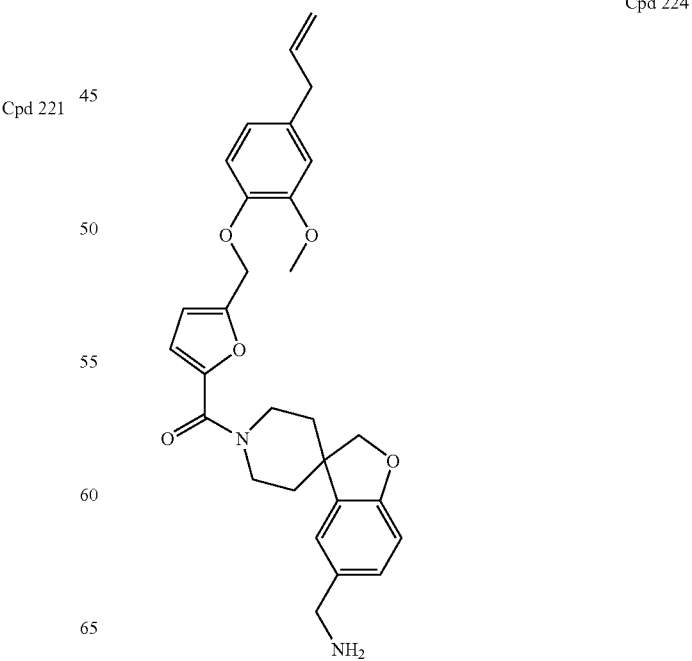

Cpd 225
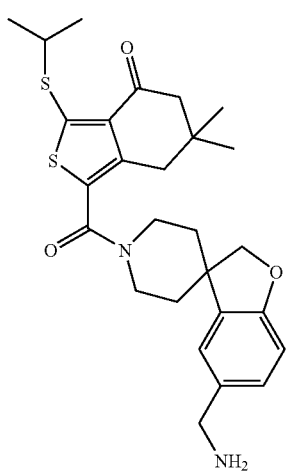
Cpd 228
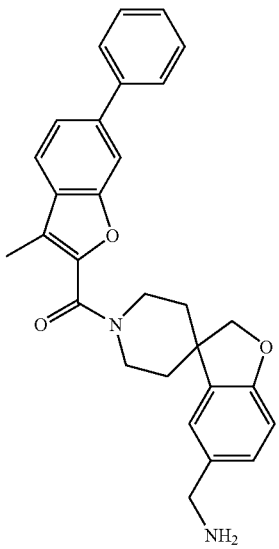
Cpd 226
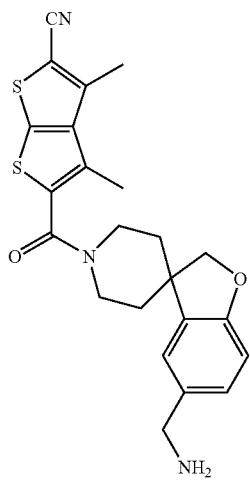
Cpd 229
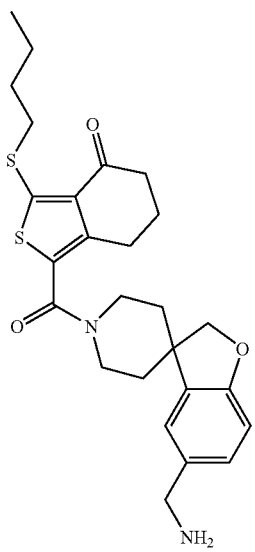
Cpd 227
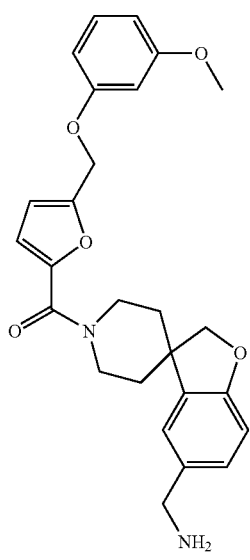
Cpd 230
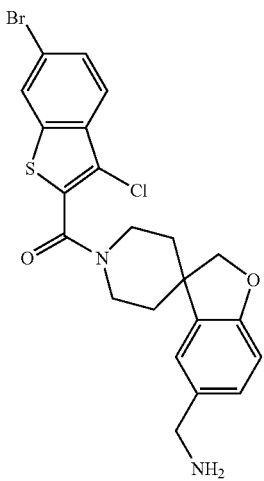

91
-continued
Cpd 231
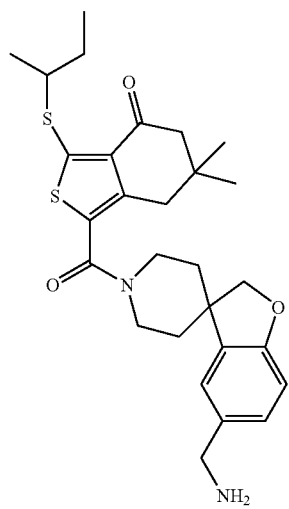
Cpd 232
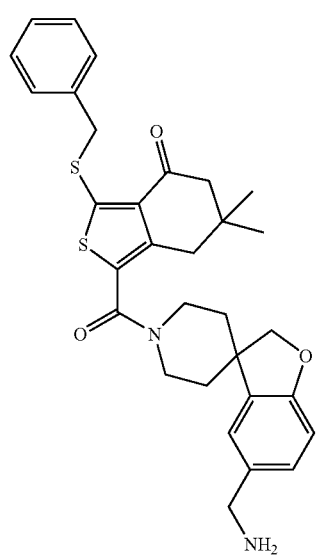
Cpd 233
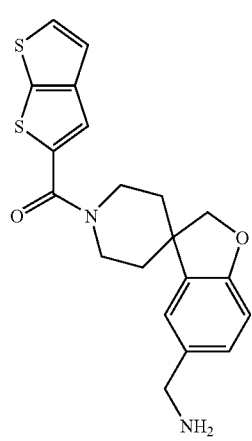
92
-continued
Cpd 234
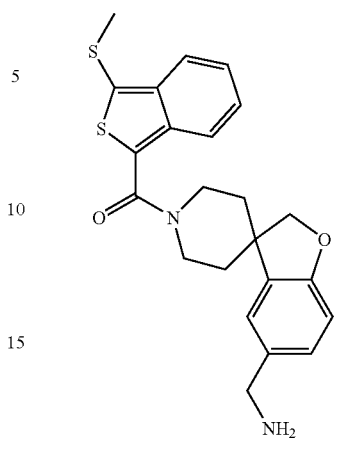
Cpd 235
Cpd 236

Cpd 237
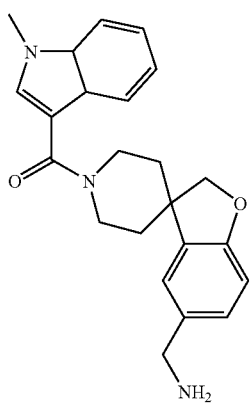
Cpd 240
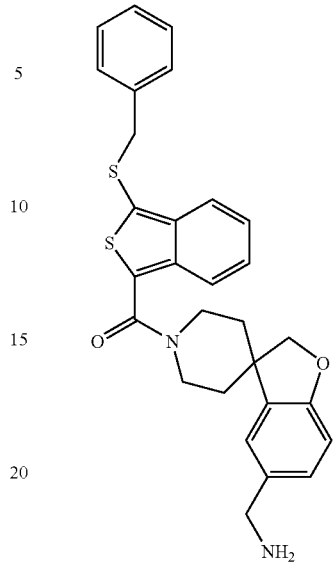
Cpd 238
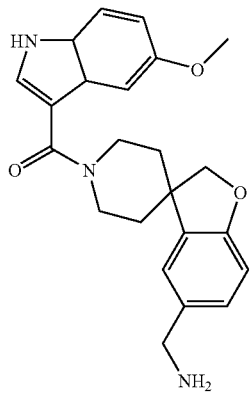
Cpd 241
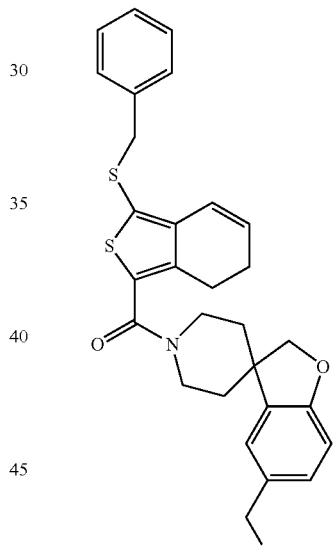
Cpd 239
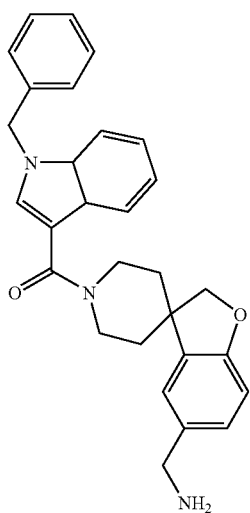
Cpd 242
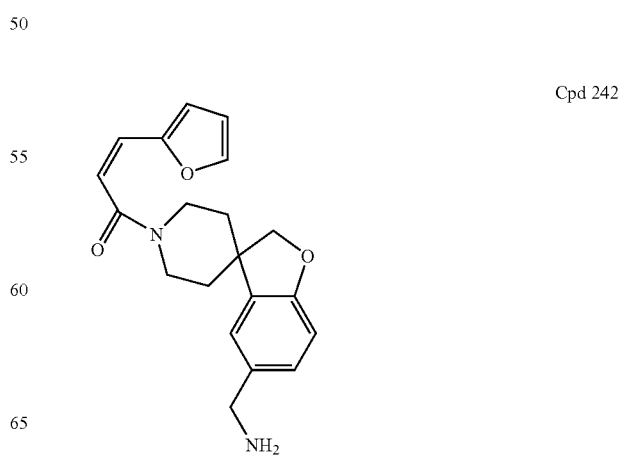

Cpd 243
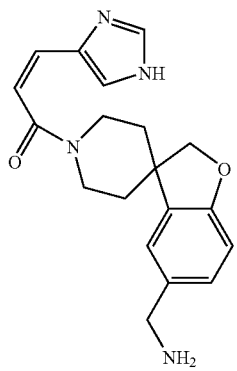
Cpd 244
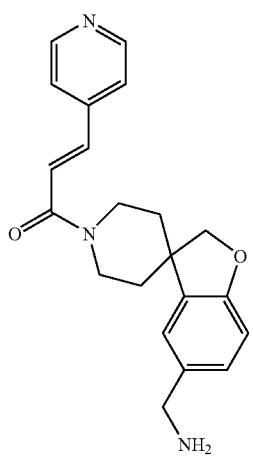
Cpd 245
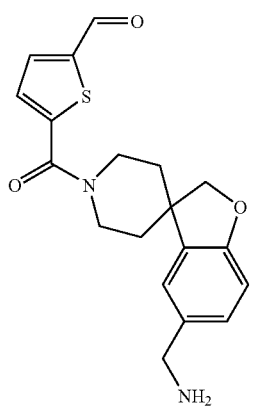
Cpd 246
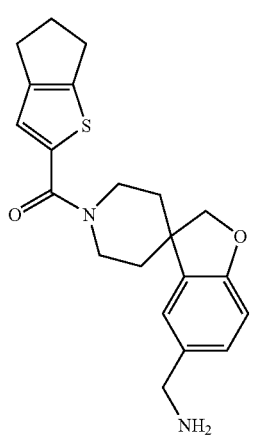
Cpd 247
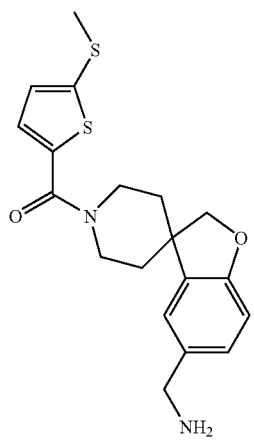
Cpd 248
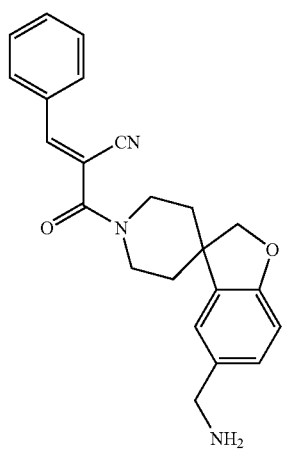
Cpd 249
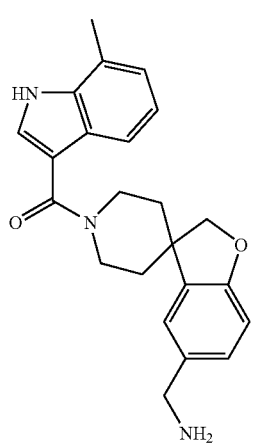

Cpd 250
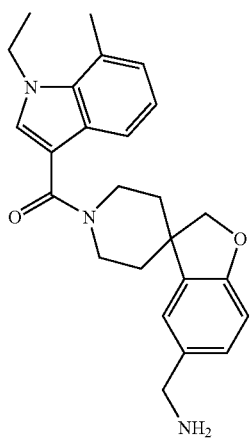
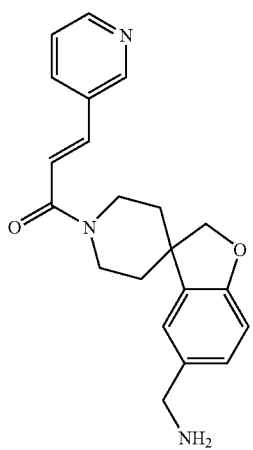
Cpd 253
Cpd 251
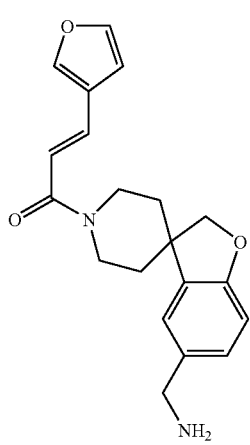
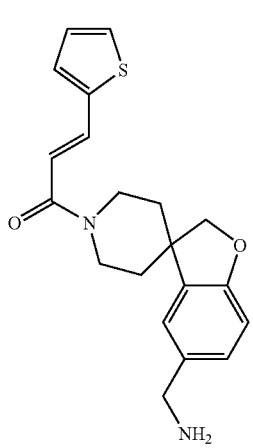
Cpd 254
Cpd 252
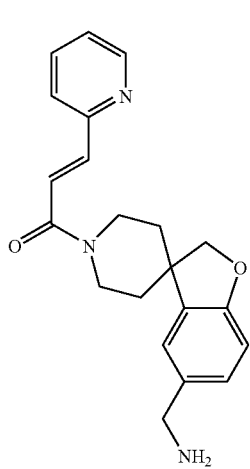
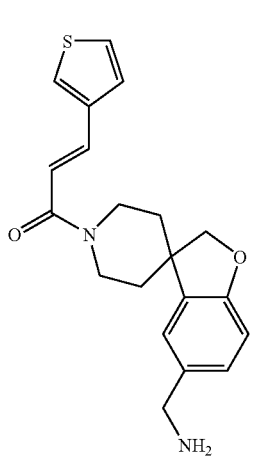
Cpd 255

Cpd 256
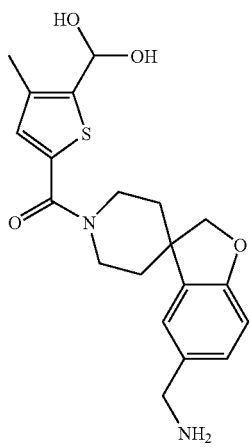
Cpd 259
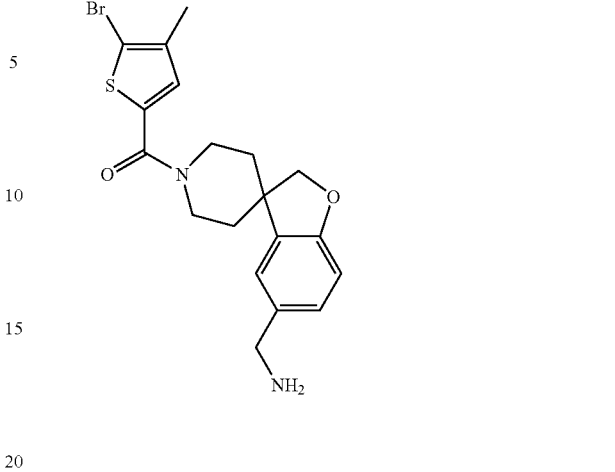
Cpd 257
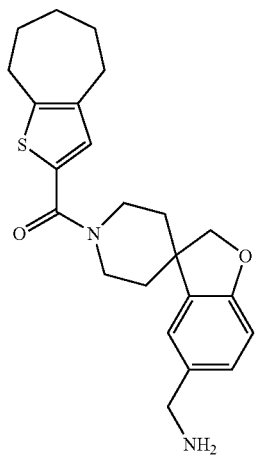
Cpd 260
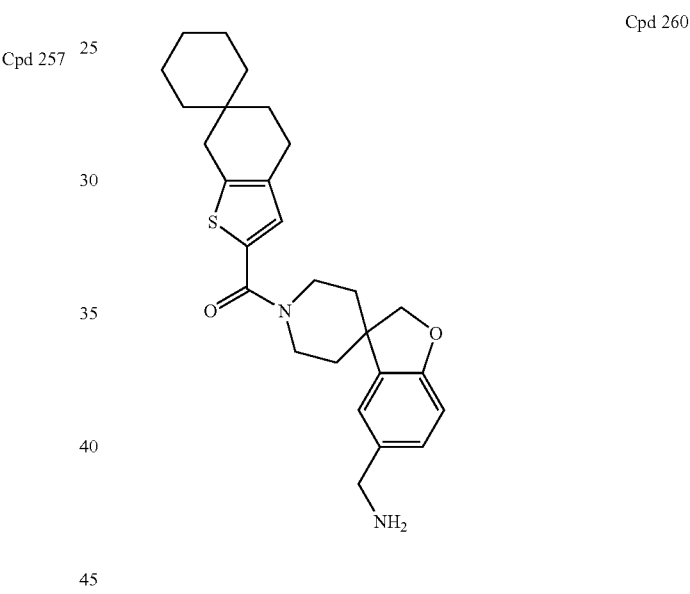
Cpd 258
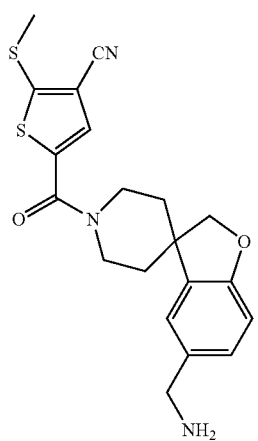
Cpd 261
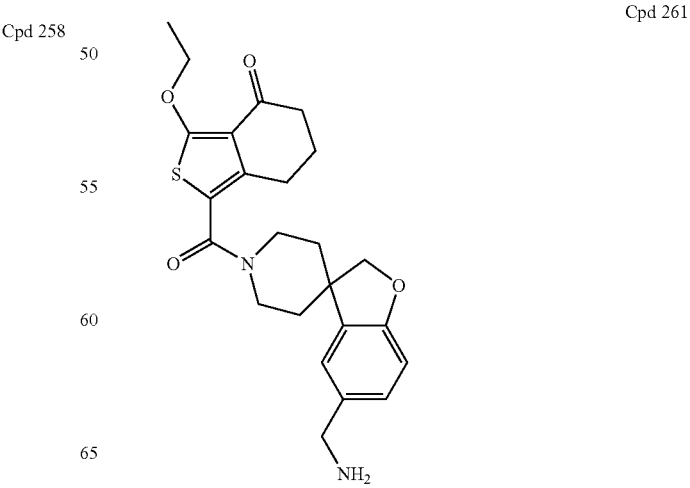

Cpd 262
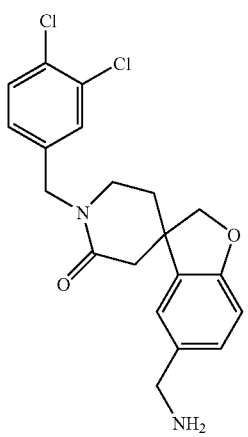
Cpd 265
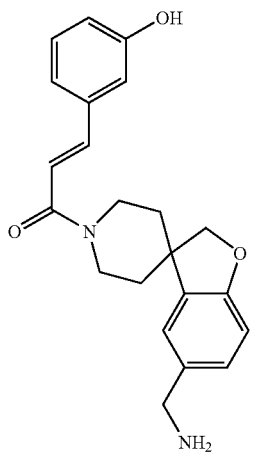
Cpd 263
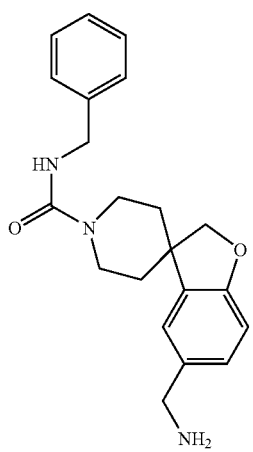
Cpd 266
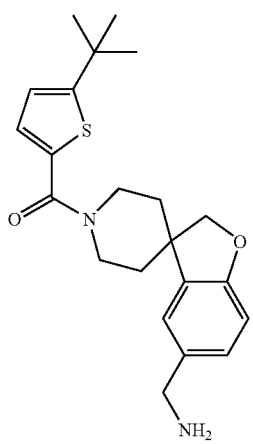
Cpd 264
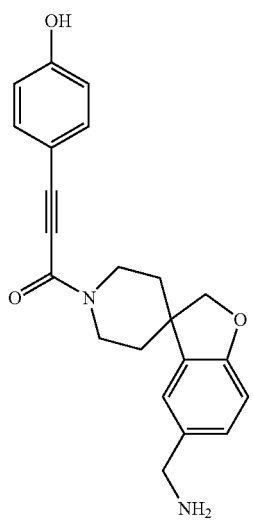
Cpd 267
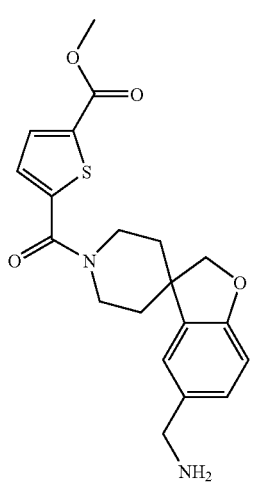

Cpd 268
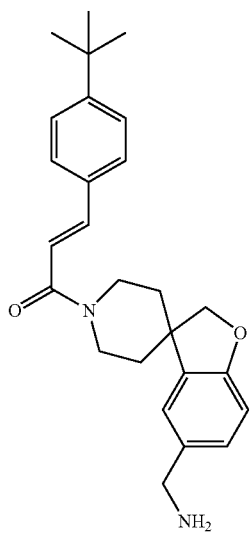
Cpd 269
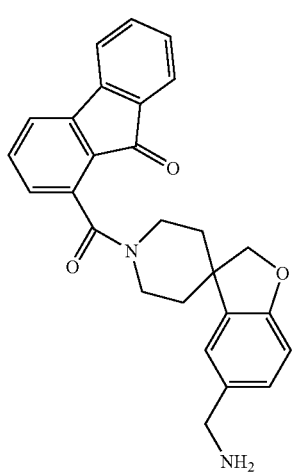
Cpd 270
Cpd 271
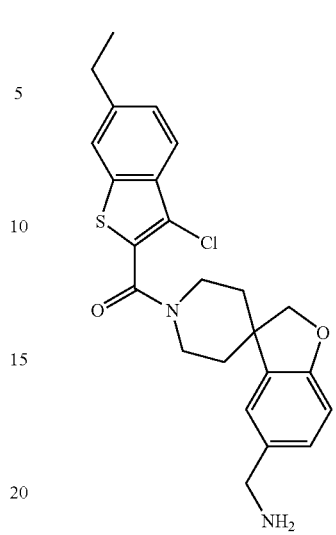
Cpd 272
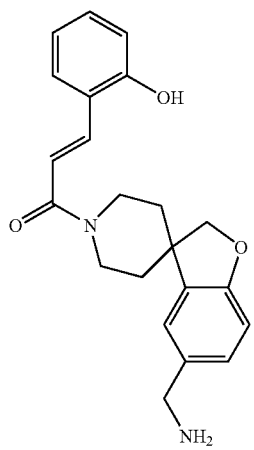
Cpd 273
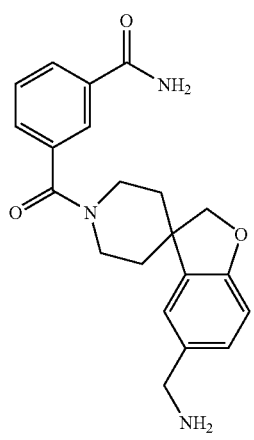

Cpd 274
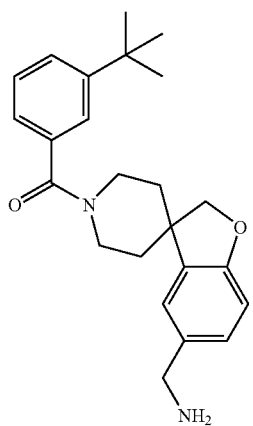
Cpd 277
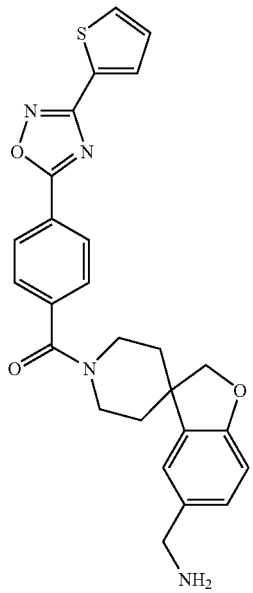
Cpd 275
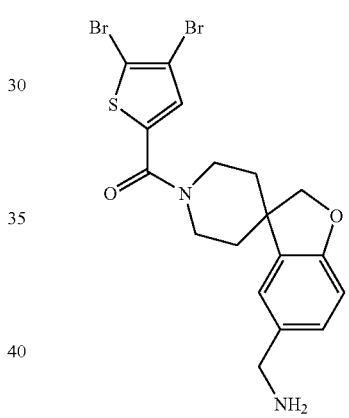
Cpd 278
Cpd 276
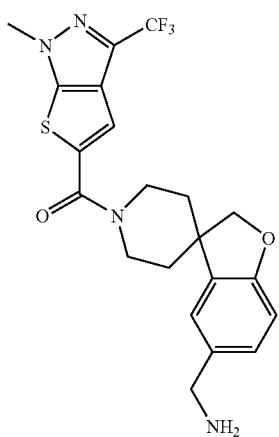
Cpd 279
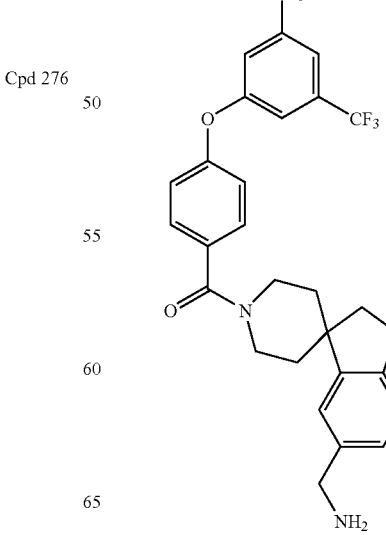

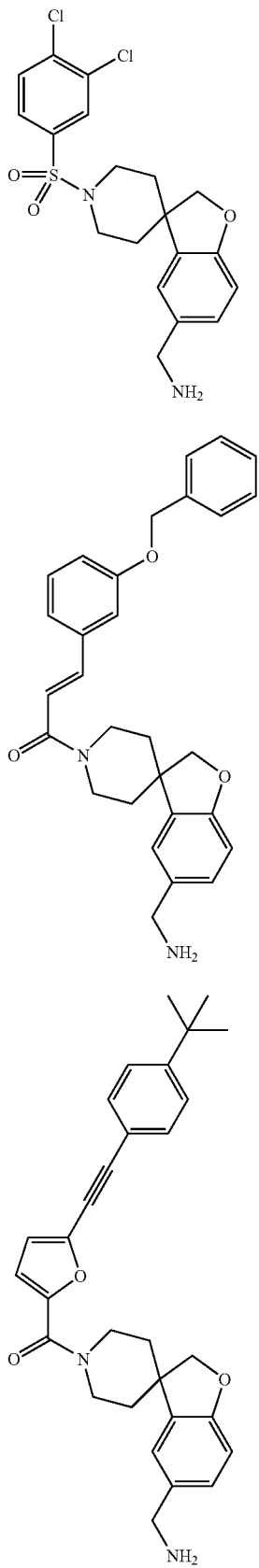
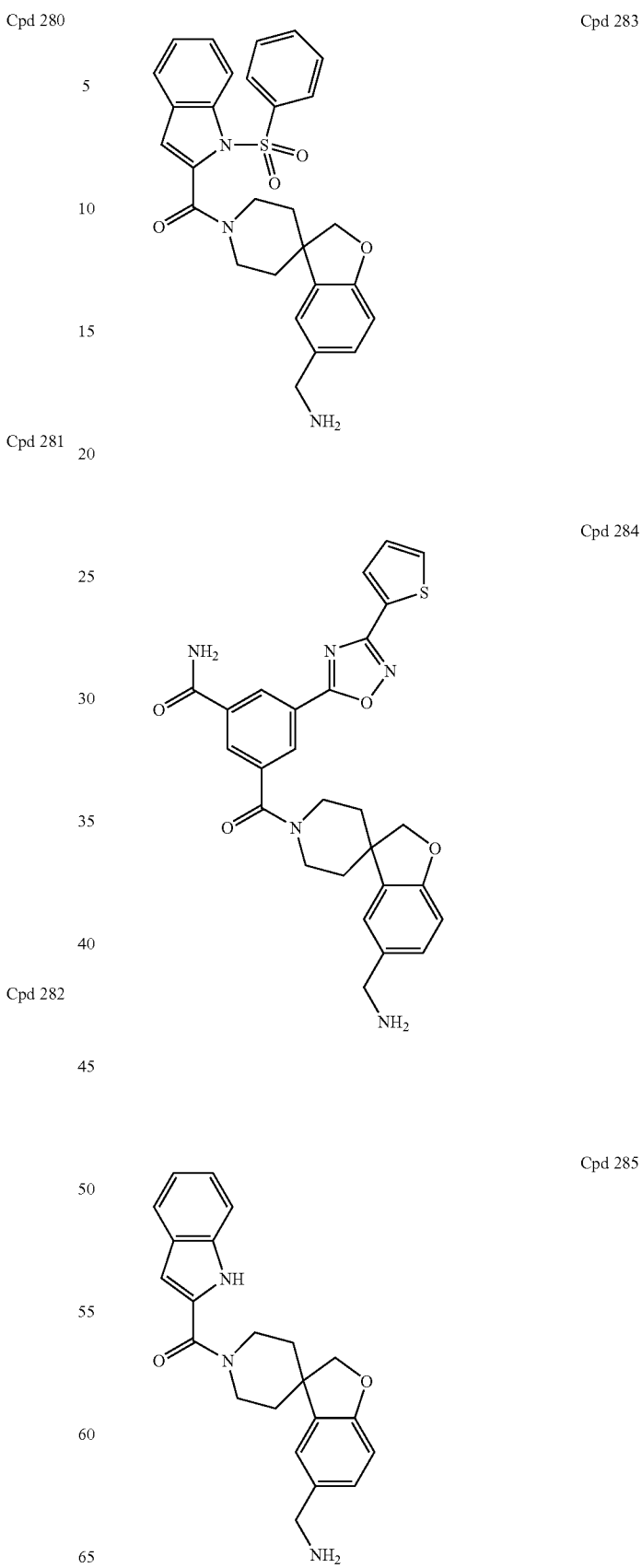

Cpd 286
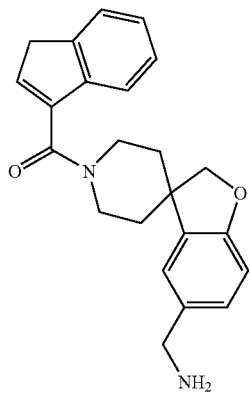
Cpd 289
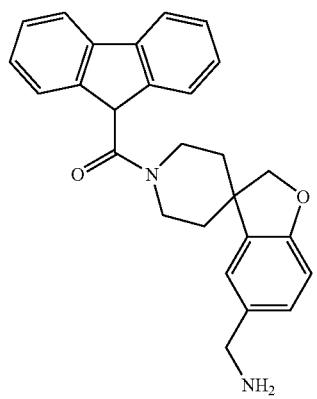
Cpd 287
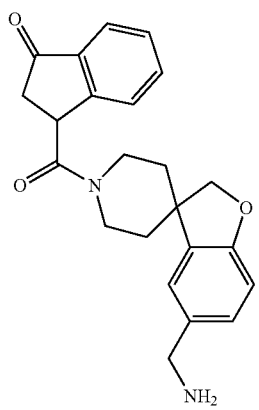
Cpd 290
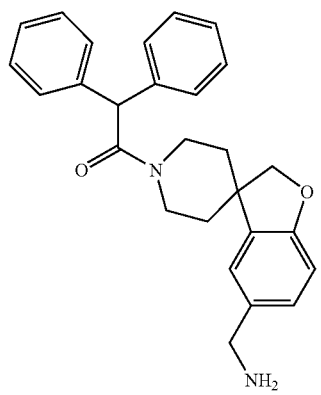
Cpd 288
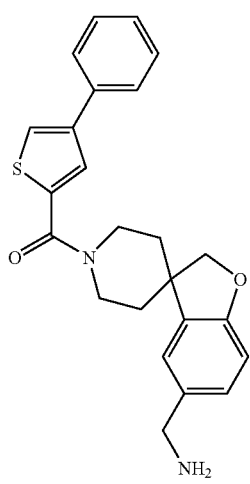
Cpd 291
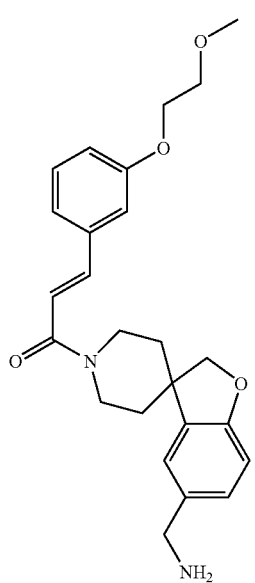

Cpd 292
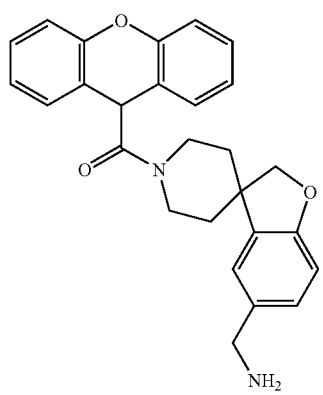
Cpd 295
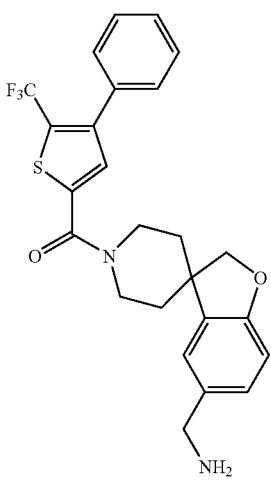
Cpd 293
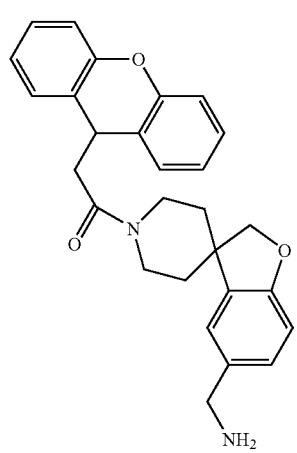
Cpd 296
Cpd 294
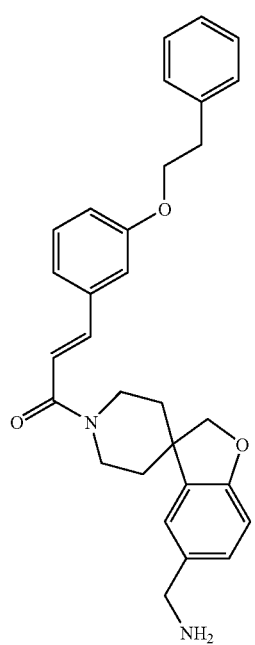
Cpd 297

Cpd 298
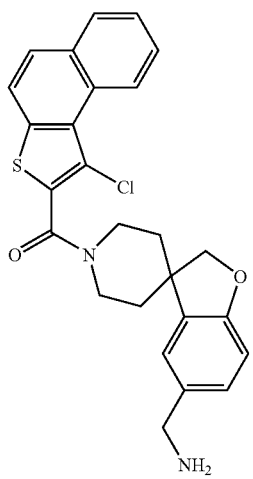
Cpd 299
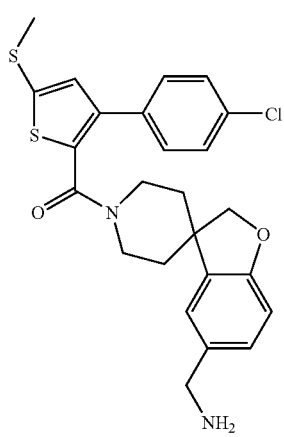
Cpd 300
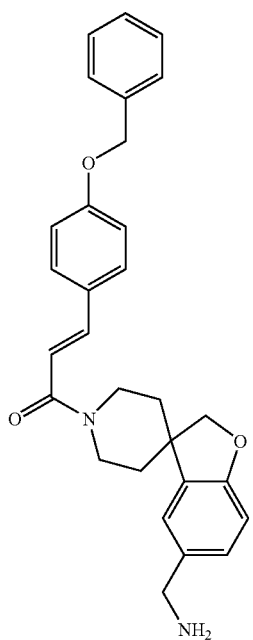
Cpd 301
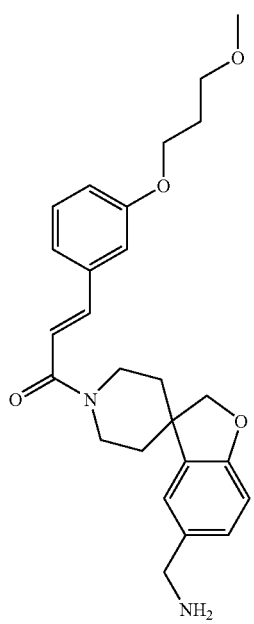
Cpd 302
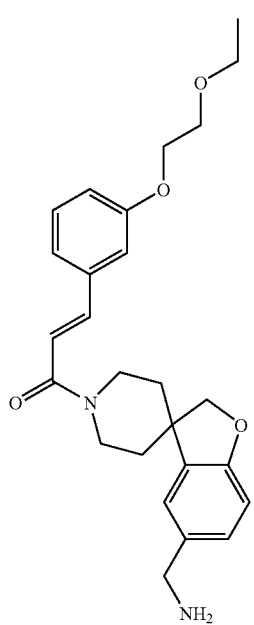

-continued
Cpd 303
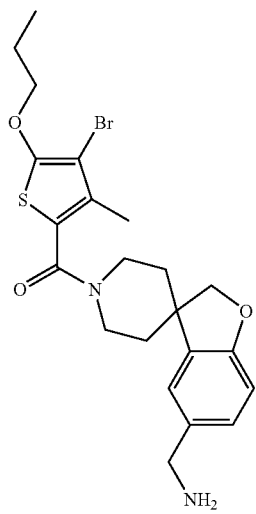
Cpd 304
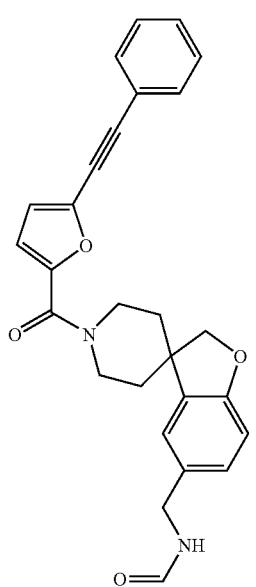
-continued
Cpd 305
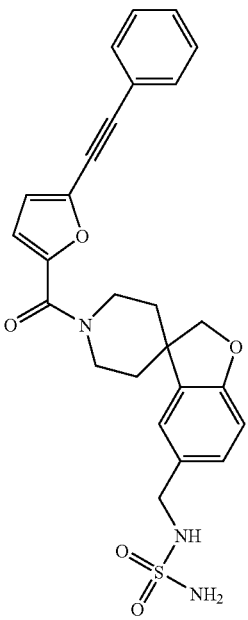
Cpd 306
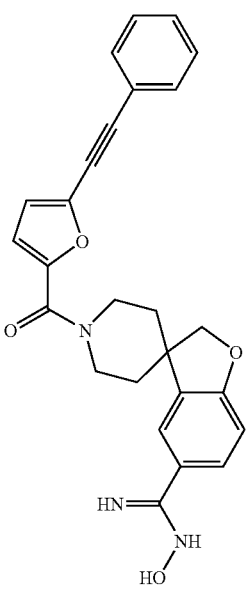

Cpd 307
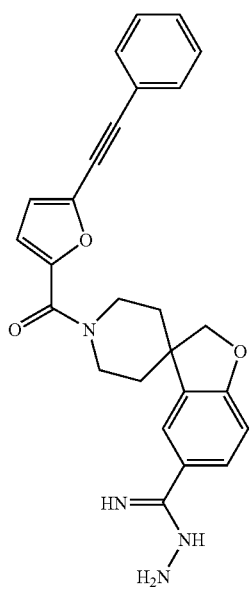
Cpd 310
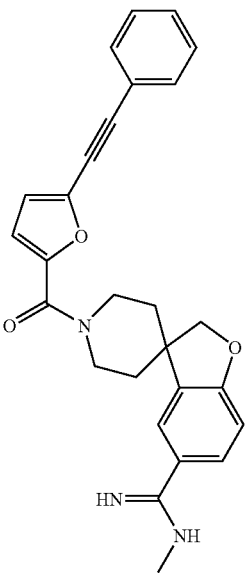
Cpd 308
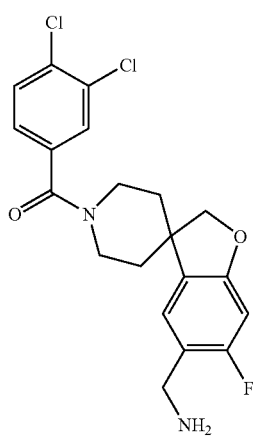
Cpd 311
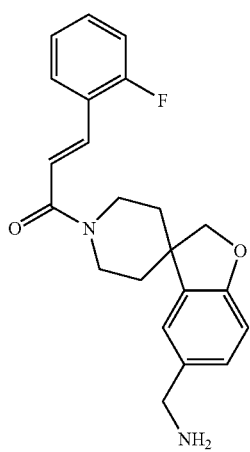
Cpd 309
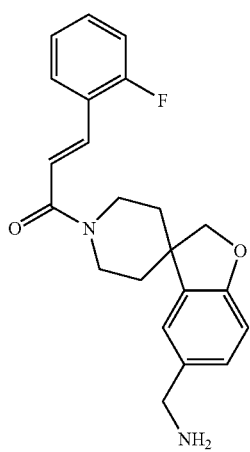
Cpd 312
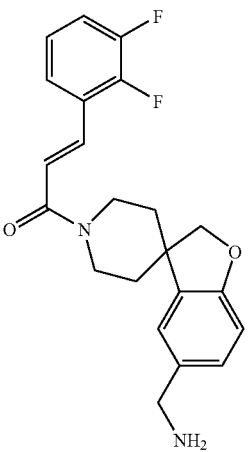

Cpd 313
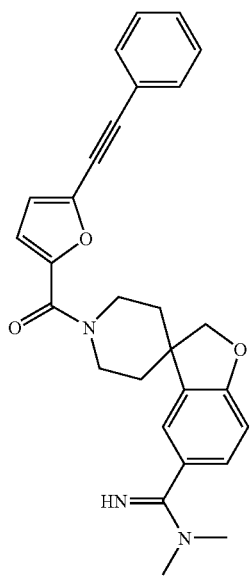
Cpd 316
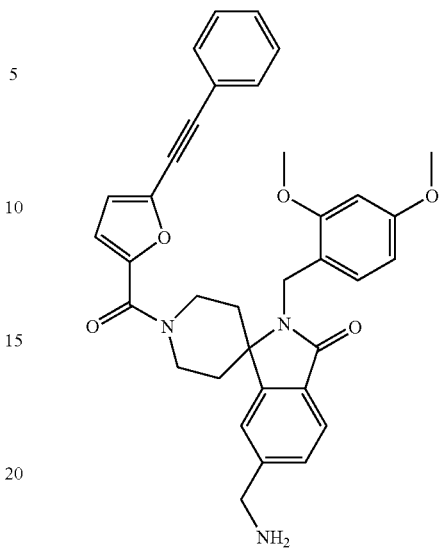
Cpd 314
Cpd 317
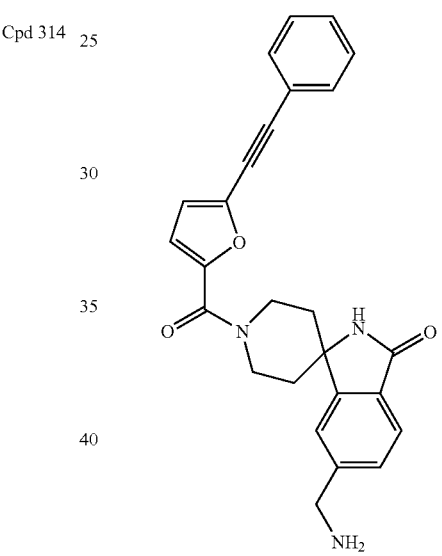
Cpd 315
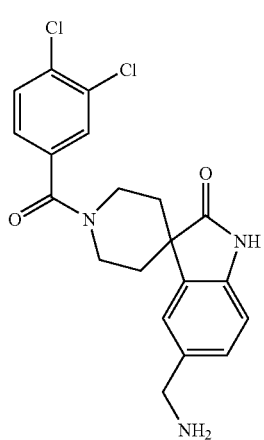
Cpd 318
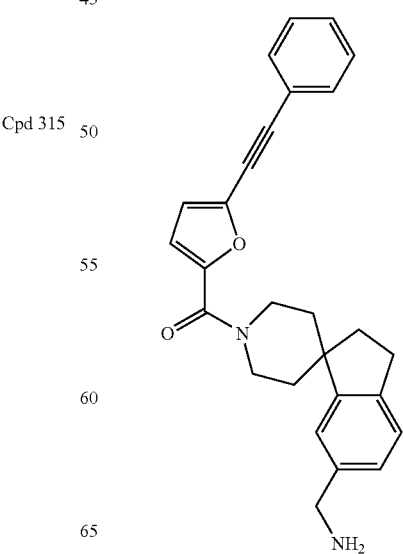

Cpd 319
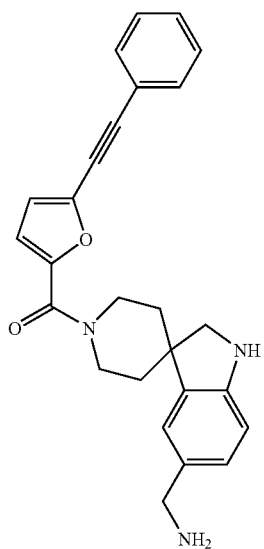
Cpd 322
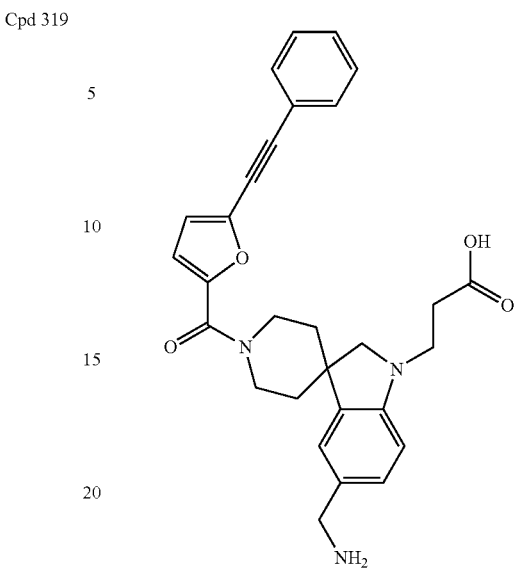
Cpd 320
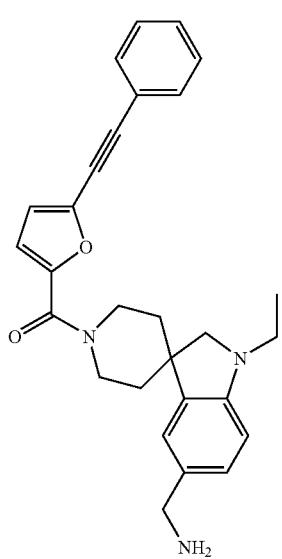
Cpd 323
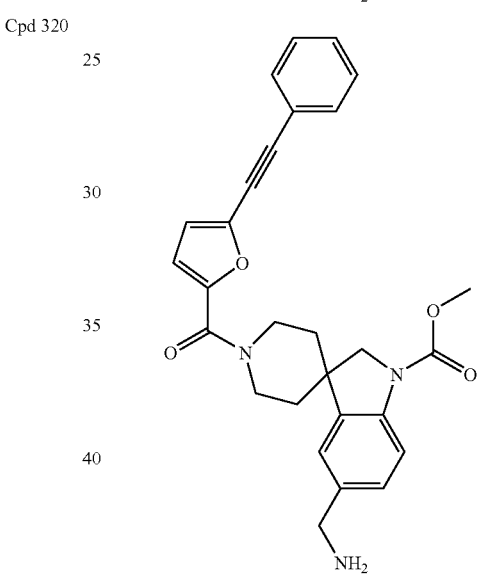
Cpd 321
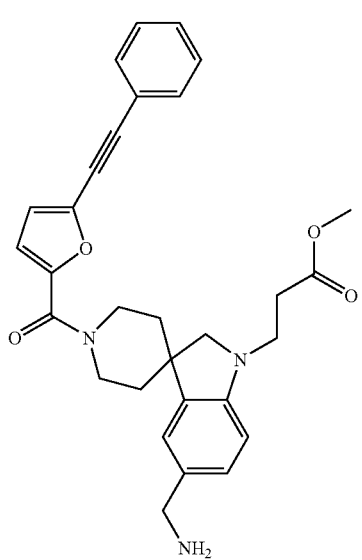
Cpd 324
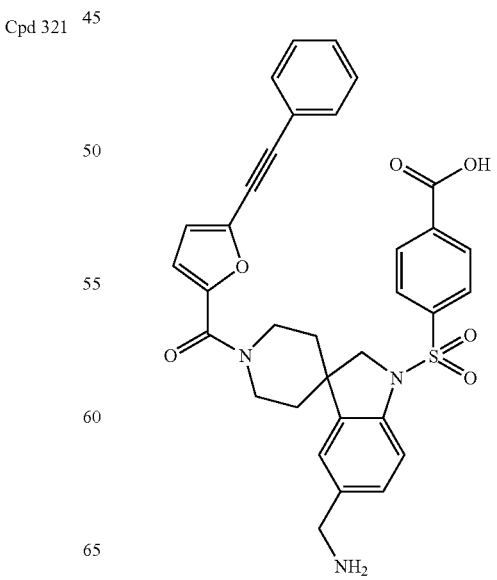

Cpd 325
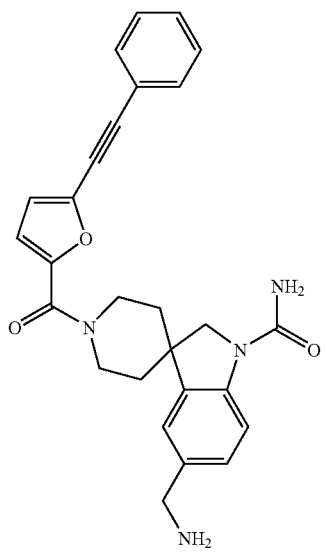
Cpd 328
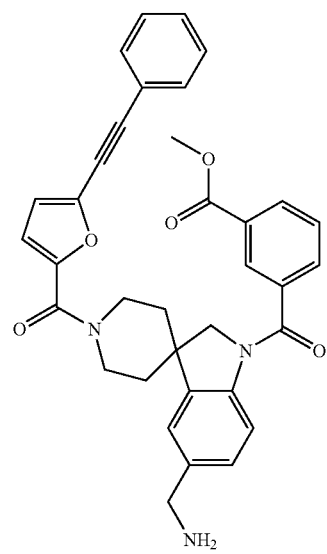
Cpd 326
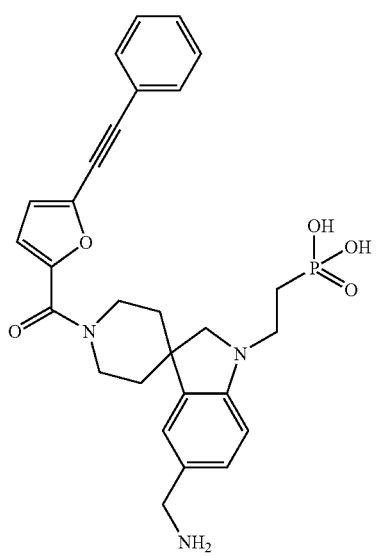
Cpd 329
Cpd 327
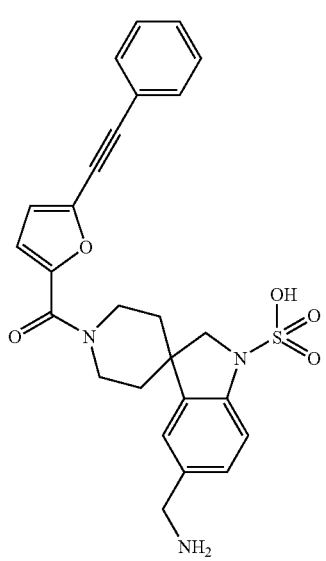
Cpd 330
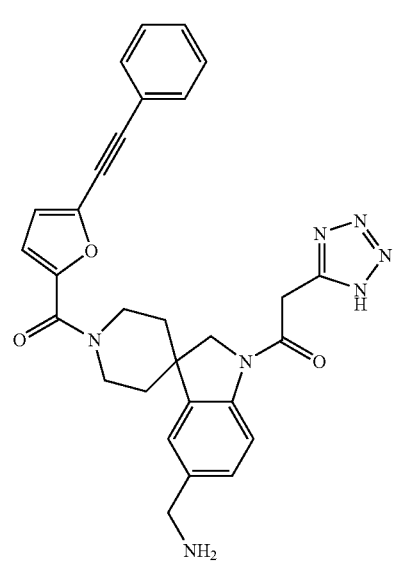

125
-continued
Cpd 331
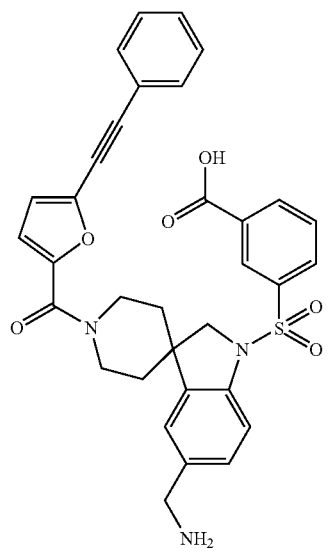
Cpd 332
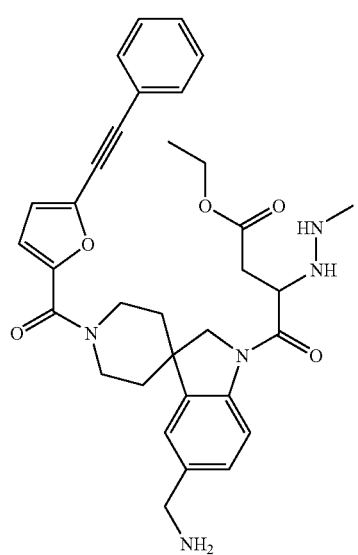
Cpd 333
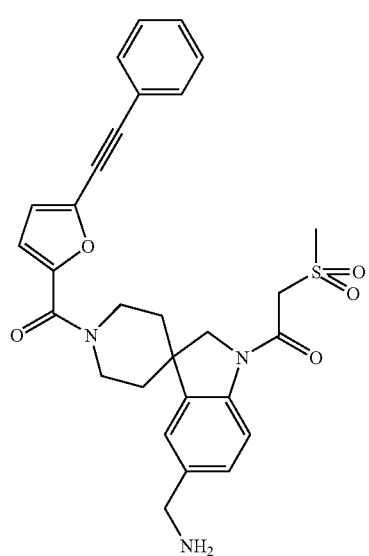
126
-continued
Cpd 334
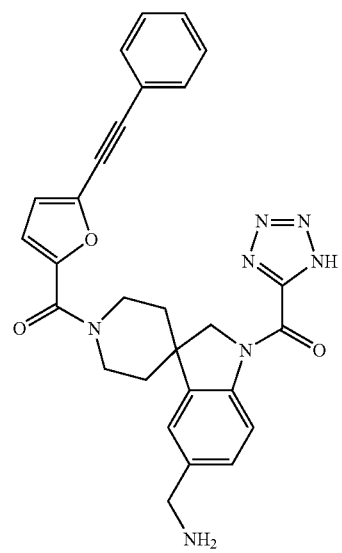
Cpd 335
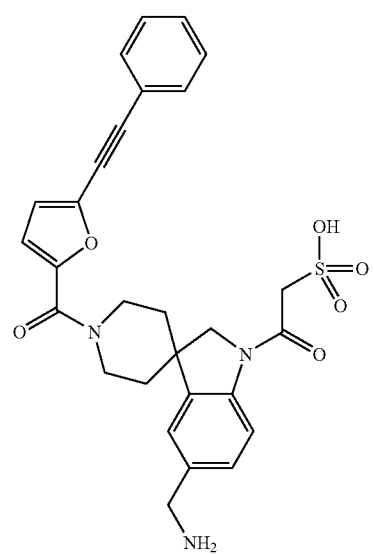
Cpd 336
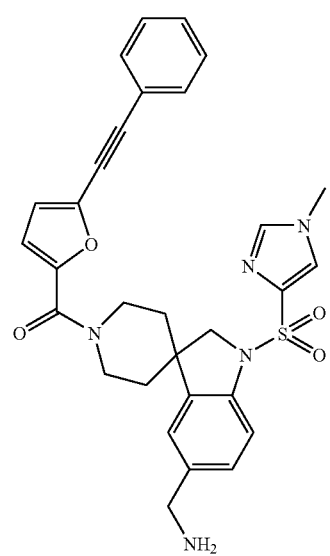

Cpd 337
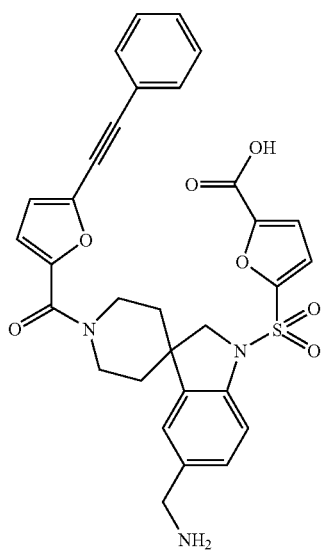
Cpd 338
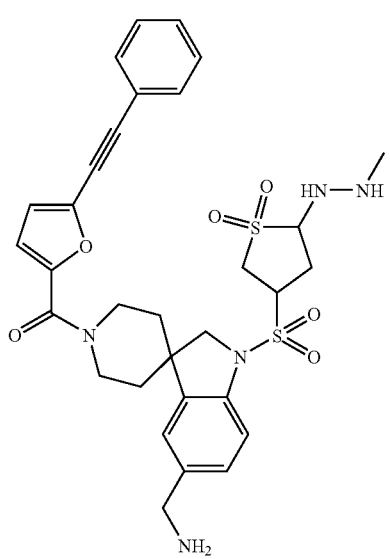
Cpd 339
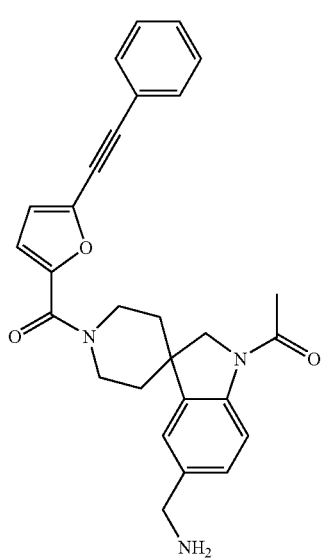
Cpd 340
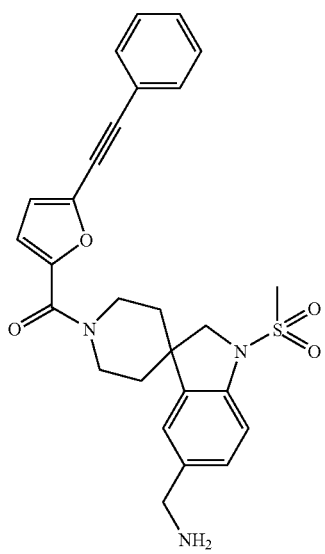
Cpd 341
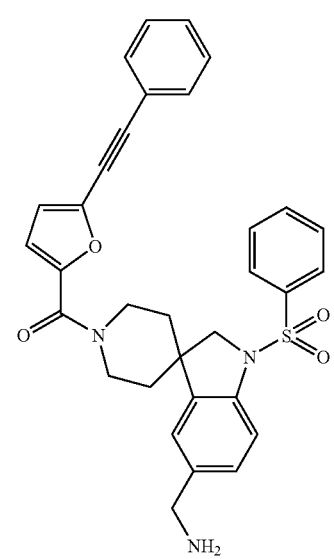
Cpd 342
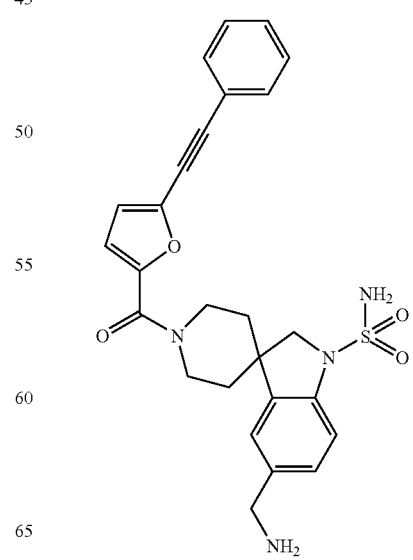

Cpd 343
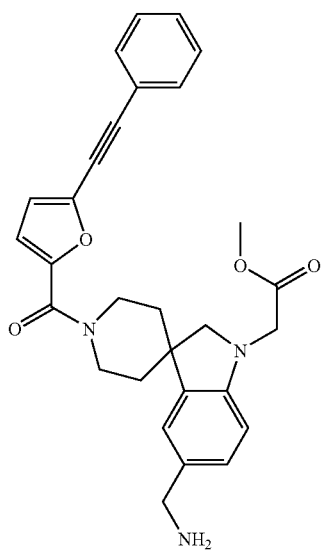
Cpd 344
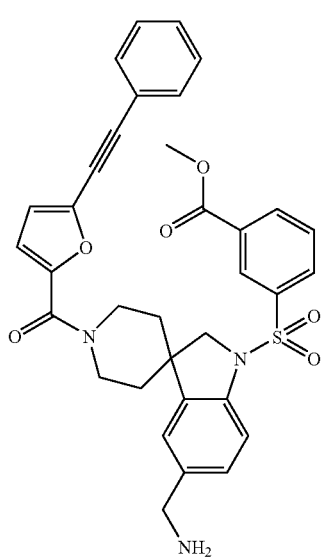
Cpd 345
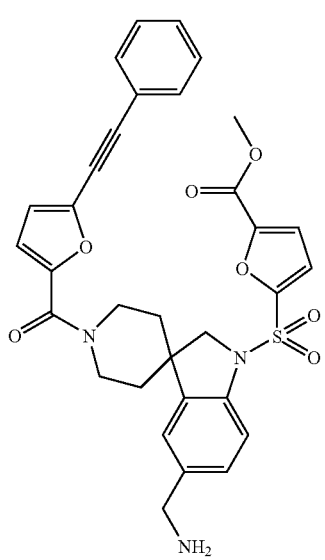
Cpd 346
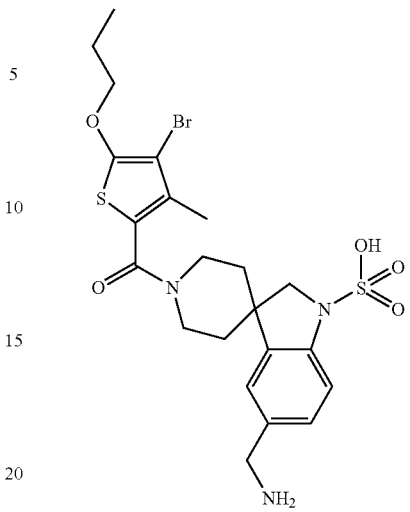
Cpd 347
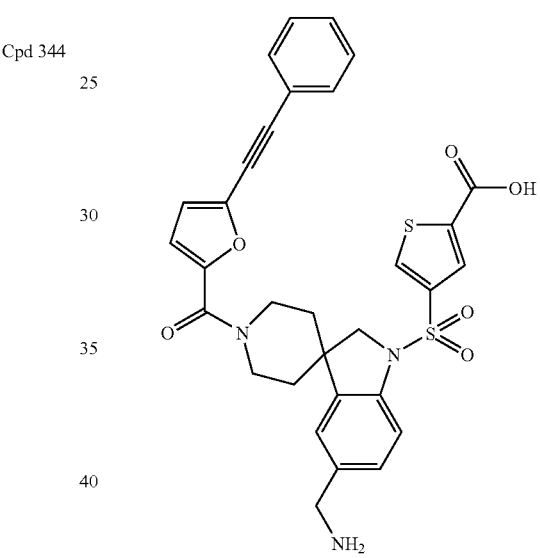
Cpd 348
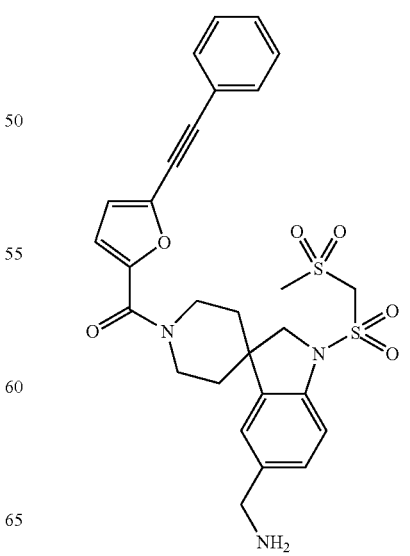

Cpd 349
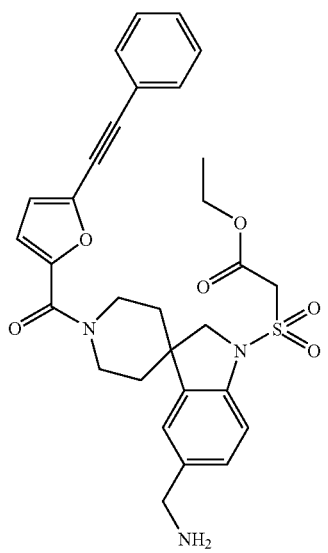
Cpd 350
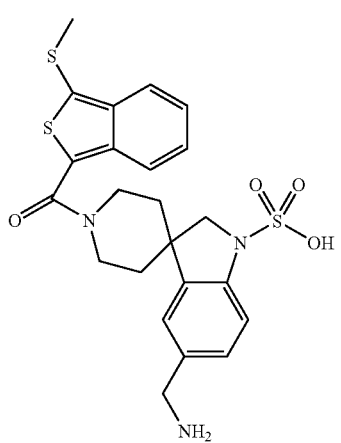
Cpd 351
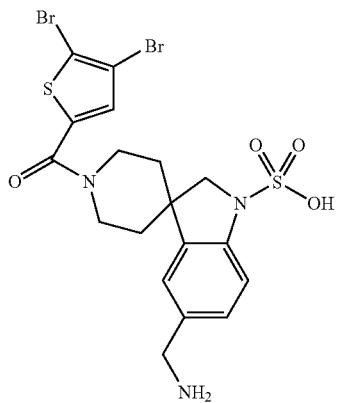
Cpd 352
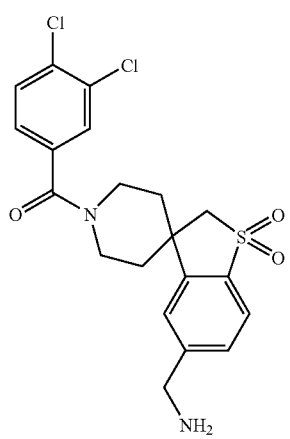
Cpd 353
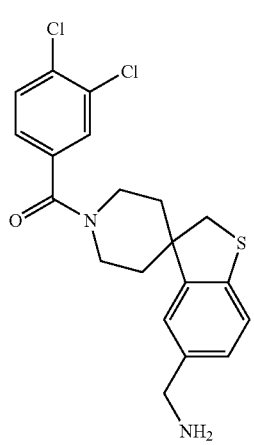
Cpd 354
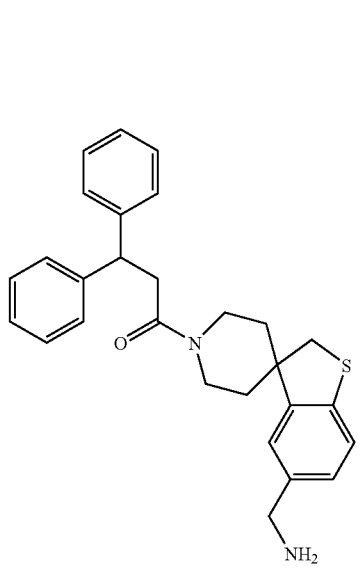

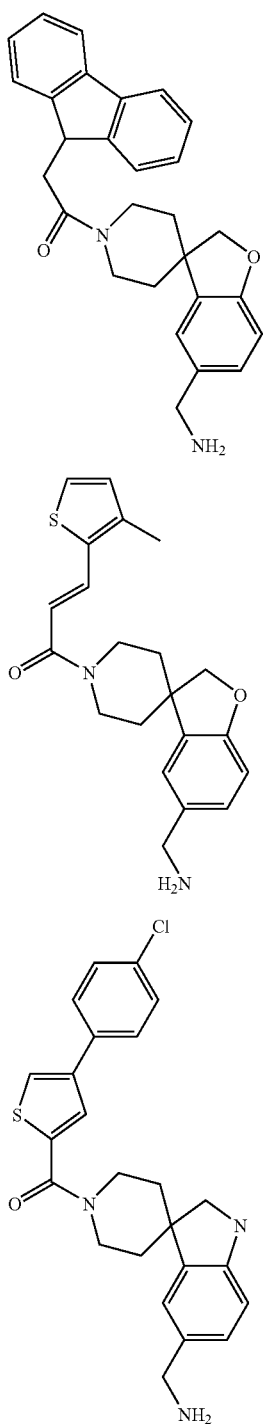
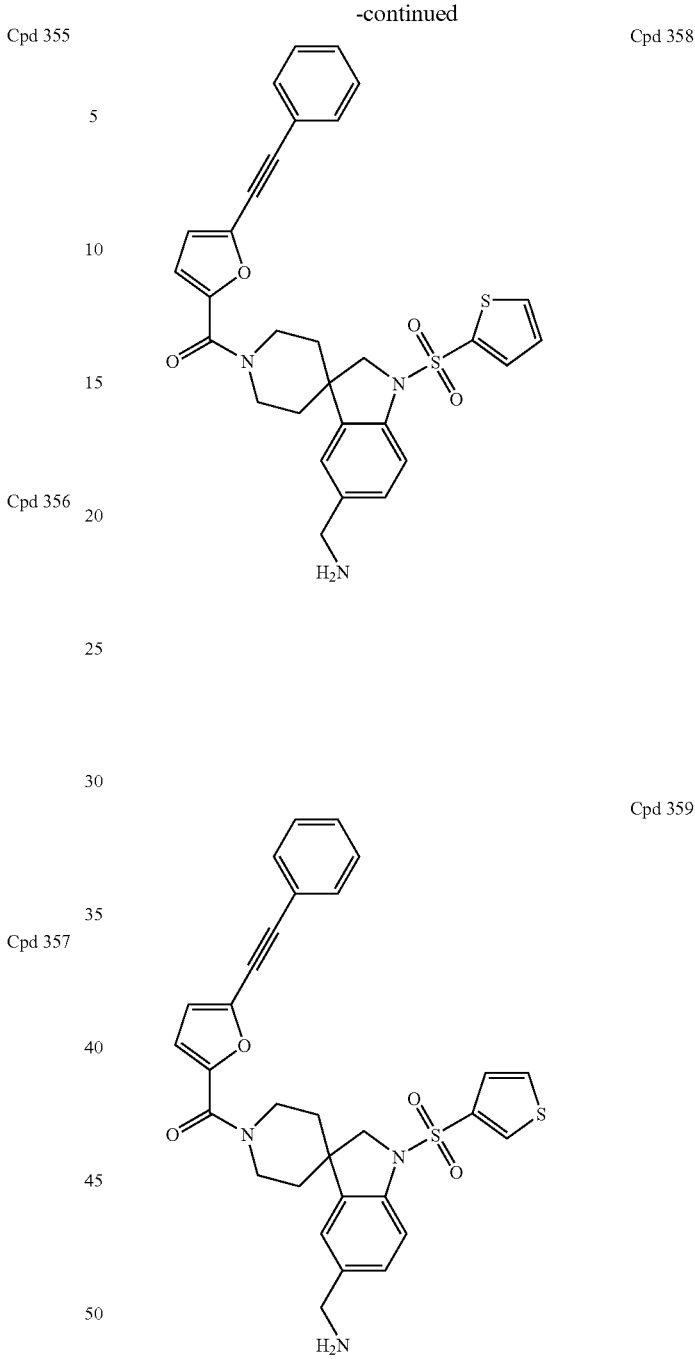
A representative compound of Formula (I) or a form thereof includes a compound selected from the group consisting of:
| Cpd | Name |
|---|---|
| 1 | 1-(3,4-dichlorophenyl)carbonyl-5'-aminomethyl-spiro[piperidine-4,3'-(2H)-benzo[b]furan], |
| 2 | 5'-(3,4-dichlorophenylcarbonylaminomethyl)-spiro[piperidine-4,3'-(2H)-benzo[b]furan], |
| 3 | 1-(5-phenylethynyl-furan-2-yl)carbonyl-5'-aminomethyl-spiro[piperidine-4,3'-(2H)-benzo[b]furan], |

| Cpd | Name |
|---|---|
| 4 | 1-(3-benzoyl-phenyl)carbonyl-5'-aminomethyl-spiro[piperidine-4,3'-(2H)-benzo[b]furan], |
| 5 | 1-(3-aminothiocarbonylamino-phenyl)carbonyl-5'-aminomethyl-spiro[piperidine-4,3'-(2H)-benzo[b]furan], |
| 6 | 1-(4-benzoyl-phenyl)carbonyl-5'-aminomethyl-spiro[piperidine-4,3'-(2H)-benzo[b]furan], |
| 7 | 1-(9-oxo-10,10-dioxo-thioxanthen-3-yl)carbonyl-5'-aminomethyl-spiro[piperidine-4,3'-(2H)-benzo[b]furan], |
| 8 | 1-(9-oxo-fluoren-2-yl)carbonyl-5'-aminomethyl-spiro[piperidine-4,3'-(2H)-benzo[b]furan], |
| 9 | 1-(4-benzoimidazol-1-ylmethylcarbonylamino-phenyl)carbonyl-5'-aminomethyl-spiro[piperidine-4,3'-(2H)-benzo[b]furan], |
| 10 | 1-(4-benzoimidazol-1-ylmethyl-phenyl)carbonyl-5'-aminomethyl-spiro[piperidine-4,3'-(2H)-benzo[b]furan], |
| 11 | 1-(4-aminosulfonyl-phenyl)carbonyl-5'-aminomethyl-spiro[piperidine-4,3'-(2H)-benzo[b]furan], |
| 12 | 1-[5-(4-chloro-phenyl)-furan-2-yl]carbonyl-5'-aminomethyl-spiro[piperidine-4,3'-(2H)-benzo[b]furan], |
| 13 | 1-(5-chloro-benzo[b]-furan-2-yl)carbonyl-5'-aminomethyl-spiro[piperidine-4,3'-(2H)-benzo[b]furan], |
| 14 | 1-(1-phenyl-2-methyl-benzoimidazol-5-yl)carbonyl-5'-aminomethyl-spiro[piperidine-4,3'-(2H)-benzo[b]furan], |
| 15 | 1-[4-(3-trifluoromethyl-phenyl)-phenyl]carbonyl-5'-aminomethyl-spiro[piperidine-4,3'-(2H)-benzo[b]furan], |
| 16 | 1-benzothiazol-6-ylcarbonyl-5'-aminomethyl-spiro[piperidine-4,3'-(2H)-benzo[b]furan], |
| 17 | 1-{4-[(4-benzoxazol-2-yl)-pyrazol-1-yl]-phenyl}carbonyl-5'-aminomethyl-spiro[piperidine-4,3'-(2H)-benzo[b]furan], |
| 18 | 1-(3-phenylsulfonylamino-phenyl)carbonyl-5'-aminomethyl-spiro[piperidine-4,3'-(2H)-benzo[b]furan], |
| 19 | 1-(3-thien-2-ylmethylcarbonylamino-phenyl)carbonyl-5'-aminomethyl-spiro[piperidine-4,3'-(2H)-benzo[b]furan], |
| 20 | 1-(3-benzodioxol-5-yl-phenyl)carbonyl-5'-aminomethyl-spiro[piperidine-4,3'-(2H)-benzo[b]furan], |
| 21 | 1-[3-(5-chloro-pyrimidin-2-yl)thiophenyl]carbonyl-5'-aminomethyl-spiro[piperidine-4,3'-(2H)-benzo[b]furan], |
| 22 | 1-(5-trifluoromethyl-furan-2-yl)carbonyl-5'-aminomethyl-spiro[piperidine-4,3'-(2H)-benzo[b]furan], |
| 23 | 1-[(5-phenylthio)-furan-2-yl]carbonyl-5'-aminomethyl-spiro[piperidine-4,3'-(2H)-benzo[b]furan], |
| 24 | 1-(3,4-dimethyl-phenyl)carbonyl-5'-aminomethyl-spiro[piperidine-4,3'-(2H)-benzo[b]furan], |
| 25 | 1-(3-methyl-4-chloro-phenyl)carbonyl-5'-aminomethyl-spiro[piperidine-4,3'-(2H)-benzo[b]furan], |
| 26 | 1-(3,4-difluoro-phenyl)carbonyl-5'-aminomethyl-spiro[piperidine-4,3'-(2H)-benzo[b]furan], |
| 27 | 1-(3-chloro-4-fluoro-phenyl)carbonyl-5'-aminomethyl-spiro[piperidine-4,3'-(2H)-benzo[b]furan], |
| 28 | 1-(3-chloro-4-methoxy-phenyl)carbonyl-5'-aminomethyl-spiro[piperidine-4,3'-(2H)-benzo[b]furan], |
| 29 | 1-(3-bromo-phenyl)carbonyl-5'-aminomethyl-spiro[piperidine-4,3'-(2H)-benzo[b]furan], |
| 30 | 1-(3-methyl-4-bromo-phenyl)carbonyl-5'-aminomethyl-spiro[piperidine-4,3'-(2H)-benzo[b]furan], |
| 31 | 1-(3-bromo-4-fluoro-phenyl)carbonyl-5'-aminomethyl-spiro[piperidine-4,3'-(2H)-benzo[b]furan], |
| 32 | 1-(3-bromo-4-methoxy-phenyl)carbonyl-5'-aminomethyl-spiro[piperidine-4,3'-(2H)-benzo[b]furan], |
| 33 | 1-(3-nitro-4-bromo-phenyl)carbonyl-5'-aminomethyl-spiro[piperidine-4,3'-(2H)-benzo[b]furan], |
| 34 | 1-(3-iodo-4-chloro-phenyl)carbonyl-5'-aminomethyl-spiro[piperidine-4,3'-(2H)-benzo[b]furan], |
| 35 | 1-[5-(2-fluoro-phenylethynyl)-furan-2-yl]carbonyl-5'-aminomethyl-spiro[piperidine-4,3'-(2H)-benzo[b]furan], |
| 36 | 1-phenylcarbonyl-5'-aminomethyl-spiro[piperidine-4,3'-(2H)-benzo[b]furan], |
| 37 | 1-cyclohexylcarbonyl-5'-aminomethyl-spiro[piperidine-4,3'-(2H)-benzo[b]furan], |
| 38 | 1-(trans-4-methyl-cyclohexyl)carbonyl-5'-aminomethyl-spiro[piperidine-4,3'-(2H)-benzo[b]furan], |
| 39 | 1-(3-chloro-phenyl)carbonyl-5'-aminomethyl-spiro[piperidine-4,3'-(2H)-benzo[b]furan], |
| 40 | 1-(3,4-dimethoxy-phenyl)carbonyl-5'-aminomethyl-spiro[piperidine-4,3'-(2H)-benzo[b]furan], |
| 41 | 1-(3-methyl-phenyl)carbonyl-5'-aminomethyl-spiro[piperidine-4,3'-(2H)-benzo[b]furan], |
| 42 | 1-(3-fluoro-phenyl)carbonyl-5'-aminomethyl-spiro[piperidine-4,3'-(2H)-benzo[b]furan], |

| Cpd | Name |
|---|---|
| 43 | 1-(4-fluoro-phenyl)carbonyl-5'-aminomethyl-spiro[piperidine-4,3'-(2H)-benzo[b]furan], |
| 44 | 1-(4-chloro-phenyl)carbonyl-5'-aminomethyl-spiro[piperidine-4,3'-(2H)-benzo[b]furan], |
| 45 | 1-(4-methylthio-phenyl)carbonyl-5'-aminomethyl-spiro[piperidine-4,3'-(2H)-benzo[b]furan], |
| 46 | 1-(3-fluoro-4-chloro-phenyl)carbonyl-5'-aminomethyl-spiro[piperidine-4,3'-(2H)-benzo[b]furan], |
| 47 | 1-(3-trifluoromethyl-phenyl)carbonyl-5'-aminomethyl-spiro[piperidine-4,3'-(2H)-benzo[b]furan], |
| 48 | 1-(3-iodo-phenyl)carbonyl-5'-aminomethyl-spiro[piperidine-4,3'-(2H)-benzo[b]furan], |
| 49 | 1-(4-iodo-phenyl)carbonyl-5'-aminomethyl-spiro[piperidine-4,3'-(2H)-benzo[b]furan], |
| 50 | 1-(3-iodo-4-methyl-phenyl)carbonyl-5'-aminomethyl-spiro[piperidine-4,3'-(2H)-benzo[b]furan], |
| 51 | 1-(3-methyl-4-iodo-phenyl)carbonyl-5'-aminomethyl-spiro[piperidine-4,3'-(2H)-benzo[b]furan], |
| 52 | 1-(3-iodo-4-methoxy-phenyl)carbonyl-5'-aminomethyl-spiro[piperidine-4,3'-(2H)-benzo[b]furan], |
| 53 | 1-(3-methoxy-phenyl)carbonyl-5'-aminomethyl-spiro[piperidine-4,3'-(2H)-benzo[b]furan], |
| 54 | 1-(4-methoxy-phenyl)carbonyl-5'-aminomethyl-spiro[piperidine-4,3'-(2H)-benzo[b]furan], |
| 55 | 1-(4-dimethylamino-phenyl)carbonyl-5'-aminomethyl-spiro[piperidine-4,3'-(2H)-benzo[b]furan], |
| 56 | 1-(3-dimethylamino-phenyl)carbonyl-5'-aminomethyl-spiro[piperidine-4,3'-(2H)-benzo[b]furan], |
| 57 | 1-(3-methylthio-phenyl)carbonyl-5'-aminomethyl-spiro[piperidine-4,3'-(2H)-benzo[b]furan], |
| 58 | 1-(4-methoxycarbonyl-phenyl)carbonyl-5'-aminomethyl-spiro[piperidine-4,3'-(2H)-benzo[b]furan], |
| 59 | 1-(4-bromo-phenyl)carbonyl-5'-aminomethyl-spiro[piperidine-4,3'-(2H)-benzo[b]furan], |
| 60 | 1-(3-trifluoromethoxy-phenyl)carbonyl-5'-aminomethyl-spiro[piperidine-4,3'-(2H)-benzo[b]furan], |
| 61 | 1-(4-trifluoromethoxy-phenyl)carbonyl-5'-aminomethyl-spiro[piperidine-4,3'-(2H)-benzo[b]furan], |
| 62 | 1-(4-phenoxy-phenyl)carbonyl-5'-aminomethyl-spiro[piperidine-4,3'-(2H)-benzo[b]furan], |
| 63 | 1-(3-trifluoromethylthio-phenyl)carbonyl-5'-aminomethyl-spiro[piperidine-4,3'-(2H)-benzo[b]furan], |
| 64 | 1-[3-(4-methoxy-phenyl)-phenyl]carbonyl-5'-aminomethyl-spiro[piperidine-4,3'-(2H)-benzo[b]furan], |
| 65 | 1-(5-phenylethynyl-furan-2-yl)carbonyl-5'-aminoiminomethyl-spiro[piperidine-4,3'-(2H)-benzo[b]furan], |
| 66 | 1-(3-cyano-phenyl)carbonyl-5'-aminomethyl-spiro[piperidine-4,3'-(2H)-benzo[b]furan], |
| 67 | 1-(4-methylcarbonyl-phenyl)carbonyl-5'-aminomethyl-spiro[piperidine-4,3'-(2H)-benzo[b]furan], |
| 68 | 1-benzodioxol-5-ylcarbonyl-5'-aminomethyl-spiro[piperidine-4,3'-(2H)-benzo[b]furan], |
| 69 | 1-(4-chloromethyl-phenyl)carbonyl-5'-aminomethyl-spiro[piperidine-4,3'-(2H)-benzo[b]furan], |
| 70 | 1-naphthalen-2-ylcarbonyl-5'-aminomethyl-spiro[piperidine-4,3'-(2H)-benzo[b]furan], |
| 71 | 1-(4-trifluoromethyl-phenyl)carbonyl-5'-aminomethyl-spiro[piperidine-4,3'-(2H)-benzo[b]furan], |
| 72 | 1-(3-methylsulfonyl-phenyl)carbonyl-5'-aminomethyl-spiro[piperidine-4,3'-(2H)-benzo[b]furan], |
| 73 | 1-(4-cyclohexyl-phenyl)carbonyl-5'-aminomethyl-spiro[piperidine-4,3'-(2H)-benzo[b]furan], |
| 74 | 1-(3-trifluoromethyl-4-fluoro-phenyl)carbonyl-5'-aminomethyl-spiro[piperidine-4,3'-(2H)-benzo[b]furan], |
| 75 | 1-(4-benzyl-phenyl)carbonyl-5'-aminomethyl-spiro[piperidine-4,3'-(2H)-benzo[b]furan], |
| 76 | 1-(4-benzyloxy-phenyl)carbonyl-5'-aminomethyl-spiro[piperidine-4,3'-(2H)-benzo[b]furan], |
| 77 | (Z)-1-(5-phenylethenyl-furan-2-yl)carbonyl-5'-aminomethyl-spiro[piperidine-4,3'-(2H)-benzo[b]furan], |
| 78 | 1-benzylcarbonyl-5'-aminomethyl-spiro[piperidine-4,3'-(2H)-benzo[b]furan], |
| 79 | 1-phenethylcarbonyl-5'-aminomethyl-spiro[piperidine-4,3'-(2H)-benzo[b]furan], |
| 80 | 1-(3-fluoro-benzyl)carbonyl-5'-aminomethyl-spiro[piperidine-4,3'-(2H)-benzo[b]furan], |
| 81 | 1-(3-chloro-benzyl)carbonyl-5'-aminomethyl-spiro[piperidine-4,3'-(2H)-benzo[b]furan], |

| Cpd | Name |
| --- | --- |
| 82 | 1-(3,4-difluoro-benzyl)carbonyl-5'-aminomethyl-spiro[piperidine-4,3'-(2H)-benzo[b]furan], |
| 83 | 1-(3-chloro-phenethyl)carbonyl-5'-aminomethyl-spiro[piperidine-4,3'-(2H)-benzo[b]furan], |
| 84 | 1-naphthalen-2-ylmethylcarbonyl-5'-aminomethyl-spiro[piperidine-4,3'-(2H)-benzo[b]furan], |
| 85 | 1-(3-trifluoromethyl-benzyl)carbonyl-5'-aminomethyl-spiro[piperidine-4,3'-(2H)-benzo[b]furan], |
| 86 | 1-(3,4-dichloro-benzyl)carbonyl-5'-aminomethyl-spiro[piperidine-4,3'-(2H)-benzo[b]furan], |
| 87 | 1-(3-bromo-benzyl)carbonyl-5'-aminomethyl-spiro[piperidine-4,3'-(2H)-benzo[b]furan], |
| 88 | 1-(3-phenoxy-benzyl)carbonyl-5'-aminomethyl-spiro[piperidine-4,3'-(2H)-benzo[b]furan], |
| 89 | 1-(3-methyl-benzyl)carbonyl-5'-aminomethyl-spiro[piperidine-4,3'-(2H)-benzo[b]furan], |
| 90 | 1-(4-fluoro-benzyl)carbonyl-5'-aminomethyl-spiro[piperidine-4,3'-(2H)-benzo[b]furan], |
| 91 | 1-(4-chloro-benzyl)carbonyl-5'-aminomethyl-spiro[piperidine-4,3'-(2H)-benzo[b]furan], |
| 92 | 1-(4-phenyl-benzyl)carbonyl-5'-aminomethyl-spiro[piperidine-4,3'-(2H)-benzo[b]furan], |
| 93 | 1-(4-bromo-benzyl)carbonyl-5'-aminomethyl-spiro[piperidine-4,3'-(2H)-benzo[b]furan], |
| 94 | 1-(4-methoxy-benzyl)carbonyl-5'-aminomethyl-spiro[piperidine-4,3'-(2H)-benzo[b]furan], |
| 95 | 1-(3-bromo-benzyl)carbonyl-5'-aminomethyl-spiro[piperidine-4,3'-(2H)-benzo[b]furan], |
| 96 | 1-(4-iodo-benzyl)carbonyl-5'-aminomethyl-spiro[piperidine-4,3'-(2H)-benzo[b]furan], |
| 97 | 1-(3-iodo-phenethyl)carbonyl-5'-aminomethyl-spiro[piperidine-4,3'-(2H)-benzo[b]furan], |
| 98 | 1-(3-methyl-phenethyl)carbonyl-5'-aminomethyl-spiro[piperidine-4,3'-(2H)-benzo[b]furan], |
| 99 | 1-(3-methoxy-benzyl)carbonyl-5'-aminomethyl-spiro[piperidine-4,3'-(2H)-benzo[b]furan], |
| 100 | 1-benzodioxol-5-ylmethylcarbonyl-5'-aminomethyl-spiro[piperidine-4,3'-(2H)-benzo[b]furan], |
| 101 | 1-(3-methoxy-phenethyl)carbonyl-5'-aminomethyl-spiro[piperidine-4,3'-(2H)-benzo[b]furan], |
| 102 | 1-(3-methyl-4-methoxy-benzyl)carbonyl-5'-aminomethyl-spiro[piperidine-4,3'-(2H)-benzo[b]furan], |
| 103 | 1-(3-methylthio-benzyl)carbonyl-5'-aminomethyl-spiro[piperidine-4,3'-(2H)-benzo[b]furan], |
| 104 | 1-(benzodioxol-5-ylethyl)carbonyl-5'-aminomethyl-spiro[piperidine-4,3'-(2H)-benzo[b]furan], |
| 105 | 1-(3,4-dimethoxy-benzyl)carbonyl-5'-aminomethyl-spiro[piperidine-4,3'-(2H)-benzo[b]furan], |
| 106 | 1-(3-methoxy-4-benzyloxy-benzyl)carbonyl-5'-aminomethyl-spiro[piperidine-4,3'-(2H)-benzo[b]furan], |
| 107 | 1-(5-phenethyl-furan-2-yl)carbonyl-5'-aminomethyl-spiro[piperidine-4,3'-(2H)-benzo[b]furan], |
| 108 | 1-(phenylethynyl)carbonyl-5'-aminomethyl-spiro[piperidine-4,3'-(2H)-benzo[b]furan], |
| 109 | (E)-1-(phenylethenyl)carbonyl-5'-aminomethyl-spiro[piperidine-4,3'-(2H)-benzo[b]furan], |
| 110 | 1-benzothien-2-ylcarbonyl-5'-aminomethyl-spiro[piperidine-4,3'-(2H)-benzo[b]furan], |
| 111 | (E)-1-(3,4-difluoro-phenylethenyl)carbonyl-5'-aminomethyl-spiro[piperidine-4,3'-(2H)-benzo[b]furan], |
| 112 | (E)-1-(phenylethenyl)carbonyl-5'-aminomethyl-spiro[piperidine-4,3'-(2H)-benzo[b]furan], |
| 113 | (E)-1-(naphthalene-2-ylethenyl)carbonyl-5'-aminomethyl-spiro[piperidine-4,3'-(2H)-benzo[b]furan], |
| 114 | 1-(5-phenyl-thien-2-yl)carbonyl-5'-aminomethyl-spiro[piperidine-4,3'-(2H)-benzo[b]furan], |
| 115 | 1-(3-phenoxy-phenyl)carbonyl-5'-aminomethyl-spiro[piperidine-4,3'-(2H)-benzo[b]furan], |
| 116 | (E)-1-(3,4-dichloro-phenylethenyl)carbonyl-5'-aminomethyl-spiro[piperidine-4,3'-(2H)-benzo[b]furan], |
| 117 | (E)-1-(4-phenyl-phenylethenyl)carbonyl-5'-aminomethyl-spiro[piperidine-4,3'-(2H)-benzo[b]furan], |
| 118 | 1-(2,4-dimethyl-thiazol-5-yl)carbonyl-5'-aminomethyl-spiro[piperidine-4,3'-(2H)-benzo[b]furan], |
| 119 | 1-(6-methyl-imidazo[1,2-a]pyridin-2-yl)carbonyl-5'-aminomethyl-spiro[piperidine-4,3'-(2H)-benzo[b]furan], |
| 120 | 1-(5-pyridin-2-yl-thien-2-yl)carbonyl-5'-aminomethyl-spiro[piperidine-4,3'-(2H)-benzo[b]furan], |

-continued

| Cpd | Name |
| --- | --- |
| 121 | 1-(2-pyridin-3-yl-thiazol-4-yl)carbonyl-5'-aminomethyl-spiro[piperidine-4,3'-(2H)-benzo[b]furan], |
| 122 | 1-(2-pyridin-4-yl-thiazol-4-yl)carbonyl-5'-aminomethyl-spiro[piperidine-4,3'-(2H)-benzo[b]furan], |
| 123 | 1-(2-phenyl-4-methyl-thiazol-5-yl)carbonyl-5'-aminomethyl-spiro[piperidine-4,3'-(2H)-benzo[b]furan], |
| 124 | 1-(2-pyridin-3-yl-4-methyl-thiazol-5-yl)carbonyl-5'-aminomethyl-spiro[piperidine-4,3'-(2H)-benzo[b]furan], |
| 125 | 1-[2-(4-methyl-phenyl)-4-methyl-thiazol-5-yl]carbonyl-5'-aminomethyl-spiro[piperidine-4,3'-(2H)-benzo[b]furan], |
| 126 | 1-(6-bromo-naphthalen-2-yl)carbonyl-5'-aminomethyl-spiro[piperidine-4,3'-(2H)-benzo[b]furan], |
| 127 | 1-[5-(1-methyl-3-trifluoromethyl-pyrazol-5-yl)-thien-2-yl]carbonyl-5'-aminomethyl-spiro[piperidine-4,3'-(2H)-benzo[b]furan], |
| 128 | 1-[2-(4-trifluoromethyl-phenyl)-4-methyl-thiazol-5-yl]carbonyl-5'-aminomethyl-spiro[piperidine-4,3'-(2H)-benzo[b]furan], |
| 129 | 1-[5-(2-chloro-5-trifluoromethyl-phenyl)-furan-2-yl]carbonyl-5'-aminomethyl-spiro]piperidine-4,3'-(2H)-benzo[b]furan], |
| 130 | 1-(5-phenyl-furan-2-yl)carbonyl-5'-aminomethyl-spiro[piperidine-4,3'-(2H)-benzo[b]furan], |
| 131 | 1-[5-(4-methyl-phenyl)-furan-2-yl]carbonyl-5'-aminomethyl-spiro[piperidine-4,3'-(2H)-benzo[b]furan], |
| 132 | 1-[5-(4-methoxy-phenyl)-furan-2-yl]carbonyl-5'-aminomethyl-spiro[piperidine-4,3'-(2H)-benzo[b]furan], |
| 133 | 1-(3,5-di-tert-butyl-phenyl)carbonyl-5'-aminomethyl-spiro[piperidine-4,3'-(2H)-benzo[b]furan], |
| 134 | 1-[5-(3-chloro-phenoxymethyl)-furan-2-yl]carbonyl-5'-aminomethyl-spiro[piperidine-4,3'-(2H)-benzo[b]furan], |
| 135 | 1-[5-(3-trifluoromethyl-phenyl)-furan-2-yl]carbonyl-5'-aminomethyl-spiro[piperidine-4,3'-(2H)-benzo[b]furan], |
| 136 | 1-[5-(2,4-dichloro-phenyl)-furan-2-yl]carbonyl-5'-aminomethyl-spiro[piperidine-4,3'-(2H)-benzo[b]furan], |
| 137 | 1-[5-(2,5-dichloro-phenyl)-furan-2-yl]carbonyl-5'-aminomethyl-spiro[piperidine-4,3'-(2H)-benzo[b]furan], |
| 138 | 1-[5-(3,4-dichloro-phenyl)-furan-2-yl]carbonyl-5'-aminomethyl-spiro[piperidine-4,3'-(2H)-benzo[b]furan], |
| 139 | 1-[5-(3-methyl-4-chloro-phenoxymethyl)-furan-2-yl]carbonyl-5'-aminomethyl-spiro[piperidine-4,3'-(2H)-benzo[b]furan], |
| 140 | 1-[5-(4-bromo-phenyl)-furan-2-yl]carbonyl-5'-aminomethyl-spiro[piperidine-4,3'-(2H)-benzo[b]furan], |
| 141 | 1-(trans-2-phenyl-cyclopropyl)carbonyl-5'-aminomethyl-spiro[piperidine-4,3'-(2H)-benzo[b]furan], |
| 142 | 1-(5-phenyl-pyridin-3-yl)carbonyl-5'-aminomethyl-spiro[piperidine-4,3'-(2H)-benzo[b]furan], |
| 143 | 1-(5-thien-2-yl-pyridin-3-yl)carbonyl-5'-aminomethyl-spiro[piperidine-4,3'-(2H)-benzo[b]furan], |
| 144 | 1-[5-(3-methoxy-phenyl)-furan-2-yl]carbonyl-5'-aminomethyl-spiro[piperidine-4,3'-(2H)-benzo[b]furan], |
| 145 | 1-[5-(4-chloro-pyrazol-1-ylmethyl)-furan-2-yl]carbonyl-5'-aminomethyl-spiro[piperidine-4,3'-(2H)-benzo[b]furan], |
| 146 | 1-[5-(2-chloro-phenylethynyl)-furan-2-yl]carbonyl-5'-aminomethyl-spiro[piperidine-4,3'-(2H)-benzo[b]furan], |
| 147 | 1-[5-(benzylthiomethyl)-furan-2-yl]carbonyl-5'-aminomethyl-spiro[piperidine-4,3'-(2H)-benzo[b]furan], |
| 148 | 1-[5-(4,6-dimethyl-pyrimidin-2-ylthiomethyl)-furan-2-yl]carbonyl-5'-aminomethyl-spiro[piperidine-4,3'-(2H)-benzo[b]furan], |
| 149 | 1-[5-(3,5-dichloro-phenoxy)-furan-2-yl]carbonyl-5'-aminomethyl-spiro[piperidine-4,3'-(2H)-benzo[b]furan], |
| 150 | 1-[5-(3,5-dimethyl-4-bromo-pyrazol-1-yl)-furan-2-yl]carbonyl-5'-aminomethyl-spiro[piperidine-4,3'-(2H)-benzo[b]furan], |
| 151 | 1-[5-(5-trifluoromethyl-pyridin-2-ylthiomethyl)-furan-2-yl]carbonyl-5'-aminomethyl-spiro[piperidine-4,3'-(2H)-benzo[b]furan], |
| 152 | 1-[4-phenylethynyl-pyridin-2-yl]carbonyl-5'-aminomethyl-spiro[piperidine-4,3'-(2H)-benzo[b]furan], |
| 153 | 1-[5-(2-methyl-phenylethynyl)-furan-2-yl]carbonyl-5'-aminomethyl-spiro[piperidine-4,3'-(2H)-benzo[b]furan], |
| 154 | 1-[5-(4-fluoro-phenoxymethyl)-furan-2-yl]carbonyl-5'-aminomethyl-spiro[piperidine-4,3'-(2H)-benzo[b]furan], |
| 155 | 1-(3-methylthio-4-oxo-5,6,7-trihydro-4H-benzo[c]thien-1-yl)carbonyl-5'-aminomethyl-spiro[piperidine-4,3'-(2H)-benzo[b]furan], |
| 156 | 1-[5-(2,5-dimethyl-furan-3-yl-carbonylaminomethyl)-furan-2-yl]carbonyl-5'-aminomethyl-spiro[piperidine-4,3'-(2H)-benzo[b]furan], |
| 157 | 1-(3-chloro-4-isopropylsulfonyl-5-methylthio-thien-2-yl)carbonyl-5'-aminomethyl-spiro[piperidine-4,3'-(2H)-benzo[b]furan], |
| 158 | 1-(3,4-dichloro-benzyl)-5'-aminomethyl-spiro[piperidine-4,3'-(2H)-benzo[b]furan], |
| 159 | 1-thien-2-ylcarbonyl-5'-aminomethyl-spiro[piperidine-4,3'-(2H)-benzo[b]furan], |

| Cpd | Name |
|---|---|
| 160 | 1-benzo[b]furan-2-ylcarbonyl-5'-aminomethyl-spiro[piperidine-4,3'-(2H)-benzo[b]furan], |
| 161 | (E)-1-(3-fluoro-phenylethenyl)carbonyl-5'-aminomethyl-spiro[piperidine-4,3'-(2H)-benzo[b]furan], |
| 162 | (Z)-1-(1-fluoro-2-phenylethenyl)carbonyl-5'-aminomethyl-spiro[piperidine-4,3'-(2H)-benzo[b]furan], |
| 163 | 1-(5,6,7-trihydro-4H-benzo[b]thien-2-yl)carbonyl-5'-aminomethyl-spiro[piperidine-4,3'-(2H)-benzo[b]furan], |
| 164 | (E)-1-(3-chloro-phenylethenyl)carbonyl-5'-aminomethyl-spiro[piperidine-4,3'-(2H)-benzo[b]furan], |
| 165 | (E)-1-(4-chloro-phenylethenyl)carbonyl-5'-aminomethyl-spiro[piperidine-4,3'-(2H)-benzo[b]furan], |
| 166 | 1-(3-chloro-benzo[b]thien-2-yl)carbonyl-5'-aminomethyl-spiro[piperidine-4,3'-(2H)-benzo[b]furan], |
| 167 | (E)-1-(3-trifluoromethoxy-phenylethenyl)carbonyl-5'-aminomethyl-spiro[piperidine-4,3'-(2H)-benzo[b]furan], |
| 168 | 1-(4-fluoro-benzo[b]thien-2-yl)carbonyl-5'-aminomethyl-spiro[piperidine-4,3'-(2H)-benzo[b]furan], |
| 169 | 1-(5-methylsulfonyl-thien-2-yl)carbonyl-5'-aminomethyl-spiro[piperidine-4,3'-(2H)-benzo[b]furan], |
| 170 | 1-[5-(4-methyl-phenylethynyl)-furan-2-yl]carbonyl-5'-aminomethyl-spiro[piperidine-4,3'-(2H)-benzo[b]furan], |
| 171 | 1-(3-chloro-6-fluoro-benzo[b]thien-2-yl)carbonyl-5'-aminomethyl-spiro[piperidine-4,3'-(2H)-benzo[b]furan], |
| 172 | 1-[5-(2,5-dimethyl-phenylethynyl)-furan-2-yl]carbonyl-5'-aminomethyl-spiro[piperidine-4,3'-(2H)-benzo[b]furan], |
| 173 | 1-[5-(2-methoxy-phenylethynyl)-furan-2-yl]carbonyl-5'-aminomethyl-spiro[piperidine-4,3'-(2H)-benzo[b]furan], |
| 174 | 1-[5-(2,5-dimethyl-phenoxymethyl)-furan-2-yl]carbonyl-5'-aminomethyl-spiro[piperidine-4,3'-(2H)-benzo[b]furan], |
| 175 | 1-(3,4-dichloro-benzo[b]thien-2-yl)carbonyl-5'-aminomethyl-spiro[piperidine-4,3'-(2H)-benzo[b]furan], |
| 176 | 1-[5-(3,5-difluoro-phenylethynyl)-furan-2-yl]carbonyl-5'-aminomethyl-spiro[piperidine-4,3'-(2H)-benzo[b]furan], |
| 177 | 1-(5-naphthalen-1-ylethynyl-furan-2-yl)carbonyl-5'-aminomethyl-spiro[piperidine-4,3'-(2H)-benzo[b]furan], |
| 178 | 1-[5-(4-tert-butyl-phenoxymethyl)-furan-2-yl]carbonyl-5'-aminomethyl-spiro[piperidine-4,3'-(2H)-benzo[b]furan], |
| 179 | (E)-1-(3-methyl-phenylethenyl)carbonyl-5'-aminomethyl-spiro[piperidine-4,3'-(2H)-benzo[b]furan], |
| 180 | (E)-1-(4-methyl-phenylethenyl)carbonyl-5'-aminomethyl-spiro[piperidine-4,3'-(2H)-benzo[b]furan], |
| 181 | (Z)-1-(1-methyl-2-phenylethenyl)carbonyl-5'-aminomethyl-spiro[piperidine-4,3'-(2H)-benzo[b]furan], |
| 182 | (E)-1-(4-fluoro-phenylethenyl)carbonyl-5'-aminomethyl-spiro[piperidine-4,3'-(2H)-benzo[b]furan], |
| 183 | (Z)-1-(2-methoxy-phenylethenyl)carbonyl-5'-aminomethyl-spiro[piperidine-4,3'-(2H)-benzo[b]furan], |
| 184 | (E)-1-(3-methoxy-phenylethenyl)carbonyl-5'-aminomethyl-spiro[piperidine-4,3'-(2H)-benzo[b]furan], |
| 185 | (E)-1-(4-methoxy-phenylethenyl)carbonyl-5'-aminomethyl-spiro[piperidine-4,3'-(2H)-benzo[b]furan], |
| 186 | (E)-1-(2-chloro-phenylethenyl)carbonyl-5'-aminomethyl-spiro[piperidine-4,3'-(2H)-benzo[b]furan], |
| 187 | (E)-1-(benzodioxol-5-ylethenyl)carbonyl-5'-aminomethyl-spiro[piperidine-4,3'-(2H)-benzo[b]furan], |
| 188 | (E)-1-(naphthalen-1-ylethenyl)carbonyl-5'-aminomethyl-spiro[piperidine-4,3'-(2H)-benzo[b]furan], |
| 189 | 1-(1-oxo-2-fluoren-9-ylidene-ethyl)-5'-aminomethyl-spiro[piperidine-4,3'-(2H)-benzo[b]furan], |
| 190 | (E)-1-(1-phenyl-2-phenylethenyl)carbonyl-5'-aminomethyl-spiro[piperidine-4,3'-(2H)-benzo[b]furan], |
| 191 | (E)-1-(2-methyl-phenylethenyl)carbonyl-5'-aminomethyl-spiro[piperidine-4,3'-(2H)-benzo[b]furan], |
| 192 | 1-(1-methyl-3H-inden-2-yl)carbonyl-5'-aminomethyl-spiro[piperidine-4,3'-(2H)-benzo[b]furan], |
| 193 | 1-(1-methyl-indol-2-yl)carbonyl-5'-aminomethyl-spiro[piperidine-4,3'-(2H)-benzo[b]furan], |
| 194 | (E)-1-(2-methoxy-phenylethenyl)carbonyl-5'-aminomethyl-spiro[piperidine-4,3'-(2H)-benzo[b]furan], |
| 195 | (E)-1-(2,6-difluoro-phenylethenyl)carbonyl-5'-aminomethyl-spiro[piperidine-4,3'-(2H)-benzo[b]furan], |
| 196 | 1-(2-oxo-(2H)-chromen-3-yl)carbonyl-5'-aminomethyl-spiro[piperidine-4,3'-(2H)-benzo[b]furan], |
| 197 | 1-(8-methoxy-(2H)-chromen-3-yl)carbonyl-5'-aminomethyl-spiro[piperidine-4,3'-(2H)-benzo[b]furan], |
| 198 | 1-(5-bromo-thien-2-yl)carbonyl-5'-aminomethyl-spiro[piperidine-4,3'-(2H)-benzo[b]furan], |

-continued

| Cpd | Name |
|---|---|
| 199 | (E)-1-(2-bromo-phenylethenyl)carbonyl-5'-aminomethyl-spiro[piperidine-4,3'-(2H)-benzo[b]furan], |
| 200 | 1-(5-trifluoromethyl-benzo[b]thien-2-yl)carbonyl-5'-aminomethyl-spiro[piperidine-4,3'-(2H)-benzo[b]furan], |
| 201 | 1-[3-(4-methoxy-phenyl)-4-cyano-5-methylthio-thien-2-yl]carbonyl-5'-aminomethyl-spiro[piperidine-4,3'-(2H)-benzo[b]furan], |
| 202 | 1-[3-(4-chloro-phenyl)-4-cyano-5-methylthio-thien-2-yl]carbonyl-5'-aminomethyl-spiro[piperidine-4,3'-(2H)-benzo[b]furan], |
| 203 | 1-(5,6,7-trihydro-4H-benzo[c]thien-1-yl)carbonyl-5'-aminomethyl-spiro[piperidine-4,3'-(2H)-benzo[b]furan], |
| 204 | 1-thieno[3,2-b]thien-2-ylcarbonyl-5'-aminomethyl-spiro[piperidine-4,3'-(2H)-benzo[b]furan], |
| 205 | (Z)-1-(1-methylcarbonylamino-2-phenylethenyl)carbonyl-5'-aminomethyl-spiro[piperidine-4,3'-(2H)-benzo[b]furan], |
| 206 | 1-[5-(2-methyl-thiazol-4-yl)-thien-2-yl]carbonyl-5'-aminomethyl-spiro[piperidine-4,3'-(2H)-benzo[b]furan], |
| 207 | 1-(3-chloro-6-methyl-benzo[b]thien-2-yl)carbonyl-5'-aminomethyl-spiro[piperidine-4,3'-(2H)-benzo[b]furan], |
| 208 | 1-[3-(2-methyl-phenoxy)-benzyl]carbonyl-5'-aminomethyl-spiro[piperidine-4,3'-(2H)-benzo[b]furan], |
| 209 | 1-(3-chloro-6-methoxy-benzo[b]thien-2-yl)carbonyl-5'-aminomethyl-spiro[piperidine-4,3'-(2H)-benzo[b]furan], |
| 210 | 1-[3-(2-fluoro-phenoxy)-benzyl]carbonyl-5'-aminomethyl-spiro[piperidine-4,3'-(2H)-benzo[b]furan], |
| 211 | 1-(3-propylthio-4-oxo-5,6,7-trihydro-4H-benzo[c]thien-1-yl)carbonyl-5'-aminomethyl-spiro[piperidine-4,3'-(2H)-benzo[b]furan], |
| 212 | 1-[5-(2-methoxy-4-propyl-phenoxymethyl)-furan-2-yl]carbonyl-5'-aminomethyl-spiro[piperidine-4,3'-(2H)-benzo[b]furan], |
| 213 | 1-[5-(2-bromo-phenoxymethyl)-furan-2-yl]carbonyl-5'-aminomethyl-spiro[piperidine-4,3'-(2H)-benzo[b]furan], |
| 214 | 1-(3-benzylthio-4-oxo-5,6,7-trihydro-4H-benzo[c]thien-1-yl)carbonyl-5'-aminomethyl-spiro[piperidine-4,3'-(2H)-benzo[b]furan], |
| 215 | 1-[1-oxo-2-(3-oxo-3H-isobenzofuran-1-ylidene)-ethyl]-5'-aminomethyl-spiro[piperidine-4,3'-(2H)-benzo[b]furan], |
| 216 | 1-(5-morpholin-4-ylmethyl-furan-2-yl)carbonyl-5'-aminomethyl-spiro[piperidine-4,3'-(2H)-benzo[b]furan], |
| 217 | 1-(4-phenyl-[1,2,3]thiadiazol-5-yl)carbonyl-5'-aminomethyl-spiro[piperidine-4,3'-(2H)-benzo[b]furan], |
| 218 | 1-(3-methylthio-5,6,7-trihydro-4H-benzo[c]thien-1-yl)carbonyl-5'-aminomethyl-spiro[piperidine-4,3'-(2H)-benzo[b]furan], |
| 219 | 1-(3-methylthio-7-hydro-6H-benzo[c]thien-1-yl)carbonyl-5'-aminomethyl-spiro[piperidine-4,3'-(2H)-benzo[b]furan], |
| 220 | 1-[5-(2-methyl-furan-3-yl-carbonylaminomethyl)-furan-2-yl]carbonyl-5'-aminomethyl-spiro[piperidine-4,3'-(2H)-benzo[b]furan], |
| 221 | 1-[5-(3,5-dimethyl-4-chloro-pyrazol-1-yl)-furan-2-yl]carbonyl-5'-aminomethyl-spiro[piperidine-4,3'-(2H)-benzo[b]furan], |
| 222 | 1-(3-methyl-4-oxo-6-phenyl-5,6,7-trihydro-4H-benzo[b]furan-2-yl)carbonyl-5'-aminomethyl-spiro[piperidine-4,3'-(2H)-benzo[b]furan], |
| 223 | 1-(3-ethylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 224 | 1-[5-(2-methoxy-4-allyl-phenoxymethyl)-furan-2-yl]carbonyl-5'-aminomethyl-spiro[piperidine-4,3'-(2H)-benzo[b]furan], |
| 225 | 1-(3-isopropylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 226 | 1-(3,4-dimethyl-5-cyano-thieno[2,3-b]thien-2-yl)carbonyl-5'-aminomethyl-spiro[piperidine-4,3'-(2H)-benzo[b]furan], |
| 227 | 1-[5-(3-methoxy-phenoxymethyl)-furan-2-yl]carbonyl-5'-aminomethyl-spiro[piperidine-4,3'-(2H)-benzo[b]furan], |
| 228 | 1-(3-methyl-6-phenyl-benzo[b]furan-2-yl)carbonyl-5'-aminomethyl-spiro[piperidine-4,3'-(2H)-benzo[b]furan], |
| 229 | 1-(3-butylthio-4-oxo-5,6,7-trihydro-4H-benzo[c]thien-1-yl)carbonyl-5'-aminomethyl-spiro[piperidine-4,3'-(2H)-benzo[b]furan], |
| 230 | 1-(3-chloro-6-bromo-benzo[b]thien-2-yl)carbonyl-5'-aminomethyl-spiro[piperidine-4,3'-(2H)-benzo[b]furan], |
| 231 | 1-(3-sec-butylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 232 | 1-(3-benzylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 233 | 1-thieno[2,3-b]thien-2-ylcarbonyl-5'-aminomethyl-spiro[piperidine-4,3'-(2H)-benzo[b]furan], |
| 234 | 1-(3-methylthio-benzo[c]thien-1-yl)carbonyl-5'-aminomethyl-spiro[piperidine-4,3'-(2H)-benzo[b]furan], |
| 235 | 1-(3-methylthio-4-methoxy-benzo[c]thien-1-yl)carbonyl-5'-aminomethyl-spiro[piperidine-4,3'-(2H)-benzo[b]furan], |
| 236 | 1-indol-3-ylcarbonyl-5'-aminomethyl-spiro[piperidine-4,3'-(2H)-benzo[b]furan], |
| 237 | 1-(1-methyl-indol-3-yl)carbonyl-5'-aminomethyl-spiro[piperidine-4,3'-(2H)-benzo[b]furan], |

-continued

| Cpd | Name |
|---|---|
| 238 | 1-(5-methoxy-indol-3-yl)carbonyl-5'-aminomethyl-spiro[piperidine-4,3'-(2H)-benzo[b]furan], |
| 239 | 1-(1-benzyl-indol-3-yl)carbonyl-5'-aminomethyl-spiro[piperidine-4,3'-(2H)-benzo[b]furan], |
| 240 | 1-(3-benzylthio-benzo[c]thien-1-yl)carbonyl-5'-aminomethyl-spiro[piperidine-4,3'-(2H)-benzo[b]furan], |
| 241 | 1-(3-benzylthio-7-hydro-6H-benzo[c]thien-1-yl)carbonyl-5'-aminomethyl-spiro[piperidine-4,3'-(2H)-benzo[b]furan], |
| 242 | (Z)-1-(furan-2-ylethenyl)carbonyl-5'-aminomethyl-spiro[piperidine-4,3'-(2H)-benzo[b]furan], |
| 243 | (Z)-1-(imidazol-4-ylethenyl)carbonyl-5'-aminomethyl-spiro[piperidine-4,3'-(2H)-benzo[b]furan], |
| 244 | (E)-1-(pyridin-4-ylethenyl)carbonyl-5'-aminomethyl-spiro[piperidine-4,3'-(2H)-benzo[b]furan], |
| 245 | 1-(5-formyl-thien-2-yl)carbonyl-5'-aminomethyl-spiro[piperidine-4,3'-(2H)-benzo[b]furan], |
| 246 | 1-(5,6-dihydro-4H-cyclopenta[b]thien-2-yl)carbonyl-5'-aminomethyl-spiro[piperidine-4,3'-(2H)-benzo[b]furan], |
| 247 | 1-(5-methylthio-thien-2-yl)carbonyl-5'-aminomethyl-spiro[piperidine-4,3'-(2H)-benzo[b]furan], |
| 248 | (E)-1-(1-cyano-2-phenylethenyl)carbonyl-5'-aminomethyl-spiro[piperidine-4,3'-(2H)-benzo[b]furan], |
| 249 | 1-(7-methyl-indol-3-yl)carbonyl-5'-aminomethyl-spiro[piperidine-4,3'-(2H)-benzo[b]furan], |
| 250 | 1-(1-ethyl-7-methyl-indol-3-yl)carbonyl-5'-aminomethyl-spiro[piperidine-4,3'-(2H)-benzo[b]furan], |
| 251 | (E)-1-(furan-3-ylethenyl)carbonyl-5'-aminomethyl-spiro[piperidine-4,3'-(2H)-benzo[b]furan], |
| 252 | (E)-1-(pyridin-2-ylethenyl)carbonyl-5'-aminomethyl-spiro[piperidine-4,3'-(2H)-benzo[b]furan], |
| 253 | (E)-1-(pyridin-3-ylethenyl)carbonyl-5'-aminomethyl-spiro[piperidine-4,3'-(2H)-benzo[b]furan], |
| 254 | (E)-1-(thien-2-ylethenyl)carbonyl-5'-aminomethyl-spiro[piperidine-4,3'-(2H)-benzo[b]furan], |
| 255 | (E)-1-(thien-3-ylethenyl)carbonyl-5'-aminomethyl-spiro[piperidine-4,3'-(2H)-benzo[b]furan], |
| 256 | 1-(5-dihydroxymethyl-4-methyl-thien-2-yl)carbonyl-5'-aminomethyl-spiro[piperidine-4,3'-(2H)-benzo[b]furan], |
| 257 | 1-(5,6,7,8-tetrahydro-4H-cyclohepta[b]thien-2-yl)carbonyl-5'-aminomethyl-spiro[piperidine-4,3'-(2H)-benzo[b]furan], |
| 258 | 1-(4-cyano-5-methylthio-thien-2-yl)carbonyl-5'-aminomethyl-spiro[piperidine-4,3'-(2H)-benzo[b]furan], |
| 259 | 1-(4-methyl-5-bromo-thien-2-yl)carbonyl-5'-aminomethyl-spiro[piperidine-4,3'-(2H)-benzo[b]furan], |
| 260 | spiro[cyclohexane-1,6'-5,7-dihydro-4H-benzo[b]thiophene]-2'-carbonyl-5'-aminomethyl-spiro[piperidine-4,3'-(2H)-benzo[b]furan], |
| 261 | 1-(3-ethoxy-4-oxo-5,6,7-trihydro-4H-benzo[c]thien-1-yl)carbonyl-5'-aminomethyl-spiro[piperidine-4,3'-(2H)-benzo[b]furan], |
| 262 | 1-(3,4-dichlorophenyl)carbonyl-2-oxo-5'-aminomethyl-spiro[piperidine-4,3'-(2H)-benzo[b]furan], |
| 263 | 1-benzylaminocarbonyl-5'-aminomethyl-spiro[piperidine-4,3'-(2H)-benzo[b]furan], |
| 264 | 1-(4-hydroxy-phenylethynyl)carbonyl-5'-aminomethyl-spiro[piperidine-4,3'-(2H)-benzo[b]furan], |
| 265 | (E)-1-(3-hydroxy-phenylethenyl)carbonyl-5'-aminomethyl-spiro[piperidine-4,3'-(2H)-benzo[b]furan], |
| 266 | 1-(5-tert-butyl-thien-2-yl)carbonyl-5'-aminomethyl-spiro[piperidine-4,3'-(2H)-benzo[b]furan], |
| 267 | 1-(5-methoxycarbonyl-thien-2-yl)carbonyl-5'-aminomethyl-spiro[piperidine-4,3'-(2H)-benzo[b]furan], |
| 268 | (E)-1-(4-tert-butyl-phenylethenyl)carbonyl-5'-aminomethyl-spiro[piperidine-4,3'-(2H)-benzo[b]furan], |
| 269 | 1-fluoren-1-ylcarbonyl-5'-aminomethyl-spiro[piperidine-4,3'-(2H)-benzo[b]furan], |
| 270 | 1-(9-oxo-fluoren-1-yl)carbonyl-5'-aminomethyl-spiro[piperidine-4,3'-(2H)-benzo[b]furan], |
| 271 | 1-(3-chloro-6-ethyl-benzo[b]thien-2-yl)carbonyl-5'-aminomethyl-spiro[piperidine-4,3'-(2H)-benzo[b]furan], |
| 272 | (E)-1-(2-hydroxy-phenylethenyl)carbonyl-5'-aminomethyl-spiro[piperidine-4,3'-(2H)-benzo[b]furan], |
| 273 | 1-(3-aminocarbonyl-phenyl)carbonyl-5'-aminomethyl-spiro[piperidine-4,3'-(2H)-benzo[b]furan], |
| 274 | 1-(3-tert-butyl-phenyl)carbonyl-5'-aminomethyl-spiro[piperidine-4,3'-(2H)-benzo[b]furan], |
| 275 | 1-(3,4,5-trichloro-thien-2-yl)carbonyl-5'-aminomethyl-spiro[piperidine-4,3'-(2H)-benzo[b]furan], |
| 276 | 1-(4-trifluoromethyl-6-methyl-1H-thieno[2,3-c]pyrazol-2-yl)carbonyl-5'-aminomethyl-spiro[piperidine-4,3'-(2H)-benzo[b]furan], |

| Cpd | Name |
|---|---|
| 277 | 1-(3-thien-2-yl-[1,2,4]oxadiazol-5-yl)carbonyl-5'-aminomethyl-spiro[piperidine-4,3'-(2H)-benzo[b]furan], |
| 278 | 1-(4,5-dibromo-thien-2-yl)carbonyl-5'-aminomethyl-spiro[piperidine-4,3'-(2H)-benzo[b]furan], |
| 279 | 1-[4-(3,5-bis-trifluoromethyl-phenoxy)-phenyl]carbonyl-5'-aminomethyl-spiro[piperidine-4,3'-(2H)-benzo[b]furan], |
| 280 | 1-(3,4-dichlorophenyl)sulfonyl-5'-aminomethyl-spiro[piperidine-4,3'-(2H)-benzo[b]furan], |
| 281 | (E)-1-(3-benzyloxy-phenylethenyl)carbonyl-5'-aminomethyl-spiro[piperidine-4,3'-(2H)-benzo[b]furan], |
| 282 | 1-[5-(4-tert-butyl-phenylethynyl)-furan-2-yl]carbonyl-5'-aminomethyl-spiro[piperidine-4,3'-(2H)-benzo[b]furan], |
| 283 | 1-(1-phenylsulfonyl-1H-indol-2-yl)carbonyl-5'-aminomethyl-spiro[piperidine-4,3'-(2H)-benzo[b]furan], |
| 284 | 1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan], |
| 285 | 1-1H-indol-2-ylcarbonyl-5'-aminomethyl-spiro[piperidine-4,3'-(2H)-benzo[b]furan], |
| 286 | 1-3H-inden-1-ylcarbonyl-5'-aminomethyl-spiro[piperidine-4,3'-(2H)-benzo[b]furan], |
| 287 | 1-(3-oxo-indan-1-yl)carbonyl-5'-aminomethyl-spiro[piperidine-4,3'-(2H)-benzo[b]furan], |
| 288 | 1-(4-phenyl-thien-2-yl)carbonyl-5'-aminomethyl-spiro[piperidine-4,3'-(2H)-benzo[b]furan], |
| 289 | 1-fluoren-9-ylcarbonyl-5'-aminomethyl-spiro[piperidine-4,3'-(2H)-benzo[b]furan], |
| 290 | 1-(1-oxo-2,2-diphenyl-ethyl)-5'-aminomethyl-spiro[piperidine-4,3'-(2H)-benzo[b]furan], |
| 291 | (E)-1-[3-(2-methoxy-ethoxy)-phenylethenyl]carbonyl-5'-aminomethyl-spiro[piperidine-4,3'-(2H)-benzo[b]furan], |
| 292 | 1-9H-xanthen-9-ylcarbonyl-5'-aminomethyl-spiro[piperidine-4,3'-(2H)-benzo[b]furan], |
| 293 | 1-9H-xanthen-9-ylmethylcarbonyl-5'-aminomethyl-spiro[piperidine-4,3'-(2H)-benzo[b]furan], |
| 294 | (E)-1-(3-phenethoxy-phenylethenyl)carbonyl-5'-aminomethyl-spiro[piperidine-4,3'-(2H)-benzo[b]furan], |
| 295 | 1-(4-phenyl-5-trifluoromethyl-thien-2-yl)carbonyl-5'-aminomethyl-spiro[piperidine-4,3'-(2H)-benzo[b]furan], |
| 296 | 1-phenylethynylcarbonyl-5'-aminomethyl-spiro[piperidine-4,3'-(2H)-benzo[b]furan], |
| 297 | 1-(5-phenylethynyl-furan-2-yl)carbonyl-spiro[piperidine-4,3'-(2H)-benzo[b]furan]-5'-[methyl-(trimethyl)ammonium], |
| 298 | 1-(1-chloro-naphtho[2,1-b]thien-2-yl)carbonyl-5'-aminomethyl-spiro[piperidine-4,3'-(2H)-benzo[b]furan], |
| 299 | 1-[3-(4-chloro-phenyl)-5-methylthio-thien-2-yl]carbonyl-5'-aminomethyl-spiro[piperidine-4,3'-(2H)-benzo[b]furan], |
| 300 | (E)-1-(4-benzyloxy-phenylethenyl)carbonyl-5'-aminomethyl-spiro[piperidine-4,3'-(2H)-benzo[b]furan], |
| 301 | (E)-1-[3-(3-methoxy-propoxy)-phenylethenyl]carbonyl-5'-aminomethyl-spiro[piperidine-4,3'-(2H)-benzo[b]furan], |
| 302 | (E)-1-[3-(2-ethoxy-ethoxy)-phenylethenyl]carbonyl-5'-aminomethyl-spiro[piperidine-4,3'-(2H)-benzo[b]furan], |
| 303 | 1-(3-methyl-4-bromo-5-propoxy-thien-2-yl)carbonyl-5'-aminomethyl-spiro[piperidine-4,3'-(2H)-benzo[b]furan], |
| 304 | 1-(5-phenylethynyl-furan-2-yl)carbonyl-5'-formylaminomethyl-spiro[piperidine-4,3'-(2H)-benzo[b]furan], |
| 305 | 1-(5-phenylethynyl-furan-2-yl)carbonyl-5'-aminosulfonylaminomethyl-spiro[piperidine-4,3'-(2H)-benzo[b]furan], |
| 306 | 1-(5-phenylethynyl-furan-2-yl)carbonyl-5'-[hydroxyamino(imino)methyl]-spiro[piperidine-4,3'-(2H)-benzo[b]furan], |
| 307 | 1-(5-phenylethynyl-furan-2-yl)carbonyl-5'-[hydrazino(imino)methyl]-spiro[piperidine-4,3'-(2H)-benzo[b]furan], |
| 308 | 1-(3,4-dichlorophenyl)carbonyl-5'-aminomethyl-6'-fluoro-spiro[piperidine-4,3'-(2H)-benzo[b]furan], |
| 309 | (E)-1-(2-fluoro-phenylethenyl)carbonyl-5'-aminomethyl-spiro[piperidine-4,3'-(2H)-benzo[b]furan], |
| 310 | 1-(5-phenylethynyl-furan-2-yl)carbonyl-5'-[methylamino(imino)methyl]-spiro[piperidine-4,3'-(2H)-benzo[b]furan], |
| 311 | 1-(5-phenylethynyl-furan-2-yl)carbonyl-5'-aminomethyl-6'-fluoro-spiro[piperidine-4,3'-(2H)-benzo[b]furan], |
| 312 | (E)-1-(2,3-difluoro-phenylethenyl)carbonyl-5'-aminomethyl-spiro[piperidine-4,3'-(2H)-benzo[b]furan], |
| 313 | 1-(5-phenylethynyl-furan-2-yl)carbonyl-5'-[dimethylamino(imino)methyl]-spiro[piperidine-4,3'-(2H)-benzo[b]furan], |
| 314 | 1-(5-phenylethynyl-furan-2-yl)carbonyl-5'-aminoethyl-spiro[piperidine-4,3'-(2H)-benzo[b]furan], |
| 315 | 1-(3,4-dichlorophenyl)carbonyl-2'-oxo-5'-aminomethyl-spiro[piperidine-4,3'-(2H)-indole], |

-continued

| Cpd | Name |
|---|---|
| 316 | 1-(5-phenylethynyl-furan-2-yl)carbonyl-1'-oxo-2'-(2,4-dimethoxy-benzyl)-5'-aminomethyl-spiro[piperidine-4,3'-1H-isoindole], |
| 317 | 1-(5-phenylethynyl-furan-2-yl)carbonyl-1'-oxo-5'-aminomethyl-spiro[piperidine-4,3'-1H-isoindole], |
| 318 | 1-(5-phenylethynyl-furan-2-yl)carbonyl-spiro[piperidine-4,3'-indane], |
| 319 | 1-(5-phenylethynyl-furan-2-yl)carbonyl-5'-aminomethyl-spiro[piperidine-4,3'-(2H)-indole], |
| 320 | 1-(5-phenylethynyl-furan-2-yl)carbonyl-1'-ethyl-5'-aminomethyl-spiro[piperidine-4,3'-(2H)-indole], |
| 321 | 1-(5-phenylethynyl-furan-2-yl)carbonyl-1'-(2-methoxycarbonyl-ethyl)-5'-aminomethyl-spiro[piperidine-4,3'-(2H)-indole], |
| 322 | 1-(5-phenylethynyl-furan-2-yl)carbonyl-1'-(2-carboxy-ethyl)-5'-aminomethyl-spiro[piperidine-4,3'-(2H)-indole], |
| 323 | 1-(5-phenylethynyl-furan-2-yl)carbonyl-1'-methoxycarbonyl-5'-aminomethyl-spiro[piperidine-4,3'-(2H)-indole], |
| 324 | 1-(5-phenylethynyl-furan-2-yl)carbonyl-1'-(4-carboxy-phenyl)sulfonyl-5'-aminomethyl-spiro[piperidine-4,3'-(2H)-indole], |
| 325 | 1-(5-phenylethynyl-furan-2-yl)carbonyl-1'-aminocarbonyl-5'-aminomethyl-spiro[piperidine-4,3'-(2H)-indole], |
| 326 | 1-(5-phenylethynyl-furan-2-yl)carbonyl-5'-aminomethyl-spiro[piperidine-4,3'-(2H)-indole]-1'-(2-ethyl-phosphonic acid), |
| 327 | 1-(5-phenylethynyl-furan-2-yl)carbonyl-1'-hydroxysulfonyl-5'-aminomethyl-spiro[piperidine-4,3'-(2H)-indole], |
| 328 | 1-(5-phenylethynyl-furan-2-yl)carbonyl-1'-(3-methoxycarbonyl-phenyl)carbonyl-5'-aminomethyl-spiro[piperidine-4,3'-(2H)-indole], |
| 329 | 1-(5-phenylethynyl-furan-2-yl)carbonyl-1'-(2-ethoxy-1,2-dioxo-ethyl)-5'-aminomethyl-spiro[piperidine-4,3'-(2H)-indole], |
| 330 | 1-(5-phenylethynyl-furan-2-yl)carbonyl-1'-(2-1H-tetrazol-5-yl-1-oxo-ethyl)-5'-aminomethyl-spiro[piperidine-4,3'-(2H)-indole], |
| 331 | 1-(5-phenylethynyl-furan-2-yl)carbonyl-1'-(3-carboxy-phenyl)sulfonyl-5'-aminomethyl-spiro[piperidine-4,3'-(2H)-indole], |
| 332 | 1-(5-phenylethynyl-furan-2-yl)carbonyl-1'-[4-ethoxy-2-(methylamino)amino-1,4-dioxo-butyl]-5'-aminomethyl-spiro[piperidine-4,3'-(2H)-indole], |
| 333 | 1-(5-phenylethynyl-furan-2-yl)carbonyl-1'-(methylsulfonylmethyl)carbonyl-5'-aminomethyl-spiro[piperidine-4,3'-(2H)-indole], |
| 334 | 1-(5-phenylethynyl-furan-2-yl)carbonyl-1'-(1H-tetrazol-5-yl)carbonyl-5'-aminomethyl-spiro[piperidine-4,3'-(2H)-indole], |
| 335 | 1-(5-phenylethynyl-furan-2-yl)carbonyl-1'-(hydroxysulfonylmethyl)carbonyl-5'-aminomethyl-spiro[piperidine-4,3'-(2H)-indole], |
| 336 | 1-(5-phenylethynyl-furan-2-yl)carbonyl-1'-(1-methyl-imidazol-4-yl)sulfonyl-5'-aminomethyl-spiro[piperidine-4,3'-(2H)-indole], |
| 337 | 1-(5-phenylethynyl-furan-2-yl)carbonyl-1'-(5-carboxy-furan-2-yl)sulfonyl-5'-aminomethyl-spiro[piperidine-4,3'-(2H)-indole], |
| 338 | 1-(5-phenylethynyl-furan-2-yl)carbonyl-1'-[5-(N'-methyl-hydrazino)-1,1-dioxo-3,4,5-trihydro-(2H)-thien-3-yl]sulfonyl-5'-aminomethyl-spiro[piperidine-4,3'-(2H)-indole], |
| 339 | 1-(5-phenylethynyl-furan-2-yl)carbonyl-1'-methylcarbonyl-5'-aminomethyl-spiro[piperidine-4,3'-(2H)-indole], |
| 340 | 1-(5-phenylethynyl-furan-2-yl)carbonyl-1'-methylsulfonyl-5'-aminomethyl-spiro[piperidine-4,3'-(2H)-indole], |
| 341 | 1-(5-phenylethynyl-furan-2-yl)carbonyl-1'-phenylsulfonyl-5'-aminomethyl-spiro[piperidine-4,3'-(2H)-indole], |
| 342 | 1-(5-phenylethynyl-furan-2-yl)carbonyl-1'-aminosulfonyl-5'-aminomethyl-spiro[piperidine-4,3'-(2H)-indole], |
| 343 | 1-(5-phenylethynyl-furan-2-yl)carbonyl-1'-[(methoxycarbonyl)methyl]-5'-aminomethyl-spiro[piperidine-4,3'-(2H)-indole], |
| 344 | 1-(5-phenylethynyl-furan-2-yl)carbonyl-1'-(3-methoxycarbonyl-phenyl)sulfonyl-5'-aminomethyl-spiro[piperidine-4,3'-(2H)-indole], |
| 345 | 1-(5-phenylethynyl-furan-2-yl)carbonyl-1'-(5-methoxycarbonyl-furan-2-yl)sulfonyl-5'-aminomethyl-spiro[piperidine-4,3'-(2H)-indole], |
| 346 | 1-(3-methyl-4-bromo-5-propoxy-thien-2-yl)carbonyl-1'-hydroxysulfonyl-5'-aminomethyl-spiro[piperidine-4,3'-(2H)-indole], |
| 347 | 1-(5-phenylethynyl-furan-2-yl)carbonyl-1'-(5-carboxy-thien-3-yl)sulfonyl-5'-aminomethyl-spiro[piperidine-4,3'-(2H)-indole], |
| 348 | 1-(5-phenylethynyl-furan-2-yl)carbonyl-1'-(methylsulfonylmethyl)sulfonyl-5'-aminomethyl-spiro[piperidine-4,3'-(2H)-indole], |
| 349 | 1-(5-phenylethynyl-furan-2-yl)carbonyl-1'-(N'-methylhydrazino-carbonylmethyl)sulfonyl-5'-aminomethyl-spiro[piperidine-4,3'-(2H)-indole], |
| 350 | 1-(3-methylthio-benzo[c]thien-1-yl)carbonyl-1'-hydroxysulfonyl-5'-aminomethyl-spiro[piperidine-4,3'-(2H)-indole], |
| 351 | 1-(4,5-dibromo-thien-2-yl)carbonyl-1'-hydroxysulfonyl-5'-aminomethyl-spiro[piperidine-4,3'-(2H)-indole], |
| 352 | 1-(3,4-dichlorophenyl)carbonyl-5'-aminomethyl-spiro[piperidine-4,3'-(1,1-dioxo-(2H)-benzo[b]thiophene)], |
| 353 | 1-(3,4-dichlorophenyl)carbonyl-5'-aminomethyl-spiro[piperidine-4,3'-(2H)-benzo[b]thiophene], |
| 354 | 1-(2,2-diphenylethyl)carbonyl-5'-aminomethyl-spiro[piperidine-4,3'-(2H)-benzo[b]furan], |

-continued

| Cpd | Name |
|---|---|
| 355 | 1-(9H-fluoren-9-ylmethyl)carbonyl-5'-aminomethyl-spiro[piperidine-4,3'-(2H)-benzo[b]furan], |
| 356 | (E)-1-(3-methyl-thien-2-ylethenyl)carbonyl-5'-aminomethyl-spiro[piperidine-4,3'-(2H)-benzo[b]furan], |
| 357 | 1-[4-(4-chloro-phenyl)-thien-2-yl]carbonyl-5'-aminomethyl-spiro[piperidine-4,3'-(2H)-benzo[b]furan], |
| 358 | 1-(5-phenylethynyl-furan-2-yl)carbonyl-1'-thien-2-ylsulfonyl-5'-aminomethyl-spiro[piperidine-4,3'-(2H)-indole], and |
| 359 | 1-(5-phenylethynyl-furan-2-yl)carbonyl-1'-thien-3-ylsulfonyl-5'-aminomethyl-spiro[piperidine-4,3'-(2H)-indole]. |

A representative compound of Formula (I) or a form thereof includes a compound selected from the group consisting of:

| Cpd | Name |
|---|---|
| 1 | 1-(3,4-dichlorophenyl)carbonyl-5'-aminomethyl-spiro[piperidine-4,3'-(2H)-benzo[b]furan], |
| 3 | 1-(5-phenylethynyl-furan-2-yl)carbonyl-5'-aminomethyl-spiro[piperidine-4,3'-(2H)-benzo[b]furan], |
| 4 | 1-(3-benzoyl-phenyl)carbonyl-5'-aminomethyl-spiro[piperidine-4,3'-(2H)-benzo[b]furan], |
| 5 | 1-(3-aminothiocarbonylamino-phenyl)carbonyl-5'-aminomethyl-spiro[piperidine-4,3'-(2H)-benzo[b]furan], |
| 7 | 1-(9-oxo-10,10-dioxo-thioxanthen-3-yl)carbonyl-5'-aminomethyl-spiro[piperidine-4,3'-(2H)-benzo[b]furan], |
| 12 | 1-[5-(4-chloro-phenyl)-furan-2-yl]carbonyl-5'-aminomethyl-spiro[piperidine-4,3'-(2H)-benzo[b]furan], |
| 16 | 1-benzothiazol-6-ylcarbonyl-5'-aminomethyl-spiro[piperidine-4,3'-(2H)-benzo[b]furan], |
| 17 | 1-{4-[(4-benzoxazol-2-yl)-pyrazol-1-yl]-phenyl}carbonyl-5'-aminomethyl-spiro[piperidine-4,3'-(2H)-benzo[b]furan], |
| 19 | 1-(3-thien-2-ylmethylcarbonylamino-phenyl)carbonyl-5'-aminomethyl-spiro[piperidine-4,3'-(2H)-benzo[b]furan], |
| 20 | 1-(3-benzodioxol-5-yl-phenyl)carbonyl-5'-aminomethyl-spiro[piperidine-4,3'-(2H)-benzo[b]furan], |
| 21 | 1-[3-(5-chloro-pyrimidin-2-yl)thiophenyl]carbonyl-5'-aminomethyl-spiro[piperidine-4,3'-(2H)-benzo[b]furan], |
| 23 | 1-[(5-phenylthio)-furan-2-yl]carbonyl-5'-aminomethyl-spiro[piperidine-4,3'-(2H)-benzo[b]furan], |
| 24 | 1-(3,4-dimethyl-phenyl)carbonyl-5'-aminomethyl-spiro[piperidine-4,3'-(2H)-benzo[b]furan], |
| 25 | 1-(3-methyl-4-chloro-phenyl)carbonyl-5'-aminomethyl-spiro[piperidine-4,3'-(2H)-benzo[b]furan], |
| 26 | 1-(3,4-difluoro-phenyl)carbonyl-5'-aminomethyl-spiro[piperidine-4,3'-(2H)-benzo[b]furan], |
| 27 | 1-(3-chloro-4-fluoro-phenyl)carbonyl-5'-aminomethyl-spiro[piperidine-4,3'-(2H)-benzo[b]furan], |
| 28 | 1-(3-chloro-4-methoxy-phenyl)carbonyl-5'-aminomethyl-spiro[piperidine-4,3'-(2H)-benzo[b]furan], |
| 29 | 1-(3-bromo-phenyl)carbonyl-5'-aminomethyl-spiro[piperidine-4,3'-(2H)-benzo[b]furan], |
| 30 | 1-(3-methyl-4-bromo-phenyl)carbonyl-5'-aminomethyl-spiro[piperidine-4,3'-(2H)-benzo[b]furan], |
| 31 | 1-(3-bromo-4-fluoro-phenyl)carbonyl-5'-aminomethyl-spiro[piperidine-4,3'-(2H)-benzo[b]furan], |
| 32 | 1-(3-bromo-4-methoxy-phenyl)carbonyl-5'-aminomethyl-spiro[piperidine-4,3'-(2H)-benzo[b]furan], |
| 33 | 1-(3-nitro-4-bromo-phenyl)carbonyl-5'-aminomethyl-spiro[piperidine-4,3'-(2H)-benzo[b]furan], |
| 34 | 1-(3-iodo-4-chloro-phenyl)carbonyl-5'-aminomethyl-spiro[piperidine-4,3'-(2H)-benzo[b]furan], |
| 35 | 1-[5-(2-fluoro-phenylethynyl)-furan-2-yl]carbonyl-5'-aminomethyl-spiro[piperidine-4,3'-(2H)-benzo[b]furan], |
| 36 | 1-phenylcarbonyl-5'-aminomethyl-spiro[piperidine-4,3'-(2H)-benzo[b]furan], |
| 37 | 1-cyclohexylcarbonyl-5'-aminomethyl-spiro[piperidine-4,3'-(2H)-benzo[b]furan], |
| 38 | 1-(trans-4-methyl-cyclohexyl)carbonyl-5'-aminomethyl-spiro[piperidine-4,3'-(2H)-benzo[b]furan], |
| 40 | 1-(3,4-dimethoxy-phenyl)carbonyl-5'-aminomethyl-spiro[piperidine-4,3'-(2H)-benzo[b]furan], |

-continued

| Cpd | Name |
|---|---|
| 41 | 1-(3-methyl-phenyl)carbonyl-5'-aminomethyl-spiro[piperidine-4,3'-(2H)-benzo[b]furan], |
| 42 | 1-(3-fluoro-phenyl)carbonyl-5'-aminomethyl-spiro[piperidine-4,3'-(2H)-benzo[b]furan], |
| 43 | 1-(4-fluoro-phenyl)carbonyl-5'-aminomethyl-spiro[piperidine-4,3'-(2H)-benzo[b]furan], |
| 44 | 1-(4-chloro-phenyl)carbonyl-5'-aminomethyl-spiro[piperidine-4,3'-(2H)-benzo[b]furan], |
| 45 | 1-(4-methylthio-phenyl)carbonyl-5'-aminomethyl-spiro[piperidine-4,3'-(2H)-benzo[b]furan], |
| 46 | 1-(3-fluoro-4-chloro-phenyl)carbonyl-5'-aminomethyl-spiro[piperidine-4,3'-(2H)-benzo[b]furan], |
| 47 | 1-(3-trifluoromethyl-phenyl)carbonyl-5'-aminomethyl-spiro[piperidine-4,3'-(2H)-benzo[b]furan], |
| 48 | 1-(3-iodo-phenyl)carbonyl-5'-aminomethyl-spiro[piperidine-4,3'-(2H)-benzo[b]furan], |
| 49 | 1-(4-iodo-phenyl)carbonyl-5'-aminomethyl-spiro[piperidine-4,3'-(2H)-benzo[b]furan], |
| 50 | 1-(3-iodo-4-methyl-phenyl)carbonyl-5'-aminomethyl-spiro[piperidine-4,3'-(2H)-benzo[b]furan], |
| 51 | 1-(3-methyl-4-iodo-phenyl)carbonyl-5'-aminomethyl-spiro[piperidine-4,3'-(2H)-benzo[b]furan], |
| 52 | 1-(3-iodo-4-methoxy-phenyl)carbonyl-5'-aminomethyl-spiro[piperidine-4,3'-(2H)-benzo[b]furan], |
| 53 | 1-(3-methoxy-phenyl)carbonyl-5'-aminomethyl-spiro[piperidine-4,3'-(2H)-benzo[b]furan], |
| 54 | 1-(4-methoxy-phenyl)carbonyl-5'-aminomethyl-spiro[piperidine-4,3'-(2H)-benzo[b]furan], |
| 56 | 1-(3-dimethylamino-phenyl)carbonyl-5'-aminomethyl-spiro[piperidine-4,3'-(2H)-benzo[b]furan], |
| 57 | 1-(3-methylthio-phenyl)carbonyl-5'-aminomethyl-spiro[piperidine-4,3'-(2H)-benzo[b]furan], |
| 58 | 1-(4-methoxycarbonyl-phenyl)carbonyl-5'-aminomethyl-spiro[piperidine-4,3'-(2H)-benzo[b]furan], |
| 59 | 1-(4-bromo-phenyl)carbonyl-5'-aminomethyl-spiro[piperidine-4,3'-(2H)-benzo[b]furan], |
| 62 | 1-(4-phenoxy-phenyl)carbonyl-5'-aminomethyl-spiro[piperidine-4,3'-(2H)-benzo[b]furan], |
| 63 | 1-(3-trifluoromethylthio-phenyl)carbonyl-5'-aminomethyl-spiro[piperidine-4,3'-(2H)-benzo[b]furan], |
| 64 | 1-[3-(4-methoxy-phenyl)-phenyl]carbonyl-5'-aminomethyl-spiro[piperidine-4,3'-(2H)-benzo[b]furan], |
| 65 | 1-(5-phenylethynyl-furan-2-yl)carbonyl-5'-aminoiminomethyl-spiro[piperidine-4,3'-(2H)-benzo[b]furan], |
| 68 | 1-benzodioxol-5-ylcarbonyl-5'-aminomethyl-spiro[piperidine-4,3'-(2H)-benzo[b]furan], |
| 70 | 1-naphthalen-2-ylcarbonyl-5'-aminomethyl-spiro[piperidine-4,3'-(2H)-benzo[b]furan], |
| 71 | 1-(4-trifluoromethyl-phenyl)carbonyl-5'-aminomethyl-spiro[piperidine-4,3'-(2H)-benzo[b]furan], |
| 72 | 1-(3-methylsulfonyl-phenyl)carbonyl-5'-aminomethyl-spiro[piperidine-4,3'-(2H)-benzo[b]furan], |
| 74 | 1-(3-trifluoromethyl-4-fluoro-phenyl)carbonyl-5'-aminomethyl-spiro[piperidine-4,3'-(2H)-benzo[b]furan], |
| 75 | 1-(4-benzyl-phenyl)carbonyl-5'-aminomethyl-spiro[piperidine-4,3'-(2H)-benzo[b]furan], |
| 76 | 1-(4-benzyloxy-phenyl)carbonyl-5'-aminomethyl-spiro[piperidine-4,3'-(2H)-benzo[b]furan], |
| 77 | (Z)-1-(5-phenylethenyl-furan-2-yl)carbonyl-5'-aminomethyl-spiro[piperidine-4,3'-(2H)-benzo[b]furan], |
| 86 | 1-(3,4-dichloro-benzyl)carbonyl-5'-aminomethyl-spiro[piperidine-4,3'-(2H)-benzo[b]furan], |
| 88 | 1-(3-phenoxy-benzyl)carbonyl-5'-aminomethyl-spiro[piperidine-4,3'-(2H)-benzo[b]furan], |
| 90 | 1-(4-fluoro-benzyl)carbonyl-5'-aminomethyl-spiro[piperidine-4,3'-(2H)-benzo[b]furan], |
| 91 | 1-(4-chloro-benzyl)carbonyl-5'-aminomethyl-spiro[piperidine-4,3'-(2H)-benzo[b]furan], |
| 92 | 1-(4-phenyl-benzyl)carbonyl-5'-aminomethyl-spiro[piperidine-4,3'-(2H)-benzo[b]furan], |
| 93 | 1-(4-bromo-benzyl)carbonyl-5'-aminomethyl-spiro[piperidine-4,3'-(2H)-benzo[b]furan], |
| 94 | 1-(4-methoxy-benzyl)carbonyl-5'-aminomethyl-spiro[piperidine-4,3'-(2H)-benzo[b]furan], |
| 96 | 1-(4-iodo-benzyl)carbonyl-5'-aminomethyl-spiro[piperidine-4,3'-(2H)-benzo[b]furan], |
| 99 | 1-(3-methoxy-benzyl)carbonyl-5'-aminomethyl-spiro[piperidine-4,3'-(2H)-benzo[b]furan], |

| Cpd | Name |
|---|---|
| 100 | 1-benzodioxol-5-ylmethylcarbonyl-5'-aminomethyl-spiro[piperidine-4,3'-(2H)-benzo[b]furan], |
| 102 | 1-(3-methyl-4-methoxy-benzyl)carbonyl-5'-aminomethyl-spiro[piperidine-4,3'-(2H)-benzo[b]furan], |
| 103 | 1-(3-methylthio-benzyl)carbonyl-5'-aminomethyl-spiro[piperidine-4,3'-(2H)-benzo[b]furan], |
| 105 | 1-(3,4-dimethoxy-benzyl)carbonyl-5'-aminomethyl-spiro[piperidine-4,3'-(2H)-benzo[b]furan], |
| 106 | 1-(3-methoxy-4-benzyloxy-benzyl)carbonyl-5'-aminomethyl-spiro[piperidine-4,3'-(2H)-benzo[b]furan], |
| 107 | 1-(5-phenethyl-furan-2-yl)carbonyl-5'-aminomethyl-spiro[piperidine-4,3'-(2H)-benzo[b]furan], |
| 108 | 1-(phenylethynyl)carbonyl-5'-aminomethyl-spiro[piperidine-4,3'-(2H)-benzo[b]furan], |
| 109 | (E)-1-(phenylethenyl)carbonyl-5'-aminomethyl-spiro[piperidine-4,3'-(2H)-benzo[b]furan], |
| 110 | 1-benzothien-2-ylcarbonyl-5'-aminomethyl-spiro[piperidine-4,3'-(2H)-benzo[b]furan], |
| 111 | (E)-1-(3,4-difluoro-phenylethenyl)carbonyl-5'-aminomethyl-spiro[piperidine-4,3'-(2H)-benzo[b]furan], |
| 112 | (E)-1-(phenylethenyl)carbonyl-5'-aminomethyl-spiro[piperidine-4,3'-(2H)-benzo[b]furan], |
| 113 | (E)-1-(naphthalene-2-ylethenyl)carbonyl-5'-aminomethyl-spiro[piperidine-4,3'-(2H)-benzo[b]furan], |
| 114 | 1-(5-phenyl-thien-2-yl)carbonyl-5'-aminomethyl-spiro[piperidine-4,3'-(2H)-benzo[b]furan], |
| 115 | 1-(3-phenoxy-phenyl)carbonyl-5'-aminomethyl-spiro[piperidine-4,3'-(2H)-benzo[b]furan], |
| 116 | (E)-1-(3,4-dichloro-phenylethenyl)carbonyl-5'-aminomethyl-spiro[piperidine-4,3'-(2H)-benzo[b]furan], |
| 117 | (E)-1-(4-phenyl-phenylethenyl)carbonyl-5'-aminomethyl-spiro[piperidine-4,3'-(2H)-benzo[b]furan], |
| 118 | 1-(2,4-dimethyl-thiazol-5-yl)carbonyl-5'-aminomethyl-spiro[piperidine-4,3'-(2H)-benzo[b]furan], |
| 120 | 1-(5-pyridin-2-yl-thien-2-yl)carbonyl-5'-aminomethyl-spiro[piperidine-4,3'-(2H)-benzo[b]furan], |
| 121 | 1-(2-pyridin-3-yl-thiazol-4-yl)carbonyl-5'-aminomethyl-spiro[piperidine-4,3'-(2H)-benzo[b]furan], |
| 122 | 1-(2-pyridin-4-yl-thiazol-4-yl)carbonyl-5'-aminomethyl-spiro[piperidine-4,3'-(2H)-benzo[b]furan], |
| 123 | 1-(2-phenyl-4-methyl-thiazol-5-yl)carbonyl-5'-aminomethyl-spiro[piperidine-4,3'-(2H)-benzo[b]furan], |
| 126 | 1-(6-bromo-naphthalen-2-yl)carbonyl-5'-aminomethyl-spiro[piperidine-4,3'-(2H)-benzo[b]furan], |
| 128 | 1-[2-(4-trifluoromethyl-phenyl)-4-methyl-thiazol-5-yl]carbonyl-5'-aminomethyl-spiro[piperidine-4,3'-(2H)-benzo[b]furan], |
| 129 | 1-[5-(2-chloro-5-trifluoromethyl-phenyl)-furan-2-yl]carbonyl-5'-aminomethyl-spiro[piperidine-4,3'-(2H)-benzo[b]furan], |
| 130 | 1-(5-phenyl-furan-2-yl)carbonyl-5'-aminomethyl-spiro[piperidine-4,3'-(2H)-benzo[b]furan], |
| 131 | 1-[5-(4-methyl-phenyl)-furan-2-yl]carbonyl-5'-aminomethyl-spiro[piperidine-4,3'-(2H)-benzo[b]furan], |
| 132 | 1-[5-(4-methoxy-phenyl)-furan-2-yl]carbonyl-5'-aminomethyl-spiro[piperidine-4,3'-(2H)-benzo[b]furan], |
| 133 | 1-(3,5-di-tert-butyl-phenyl)carbonyl-5'-aminomethyl-spiro[piperidine-4,3'-(2H)-benzo[b]furan], |
| 134 | 1-[5-(3-chloro-phenoxymethyl)-furan-2-yl]carbonyl-5'-aminomethyl-spiro[piperidine-4,3'-(2H)-benzo[b]furan], |
| 135 | 1-[5-(3-trifluoromethyl-phenyl)-furan-2-yl]carbonyl-5'-aminomethyl-spiro[piperidine-4,3'-(2H)-benzo[b]furan], |
| 136 | 1-[5-(2,4-dichloro-phenyl)-furan-2-yl]carbonyl-5'-aminomethyl-spiro[piperidine-4,3'-(2H)-benzo[b]furan], |
| 137 | 1-[5-(2,5-dichloro-phenyl)-furan-2-yl]carbonyl-5'-aminomethyl-spiro[piperidine-4,3'-(2H)-benzo[b]furan], |
| 138 | 1-[5-(3,4-dichloro-phenyl)-furan-2-yl]carbonyl-5'-aminomethyl-spiro[piperidine-4,3'-(2H)-benzo[b]furan], |
| 139 | 1-[5-(3-methyl-4-chloro-phenoxymethyl)-furan-2-yl]carbonyl-5'-aminomethyl-spiro[piperidine-4,3'-(2H)-benzo[b]furan], |
| 140 | 1-[5-(4-bromo-phenyl)-furan-2-yl]carbonyl-5'-aminomethyl-spiro[piperidine-4,3'-(2H)-benzo[b]furan], |
| 141 | 1-(trans-2-phenyl-cyclopropyl)carbonyl-5'-aminomethyl-spiro[piperidine-4,3'-(2H)-benzo[b]furan], |
| 142 | 1-(5-phenyl-pyridin-3-yl)carbonyl-5'-aminomethyl-spiro[piperidine-4,3'-(2H)-benzo[b]furan], |
| 143 | 1-(5-thien-2-yl-pyridin-3-yl)carbonyl-5'-aminomethyl-spiro[piperidine-4,3'-(2H)-benzo[b]furan], |
| 144 | 1-[5-(3-methoxy-phenyl)-furan-2-yl]carbonyl-5'-aminomethyl-spiro[piperidine-4,3'-(2H)-benzo(b)furan], |

| Cpd | Name |
|---|---|
| 145 | 1-[5-(4-chloro-pyrazol-1-ylmethyl)-furan-2-yl]carbonyl-5'-aminomethyl-spiro[piperidine-4,3'-(2H)-benzo[b]furan], |
| 146 | 1-[5-(2-chloro-phenylethynyl)-furan-2-yl]carbonyl-5'-aminomethyl-spiro[piperidine-4,3'-(2H)-benzo[b]furan], |
| 147 | 1-[5-(benzylthiomethyl)-furan-2-yl]carbonyl-5'-aminomethyl-spiro[piperidine-4,3'-(2H)-benzo(b]furan], |
| 148 | 1-[5-(4,6-dimethyl-pyrimidin-2-ylthiomethyl)-furan-2-yl]carbonyl-5'-aminomethyl-spiro[piperidine-4,3'-(2H)-benzo[b]furan], |
| 149 | 1-[5-(3,5-dichloro-phenoxy)-furan-2-yl]carbonyl-5'-aminomethyl-spiro[piperidine-4,3'-(2H)-benzo[b]furan], |
| 150 | 1-[5-(3,5-dimethyl-4-bromo-pyrazol-1-yl)-furan-2-yl]carbonyl-5'-aminomethyl-spiro[piperidine-4,3'-(2H)-benzo[b]furan], |
| 151 | 1-[5-(5-trifluoromethyl-pyridin-2-ylthiomethyl)-furan-2-yl]carbonyl-5'-aminomethyl-spiro[piperidine-4,3'-(2H)-benzo[b]furan], |
| 152 | 1-[4-phenylethynyl-pyridin-2-yl]carbonyl-5'-aminomethyl-spiro[piperidine-4,3'-(2H)-benzo[b]furan], |
| 153 | 1-[5-(2-methyl-phenylethynyl)-furan-2-yl]carbonyl-5'-aminomethyl-spiro[piperidine-4,3'-(2H)-benzo[b]furan], |
| 154 | 1-[5-(4-fluoro-phenoxymethyl)-furan-2-yl]carbonyl-5'-aminomethyl-spiro[piperidine-4,3'-(2H)-benzo[b]furan], |
| 155 | 1-(3-methylthio-4-oxo-5,6,7-trihydro-4H-benzo[c]thien-1-yl)carbonyl-5'-aminomethyl-spiro[piperidine-4,3'-(2H)-benzo[b]furan], |
| 156 | 1-[5-(2,5-dimethyl-furan-3-yl-carbonylaminomethyl)-furan-2-yl]carbonyl-5'-aminomethyl-spiro[piperidine-4,3'-(2H)-benzo[b]furan], |
| 157 | 1-(3-chloro-4-isopropylsulfonyl-5-methylthio-thien-2-yl)carbonyl-5'-aminomethyl-spiro[piperidine-4,3'-(2H)-benzo[b]furan], |
| 159 | 1-thien-2-ylcarbonyl-5'-aminomethyl-spiro[piperidine-4,3'-(2H)-benzo[b]furan], |
| 160 | 1-benzo[b]furan-2-ylcarbonyl-5'-aminomethyl-spiro[piperidine-4,3'-(2H)-benzo[b]furan], |
| 161 | (E)-1-(3-fluoro-phenylethenyl)carbonyl-5'-aminomethyl-spiro[piperidine-4,3'-(2H)-benzo[b]furan], |
| 162 | (Z)-1-(1-fluoro-2-phenylethenyl)carbonyl-5'-aminomethyl-spiro[piperidine-4,3'-(2H)-benzo[b]furan], |
| 163 | 1-(5,6,7-trihydro-4H-benzo[b]thien-2-yl)carbonyl-5'-aminomethyl-spiro[piperidine-4,3'-(2H)-benzo[b]furan], |
| 164 | (E)-1-(3-chloro-phenylethenyl)carbonyl-5'-aminomethyl-spiro[piperidine-4,3'-(2H)-benzo[b]furan], |
| 165 | (E)-1-(4-chloro-phenylethenyl)carbonyl-5'-aminomethyl-spiro[piperidine-4,3'-(2H)-benzo[b]furan], |
| 166 | 1-(3-chloro-benzo[b]thien-2-yl)carbonyl-5'-aminomethyl-spiro[piperidine-4,3'-(2H)-benzo[b]furan], |
| 167 | (E)-1-(3-trifluoromethoxy-phenylethenyl)carbonyl-5'-aminomethyl-spiro[piperidine-4,3'-(2H)-benzo[b]furan], |
| 168 | 1-(4-fluoro-benzo[b]thien-2-yl)carbonyl-5'-aminomethyl-spiro[piperidine-4,3'-(2H)-benzo[b]furan], |
| 170 | 1-[5-(4-methyl-phenylethynyl)-furan-2-yl]carbonyl-5'-aminomethyl-spiro[piperidine-4,3'-(2H)-benzo[b]furan], |
| 171 | 1-(3-chloro-6-fluoro-benzo[b]thien-2-yl)carbonyl-5'-aminomethyl-spiro[piperidine-4,3'-(2H)-benzo[b]furan], |
| 172 | 1-[5-(2,5-dimethyl-phenylethynyl)-furan-2-yl]carbonyl-5'-aminomethyl-spiro[piperidine-4,3'-(2H)-benzo[b]furan], |
| 173 | 1-[5-(2-methoxy-phenylethynyl)-furan-2-yl]carbonyl-5'-aminomethyl-spiro[piperidine-4,3'-(2H)-benzo[b]furan], |
| 174 | 1-[5-(2,5-dimethyl-phenoxymethyl)-furan-2-yl]carbonyl-5'-aminomethyl-spiro[piperidine-4,3'-(2H)-benzo[b]furan], |
| 175 | 1-(3,4-dichloro-benzo[b]thien-2-yl)carbonyl-5'-aminomethyl-spiro[piperidine-4,3'-(2H)-benzo[b]furan], |
| 176 | 1-[5-(3,5-difluoro-phenylethynyl)-furan-2-yl]carbonyl-5'-aminomethyl-spiro[piperidine-4,3'-(2H)-benzo[b]furan], |
| 177 | 1-(5-naphthalen-1-ylethynyl-furan-2-yl)carbonyl-5'-aminomethyl-spiro[piperidine-4,3'-(2H)-benzo[b]furan], |
| 178 | 1-[5-(4-tert-butyl-phenoxymethyl)-furan-2-yl]carbonyl-5'-aminomethyl-spiro[piperidine-4,3'-(2H)-benzo[b]furan], |
| 179 | (E)-1-(3-methyl-phenylethenyl)carbonyl-5'-aminomethyl-spiro[piperidine-4,3'-(2H)-benzo[b]furan], |
| 180 | (E)-1-(4-methyl-phenylethenyl)carbonyl-5'-aminomethyl-spiro[piperidine-4,3'-(2H)-benzo[b]furan], |
| 182 | (E)-1-(4-fluoro-phenylethenyl)carbonyl-5'-aminomethyl-spiro[piperidine-4,3'-(2H)-benzo[b]furan], |
| 184 | (E)-1-(3-methoxy-phenylethenyl)carbonyl-5'-aminomethyl-spiro[piperidine-4,3'-(2H)-benzo[b]furan], |
| 186 | (E)-1-(2-chloro-phenylethenyl)carbonyl-5'-aminomethyl-spiro[piperidine-4,3'-(2H)-benzo[b]furan], |
| 187 | (E)-1-(benzodioxol-5-ylethenyl)carbonyl-5'-aminomethyl-spiro[piperidine-4,3'-(2H)-benzo[b]furan], |
| 188 | (E)-1-(naphthalen-1-ylethenyl)carbonyl-5'-aminomethyl-spiro[piperidine-4,3'-(2H)-benzo[b]furan], |

| Cpd | Name |
|---|---|
| 189 | 1-(1-oxo-2-fluoren-9-ylidene-ethyl)-5'-aminomethyl-spiro[piperidine-4,3'-(2H)-benzo[b]furan], |
| 190 | (E)-1-(1-phenyl-2-phenylethenyl)carbonyl-5'-aminomethyl-spiro[piperidine-4,3'-(2H)-benzo[b]furan], |
| 191 | (E)-1-(2-methyl-phenylethenyl)carbonyl-5'-aminomethyl-spiro[piperidine-4,3'-(2H)-benzo[b]furan], |
| 192 | 1-(1-methyl-3H-inden-2-yl)carbonyl-5'-aminomethyl-spiro[piperidine-4,3'-(2H)-benzo[b]furan], |
| 193 | 1-(1-methyl-indol-2-yl)carbonyl-5'-aminomethyl-spiro[piperidine-4,3'-(2H)-benzo[b]furan], |
| 194 | (E)-1-(2-methoxy-phenylethenyl)carbonyl-5'-aminomethyl-spiro[piperidine-4,3'-(2H)-benzo[b]furan], |
| 195 | (E)-1-(2,6-difluoro-phenylethenyl)carbonyl-5'-aminomethyl-spiro[piperidine-4,3'-(2H)-benzo[b]furan], |
| 196 | 1-(2-oxo-(2H)-chromen-3-yl)carbonyl-5'-aminomethyl-spiro[piperidine-4,3'-(2H)-benzo[b]furan], |
| 197 | 1-(8-methoxy-(2H)-chromen-3-yl)carbonyl-5'-aminomethyl-spiro[piperidine-4,3'-(2H)-benzo[b]furan], |
| 198 | 1-(5-bromo-thien-2-yl)carbonyl-5'-aminomethyl-spiro[piperidine-4,3'-(2H)-benzo[b]furan], |
| 199 | (E)-1-(2-bromo-phenylethenyl)carbonyl-5'-aminomethyl-spiro[piperidine-4,3'-(2H)-benzo[b]furan], |
| 201 | 1-[3-(4-methoxy-phenyl)-4-cyano-5-methylthio-thien-2-yl]carbonyl-5'-aminomethyl-spiro[piperidine-4,3'-(2H)-benzo[b]furan], |
| 202 | 1-[3-(4-chloro-phenyl)-4-cyano-5-methylthio-thien-2-yl]carbonyl-5'-aminomethyl-spiro[piperidine-4,3'-(2H)-benzo[b]furan], |
| 203 | 1-(5,6,7-trihydro-4H-benzo[c]thien-1-yl)carbonyl-5'-aminomethyl-spiro[piperidine-4,3'-(2H)-benzo[b]furan], |
| 204 | 1-thieno[3,2-b]thien-2-ylcarbonyl-5'-aminomethyl-spiro[piperidine-4,3'-(2H)-benzo[b]furan], |
| 205 | (Z)-1-(1-methylcarbonylamino-2-phenylethenyl)carbonyl-5'-aminomethyl-spiro[piperidine-4,3'-(2H)-benzo[b]furan], |
| 206 | 1-[5-(2-methyl-thiazol-4-yl)-thien-2-yl]carbonyl-5'-aminomethyl-spiro[piperidine-4,3'-(2H)-benzo[b]furan], |
| 208 | 1-[3-(2-methyl-phenoxy)-benzyl]carbonyl-5'-aminomethyl-spiro[piperidine-4,3'-(2H)-benzo[b]furan], |
| 210 | 1-[3-(2-fluoro-phenoxy)-benzyl]carbonyl-5'-aminomethyl-spiro[piperidine-4,3'-(2H)-benzo[b]furan], |
| 211 | 1-(3-propylthio-4-oxo-5,6,7-trihydro-4H-benzo[c]thien-1-yl)carbonyl-5'-aminomethyl-spiro[piperidine-4,3'-(2H)-benzo[b]furan], |
| 212 | 1-[5-(2-methoxy-4-propyl-phenoxymethyl)-furan-2-yl]carbonyl-5'-aminomethyl-spiro[piperidine-4,3'-(2H)-benzo[b]furan], |
| 213 | 1-[5-(2-bromo-phenoxymethyl)-furan-2-yl]carbonyl-5'-aminomethyl-spiro[piperidine-4,3'-(2H)-benzo[b]furan], |
| 214 | 1-(3-benzylthio-4-oxo-5,6,7-trihydro-4H-benzo[c]thien-1-yl)carbonyl-5'-aminomethyl-spiro[piperidine-4,3'-(2H)-benzo[b]furan], |
| 215 | 1-[1-oxo-2-(3-oxo-3H-isobenzofuran-1-ylidene)-ethyl]-5'-aminomethyl-spiro[piperidine-4,3'-(2H)-benzo[b]furan], |
| 217 | 1-(4-phenyl-[1,2,3]thiadiazol-5-yl)carbonyl-5'-aminomethyl-spiro[piperidine-4,3'-(2H)-benzo[b]furan], |
| 218 | 1-(3-methylthio-5,6,7-trihydro-4H-benzo[c]thien-1-yl)carbonyl-5'-aminomethyl-spiro[piperidine-4,3'-(2H)-benzo[b]furan], |
| 219 | 1-(3-methylthio-7-hydro-6H-benzo[c]thien-1-yl)carbonyl-5'-aminomethyl-spiro[piperidine-4,3'-(2H)-benzo[b]furan], |
| 220 | 1-[5-(2-methyl-furan-3-yl-carbonylaminomethyl)-furan-2-yl]carbonyl-5'-aminomethyl-spiro[piperidine-4,3'-(2H)-benzo[b]furan], |
| 221 | 1-[5-(3,5-dimethyl-4-chloro-pyrazol-1-yl)-furan-2-yl]carbonyl-5'-aminomethyl-spiro[piperidine-4,3'-(2H)-benzo[b]furan], |
| 222 | 1-(3-methyl-4-oxo-6-phenyl-5,6,7-trihydro-4H-benzo[b]furan-2-yl)carbonyl-5'-aminomethyl-spiro[piperidine-4,3'-(2H)-benzo[b]furan], |
| 223 | 1-(3-ethylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 224 | 1-[5-(2-methoxy-4-allyl-phenoxymethyl)-furan-2-yl]carbonyl-5'-aminomethyl-spiro[piperidine-4,3'-(2H)-benzo[b]furan], |
| 225 | 1-(3-isopropylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 227 | 1-[5-(3-methoxy-phenoxymethyl)-furan-2-yl]carbonyl-5'-aminomethyl-spiro[piperidine-4,3'-(2H)-benzo[b]furan], |
| 228 | 1-(3-methyl-6-phenyl-benzo[b]furan-2-yl)carbonyl-5'-aminomethyl-spiro[piperidine-4,3'-(2H)-benzo[b]furan], |
| 229 | 1-(3-butylthio-4-oxo-5,6,7-trihydro-4H-benzo[c]thien-1-yl)carbonyl-5'-aminomethyl-spiro[piperidine-4,3'-(2H)-benzo[b]furan], |
| 230 | 1-(3-chloro-6-bromo-benzo[b]thien-2-yl)carbonyl-5'-aminomethyl-spiro[piperidine-4,3'-(2H)-benzo[b]furan], |
| 231 | 1-(3-sec-butylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |
| 232 | 1-(3-benzylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], |

-continued

| Cpd | Name |
|---|---|
| 233 | 1-thieno[2,3-b]thien-2-ylcarbonyl-5'-aminomethyl-spiro[piperidine-4,3'-(2H)-benzo[b]furan], |
| 234 | 1-(3-methylthio-benzo[c]thien-1-yl)carbonyl-5'-aminomethyl-spiro[piperidine-4,3'-(2H)-benzo[b]furan], |
| 235 | 1-(3-methylthio-4-methoxy-benzo[c]thien-1-yl)carbonyl-5'-aminomethyl-spiro[piperidine-4,3'-(2H)-benzo[b]furan], |
| 236 | 1-indol-3-ylcarbonyl-5'-aminomethyl-spiro[piperidine-4,3'-(2H)-benzo[b]furan], |
| 237 | 1-(1-methyl-indol-3-yl)carbonyl-5'-aminomethyl-spiro[piperidine-4,3'-(2H)-benzo[b]furan], |
| 238 | 1-(5-methoxy-indol-3-yl)carbonyl-5'-aminomethyl-spiro[piperidine-4,3'-(2H)-benzo[b]furan], |
| 239 | 1-(1-benzyl-indol-3-yl)carbonyl-5'-aminomethyl-spiro[piperidine-4,3'-(2H)-benzo[b]furan], |
| 240 | 1-(3-benzylthio-benzo[c]thien-1-yl)carbonyl-5'-aminomethyl-spiro[piperidine-4,3'-(2H)-benzo[b]furan], |
| 241 | 1-(3-benzylthio-7-hydro-6H-benzo[c]thien-1-yl)carbonyl-5'-aminomethyl-spiro[piperidine-4,3'-(2H)-benzo[b]furan], |
| 242 | (Z)-1-(furan-2-ylethenyl)carbonyl-5'-aminomethyl-spiro[piperidine-4,3'-(2H)-benzo[b]furan], |
| 245 | 1-(5-formyl-thien-2-yl)carbonyl-5'-aminomethyl-spiro[piperidine-4,3'-(2H)-benzo[b]furan], |
| 246 | 1-(5,6-dihydro-4H-cyclopenta[b]thien-2-yl)carbonyl-5'-aminomethyl-spiro[piperidine-4,3'-(2H)-benzo[b]furan], |
| 247 | 1-(5-methylthio-thien-2-yl)carbonyl-5'-aminomethyl-spiro[piperidine-4,3'-(2H)-benzo[b]furan], |
| 248 | (E)-1-(1-cyano-2-phenylethenyl)carbonyl-5'-aminomethyl-spiro[piperidine-4,3'-(2H)-benzo[b]furan], |
| 249 | 1-(7-methyl-indol-3-yl)carbonyl-5'-aminomethyl-spiro[piperidine-4,3'-(2H)-benzo[b]furan], |
| 250 | 1-(1-ethyl-7-methyl-indol-3-yl)carbonyl-5'-aminomethyl-spiro[piperidine-4,3'-(2H)-benzo[b]furan], |
| 254 | (E)-1-(thien-2-ylethenyl)carbonyl-5'-aminomethyl-spiro[piperidine-4,3'-(2H)-benzo[b]furan], |
| 255 | (E)-1-(thien-3-ylethenyl)carbonyl-5'-aminomethyl-spiro[piperidine-4,3'-(2H)-benzo[b]furan], |
| 256 | 1-(5-dihydroxymethyl-4-methyl-thien-2-yl)carbonyl-5'-aminomethyl-spiro[piperidine-4,3'-(2H)-benzo[b]furan], |
| 257 | 1-(5,6,7,8-tetrahydro-4H-cyclohepta[b]thien-2-yl)carbonyl-5'-aminomethyl-spiro[piperidine-4,3'-(2H)-benzo[b]furan], |
| 258 | 1-(4-cyano-5-methylthio-thien-2-yl)carbonyl-5'-aminomethyl-spiro[piperidine-4,3'-(2H)-benzo[b]furan], |
| 259 | 1-(4-methyl-5-bromo-thien-2-yl)carbonyl-5'-aminomethyl-spiro[piperidine-4,3'-(2H)-benzo[b]furan], |
| 261 | 1-(3-ethoxy-4-oxo-5,6,7-trihydro-4H-benzo[c]thien-1-yl)carbonyl-5'-aminomethyl-spiro[piperidine-4,3'-(2H)-benzo[b]furan], |
| 265 | (E)-1-(3-hydroxy-phenylethenyl)carbonyl-5'-aminomethyl-spiro[piperidine-4,3'-(2H)-benzo[b]furan], |
| 266 | 1-(5-tert-butyl-thien-2-yl)carbonyl-5'-aminomethyl-spiro[piperidine-4,3'-(2H)-benzo[b]furan], |
| 267 | 1-(5-methoxycarbonyl-thien-2-yl)carbonyl-5'-aminomethyl-spiro[piperidine-4,3'-(2H)-benzo[b]furan], |
| 272 | (E)-1-(2-hydroxy-phenylethenyl)carbonyl-5'-aminomethyl-spiro[piperidine-4,3'-(2H)-benzo[b]furan], |
| 275 | 1-(3,4,5-trichloro-thien-2-yl)carbonyl-5'-aminomethyl-spiro[piperidine-4,3'-(2H)-benzo[b]furan], |
| 276 | 1-(4-trifluoromethyl-6-methyl-1H-thieno[2,3-c]pyrazol-2-yl)carbonyl-5'-aminomethyl-spiro[piperidine-4,3'-(2H)-benzo[b]furan], |
| 277 | 1-(3-thien-2-yl-[1,2,4]oxadiazol-5-yl)carbonyl-5'-aminomethyl-spiro[piperidine-4,3'-(2H)-benzo[b]furan], |
| 278 | 1-(4,5-dibromo-thien-2-yl)carbonyl-5'-aminomethyl-spiro[piperidine-4,3'-(2H)-benzo[b]furan], |
| 280 | 1-(3,4-dichlorophenyl)sulfonyl-5'-aminomethyl-spiro[piperidine-4,3'-(2H)-benzo[b]furan], |
| 281 | (E)-1-(3-benzyloxy-phenylethenyl)carbonyl-5'-aminomethyl-spiro[piperidine-4,3'-(2H)-benzo[b]furan], |
| 282 | 1-[5-(4-tert-butyl-phenylethynyl)-furan-2-yl]carbonyl-5'-aminomethyl-spiro[piperidine-4,3'-(2H)-benzo[b]furan], |
| 283 | 1-(1-phenylsulfonyl-1H-indol-2-yl)carbonyl-5'-aminomethyl-spiro[piperidine-4,3'-(2H)-benzo[b]furan], |
| 284 | 1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan], |
| 285 | 1-1H-indol-2-ylcarbonyl-5'-aminomethyl-spiro[piperidine-4,3'-(2H)-benzo[b]furan], |
| 286 | 1-3H-inden-1-ylcarbonyl-5'-aminomethyl-spiro[piperidine-4,3'-(2H)-benzo[b]furan], |
| 288 | 1-(4-phenyl-thien-2-yl)carbonyl-5'-aminomethyl-spiro[piperidine-4,3'-(2H)-benzo[b]furan], |

| Cpd | Name |
|---|---|
| 290 | 1-(1-oxo-2,2-diphenyl-ethyl)-5'-aminomethyl-spiro[piperidine-4,3'-(2H)-benzo[b]furan], |
| 291 | (E)-1-[3-(2-methoxy-ethoxy)-phenylethenyl]carbonyl-5'-aminomethyl-spiro[piperidine-4,3'-(2H)-benzo[b]furan], |
| 294 | (E)-1-(3-phenethoxy-phenylethenyl)carbonyl-5'-aminomethyl-spiro[piperidine-4,3'-(2H)-benzo[b]furan], |
| 295 | 1-(4-phenyl-5-trifluoromethyl-thien-2-yl)carbonyl-5'-aminomethyl-spiro[piperidine-4,3'-(2H)-benzo[b]furan], |
| 298 | 1-(1-chloro-naphtho[2,1-b]thien-2-yl)carbonyl-5'-aminomethyl-spiro[piperidine-4,3'-(2H)-benzo[b]furan], |
| 299 | 1-[3-(4-chloro-phenyl)-5-methylthio-thien-2-yl]carbonyl-5'-aminomethyl-spiro[piperidine-4,3'-(2H)-benzo[b]furan], |
| 302 | (E)-1-[3-(2-ethoxy-ethoxy)-phenylethenyl]carbonyl-5'-aminomethyl-spiro[piperidine-4,3'-(2H)-benzo[b]furan], |
| 303 | 1-(3-methyl-4-bromo-5-propoxy-thien-2-yl)carbonyl-5'-aminomethyl-spiro[piperidine-4,3'-(2H)-benzo[b]furan], |
| 304 | 1-(5-phenylethynyl-furan-2-yl)carbonyl-5'-formylaminomethyl-spiro[piperidine-4,3'-(2H)-benzo[b]furan], |
| 306 | 1-(5-phenylethynyl-furan-2-yl)carbonyl-5'-[hydroxyamino(imino)methyl]-spiro[piperidine-4,3'-(2H)-benzo[b]furan], |
| 307 | 1-(5-phenylethynyl-furan-2-yl)carbonyl-5'-[hydrazino(imino)methyl]-spiro[piperidine-4,3'-(2H)-benzo[b]furan], |
| 309 | (E)-1-(2-fluoro-phenylethenyl)carbonyl-5'-aminomethyl-spiro[piperidine-4,3'-(2H)-benzo[b]furan], |
| 310 | 1-(5-phenylethynyl-furan-2-yl)carbonyl-5'-[methylamino(imino)methyl]-spiro[piperidine-4,3'-(2H)-benzo[b]furan], |
| 311 | 1-(5-phenylethynyl-furan-2-yl)carbonyl-5'-aminomethyl-6'-fluoro-spiro[piperidine-4,3'-(2H)-benzo[b]furan], |
| 312 | (E)-1-(2,3-difluoro-phenylethenyl)carbonyl-5'-aminomethyl-spiro[piperidine-4,3'-(2H)-benzo[b]furan], |
| 313 | 1-(5-phenylethynyl-furan-2-yl)carbonyl-5'-[dimethylamino(imino)methyl]-spiro[piperidine-4,3'-(2H)-benzo[b]furan], |
| 315 | 1-(3,4-dichlorophenyl)carbonyl-2'-oxo-5'-aminomethyl-spiro[piperidine-4,3'-(2H)-indole], |
| 316 | 1-(5-phenylethynyl-furan-2-yl)carbonyl-1'-oxo-2'-(2,4-dimethoxy-benzyl)-5'-aminomethyl-spiro[piperidine-4,3'-1H-isoindole], |
| 317 | 1-(5-phenylethynyl-furan-2-yl)carbonyl-1'-oxo-5'-aminomethyl-spiro[piperidine-4,3'-1H-isoindole], |
| 318 | 1-(5-phenylethynyl-furan-2-yl)carbonyl-spiro[piperidine-4,3'-indane], |
| 319 | 1-(5-phenylethynyl-furan-2-yl)carbonyl-5'-aminomethyl-spiro[piperidine-4,3'-(2H)-indole], |
| 320 | 1-(5-phenylethynyl-furan-2-yl)carbonyl-1'-ethyl-5'-aminomethyl-spiro[piperidine-4,3'-(2H)-indole], |
| 321 | 1-(5-phenylethynyl-furan-2-yl)carbonyl-1'-(2-methoxycarbonyl-ethyl)-5'-aminomethyl-spiro[piperidine-4,3'-(2H)-indole], |
| 322 | 1-(5-phenylethynyl-furan-2-yl)carbonyl-1'-(2-carboxy-ethyl)-5'-aminomethyl-spiro[piperidine-4,3'-(2H)-indole], |
| 323 | 1-(5-phenylethynyl-furan-2-yl)carbonyl-1'-methoxycarbonyl-5'-aminomethyl-spiro[piperidine-4,3'-(2H)-indole], |
| 324 | 1-(5-phenylethynyl-furan-2-yl)carbonyl-1'-(4-carboxy-phenyl)sulfonyl-5'-aminomethyl-spiro[piperidine-4,3'-(2H)-indole], |
| 325 | 1-(5-phenylethynyl-furan-2-yl)carbonyl-1'-aminocarbonyl-5'-aminomethyl-spiro[piperidine-4,3'-(2H)-indole], |
| 326 | 1-(5-phenylethynyl-furan-2-yl)carbonyl-5'-aminomethyl-spiro[piperidine-4,3'-(2H)-indole]-1'-(2-ethyl-phosphonic acid), |
| 327 | 1-(5-phenylethynyl-furan-2-yl)carbonyl-1'-hydroxysulfonyl-5'-aminomethyl-spiro[piperidine-4,3'-(2H)-indole], |
| 328 | 1-(5-phenylethynyl-furan-2-yl)carbonyl-1'-(3-methoxycarbonyl-phenyl)carbonyl-5'-aminomethyl-spiro[piperidine-4,3'-(2H)-indole], |
| 329 | 1-(5-phenylethynyl-furan-2-yl)carbonyl-1'-(2-ethoxy-1,2-dioxo-ethyl)-5'-aminomethyl-spiro[piperidine-4,3'-(2H)-indole], |
| 330 | 1-(5-phenylethynyl-furan-2-yl)carbonyl-1'-(2-1H-tetrazol-5-yl-1-oxo-ethyl)-5'-aminomethyl-spiro[piperidine-4,3'-(2H)-indole], |
| 331 | 1-(5-phenylethynyl-furan-2-yl)carbonyl-1'-(3-carboxy-phenyl)sulfonyl-5'-aminomethyl-spiro[piperidine-4,3'-(2H)-indole], |
| 332 | 1-(5-phenylethynyl-furan-2-yl)carbonyl-1'-[4-ethoxy-2-(methylamino)amino-1,4-dioxo-butyl]-5'-aminomethyl-spiro[piperidine-4,3'-(2H)-indole], |
| 333 | 1-(5-phenylethynyl-furan-2-yl)carbonyl-1'-(methylsulfonylmethyl)carbonyl-5'-aminomethyl-spiro[piperidine-4,3'-(2H)-indole], |
| 334 | 1-(5-phenylethynyl-furan-2-yl)carbonyl-1'-(1H-tetrazol-5-yl)carbonyl-5'-aminomethyl-spiro[piperidine-4,3'-(2H)-indole], |
| 335 | 1-(5-phenylethynyl-furan-2-yl)carbonyl-1'-(hydroxysulfonylmethyl)carbonyl-5'-aminomethyl-spiro[piperidine-4,3'-(2H)-indole], |
| 336 | 1-(5-phenylethynyl-furan-2-yl)carbonyl-1'-(1-methyl-imidazol-4-yl)sulfonyl-5'-aminomethyl-spiro[piperidine-4,3'-(2H)-indole], |
| 337 | 1-(5-phenylethynyl-furan-2-yl)carbonyl-1'-(5-carboxy-furan-2-yl)sulfonyl-5'-aminomethyl-spiro[piperidine-4,3'-(2H)-indole], |

| Cpd | Name |
|---|---|
| 338 | 1-(5-phenylethynyl-furan-2-yl)carbonyl-1'-[5-(N'-methyl-hydrazino)-1,1-dioxo-3,4,5-trihydro-(2H)-thien-3-yl]sulfonyl-5'-aminomethyl-spiro[piperidine-4,3'-(2H)-indole], |
| 339 | 1-(5-phenylethynyl-furan-2-yl)carbonyl-1'-methylcarbonyl-5'-aminomethyl-spiro[piperidine-4,3'-(2H)-indole], |
| 340 | 1-(5-phenylethynyl-furan-2-yl)carbonyl-1'-methylsulfonyl-5'-aminomethyl-spiro[piperidine-4,3'-(2H)-indole], |
| 341 | 1-(5-phenylethynyl-furan-2-yl)carbonyl-1'-phenylsulfonyl-5'-aminomethyl-spiro[piperidine-4,3'-(2H)-indole], |
| 342 | 1-(5-phenylethynyl-furan-2-yl)carbonyl-1'-aminosulfonyl-5'-aminomethyl-spiro[piperidine-4,3'-(2H)-indole], |
| 343 | 1-(5-phenylethynyl-furan-2-yl)carbonyl-1'-[(methoxycarbonyl)methyl]-5'-aminomethyl-spiro[piperidine-4,3'-(2H)-indole], |
| 344 | 1-(5-phenylethynyl-furan-2-yl)carbonyl-1'-(3-methoxycarbonyl-phenyl)sulfonyl-5'-aminomethyl-spiro[piperidine-4,3'-(2H)-indole], |
| 345 | 1-(5-phenylethynyl-furan-2-yl)carbonyl-1'-(5-methoxycarbonyl-furan-2-yl)sulfonyl-5'-aminomethyl-spiro[piperidine-4,3'-(2H)-indole], |
| 346 | 1-(3-methyl-4-bromo-5-propoxy-thien-2-yl)carbonyl-1'-hydroxysulfonyl-5'-aminomethyl-spiro[piperidine-4,3'-(2H)-indole], |
| 347 | 1-(5-phenylethynyl-furan-2-yl)carbonyl-1'-(5-carboxy-thien-3-yl)sulfonyl-5'-aminomethyl-spiro[piperidine-4,3'-(2H)-indole], |
| 348 | 1-(5-phenylethynyl-furan-2-yl)carbonyl-1'-(methylsulfonylmethyl)sulfonyl-5'-aminomethyl-spiro[piperidine-4,3'-(2H)-indole], |
| 349 | 1-(5-phenylethynyl-furan-2-yl)carbonyl-1'-(N'-methylhydrazino-carbonylmethyl)sulfonyl-5'-aminomethyl-spiro[piperidine-4,3'-(2H)-indole], |
| 350 | 1-(3-methylthio-benzo[c]thien-1-yl)carbonyl-1'-hydroxysulfonyl-5'-aminomethyl-spiro[piperidine-4,3'-(2H)-indole], |
| 351 | 1-(4,5-dibromo-thien-2-yl)carbonyl-1'-hydroxysulfonyl-5'-aminomethyl-spiro[piperidine-4,3'-(2H)-indole], |
| 353 | 1-(3,4-dichlorophenyl)carbonyl-5'-aminomethyl-spiro[piperidine-4,3'-(2H)-benzo[b]thiophene], |
| 354 | 1-(2,2-diphenylethyl)carbonyl-5'-aminomethyl-spiro[piperidine-4,3'-(2H)-benzo[b]furan], |
| 355 | 1-(9H-fluoren-9-ylmethyl)carbonyl-5'-aminomethyl-spiro[piperidine-4,3'-(2H)-benzo[b]furan], |
| 356 | (E)-1-(3-methyl-thien-2-ylethenyl)carbonyl-5'-aminomethyl-spiro[piperidine-4,3'-(2H)-benzo[b]furan], |
| 357 | 1-[4-(4-chloro-phenyl)-thien-2-yl]carbonyl-5'-aminomethyl-spiro[piperidine-4,3'-(2H)-benzo[b]furan], |
| 358 | 1-(5-phenylethynyl-furan-2-yl)carbonyl-1'-thien-2-ylsulfonyl-5'-aminomethyl-spiro[piperidine-4,3'-(2H)-indole], and |
| 359 | 1-(5-phenylethynyl-furan-2-yl)carbonyl-1'-thien-3-ylsulfonyl-5'-aminomethyl-spiro[piperidine-4,3'-(2H)-indole]. |

40

A representative compound of Formula (I) or a form thereof includes a compound selected from the group consisting of:

| Cpd | Name |
|---|---|
| 3 | 1-(5-phenylethynyl-furan-2-yl)carbonyl-5'-aminomethyl-spiro[piperidine-4,3'-2H)-(benzo[b]furan], |
| 35 | 1-[5-(2-fluoro-phenylethynyl)-furan-2-yl]carbonyl-5'-aminomethyl-spiro[piperidine-4,3'-(2H)-benzo[b]furan], |
| 65 | 1-(5-phenylethynyl-furan-2-yl)carbonyl-5'-aminoiminomethyl-spiro[piperidine-4,3'-(2H)-benzo[b]furan], |
| 146 | 1-[5-(2-chloro-phenylethynyl)-furan-2-yl]carbonyl-5'-aminomethyl-spiro[piperidine-4,3'-(2H)-benzo[b]furan], |
| 152 | 1-[4-phenylethynyl-pyridin-2-yl]carbonyl-5'-aminomethyl-spiro[piperidine-4,3'-(2H)-benzo[b]furan], |
| 153 | 1-[5-(2-methyl-phenylethynyl)-furan-2-yl]carbonyl-5'-aminomethyl-spiro[piperidine-4,3'-(2H)-benzo[b]furan], |
| 170 | 1-[5-(4-methyl-phenylethynyl)-furan-2-yl]carbonyl-5'-aminomethyl-spiro[piperidine-4,3'-(2H)-benzo[b]furan], |
| 172 | 1-[5-(2,5-dimethyl-phenylethynyl)-furan-2-yl]carbonyl-5'-aminomethyl-spiro[piperidine-4,3'-(2H)-benzo[b]furan], |
| 214 | 1-(3-benzylthio-4-oxo-5,6,7-trihydro-4H-benzo[c]thien-1-yl)carbonyl-5'-aminomethyl-spiro[piperidine-4,3'-(2H)-benzo[b]furan], |
| 218 | 1-(3-methylthio-5,6,7-trihydro-4H-benzo[c]thien-1-yl)carbonyl-5'-aminomethyl-spiro[piperidine-4,3'-(2H)-benzo[b]furan], |
| 219 | 1-(3-methylthio-7-hydro-6H-benzo[c]thien-1-yl)carbonyl-5'-aminomethyl-spiro[piperidine-4,3'-(2H)-benzo[b]furan], |

-continued

| Cpd | Name |
|---|---|
| 229 | 1-(3-butylthio-4-oxo-5,6,7-trihydro-4H-benzo[c]thien-1-yl)carbonyl-5'-aminomethyl-spiro[piperidine-4,3'-(2H)-benzo[b]furan], |
| 234 | 1-(3-methylthio-benzo[c]thien-1-yl)carbonyl-5'-aminomethyl-spiro[piperidine-4,3'-(2H)-benzo[b]furan], |
| 235 | 1-(3-methylthio-4-methoxy-benzo[c]thien-1-yl)carbonyl-5'-aminomethyl-spiro[piperidine-4,3'-(2H)-benzo[b]furan], |
| 240 | 1-(3-benzylthio-benzo[c]thien-1-yl)carbonyl-5'-aminomethyl-spiro[piperidine-4,3'-(2H)-benzo[b]furan], |
| 241 | 1-(3-benzylthio-7-hydro-6H-benzo[c]thien-1-yl)carbonyl-5'-aminomethyl-spiro[piperidine-4,3'-(2H)-benzo[b]furan], |
| 277 | 1-(3-thien-2-yl-[1,2,4]oxadiazol-5-yl)carbonyl-5'-aminomethyl-spiro[piperidine-4,3'-(2H)-benzo[b]furan], |
| 284 | 1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan], |
| 303 | 1-(3-methyl-4-bromo-5-propoxy-thien-2-yl)carbonyl-5'-aminomethyl-spiro[piperidine-4,3'-(2H)-benzo[b]furan], |
| 317 | 1-(5-phenylethynyl-furan-2-yl)carbonyl-1'-oxo-5'-aminomethyl-spiro[piperidine-4,3'-1H-isoindole], |
| 318 | 1-(5-phenylethynyl-furan-2-yl)carbonyl-spiro[piperidine-4,3'-indane], |
| 340 | 1-(5-phenylethynyl-furan-2-yl)carbonyl-1'-methylsulfonyl-5'-aminomethyl-spiro[piperidine-4,3'-(2H)-indole], |
| 341 | 1-(5-phenylethynyl-furan-2-yl)carbonyl-1'-phenylsulfonyl-5'-aminomethyl-spiro[piperidine-4,3'-(2H)-indole], and |
| 342 | 1-(5-phenylethynyl-furan-2-yl)carbonyl-1'-aminosulfonyl-5'-aminomethyl-spiro[piperidine-4,3'-(2H)-indole]. |

Chemical Definitions & Nomenclature

It should also be noted that any atom with unsatisfied valences in the text, schemes, examples, structural formulae and any tables herein is assumed to have the hydrogen atom or atoms to satisfy the valences.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-4}$alkyl" means a saturated branched or straight-chain hydrocarbon radical having from 1 up to 4 carbon atoms in a linear or branched arrangement. The term includes atom groups such as methyl, ethyl, 1-propyl, 2-propyl, 1-butyl, 2-butyl, tert-butyl and the like. An alkyl radical may be attached to a core molecule by any atom where allowed by available valences.

The term "$C_{2-4}$alkenyl" means a saturated branched or straight-chain hydrocarbon radical having from 1 up to 4 carbon atoms in a linear or branched arrangement and at least one double bond between two adjacent straight-chain carbon atoms. The term includes atom groups such as ethenyl, propenyl, butenyl and the like. An alkenyl radical may be attached to a core molecule by any atom where allowed by available valences.

The term "$C_{2-4}$alkynyl" means a saturated branched or straight-chain hydrocarbon radical having from 1 up to 4 carbon atoms in a linear or branched arrangement and at least one triple bond between two adjacent straight-chain carbon atoms. The term includes atom groups such as ethynyl, propynyl, butynyl and the like. An alkynyl radical may be attached to a core molecule by any atom where allowed by available valences.

The term "$C_{1-4}$alkoxy" means an alkyl radical having from 1 up to 4 carbon atoms in a linear or branched arrangement, as in the formula: —O—$C_{1-4}$alkyl. The term includes atom groups such as methoxy, ethoxy, propoxy, butoxy and the like. An alkoxy radical may be attached to a core molecule by any atom where allowed by available valences.

The term "$C_{3-14}$cycloalkyl" means a saturated or partially unsaturated, monocyclic, polycyclic or benzofused hydrocarbon ring system radical. The term also includes $C_{3-8}$cycloalkyl, $C_{5-6}$cycloalkyl, $C_{5-8}$cycloalkyl and benzofused $C_{3-14}$cycloalkyl ring systems. Examples include cyclopropyl, cyclobutyl, cyclopentyl, cyclohexyl, cyclohexyl, cyclohexenyl, cycloheptyl, cyclooctyl, 1H-indenyl, indanyl, 9H-fluorenyl, bicyclo[2.2.1]heptyl, bicyclo[2.2.1]heptanyl and the like. A $C_{3-14}$cycloalkyl radical may be attached to a core molecule by any atom where allowed by available valences.

The term "aryl" means an unsaturated, aromatic monocyclic or polycyclic hydrocarbon ring system radical. Examples of aryl ring systems include phenyl, naphthalenyl, azulenyl, anthracenyl and the like. An aryl radical may be attached to a core molecule by any atom where allowed by available valences.

The term "hetero", when used as a prefix for a ring system, refers to the replacement of at least one carbon atom member in the ring system with a heteroatom selected from N, O, S, S(O), or $SO_2$. A hetero ring may have 1, 2, 3 or 4 carbon atom members replaced by a nitrogen atom. Alternatively, a ring may have 1, 2 or 3 nitrogen atom members and 1 oxygen or sulfur atom member. Alternatively, a ring may have 1 oxygen or sulfur atom member. Alternatively, up to two adjacent ring members may be heteroatoms, wherein one heteroatom is nitrogen and the other heteroatom is selected from N, S or O.

The term "heterocyclyl" means a saturated or partially unsaturated, monocyclic or polycyclic "hetero" ring system radical. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl, 2,5-diaza-bicyclo[2.2.1]heptanyl, 2-oxa-5-aza-bicyclo[2.2.1]heptanyl and the like. A heterocyclyl radical may be attached to a core molecule by any atom where allowed by available valences.

The term "heterocyclyl" also includes a benzofused-heterocyclyl ring system radical. The term "benzofused-heterocyclyl" means a heterocyclyl ring system radical having a benzene ring fused on the ring system on adjacent carbons, such as indolinyl (also referred to as 2,3-dihydro-indolyl), benzo[1,3]dioxolyl, 2,3-dihydro-1,4-benzodioxinyl, 2,3-dihydro-benzofuranyl, 1,2-dihydro-phthalazinyl and the like. A benzofused-heterocyclyl radical may be attached to a core molecule by any atom where allowed by available valences.

The term "heteroaryl" means an unsaturated monocyclic, polycyclic aromatic "hetero" ring system radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like. A heteroaryl radical may be attached to a core molecule by any atom where allowed by available valences.

The term "heteroaryl" also includes a benzofused-heteroaryl ring system radical. The term "benzofused-heteroaryl" means a heteroaryl ring system radical having a benzene ring fused on the ring system on adjacent carbons, such as indolizinyl, indolyl, azaindolyl, isoindolyl, benzofuranyl, benzothienyl, indazolyl, azaindazolyl, benzoimidazolyl, benzothiazolyl, benzoxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. A benzofused-heteroaryl radical may be attached to a core molecule by any atom where when allowed by available valences.

The term "$C_{1-4}$alkoxy$C_{1-4}$alkoxy" means a radical of the formula: —O—$C_{1-4}$alkyl-O—$C_{1-4}$alkyl.

The term "$C_{1-4}$alkoxy$C_{1-4}$alkyl" means a radical of the formula: —$C_{1-4}$alkyl-O—$C_{1-4}$alkyl.

The term "$C_{1-4}$alkoxycarbonyl" means a radical of the formula: —C(O)—O—$C_{1-4}$alkyl.

The term "$C_{1-4}$alkoxycarbonyl$C_{1-4}$alkyl" means a radical of the formula: —$C_{1-4}$alkyl-C(O)—O—$C_{1-4}$alkyl.

The term "$C_{1-4}$alkoxycarbonyl$C_{1-4}$alkylcarbonyl" means a radical of the formula: —C(O)—$C_{1-4}$alkyl-C(O)—O—$C_{1-4}$alkyl.

The term "$C_{1-4}$alkoxycarbonyl$C_{1-4}$alkylsulfonyl" means a radical of the formula: —$SO_2$—$C_{1-4}$alkyl-C(O)—O—$C_{1-4}$alkyl.

The term "$C_{1-4}$alkoxycarbonylcarbonyl" means a radical of the formula: —C(O)—C(O)—O—$C_{1-4}$alkyl.

The term "($C_{1-4}$alkyl)aminoamino" means a radical of the formula: —NH—NH—$C_{1-4}$alkyl.

The term "$C_{1-4}$alkylcarbonyl" means a radical of the formula: —C(O)—$C_{1-4}$alkyl.

The term "$C_{1-4}$alkylcarbonylamino" means a radical of the formula: —NH—C(O)—$C_{1-4}$alkyl.

The term "$C_{1-4}$alkylsulfonyl" means a radical of the formula: —$SO_2$—$C_{1-4}$alkyl.

The term "$C_{1-4}$alkylsulfonyl$C_{1-4}$alkylcarbonyl" means a radical of the formula: —C(O)—$C_{1-4}$alkyl-$SO_2$—$C_{1-4}$alkyl.

The term "$C_{1-4}$alkylsulfonyl$C_{1-4}$alkylsulfonyl" means a radical of the formula: —$SO_2$—$C_{1-4}$alkyl-$SO_2$—$C_{1-4}$alkyl.

The term "$C_{1-4}$alkylthio" means a radical of the formula: —S—$C_{1-4}$alkyl.

The terms "amino," "($C_{1-4}$alkyl)amino" and "($C_{1-4}$alkyl)$_2$-amino" mean a radical of the formula: —$NH_2$, —NH—$C_{1-4}$alkyl and —N($C_{1-4}$alkyl)$_2$, respectively.

The terms "amino$C_{1-4}$alkyl," "($C_{1-4}$alkyl)amino$C_{1-4}$alkyl," "($C_{1-4}$alkyl)$_2$-amino$C_{1-4}$alkyl" and "($C_{1-4}$alkyl)$_3$-amino$C_{1-4}$alkyl" mean a radical of the formula: —$C_{1-4}$alkyl-$NH_2$, —$C_{1-4}$alkyl-NH—$C_{1-4}$alkyl, —$C_{1-4}$alkyl-N($C_{1-4}$alkyl)$_2$ and —$C_{1-4}$alkyl-$N^+$($C_{1-4}$alkyl)$_3$, respectively.

The term "aminocarbonyl" means a radical of the formula: —C(O)—$NH_2$.

The terms "aminoimino," "hydroxyaminoimino," "($C_{1-4}$alkyl)aminoimino," "($C_{1-4}$alkyl)$_2$-aminoimino" and "aminoaminoimino" mean a radical of the formula: —C(NH)—$NH_2$, —C(NH)—NHOH, —C(NH)—N($C_{1-4}$alkyl), —C(NH)—N($C_{1-4}$alkyl)$_2$ and —C(NH)—NH—$NH_2$, respectively.

The terms "aminosulfonyl," "($C_{1-4}$alkyl)aminosulfonyl" and "($C_{1-4}$alkyl)$_2$-aminosulfonyl" mean a radical of the formula: —$SO_2$—$NH_2$, —$SO_2$—NH—$C_{1-4}$alkyl and —$SO_2$—N($C_{1-4}$alkyl)$_2$, respectively.

The term "aminosulfonylamino$C_{1-4}$alkyl" means a radical of the formula: —$C_{1-4}$alkyl-NH—$SO_2$—$NH_2$.

The term "aminothiocarbonylamino" means a radical of the formula: —NH—C(S)—$NH_2$.

The term "aryl$C_{1-4}$alkoxy" means a radical of the formula: —O—$C_{1-4}$alkyl-aryl The terms "aryl$C_{1-4}$alkyl" and "(aryl)$_{1-2}$$C_{1-4}$alkyl" mean a radical of the formula: —$C_{1-4}$alkyl-aryl and —$C_{1-4}$alkyl-(aryl)$_{1-2}$, respectively, wherein $C_{1-4}$alkyl is substituted on one or more available carbon chain atoms with one or more aryl radicals when allowed by available valences or as indicated by a subscript integer.

The term "aryl$C_{1-4}$alkylamino" means a radical of the formula: —NH—$C_{1-4}$alkyl-aryl.

The term "aryl$C_{1-4}$alkylamino$C_{1-4}$alkyl" means a radical of the formula: —$C_{1-4}$alkyl-NH—$C_{1-4}$alkyl-aryl.

The term "aryl$C_{1-4}$alkylcarbonylamino$C_{1-4}$alkyl" means a radical of the formula: —$C_{1-4}$alkyl-NH—C(O)—$C_{1-4}$alkyl-aryl.

The term "aryl$C_{1-4}$alkylthio" means a radical of the formula: —S—$C_{1-4}$alkyl-aryl.

The term "aryl$C_{1-4}$alkylthio$C_{1-4}$alkyl" means a radical of the formula: —$C_{1-4}$alkyl-S—$C_{1-4}$alkyl-aryl.

The term "aryl$C_{2-4}$alkenyl" means a radical of the formula: —$C_{2-4}$alkenyl-aryl.

The term "aryl$C_{2-4}$alkenylcarbonylamino$C_{1-4}$alkyl" means a radical of the formula: —$C_{1-4}$alkyl-NH—C(O)—$C_{2-4}$alkenyl-aryl.

The term "aryl$C_{2-4}$alkynyl" means a radical of the formula: —$C_{2-4}$alkynyl-aryl.

The term "aryl$C_{2-4}$alkynylcarbonylamino$C_{1-4}$alkyl" means a radical of the formula: —$C_{1-4}$alkyl-NH—C(O)—$C_{2-4}$alkynyl-aryl.

The term "arylcarbonyl" means a radical of the formula: —C(O)-aryl.

The term "arylcarbonylamino$C_{1-4}$alkyl" means a radical of the formula: —$C_{1-4}$alkyl-NH—C(O)-aryl.

The term "aryloxy" means a radical of the formula: —O-aryl

The term "aryloxy$C_{1-4}$alkyl" means a radical of the formula: —$C_{1-4}$alkyl-O-aryl The term "arylsulfonyl" means a radical of the formula: —$SO_2$-aryl.

The term "arylsulfonylamino" means a radical of the formula: —NH—$SO_2$-aryl.

The term "arylsulfonylamino$C_{1-4}$alkyl" means a radical of the formula: —$C_{1-4}$alkyl-NH—$SO_2$-aryl.

The term "arylthio" means a radical of the formula: —S-aryl

The term "carbonyl" means a radical of the formula: —C(O)—.

The term "carboxy" means a radical of the formula: —C(O)OH.

The term "carboxyC$_{1-4}$alkyl" means a radical of the formula: —C$_{1-4}$alkyl-C(O)OH.

The term "C$_{3-14}$cycloalkylC$_{1-4}$alkyl" means a radical of the formula: —C$_{1-4}$alkyl-C$_{3-14}$cycloalkyl.

The term "C$_{3-14}$cycloalkylcarbonylaminoC$_{1-4}$alkyl" means a radical of the formula: —C$_{1-4}$alkyl-NH—C(O)—C$_{3-14}$cycloalkyl.

The term "C$_{3-14}$cycloalkylC$_{1-4}$alkenyl" means a radical of the formula: —C$_{1-4}$alkyl-NH—C(O)-methenylene-C$_{3-14}$cycloalkyl and —C$_{1-4}$alkyl-NH—C(O)—C$_{2-4}$alkenyl-C$_{3-14}$cycloalkyl.

The term "C$_{3-14}$cycloalkylC$_{2-4}$alkenylcarbonylaminoC$_{1-4}$alkyl" means a radical of the formula: —C$_{1-4}$alkyl-NH—C(O)—C$_{2-4}$alkenyl-C$_{3-14}$cycloalkyl.

The term "formyl" means a radical of the formula: —C(O)H.

The term "formylaminoC$_{1-4}$alkyl" means a radical of the formula: —C$_{1-4}$alkyl-NH—C(O)H.

The term "halogen" or "halo" means the group chloro, bromo, fluoro or iodo.

The terms "haloC$_{1-4}$alkoxy," "haloC$_{1-4}$alkyl" and "haloC$_{1-4}$ alkylthio" mean a radical of the formula: —O—C$_{1-4}$ alkyl-halo, —C$_{1-4}$alkyl-halo and —S—C$_{1-4}$alkyl-halo, respectively, wherein C$_{1-4}$alkyl is substituted on one or more available carbon atoms with one or more halo atoms when allowed by available valences.

The term "heteroarylC$_{1-4}$alkyl" means a radical of the formula: —C$_{1-4}$alkyl-heteroaryl.

The term "heteroarylC$_{1-4}$alkylcarbonyl" means a radical of the formula: —C(O)—C$_{1-4}$alkyl-heteroaryl.

The term "heteroarylC$_{1-4}$alkylcarbonylamino" means a radical of the formula: —NH—C(O)—C$_{1-4}$alkyl-heteroaryl.

The term "heteroarylC$_{2-4}$alkenyl" means a radical of the formula: —C$_{2-4}$alkenyl-heteroaryl.

The term "heteroarylC$_{2-4}$alkenylcarbonylaminoC$_{1-4}$alkyl" means a radical of the formula: —C$_{1-4}$alkyl-NH—C(O)—C$_{2-4}$ alkenyl-heteroaryl.

The term "heteroarylcarbonyl" means a radical of the formula: —C(O)-heteroaryl.

The term "heteroarylcarbonylaminoC$_{1-4}$alkyl" means a radical of the formula: —C$_{1-4}$alkyl-NH—C(O)-heteroaryl.

The term "heteroarylsulfonyl" means a radical of the formula: —SO$_2$-heteroaryl.

The term "heteroarylthio" means a radical of the formula: —S-heteroaryl.

The term "heteroarylthioC$_{1-4}$alkyl" means a radical of the formula: —C$_{1-4}$alkyl-5-heteroaryl.

The term "heterocyclylcarbonylaminoC$_{1-4}$alkyl" means a radical of the formula: —C$_{1-4}$alkyl-NH—C(O)-heterocyclyl.

The term "heteroaryl-heteroaryl" means a radical of the formula: -heteroaryl-heteroaryl, wherein a heteroaryl ring is substituted on an available carbon atom with a second heteroaryl ring.

The term "heterocyclylC$_{1-4}$alkyl" means a radical of the formula: —C$_{1-4}$alkyl-heterocyclyl.

The term "heterocyclylC$_{1-4}$alkylcarbonylaminoC$_{1-4}$alkyl" means a radical of the formula: —C$_{1-4}$alkyl-NH—C(O)—C$_{1-4}$ alkyl-heterocyclyl.

The term "heterocyclylC$_{1-4}$alkenyl" means a radical of the formula: -methenylene-heterocyclyl and —C$_{2-4}$alkenyl-heterocyclyl.

The term "heterocyclylC$_{1-4}$alkenylcarbonylaminoC$_{1-4}$alkyl" means a radical of the formula: —C$_{1-4}$alkyl-NH—C(O)-methenylene-heterocyclyl and —C$_{1-4}$alkyl-NH—C(O)—C$_{2-4}$alkenyl-heterocyclyl.

The term "heterocyclylcarbonyl" means a radical of the formula: —C(O)-heterocyclyl.

The term "heterocyclylsulfonyl" means a radical of the formula: —SO$_2$-heterocyclyl.

The term "hydroxyC$_{1-4}$alkyl" means a radical of the formula: —C$_{1-4}$alkyl-hydroxy, wherein C$_{1-4}$alkyl is substituted on one or more available carbon atoms with one or more hydroxy groups when allowed by available valences.

The term "hydroxysulfonyl" means a radical of the formula: —SO$_2$—OH.

The term "hydroxysulfonylC$_{1-4}$alkylcarbonyl" means a radical of the formula: —C(O)—C$_{1-4}$alkyl-SO$_2$—OH.

The term "nitro" means a radical of the formula: —NO$_2$.

The term "oxo" means a radical of the formula: =O.

The term "P[(O)(OH)$_2$]-C$_{1-4}$alkyl" means a radical of the formula: —C$_{1-4}$alkyl-{P[(O)(OH)$_2$]}.

The term "sulfonyl" means a radical of the formula: —SO$_2$—.

The term "substituted" means the independent replacement of one or more hydrogen atoms within a radical with that amount of substituents allowed by available valences.

The term "each instance" means that substitution may occur on a variable when the variable is referred to in any configuration. For example, the term "wherein each instance of heteroaryl is substituted" means that substitution may occur as indicated on the heteroaryl ring in each instance heteroaryl is referred to in a heteroaryl, (heteroaryl)aryl or (heteroaryl)heteroaryl substituent. When the term "each instance" is not used, substitution may occur only on the variable referred to.

The term "each selected from" means that, for a variable having multiple substituents, each substituent may be independently selected from the indicated group.

In general, IUPAC nomenclature rules are used herein.

Compound Forms

The term "about," whether used explicitly or not in reference to a quantitative expression given herein, means that every quantity given herein qualified with the term or otherwise is meant to refer both to the actual given value and the approximation to such given value that would reasonably be inferred based on the ordinary skill in the art, including approximations due to experimental and/or measurement conditions for such given value.

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the present invention may also be present in the form of pharmaceutically acceptable salts. For use in medicine, the salts of the compounds of this invention refer to non-toxic "pharmaceutically acceptable salts" (*Ref International J. Pharm.,* 1986, 33, 201-217; *J. Pharm. Sci.,* 1997 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Therapeutic Use

The compounds of Formula (I) are useful for treating inflammatory disorders such as immunomediated inflammatory disorders and mast cell mediated inflammatory disorders. Examples of immunomediated inflammatory disorders for which the compounds of the present invention are useful include, but are not limited to, asthma, allergic rhinitis, rheumatoid arthritis, rheumatoid spondylitis, osteoarthritis, gouty arthritis, arthritic conditions in general (i.e., arthritis), peptic ulcers, ocular and vernal conjunctivitis, inflammatory bowel disease, chronic obstructive pulmonary disease ("COPD"; see Grashoff, W. F. et al., *American Journal of Pathology*, 151(6):1785-90, December 1997), Crohn's disease, urticaria, bullous pemphiguoid, schleroderma, fibrosis, dermatitis, psoriasis, angioedema, eczematous dermatitis, anaphylaxis, hyperproliferative skin disease, inflammatory skin conditions, hepatic cirrhosis, glomerulonephritis, nephritis, vascular inflammation, atherosclerosis or restenosis.

The compounds of Formula (I) have also been shown to be effective in causing skin depigmentation and therefore may be useful in the treatment and/or prevention of skin hyperpigmentation.

The compounds of Formula (I) also function as inhibitors of thrombin and factor Xa. Consequently, they may be useful for the treatment of thrombin and/or factor Xa mediated disorders, such as thrombosis.

Therapeutic agents that may be useful for administration in combination with compounds of Formula (I) include β-adrenergic agonists (e.g. albuterol, terbutaline, formoterol, fenoterol, prenaline and the like) methylxanthines (e.g. caffeine, theophylline, aminophylline, theobromine, and the like) and corticosteroids (e.g. beclomethasome, triamcinolone, flurisolide, dexamethasone, hydrocortisone, prednisone and the like). In general, one of ordinary skill in the art, acting in reliance upon personal knowledge and the disclosure of this application, will be able to ascertain the amounts of these respective therapeutic agents and the amount of the compound of Formula (I) which should be administered to a subject to treat a given immunomediated inflammatory disease.

The present invention is directed to a method for treating a tryptase mediated inflammatory, vascular or dermatological condition in a subject in need thereof comprising administering to the subject an effective amount of a compound of Formula (I).

The tryptase mediated inflammatory, vascular or dermatological condition is selected from, but not limited to, inflammatory diseases associated with the respiratory tract, such as asthma and allergic rhinitis, as well as other immunomediated inflammatory disorders, such as rheumatoid arthritis, rheumatoid spondylitis, osteoarthritis, gouty arthritis, peptic ulcers, ocular and vernal conjunctivitis, psoriasis, inflammatory bowel disease, Crohn's disease, chronic obstructive pulmonary disease, urticaria, bullous pemphiguoid, schleroderma, fibrosis, dermatitis, psoriasis, pruritis, angioedema, eczematous dermatitis, anaphylaxis, hyperproliferative skin disease, inflammatory skin conditions, hepatic cirrhosis, glomerulonephritis, nephritis, vascular inflammation, atherosclerosis or restenosis.

The tryptase mediated inflammatory, vascular or dermatological condition is further selected from asthma, allergic rhinitis, inflammatory bowel disease, Crohn's disease or pruritis.

The present invention includes the use of any of the compounds of Formula (I) for the preparation of a medicament for treating a tryptase mediated inflammatory, vascular or dermatological condition in a subject in need thereof.

The term "administering" with respect to the methods of the present invention, refers to a means for treating, ameliorating or preventing a disease as described herein with a compound specifically disclosed or a compound or prodrug thereof, which would obviously be included within the scope of the invention albeit not specifically disclosed for certain of the instant compounds.

Such methods include administering an effective amount of one or more compounds of Formula (I) or a form, composition or medicament thereof at different times during the course of a therapy or concurrently in a combination form. Such methods further include administering an effective amount of one or more compounds of Formula (I) or a form, composition or medicament thereof with one or more agents at different times during the course of a therapy or concurrently in a combination form.

The term "prodrug" refers to a metabolic precursor of a compound of Formula (I) or a form thereof. In general, a prodrug is a functional derivative of a compound which may be inactive when administered to a patient but is readily convertible in vivo into an active metabolite compound.

The term "active metabolite" refers to a metabolic product of a compound that is effective for ameliorating, treating or preventing a thrombin mediated disease, disorder or condition. Conventional procedures for the selection and preparation of suitable prodrug derivatives are described, for example, in "Design of Prodrugs", ed. H. Bundgaard, Elsevier, 1985.

The term "patient" as used herein, refers to an animal, preferably a mammal, most preferably a human, who has been the object of treatment, observation or experiment and is at risk of (or susceptible to) developing a disease or having a disease related to unregulated kinase activity.

The term "effective amount" refers to that amount of active compound or pharmaceutical agent that elicits the biological or medicinal response (such as inhibiting unregulated kinase activity) in a patient's tissue system, animal or human, that is being sought by a researcher, veterinarian, medical doctor, or other clinician.

The effective amount of a compound of Formula (I) exemplified in such a method is from about 0.001 mg/kg/day to about 300 mg/kg/day.

The term "composition" refers to a product containing one or more compounds of Formula (I) or a form thereof (such as a product comprising the specified ingredients in the specified amounts, as well as any product which results, directly or indirectly, from such combinations of the specified ingredients in the specified amounts).

The term "medicament" refers to one or more compounds of Formula (I) or a form thereof used in manufacturing a product for use in ameliorating, treating or preventing a thrombin mediated disease, disorder or condition.

A formulation of a composition or medicament of the present invention is "pharmaceutically acceptable" when the molecular entities and components used therein are of sufficient purity and quality such that, when appropriately administered to an animal or a human, the formulation does not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

Even though the compounds of the present invention (including their pharmaceutically, acceptable salts and pharmaceutically acceptable solvates) can be administered alone, they will generally be administered in admixture with a pharmaceutical carrier, excipient or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

For some applications, the compositions are administered orally in the form of tablets containing excipients such as starch or lactose, or in capsules or ovules either alone or in admixture with excipients, or in the form of elixirs, solutions or suspensions containing flavoring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as tryptase inhibitors is required for a subject in need thereof.

The invention also provides a pharmaceutical or veterinary pack or kit comprising one or more containers filled with one or more of the ingredients of the pharmaceutical and veterinary compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Optimal dosages of the compounds of Formula (I) to be administered for treating a tryptase mediated inflammatory, vascular or dermatological condition may be readily determined by those skilled in the art, and will vary with the particular compound used, the strength of the preparation, the mode of administration, and the advancement of the condition. In addition, factors associated with the particular patient being treated, including patient age, weight, diet and time of administration, will result in the need to adjust dosages.

General Synthetic Methods

Compounds of the present invention may be prepared by the application or adaptation of known methods, meaning methods used heretofore or described in the literature. Examples of such methods are described by R. C. Larock in *Comprehensive Organic Transformations*, $2^{nd}$ ed., John Wiley & Sons Ltd publishers (1999) and in *Comprehensive Organic Synthesis, Volumes* 1-9, Barry M. Trost, Ed., Pergamon Press publishers (1991).

In the reactions used to prepared compounds of the present invention, it may be necessary to protect reactive functional groups, for example, amino groups, in order to avoid their unwanted participation in the reactions. Conventional protecting groups may be used in accordance with standard practice, such as those described by T. W. Greene and P. G. M. Wuts in *Protective Groups in Organic Chemistry*, $3^{rd}$ ed., John Wiley and Sons Ltd publishers (1999).

The compounds of the present invention may be prepared more particularly in accordance with the general synthetic schemes described below. Since each scheme is an illustration, the invention should not be construed as being limited by the particular chemical reactions depicted or the specific reagents, protecting groups, solvents and reaction conditions expressed. The preparation of the various starting materials used in the schemes is well within the skill of persons versed in the art.

Abbreviations used the following sections are listed in the table below.

| Abbreviation | Meaning |
|---|---|
| ACE-Cl | α-chloroethyl chloroformate |
| ACN | Acetonitrile |
| AIBN | 2,2'-azobis(2-methylpropionitrile) |
| (+/−)-BINAP | (+/−)-2,2'-bis(diphenylphosphino)-1,1'-binaphthalene |
| Boc | tert-butyloxycarbonyl |
| BOP | benzotriazol-1-yloxy-tris(dimethylamino)phosphonium hexafluorophosphate |
| BOP-Cl | bis(2-oxo-3-oxazolidinyl)phosphinic chloride, |
| CAS# | Chemical Abstracts Service Registry Number |
| Cbz | benzyloxycarbonyl |
| Cpd | compound |
| DBU | 1,8-diazabicyclo[5.4.0]undec-7-ene |
| DCC | dicyclohexylcarbodiimide |
| DCE | dichloroethane |
| DCM | dichloromethane |
| DIBAL | diisobutylaluminum hydride |
| DIC | N,N'-dicyclohexylcarbodiimide |
| DIPEA | N,N-diisopropylethylamine |
| DMAP | dimethylaminopyridine |
| DMF | N,N-dimethylformamide |
| DMSO | dimethyl sulfoxide |
| EDC | 1-(3-dimethylaminopropyl)-3-ethylcarbodiimide hydrochloride |
| ESI | electrospray ionization |
| $Et_3N$ or TEA | triethylamine |
| EtOAc | ethyl acetate |
| Fmoc | 9-fluorenylmethyloxycarbonyl |
| h/hr/hrs | hour(s) |
| HCl | hydrogen chloride |
| HOAc | glacial acetic acid |
| HOBT | 1-hydroxybenzotriazole hydrate |
| HBTU | O-benzotriazol-1-yloxy-N,N,N',N'-tetramethyluronium hexafluorophosphate |
| LiOH | lithium hydroxide |
| min | minute(s) |
| MS | mass spectroscopy |
| Mtr | 4-methoxy-2,3,6-trimethylbenzenesufonyl |
| NMR | nuclear magnetic resonance spectroscopy |
| PG | protecting group |
| ov | overlapping |
| Pht | phthaloyl |
| PMB | para-methoxylbenzyl |
| PyBrOP | bromotris(pyrrolidino)phosphonium hexafluorophosphate, |
| RT/rt | room temperature |
| TEA | triethylamine |
| Teoc | [2-(trimethylsilyl)ethoxy]carbonyl |
| TFA | trifluoroacetic acid |
| THF | tetrahydrofuran |
| TLC | thin layer chromatography |
| TMS | trimethylsilyl |
| Tos | p-toluenesulfonyl |

Scheme A describes the solution-phase synthesis of certain 5-aminomethyl-spiro[benzofuran-3(2H), 4'-piperidine] derivatives A9 of Formula (I).

Scheme A

Treatment of methyl phenyl sulfoxide with lithium diisopropylamide (LDA) in THF at about −75° C. followed by reaction with 1-Boc-4-piperidone A1 at about 21° C. affords sulfoxide A2. Reaction of A2 with potassium tert-butoxide in refluxing tert-butanol generates allyl alcohol A3 via a [2,3]-sigmatropic rearrangement (WO94/29309). Compound A3 is subsequently reacted with thionyl chloride at about 60° C. for about 25 min to provide allyl chloride A4.

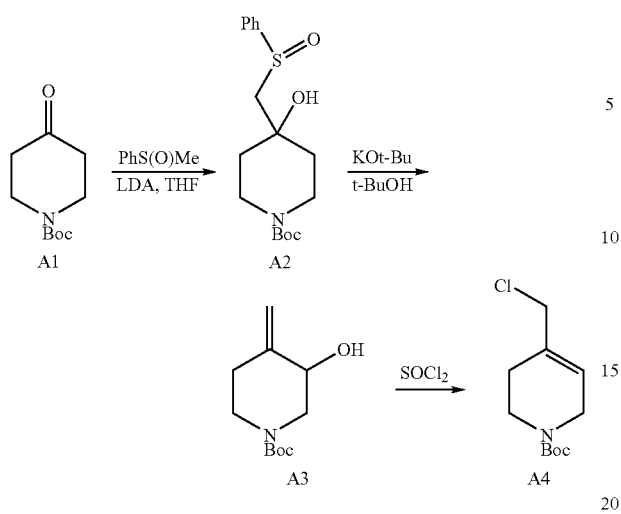

Reaction of compound A4 with 3-bromo-4-hydroxybenzonitrile in the presence of potassium carbonate in acetone furnishes ether A5. Radical-induced cyclization of A5 with tributyltin hydride in the presence of AIBN and PhMe at about 80° C. affords spiro[benzofuran-3(2H), 4'-piperidine A6 (Chen, M.-H.; Abraham, J. A. *Tetrahedron Lett.* 1996, 30, 5233-5234).

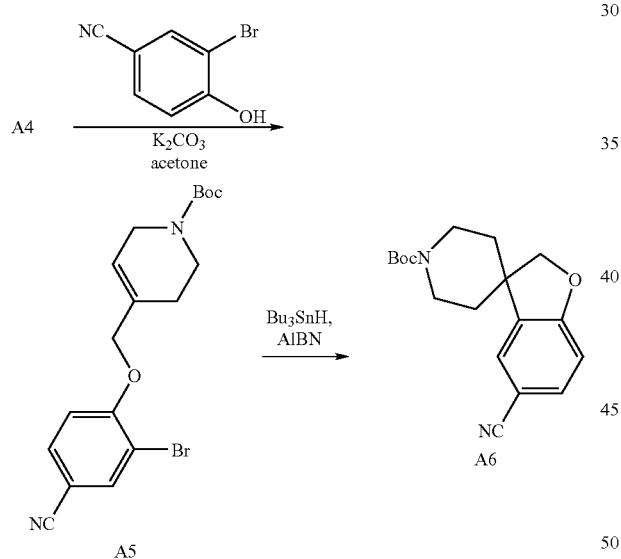

Hydrogenation of the nitrile group of A6 in the presence of Raney Nickel (AT about 60 psig $H_2$) and aqueous 3N sodium hydroxide in EtOH affords benzylamine A7.

Reaction of A7 with a reagent such as phthalic anhydride (Pht) in toluene (PhMe) or N,N-diisopropylethylamine (DIPEA), 9-fluorenyl-methylcarbonyl chloride (Fmoc-Cl) in DIPEA, 2-(trimethylsilyl)ethyl-4-nitrophenyl carbonate (Teoc) in DIPEA followed by removal of the Boc protecting group via HCl or TFA gives A8 as the corresponding salt (where PG represents a protecting group such as Pht, Fmoc or Teoc).

Coupling of A8 in the presence of a base with either carboxylic acids and a coupling agent (such as BOP-Cl) in a mixture with DIPEA and $CH_2Cl_2$ or with acid chlorides and sulfonyl chlorides in a mixture with TEA and THF at about 0° C. then deprotection with methylhydrazine in EtOH at about 40° C. or with piperidine/DMF or with TFA/$CH_2Cl_2$ affords the substituted 5-aminomethyl-spiro[benzofuran-3(2H), 4'-piperidine] A9 of Formula (I).

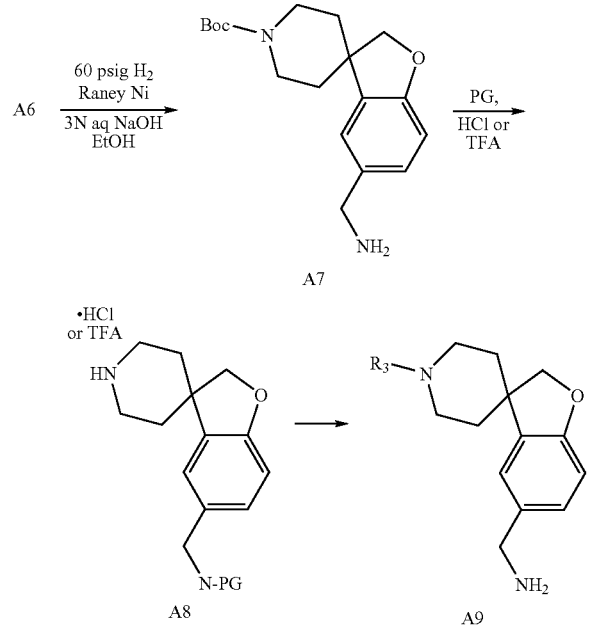

Scheme B describes the solid-phase synthesis of certain 5-aminomethyl-spiro[benzofuran-3(2H), 4'-piperidine] derivatives A9 of Formula (I) as a TFA salt.

Scheme B

Removal of the Boc protecting group from A6 with TFA:$CH_2Cl_2$ followed by reaction of the resulting piperidine with Teoc provides Teoc-protected intermediate B1 (WO/200190101). Hydrogenation of the nitrile moiety in the presence of hydrochloric acid in ethanol affords benzylamine B2 as the hydrochloride salt.

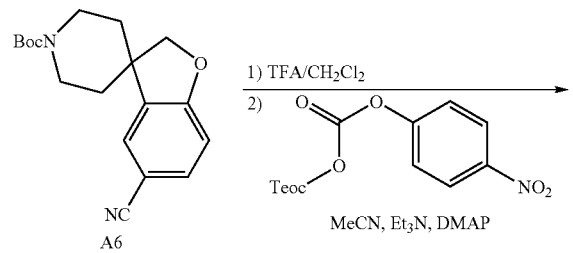

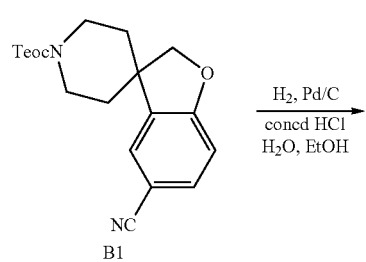

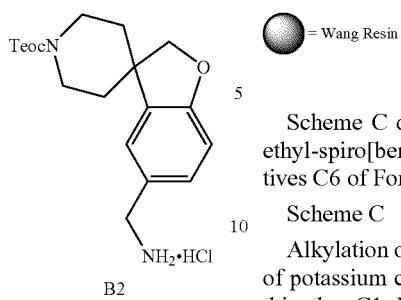

Reaction of B2 with p-nitrophenyl carbonate Wang resin in the presence of DIPEA and 4-dimethylaminopyridine (DMAP) in DMF followed by deprotection with tetrabutylammonium fluoride in THF provides the resin-bound intermediate B3. Coupling of B3 with a carboxylic acid (wherein the —C(O)R portion is incorporated into $R_3$ as a product of the reaction) with N,N'-dicyclohexylcarbodiimide (DIC) and 1-hydroxybenzotriazole hydrate (HOBt) followed by cleavage from the resin with trifluoroacetic acid (TFA) furnishes the 5-aminomethyl-spiro[benzofuran-3(2H), 4'-piperidine] A1 as the TFA salt of Formula (I), wherein $R_3$ is carbonyl.

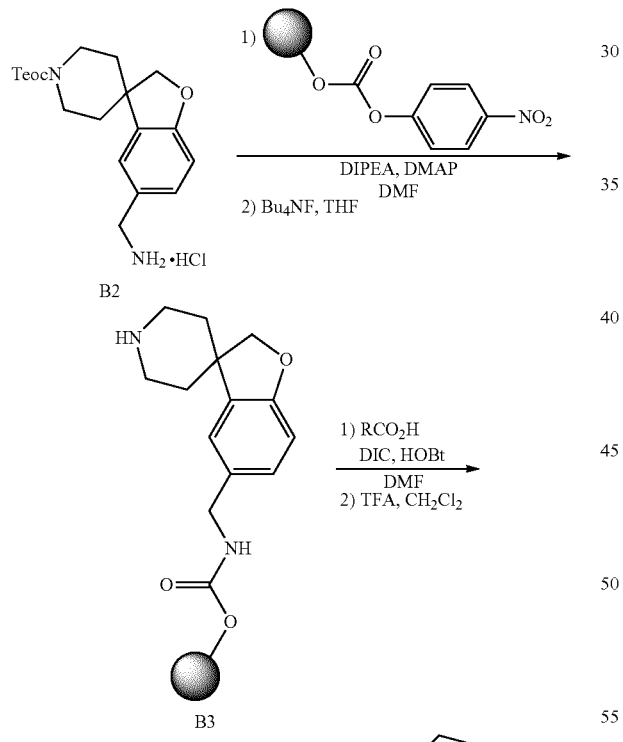

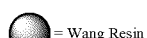 = Wang Resin

Scheme C describes the synthesis of certain 5-aminomethyl-spiro[benzo[b]thiophene-3(2H), 4'-piperidine] derivatives C6 of Formula (I).

Scheme C

Alkylation of 2-bromotihiophenol with A4 in the presence of potassium carbonate in acetone at about 65° C. provides thioether C1. Radical-induced cyclization of C1 with tributyltin hydride in the presence of AlBN in toluene at about 80° C. affords spiro[benzo[b]thiophene-3(2H), 4'-piperidine C2 (Chen, M.-H.; Abraham, J. A. *Tetrahedron Lett.* 1996, 30, 5233-5234).

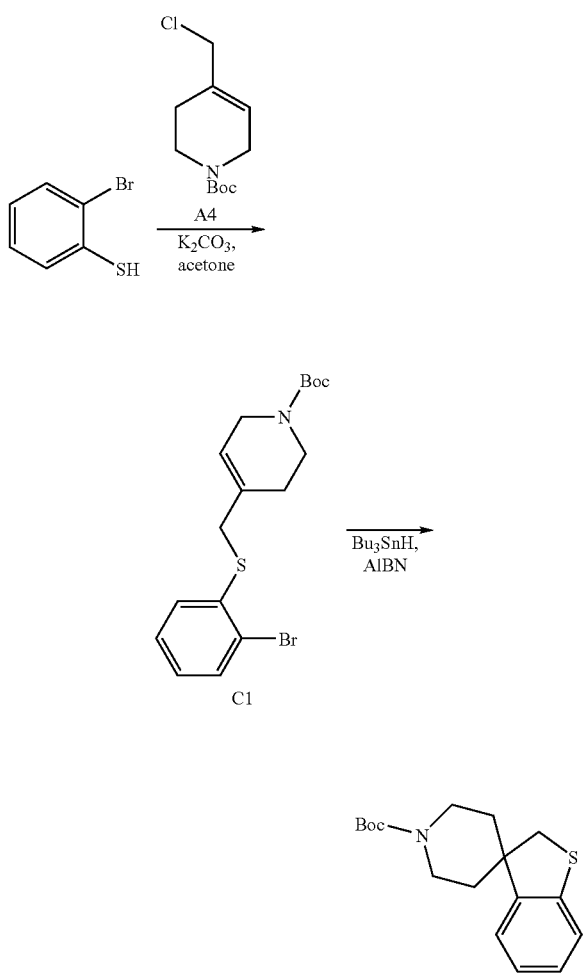

Removal of the Boc-protecting group from C2 with TFA: $CH_2Cl_2$ (1:4) followed by partitioning between 0.1 N aqueous sodium hydroxide and diethyl ether affords the freebase C3. Coupling of C3 with either a carboxylic acid and a coupling agent (such as BOP-Cl) in a mixture with DIPEA and $CH_2Cl_2$ or with a carboxylic acid chloride or a sulfonyl chloride in a mixture with TEA and $CH_2Cl_2$ at about 0° C. furnishes the corresponding amide C4.

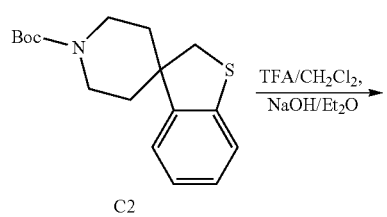

C2

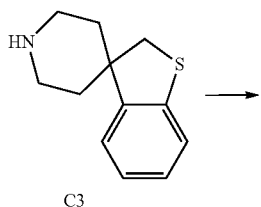

C3

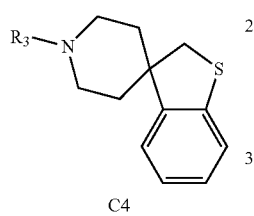

C4

Tscherniac-Einhorn amidomethylation reaction of C4 with N-(hydroxymethyl)phthalimide in either neat trifilic acid at room temperature or a mixture of sulfuric and glacial acetic acids at about 60° C. provides C6. Removal of the phthalyl protecting group with methylhydrazine in ethanol at about 40° C. yields 5-aminomethyl-spiro[benzo[b]-thiophene-3 (2H), 4'-piperidine] derivatives C6 of Formula (I).

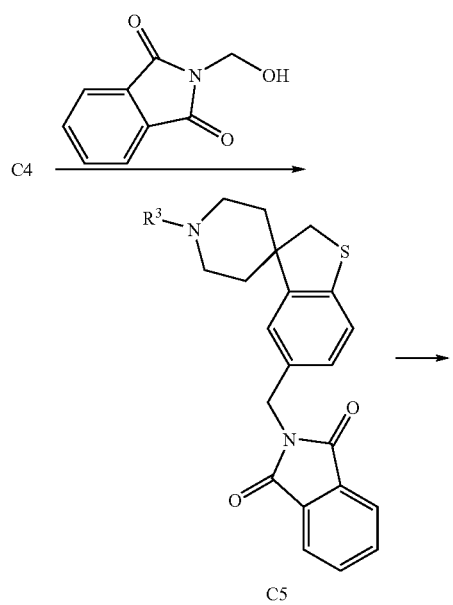

C5

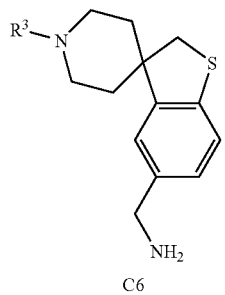

C6

Scheme D describes the synthesis of certain 5-aminomethyl-spiro[indoline-3,4'-piperidines] derivatives D8 of Formula (I).

Scheme D

Spiropiperidine D1 can be prepared according to the published method (Ong H H, Profitt J A, Fortunato J, Glamkowski E J, Ellis D B, Geyer H M, Wilker J C, and Burghard H *J. Med. Chem.*, 1983, 26 (7), 981-986). Reacting D1 with formic acid in refluxing toluene provides formamide D2. A Tscherniac-Einhorn amidomethylation reaction of D2 with N-(hydroxymethyl)phthalimide in neat sulfuric acid at room furnishes D3.

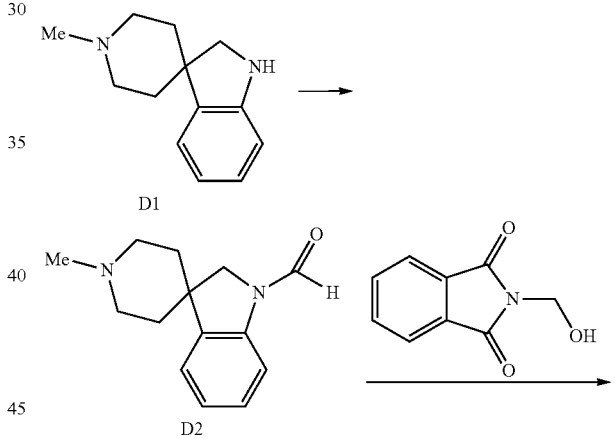

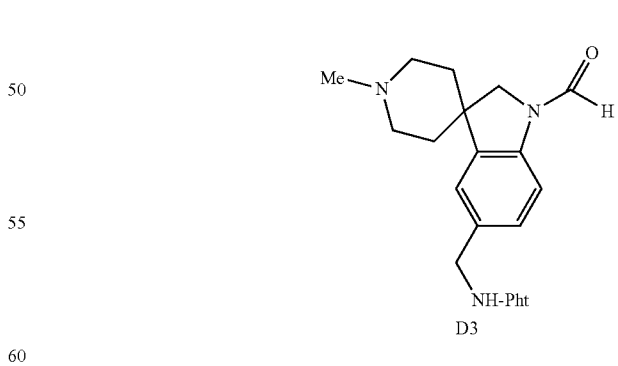

D3

Demethylation of D3 with α-chloroethyl chloroformate in the presence of 1,8-bis(dimethylamino)naphthalene in refluxing dichloroethane affords carbamate D4, which converts to piperidine D5 with hydrochloric acid in refluxing methanol (Olofson, R. A.; Martz, J. T.; Senet, J. P.; Piteau, M.; Malfroot, T. *J. Org. Chem.* 1984, 49(11), 2081-2082).

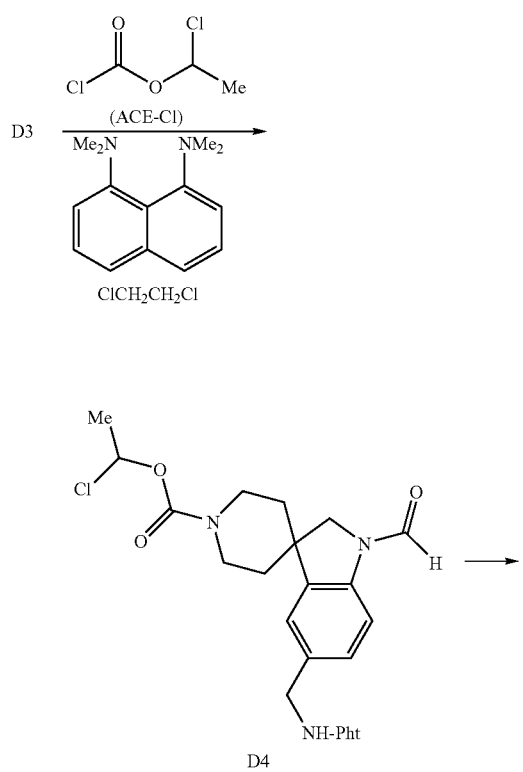

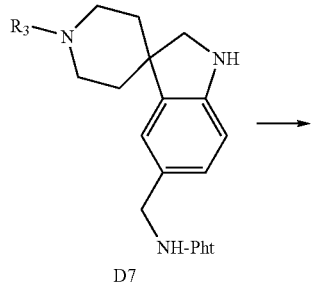

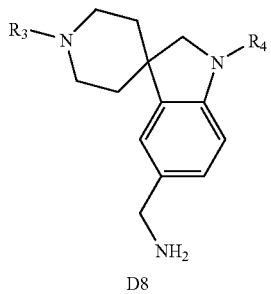

Scheme E describes the synthesis of certain 2,3-dihydrospiro[1H-indene-1,4'-piperidine] derivatives E7 of Formula (I).

Scheme E

Reduction of 5-bromo-1-indanone E1 with sodium borohydride in MeOH followed by dehydration of the resulting alcohol with sulfuric acid in refluxing benzene at about 80° C. affords 6-bromo-1H-indene E2 (CAS# 33065-61-1; see, Young J R, Huang S X, Walsh T F, Wyvratt M J, Yang Y T, Yudkovitz J B, Cui J, Mount G R, Ren R N, Wu T-J, Shen X, Lyons K A, Mao A-H, Carlin J R, Karanam B V, Vincent S H, Cheng K and Goulet M T, *Bioorg. Med. Chem. Lett.* 2002, 12 (5), 827-832).

Treatment of E2 with lithium bis(trimethylsilyl)amide at 0° C. in THF followed by alkylation with N-Boc-N,N-bis(2-chloroethyl)amine provides spiro[1H-indene-1,4'-piperidine] E3 (CAS# 158628-80-9; see, Efange S M N, Khare A B, Foulon C, Akella S K and Parsons S M, *J. Med. Chem.* 1994, 37 (16), 2574-82).

Selective coupling of the piperidine nitrogen of D5 with N-hydroxysuccinimide ester D6 in THF yields the corresponding amide D7 (Xie J-S, Huang C Q, Fang Y-Y and Zhu Y-F, *Tetrahedron* 2004, 60 (22), 4875-4878). Subsequent coupling of the D7 indoline nitrogen with either a carboxylic acid chloride or a sulfonyl chloride according to the conditions of Schemes A-C affords the corresponding carboxamides and sulfonamides of the 5-aminomethyl-spiro[indoline-3,4'-piperidine] derivatives D8 of Formula (I).

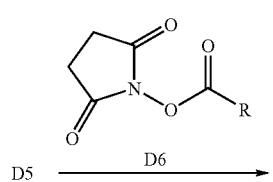

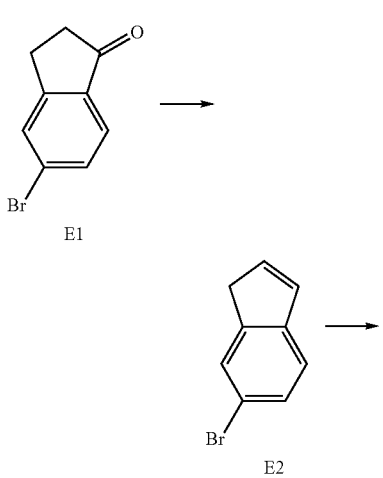

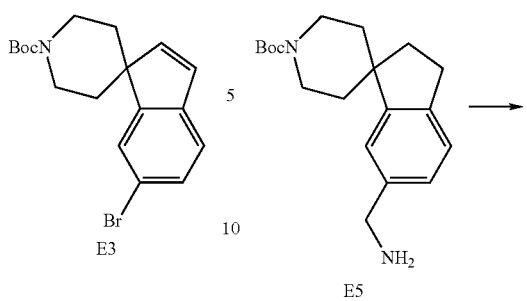

Formylation of E3 with sodium formate and carbon monoxide in the presence of tris(3-chlorophenyl)phosphine and bis(triphenylphosphine)-palladium(II) bromide in DMF at about 110° C. furnishes aldehyde E4 (Okano T, Harada N and Jitsuo Kiji J, *Bull. Chem. Soc. Jpn* 1994, 67 (8), 2329-2332). Reaction of E4 with hydrazine in EtOH followed by hydrogenation of the hydrazone and alkene moieties of E5 via $PtO_2$ in EtOH under hydrogen provides benzylamine E5.

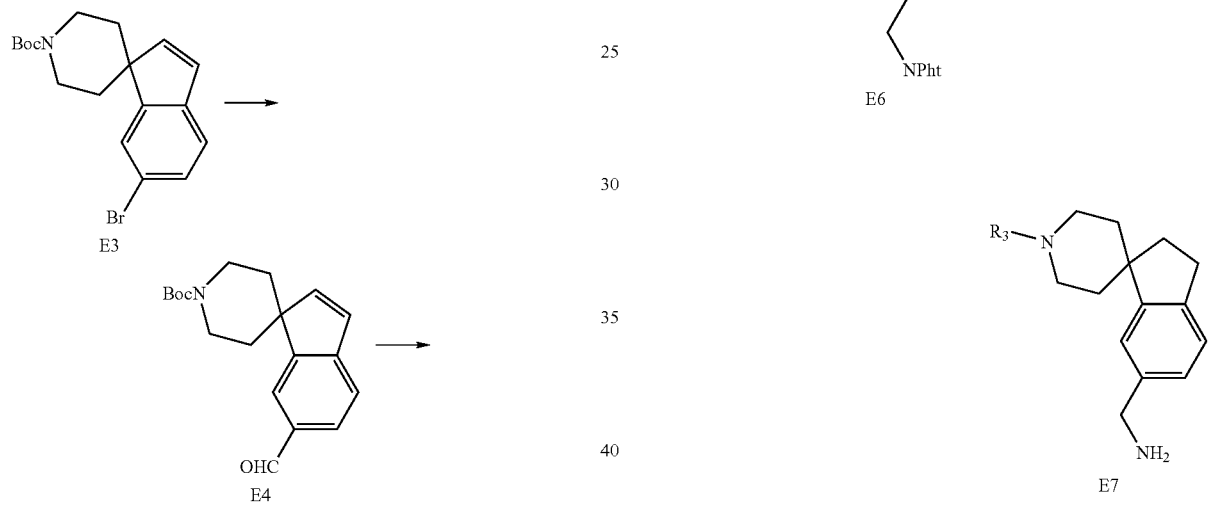

Reaction of E5 with phthalic anhydride in the presence of DIPEA in refluxing toluene followed by removal of the Boc-group with TFA in $CH_2Cl_2$ provides piperidine E6. Under foregoing conditions, coupling of E6 with either a carboxylic acid in a mixture with EDC and DMF, a carboxylic acid chloride or a sulfonyl chloride in TEA and in $CH_2Cl_2$ at about 0° C. followed by deprotection with methylhydrazine in ethanol at reflux affords the corresponding carboxamide and sulfonamide derivatives of 2,3-dihydro-spiro[1H-indene-1,4'-piperidine] E7 of Formula (I).

Scheme F describes the synthesis of certain spiro[3H-indole-3,4'-piperidin]-2(1H)-ones F7 of Formula (I).

Scheme F

Reacting 1-(tert-butoxycarbonyl)piperidine-4-carboxylic acid F1 with thionyl chloride in the presence of pyridine in $CH_2Cl_2$ provides the corresponding acid chloride, which is subsequently reacted with 4-amino-3-bromobenzonitrile in a mixture with DMAP and $CH_2Cl_2$ to furnish anilide F2. Reaction of F2 with p-methoxybenzyl chloride in the presence of potassium fluoride on alumina in refluxing acetonitrile provides F3.

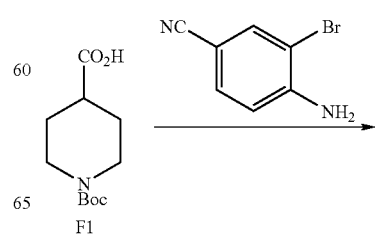

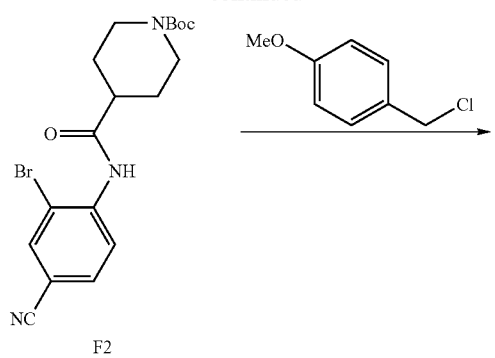

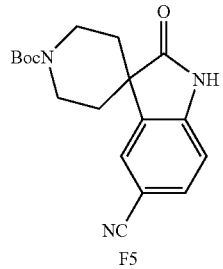

Removal of the Boc-protecting group of F5 with TFA in CH$_2$Cl$_2$ followed by coupling of the resulting piperidine with a carboxylic acid, carboxylic acid chloride, or a sulfonyl chloride according to the conditions of Scheme E affords the corresponding carboxamide and sulfonamide derivatives F6. Catalytic hydrogenation of F6 with Raney nickel under hydrogen in a mixture of 3N aqueous sodium hydroxide and ethanol furnishes the corresponding carboxamide and sulfonamide derivatives of spiro[3H-indole-3,4'-piperidin]-2 (1H)-ones F7 of Formula (I).

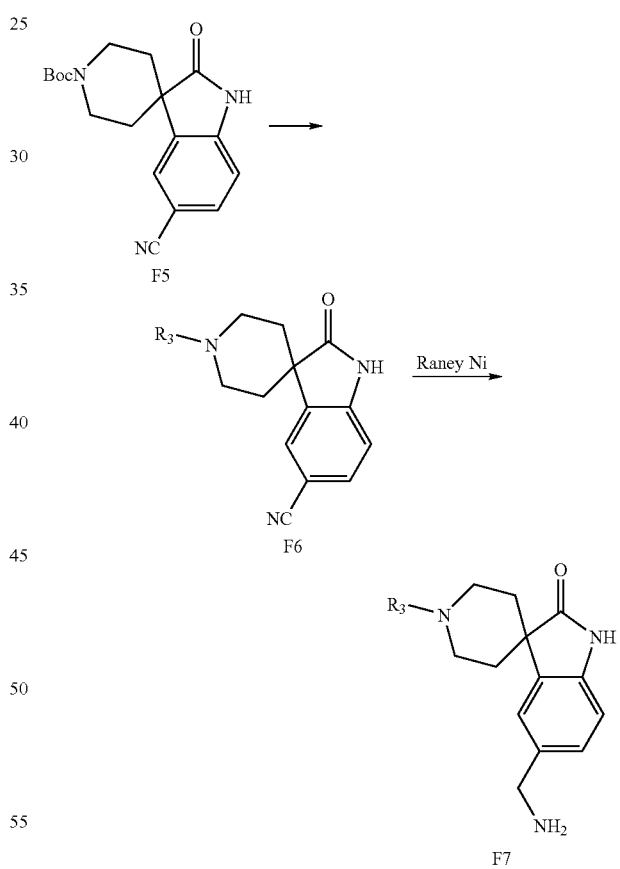

Palladium catalyzed intramolecular amide α-arylation of F3 with tris(dibenzylideneacetone)dipalladium(0) and sodium tert-butoxide in the presence of (+/−)-2,2'-bis(diphenylphosphino)-1,1'-binaphthalene (BINAP) in 1,4-dioxane at about 95-110° C. generates compound F4 (see, Freund R and Mederski W K R, *Helv. Chim. Acta* 2000, 83 (6), 1247-1255). Oxidative removal of the p-methoxybenzyl protecting group with ammonium cerium(IV) nitrate in a mixture of water and acetonitrile provides F5.

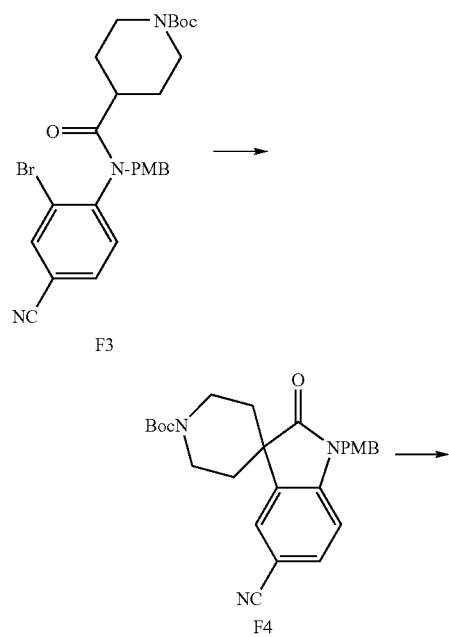

Scheme G describes the synthesis of certain spiro[1H-isoindole-1,4'-piperidin]-3(2H)-ones G7 of Formula (I).

Scheme G

Reaction of methyl 2-bromo-4-(bromomethyl)benzoate G1 (CAS# 128577-48-0) with potassium phthalimide in DMF followed by demethylation with lithium iodide in refluxing pyridine provides carboxylic acid G2. Reaction of G2 with refluxing thionyl chloride provides the acid chloride G3.

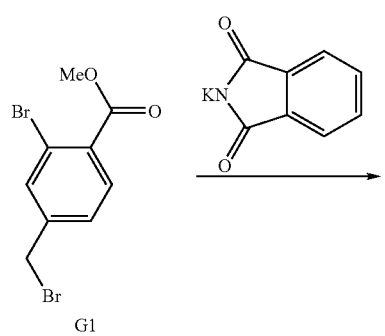

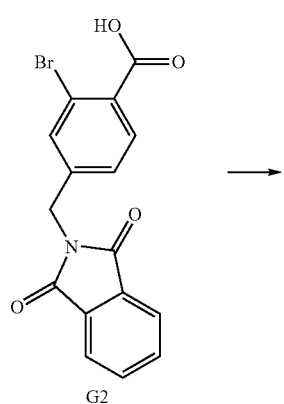

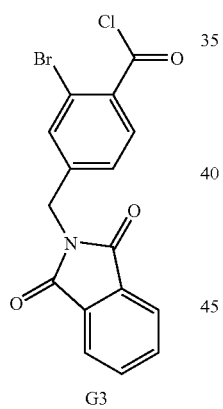

Condensation of 2,4-dimethoxybenzylamine G4 with 1-Boc-4-piperidone (CAS# 79099-07-3) in refluxing toluene furnishes imine G5. Reaction of G5 with G3 in toluene at about 80° C. provides amide G6.

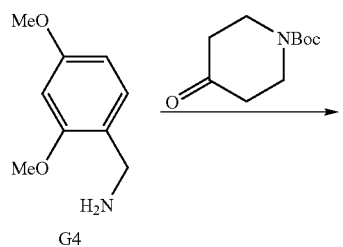

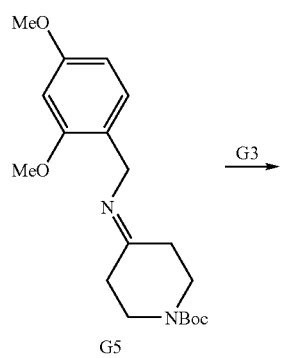

Intramolecular Heck cyclization of G6 with palladium(II) acetate in the presence of tricyclopentylphosphine, and dicyclopentylmethylamine in N,N-dimethylacetamide (DMA) at about 100° C. provides isoindolone G7. Removal of the Boc-protecting group with TFA in $CH_2Cl_2$ followed by catalytic hydrogenation via 10% Pd/C under hydrogen in EtOH affords spiropiperidine G8.

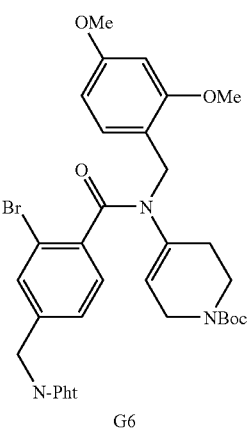

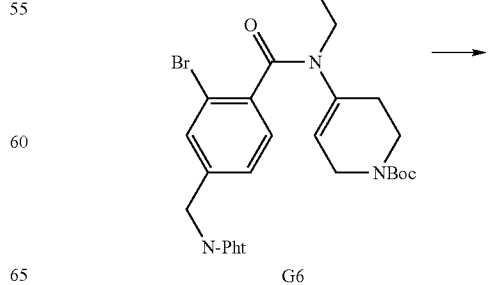

-continued

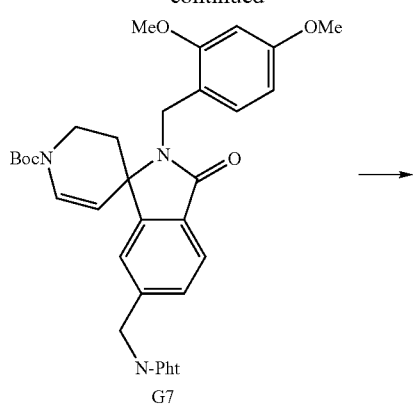

G7

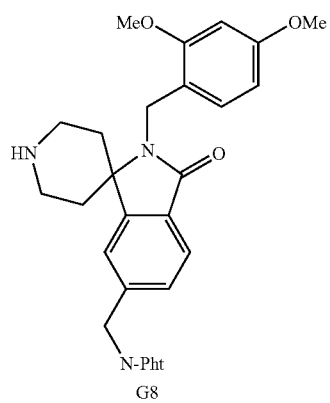

G8

Coupling of G8 with a carboxylic acid, carboxylic acid chloride, or a sulfonyl chloride according to the conditions of Scheme C affords the corresponding carboxamide and sulfonamide derivatives. Removal of the phthalyl protecting group with methylhydrazine at about 40° C. followed by removal of the dimethoxybenzyl protecting group with neat TFA provides the corresponding carboxamide and sulfonamide derivatives G9 of Formula (I).

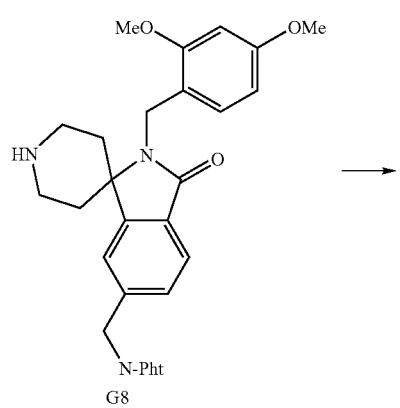

G8

-continued

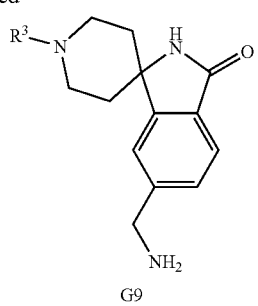

G9

Scheme H describes the solution-phase synthesis of certain 5-aminomethyl-spiro[benzofuran-3(2H), 4'-piperidine] derivatives H3, H4, H5, and H6 of Formula (I).

Scheme H

Removal of the Boc group from A6 (Scheme A) with trifluoroacetic acid followed by coupling with either carboxylic acids and a coupling agent (such as BOP-Cl) in a mixture with DIPEA and $CH_2Cl_2$ or with acid chlorides and sulfonyl chlorides in a mixture with TEA and THF at about 0° C. generates nitrile H1.

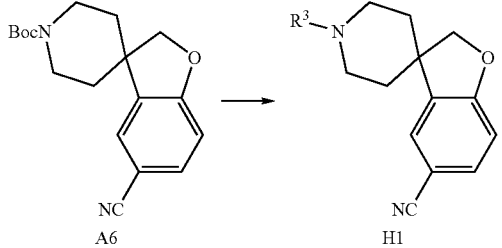

A6                H1

Pinner reaction of H1 with hydrochloric acid in ethanol at 5° C., followed by neutralization with 3 N NaOH affords ethyl imidate H2 as the free base.

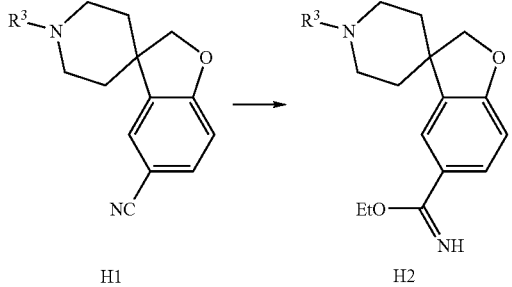

H1                H2

Compound H2 is reacted with anhydrous ammonia, mono- or dialkylamine, hydroxylamine or hydrazine with subsequent purification by reverse-phase HPLC to yield H3, H4, H5 and H6, respectively.

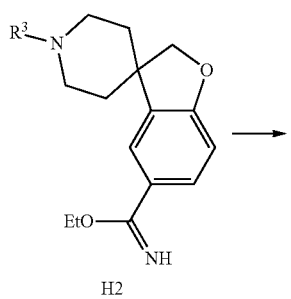

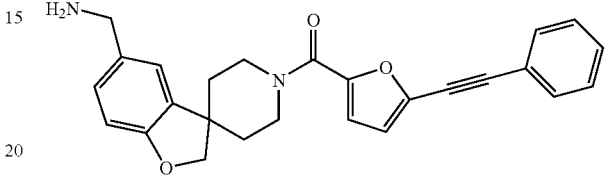

H3:Ra = —NH$_2$
H4:Ra = —NH(C$_{1-4}$alkyl), —N(C$_{1-4}$alkyl)$_2$
H5:Ra = —NHOH
H6:Ra = —NHNH$_2$

SPECIFIC EXAMPLES

General Information and Procedures

Commercially available reagents were used without purification unless specifically necessary. All reactions were conducted under argon or nitrogen in rigorously dried solvents with magnetic stirring at room temperature unless noted otherwise. Multiple extractions are designated within parentheses; e.g., "(3×)" indicates 3 extractions. Solutions and residues were not heated above 40° C. while concentrating in vacuo. Normal-phase preparative chromatography was performed either on an Isco Combiflash Separation System Sg 100 c equipped with a Biotage FLASH Si 40M silica gel cartridge (KP-Sil® Silica, 32-63 µm, 60 Å; 40×270 mm) eluting at 35 mL/min or on a Waters Delta Prep 3000 equipped with 2PrepPak® silica gel cartridges (Porasil® Silica, 55-105 µm, 57×300 mm) connected in series eluting at 120 mL/min; both systems had peak detection at 254 nm and solvent gradient times of 60 min.

Reverse-phase preparative chromatography was performed on a Gilson Preparative HPLC system equipped with a Kromasil C-18 column (2.5×50 cm; 10 µm, 100 Å) eluting at 50 mL/min with detection at 220 nm; solvent gradients were conducted over a 30 min period and fractions were collected over 40 min. Reverse-phase chromatography fractions were lyophilized on a FTS Systems Flexi-Dry MP lyophilizer. Melting points were determined on a Thomas-Hoover apparatus calibrated with a set of melting point standards. $^1$H NMR spectra were acquired at 300.14 MHz on a Bruker Avance-300 spectrometer in CD$_3$OD unless indicated otherwise, using Me$_4$Si as an internal standard. NMR abbreviations used: AB$_q$, AB quartet; br, broad; d, doublet; dd, doublet of doublets; dt, doublet of triplets; m, multiplet; ov, overlapping; q quartet; s, singlet; t, triplet. Electrospray (ES) mass spectra were obtained on a Micromass Platform LC single quadrupole mass spectrometer in the positive mode. Chemical-ionization mass spectra (CI-MS) were recorded on a Finnigan 3300 mass spectrometer with methane as the reagent gas.

The following examples are offered by way of illustration; the invention should not be construed as being limited by the chemical reactions and conditions expressed.

Example 1

1-(5-phenylethynyl-furan-2-yl)carbonyl-5'-aminomethyl-spiro[piperidine-4,3'-benzo[b]furan] (Cpd 3)

Cpd 3

Step A. 4-benzenesulfinylmethyl-4-hydroxy-piperidine-1-carboxylic Acid tert-butyl ester (CAS# 221142-274)

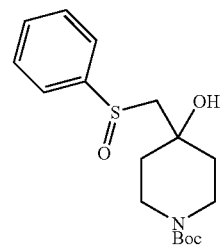

1a

A solution of n-butyllithium (96 mL of 2.5 M in hexanes, 0.240 mol) was added dropwise at −75° C. to a solution of diisopropylamine (33.2 mL, 0.237 mol) in THF (150 mL) with mechanical stirring under argon and stirred for 30 min. To this solution was added a solution of (±)-methyl phenyl sulfoxide (33.2 g, 0.237 mol) in THF (40 mL) dropwise over 15 min at −75° C. The reaction mixture was quickly warmed to 5° C., stirred for 20 min, cooled back down to −75° C., treated with a solution of 1-Boc-4-piperidone (46.9 g, 0.235 mol; CAS# 79099-07-3) in THF (200 mL) and slowly warmed to room temperature over 18 h. The resulting light yellow suspension was quenched by the addition of solid ammonium chloride (39 g, 0.729 mol) and concentrated in vacuo. The residue was partitioned between EtOAc and water. The aqueous layer was extracted with EtOAc (2×) and the combined EtOAc extracts were washed with brine (2×), dried (MgSO$_4$), filtered and concentrated in vacuo to afford 1a (64.3 g, 80%) as an off-white solid: $^1$H NMR (CDCl$_3$) δ 7.70-7.50 (m, 5H), 4.20 (br s, 1H), 4.05-3.80 (m, 2H), 3.40-

3.15 (m, 2H), 3.06, 2.70 (AB$_q$, J$_{ab}$=13.4 Hz, 2H), 2.19-2.13 (m, 1H), 1.88-1.50 (m, 3H), 1.46 (s, 9H); MS (ES) m/z 340.2 (MH)$^+$.

Step B. 3-hydroxy-4-methylene-piperidine-1-carboxylic Acid Tert-Butyl Ester (CAS# 159635-22-0)

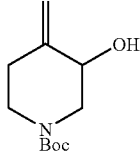

1b

Potassium tert-butoxide (21.7 g, 0.193 mol) was combined with 1a (50.5 g, 0.149 mol) in tert-butanol and the resulting yellow suspension was heated at reflux with mechanical stirring under argon for 2 h. The reaction mixture was cooled to room temperature, quenched by the addition of solid ammonium chloride (24.0 g, 0.446 mol), stirred for 10 min, and concentrated in vacuo. The residue was partitioned between water and EtOAc and the aqueous layer was extracted with EtOAc (2×). The combined EtOAc extracts were washed with brine (2×), dried (MgSO$_4$), filtered through filter agent, and concentrated in vacuo. The brown residue was purified by chromatography on silica gel on an Isco Combiflash chromatograph eluting with hexane/EtOAc (4:1) to furnish 1b as an amber solid (23.3 g, 74%): $^1$H NMR (CDCl$_3$) δ 5.03 (s, 1H), 4.88 (s, 1H), 4.20-4.05 (m, 1H), 3.75 (dd, J=12.9 Hz, 3.9 Hz, 1H), 3.65-3.40 (m, 1H), 3.35-3.10 (m, 2H), 2.50-2.46 (m, 1H), 2.20-2.05 (m, 2H), 1.95 (br s, 1H), 1.47 (s, 9H); MS (ES) m/z 236.2 (M+Na)$^+$.

Step C. 4-chloromethyl-3,6-dihydro-(2H)-pyridine-1-carboxylic Acid Tert-Butyl Ester (CAS# 159635-22-0)

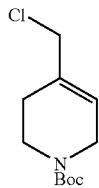

1c

A solution of 1b (6.07 g, 0.0285 mol) in toluene (150 mL) was heated to 60° C. and treated in one portion with thionyl chloride (2.50 mL, 0.0342 mol). After 25 min at 60° C., the reaction mixture was quickly cooled to 5° C. and poured into saturated aqueous NaHCO$_3$ that was previously cooled to 5° C. The layers were separated and the organic layer was extracted with saturated aqueous NaHCO$_3$ (2×), brine (2×), dried (MgSO$_4$), filtered through filer agent, and concentrated in vacuo to give 1c as a brown oil (3.84 g, 58%): $^1$H NMR (CDCl$_3$) δ 5.95-5.70 (m, 1H), 4.03 (s, 2H), 4.00-3.90 (m, 2H), 3.53 (t, J=5.7 Hz, 2H), 2.30-2.15 (m, 2H), 1.47 (s, 9H); MS (Cl) m/z 232.2 (MH)$^+$.

Step D. 4-(2-bromo-4-cyano-phenoxymethyl)-3,6-dihydro-(2H)-pyridine-1-carboxylic Acid Tert-Butyl Ester

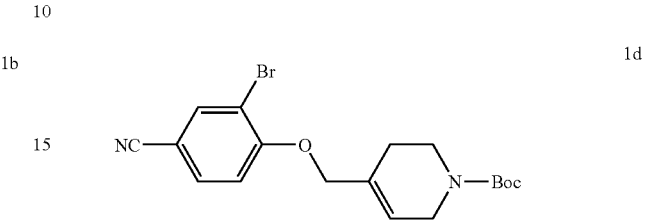

1d

Finely ground K$_2$CO$_3$ (12.5 g, 0.0906 mol) was added to a solution of 3-bromo-4-hydroxylbenzonitrile (6.58 g, 0.0332 mol) and 1c (7.00 g, 0.0302 mol) in acetone (164 mL). The reaction mixture was heated at reflux for 60 h while stirring under argon. The reaction mixture was filtered and the filtrate was concentrated in vacuo and partitioned between EtOAc and 5% aqueous K$_2$CO$_3$. The organic layer was extracted 5% aqueous K$_2$CO$_3$ (2×), brine (2×), dried (MgSO$_4$), filtered through filter agent and concentrated in vacuo to furnish 1d (10.9 g, 92%) as a tan solid: $^1$H NMR (CDCl$_3$) δ 7.84 (d, 1H, J=2.0 Hz), 7.58 (dd, 1H, J=8.6 Hz, 2.0 Hz), 6.92 (d, 1H, 8.6 Hz), 5.80-5.70 (m, 1H), 4.55 (s, 2H), 4.00-3.90 (m, 2H), 3.57 (t, 2H, J=5.7 Hz), 2.30-2.15 (m, 2H), 1.48 (s, 9H); MS (ES) m/z 415.0 (M+Na)$^+$.

Step E. 1-(tert-butyloxy)carbonyl-5'-cyano-spiro[piperidine-4,3'-benzo[b]furan]

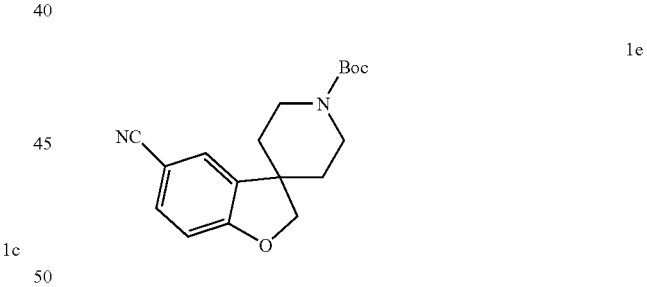

1e

A solution of 1d (10.7 g, 0.0271 mol) and Bu$_3$SnH (10.9 mL, 0.0407 mol) in toluene (1360 mL) was treated with AIBN (0.232 g, 0.0014 mol). The reaction mixture was heated at 80° C. under argon for 4 h, cooled to room temperature, and concentrated in vacuo. The residue was dissolved in 250 mL of EtOAc, cooled to 5° C. and treated with DBU (11 mL, 0.075 mol). Bromine (ca. 6 mL) was added dropwise until a brown endpoint was reached. The resulting precipitate was removed by filtration through a bed of silica gel. The filtrate was extracted with 1 N aqueous Na$_2$S$_2$O$_4$ (2×), brine (2×), dried (MgSO$_4$), filtered through filter agent and concentrated in vacuo to give a yellow solid. This solid was purified by chromatography on silica gel eluting with 10-30% EtOAc in hexane to give 1e (5.87 g, 69%) as a white solid: $^1$H NMR (CDCl$_3$) δ 7.48 (dd, 1H, J=8.3 Hz, 1.7 Hz), 7.37 (d, J=1.7 Hz), 6.86 (d, 1H, J=8.3 Hz), 4.50 (s, (2H)), 4.20-4.02 (m, 2H), 2.95-2.75 (m, 2H), 1.95-1.65 (ov m, 4H), 1.49 (s, 9H); MS (ES) m/z 314.9 (MH)+, 336.9 (M+Na)+.

Step F. 1-(tert-butyloxy)carbonyl-5'-aminomethyl-spiro[piperidine-4,3'-benzo[b]furan]

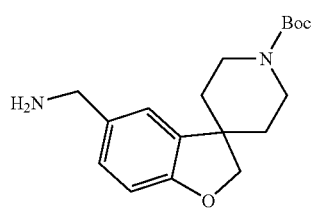

1f

A solution of 1e (4.00 g, 0.0127 mol) in mixture of ethanol (160 mL) and 3N aqueous NaOH (60 mL) was treated with a 50% aqueous suspension of Raney nickel (1.46 g) and placed on a Parr hydrogenator under 60 psig of hydrogen for 16 h. The reaction mixture was filtered through filter agent and the filtrate was concentrated in vacuo. The residue was partitioned between water and $CHCl_3$. The aqueous layer was extracted again with $CHCl_3$ (2×) and the combined $CHCl_3$ extracts were washed with brine (2×), dried ($K_2CO_3$), filtered through filter agent, and concentrated in vacuo to afford 1f (4.06 g, 100%) as a clear viscous oil: $^1$H NMR (CDCl$_3$) δ 7.10-7.00 (ov m, 2H), 6.76 (d, 1H, J=8.7 Hz), 4.41 (s, 2H), 4.40-4.00 (m, 2H), 3.80 (s, 2H), 3.05-2.80 (m, 2H), 2.00-1.60 (ov m, 4H), 1.49 (s, 9H), 1.33 (br s, 2H); MS (ES) m/z 318.9 (MH)+.

Step G. 1-(tert-butyloxy)carbonyl-5'-(1,3-dioxo-1,3-dihydro-isoindol-2-ylmethyl)-spiro[piperidine-4,3'-(2H)-benzo[b]furan]

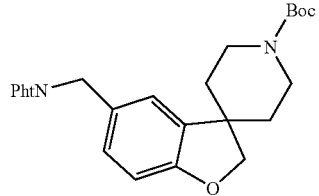

1g

A solution of phthalic anhydride (1.74 g, 0.0118 mol), 1f (3.74 g, 0.0118 mol), and N,N-diisopropylethylamine (2.87 mL, 0.0165 mol) in toluene (118 mL) was heated at reflux under argon with azeotropic removal of water for 14 h. The reaction mixture was cooled to room temperature, extracted with 10% aqueous citric acid (3×) and brine (2×), dried (MgSO$_4$), filtered through filter agent and concentrated in vacuo. The residue was purified by chromatography on silica gel on a Isco Combiflash chromatograph eluting with hexane/EtOAc (4:1) to furnish 1g as a white foam (3.56 g, 68%): $^1$H NMR (CDCl$_3$) δ 7.84 (dd, 2H, J=5.4 Hz, 3.1 Hz), 7.70 (dd, 2H, J=5.4 Hz, 3.1 Hz), 7.35-7.20 (ov m, 2H), 6.73 (d, 1H, J=8.2 Hz), 4.77 (s, 2H), 4.38 (s, 2H), 4.20-4.00 (m, 2H), 2.95-2.80 (m, 2H), 1.95-1.60 (m, 4H), 1.50 (s, 9H); MS (ES) m/z 471.2 (M+Na)+.

Step H. 5'-(1,3-dioxo-1,3-dihydro-isoindol-2-ylmethyl)-spiro[piperidine-4,3'-benzo[b]furan]Hydrochloride (1:1)

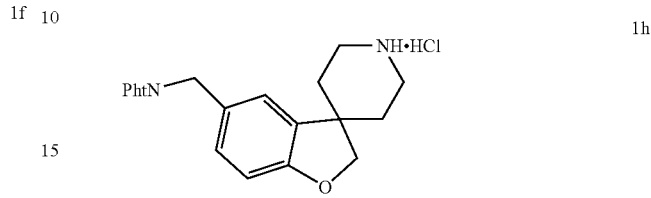

1h

A solution of 1g (3.54 g, 0.0079 mol) in dichloromethane (60 mL) was treated with trifluoromethylacetic acid (20 mL), stirred under a nitrogen atmosphere for 1 h and concentrated in vacuo. The residue was dissolved in methanol (150 mL) and treated with 4N HCl in 1,4-dioxane (6 mL). The resulting white suspension was concentrated in vacuo, partially dissolved in methanol (150 mL), treated with 4N HCl in 1,4-dioxane (6 mL) and concentrated in vacuo. The foregoing process was repeated yet again and the resulting white solid was suspended in diethyl ether (200 mL) and stirred at room temperature over 16 h. The resulting white precipitate was isolated by filtration, washed with diethylether, and dried in vacuo to give 1h (2.99 g, 98%) as a white solid: $^1$H NMR (CD$_3$OD) δ 7.95-7.80 (ov m, 4H), 7.35-7.10 (ov m, 2H), 6.76 (d, 1H, J=8.2 Hz), 4.79 (s, 2H), 4.50 (s, 2H), 3.55-3.40 (m, 2H), 3.14 (dt, 2H, J=13.0 Hz, 3.4 Hz), 2.20-2.05 (m, 2H), 2.05-1.90 (m, 2H); MS (ES) m/z 348.9 (MH)+.

Step I. 1-(5-phenylethynyl-furan-2-yl)carbonyl-5'-(1,3-dioxo-1,3-dihydro-isoindol-2-ylmethyl)-spiro[piperidine-4,3'-(2H)-benzo[b]furan]

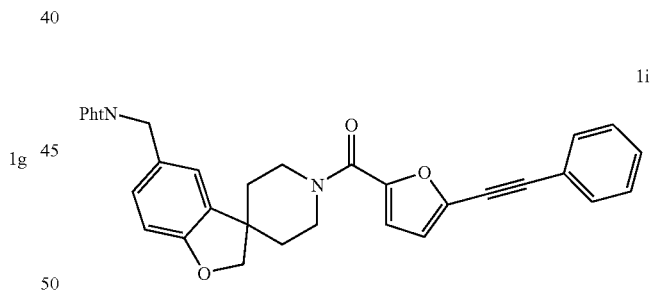

1i

Bis(2-oxo-3-oxazolidinyl)phosphinic chloride (2.37 g, 0.0093 mol) was added to a slurry of 1i (2.99 g, 0.0078 mol), 5-(2-phenyleth-1-ynyl-2-furoic acid, 1.81 g, 0.0085 mol), and N,N-diisopropylethylamine (6.00 mL, 0.0344 mol) in dichloromethane (156 mL) while stirring under argon. After 75 min, the resulting amber solution was concentrated in vacuo and partitioned between EtOAc and 10% aqueous citric acid. The organic layer was extracted with 10% aqueous citric acid (2×), saturated aqueous NaHCO$_3$ (3×), brine (3×), dried (MgSO$_4$) and concentrated in vacuo to furnish 1i (4.18 g, 99%) as a tan solid: $^1$H NMR (CDCl$_3$) δ 7.90-7.77 (m, 2H), 7.77-7.62 (m, 2H), 7.60-7.50 (m, 2H), 7.50-7.30 (ov m, 3H), 7.30-7.20 (m, 2H), 7.13 (d, 1H, J=3.5 Hz), 6.80-6.65 (ov m, 2H), 4.77 (s, 2H), 4.62-4.50 (m, 2H), 4.46 (s, 2H), 3.30-2.90 (br m, 2H), 2.08-1.90; (m, 2H); 1.90-1.75 (m, 2H); MS (ES) m/z 542.7 (MH)+.

Step J. 1-(5-phenylethynyl-furan-2-yl)carbonyl-5'-aminomethyl-spiro[piperidine-4,3'-(2H)-benzo[b]furan]Benzoate (1:1) (Cpd 3)

A slurry of 1i (4.25 g, 0.0078 mol) in ethanol (78 mL) was treated with methylhydrazine (7.8 mL, 0.1466 mol) was stirred at room temperature under argon for 16 h. Additional portions of ethanol (78 mL) and methylhydrazine (7.8 mL, 0.1466 mol) were added and the reaction mixture was heated at 40° C. for 5.5 h. The resultant yellow solution was cooled to room temperature and concentrated in vacuo. The residue was purified by reversed phase chromatography eluting with 25-90% MeCN/H$_2$O/0.2% TFA to give the TFA salt of the title compound as an off-white solid. This material was partitioned between 1 N aqueous NaOH and chloroform and the basic aqueous layer was extracted with chloroform (2×) and the combined organic extracts were washed with brine (2×), dried (Na$_2$SO$_4$), filtered through filter agent and concentrated in vacuo to provide the freebase of Compound 1 as a tan foam (2.12 g, 66%). The freebase (2.49 g, 0.0060 mol) was combined with benzoic acid (0.737 g, 0.0060 mol) was dissolved in boiling ethanol (40 mL) and allowed to crystallize first at room temperature and then at 5° C. The resulting crystals were isolated by filtration, washed with diethylether, and dried in vacuo over 16 h at 80° C. to afford Compound 3 (2.15 g, 66%) as the benzoate salt: mp 179-181° C.; $^1$H NMR (CD$_3$OD) δ 7.88-7.76 (m, 2H), 7.50-7.38 (m, 2H), 7.38-7.15 (ov m, 7H), 7.13 (dd, 1H, J=8.2 Hz, 1.9 Hz) 6.99 (d, 1H, J=3.6 Hz), 6.76 (d, 1H, J=3.6 Hz), 6.71 (d, 1H, J=8.2 Hz), 4.47 (s, 2H), 4.47-4.30 (m, 2H), 3.92 (s, 2H), 3.50-2.90 (br m, 2H), 1.97-1.80 (m, 2H), 1.80-1.65 (m, 2H); MS (ES) m/z 413.3 (MH)$^+$.

Using the procedure of Example 1 and suitable reagents, starting materials and reaction conditions, other compounds representative of the present invention may be prepared by those skilled in the art, such as:

| Cpd | Name and Data |
|---|---|
| 4 | 1-(3-benzoyl-phenyl)carbonyl-5'-aminomethyl-spiro[piperidine-4,3'-(2H)-benzo[b]furan]<br>$^1$H NMR (CD$_3$OD) δ 7.90-7.80 (m, 4H), 7.75-7.64 (m, 3H), 7.57-7.53 (m, 2H), 7.31 (d, J = 1.8 Hz, 1H), 7.23 (dd, J = 2.0 Hz, J = 8.2 Hz, 1H), 6.82 (dd, J = 3.4 Hz, J = 8.2 Hz, 1H), 4.67-4.57 (m, 3H), 4.04 (s, 2H), 3.86-3.78 (m, 1H), 3.35-3.25 (br m, 1H), 3.20-3.12 (m, 1H), 2.03-1.77 (m, 4H). C$_{27}$H$_{26}$N$_2$O$_3$; MS (ESI) m/z 427 (MH)$^+$. |
| 6 | 1-(4-benzoyl-phenyl)carbonyl-5'-aminomethyl-spiro[piperidine-4,3'-(2H)-benzo[b]furan]<br>$^1$H NMR (CD$_3$OD) δ 7.88 (d, J = 8.2 Hz, 2H), 7.80 (d, J = 7.1 Hz, 2H), 7.70 (m, 5H), 7.34 (d, J = 1.9 Hz, 1H), 7.24 (dd, J = 1.9 Hz, J = 8.2 Hz, 1H), 6.83 (d, J = 8.2 Hz, 1H), 4.58 (br s, 3H), 4.05 (s, 2H), 5.85-3.75 (m, 1H), 3.28-3.18 (m, 2H), 2.03-1.78 (m, 4H). C$_{27}$H$_{26}$N$_2$O$_3$; MS (ESI) m/z 427 (MH)$^+$. |
| 7 | 1-(9-oxo-10,10-dioxo-thioxanthen-3-yl)carbonyl-5'-aminomethyl-spiro[piperidine-4,3'-(2H)-benzo[b]furan]<br>$^1$H NMR (CD$_3$OD) δ 8.44 (d, J = 8.0 Hz, 1H), 8.36 (dd, J = 1.1 Hz, J = 7.7 Hz, 1H), 8.24 (d, J = 1.4 Hz, 1H), 8.19 (d, J = 7.7 Hz, 1H), 8.04-7.89 (m, 3H), 7.36 (d, J = 1.8 Hz, 1H), 7.24 (dd, J = 1.9 Hz, J = 8.2 Hz, 1H), 6.83 (d, J = 8.2 Hz, 1H), 4.57 (m, 3H), 4.06 (s, 2H), 3.70-3.50 (br m, 1H), 3.32-3.20 (m, 2H), 2.03-1.78 (m, 4H). C$_{27}$H$_{24}$N$_2$O$_5$S; MS (ESI) m/z 489 (MH)$^+$. |
| 8 | 1-(9-oxo-fluoren-2-yl)carbonyl-5'-aminomethyl-spiro[piperidine-4,3'-(2H)-benzo[b]furan]<br>$^1$H NMR (CD$_3$OD) δ 7.77-7.37 (m, 7H), 7.27-7.25 (m, 1H), 7.14 (s, 1H), 6.84 (d, J = 8.2 Hz, 1H), 4.82 (m, 1H), 4.64-4.51 (m, 2H), 4.05 (d, J = 15.2 Hz, 2H), 3.68 (d, J = 13.9 Hz, 1H), 3.38-3.27 (m, 2H), 2.12-2.00 (m, 2.5H), 1.69 (m, 1.5H). C$_{27}$H$_{24}$N$_2$O$_3$; MS (ESI) m/z 425 (MH)$^+$. |
| 9 | 1-(4-benzoimidazol-1-ylmethylcarbonylamino-phenyl)carbonyl-5'-aminomethyl-spiro[piperidine-4,3'-(2H)-benzo[b]furan]<br>$^1$H NMR (CD$_3$OD) δ 9.14 (s, 1H), 7.85-7.73 (m, 4H), 7.62-7.59 (m, 2H), 7.49 (d, J = 8.6 Hz, 2H), 7.33 (s, 1H), 7.23 (d, J = 8.3 Hz, 1H), 6.84 (d, J = 8.3 Hz, 1H), 5.45 (m, 3H), 4.58 (m, 4H), 4.06 (s, 2H), 3.15 (m, 1H), 2.00-1.80 (m, 4H). C29H29N5O3; MS (ESI) m/z 496 (MH)$^+$. |
| 10 | 1-(4-benzoimidazol-1-ylmethyl-phenyl)carbonyl-5'-aminomethyl-spiro[piperidine-4,3'-(2H)-benzo[b]furan]<br>$^1$H NMR (CD$_3$OD) δ 9.5 (s, 1H), 7.87 (d, J = 7.3 Hz, 1H), 7.81 (d, J = 7.2 Hz, 1H), 7.66-7.50 (m, 6H), 7.31 (d, J = 1.7 Hz, 1H), 7.26 (dd, J = 1.8 Hz, J = 8.2 Hz, 1H), 6.81 (d, J = 8.2 Hz, 1H), 5.81 (s, 2H), 4.60-4.40 (br m, 3H), 4.04 (s, 2H), 3.75-3.60 (br m, 1H), 3.20-3.05 (br m, 2H), 2.03-1.72 (m, 4H). C$_{28}$H$_{28}$N$_4$O$_2$; MS (ESI) m/z 453 (MH)$^+$. |
| 11 | 1-(4-aminosulfonyl-phenyl)carbonyl-5'-aminomethyl-spiro[piperidine-4,3'-(2H)-benzo[b]furan]<br>$^1$H NMR (CD$_3$OD) δ 8.02 (d, J = 8.4 Hz, 2H), 7.64 (d, J = 8.5 Hz, 2H), 7.35 (s, 1H), 7.26 (d, J = 8.3 Hz, 1H), 6.85 (d, J = 8.2 Hz, 1H), 4.56 (br s, 3H), 4.07 (s, 2H), 3.75-3.65 (br m, 1H), 3.33-3.31 (br m, 1H), 1.93-1.77 (m, 4H). C$_{20}$H$_{23}$N$_3$O$_4$S; MS (ESI) m/z 402 (MH)$^+$. |
| 12 | 1-[5-(4-chloro-phenyl)-furan-2-yl]carbonyl-5'-aminomethyl-spiro[piperidine-4,3'-(2H)-benzo[b]furan]<br>$^1$H NMR (CD$_3$OD) δ 7.78 (d, J = 8.6 Hz, 2H), 7.47 (d, J = 8.6 Hz, 2H), 7.33 (d, J = 1.8 Hz, 1H), 7.26 (dd, J = 1.9 Hz, J = 8.2 Hz, 1H), 7.18 (d, J = 3.7, 1H), 7.00 (d, J = 3.7, 1H), 6.86 (d, J = 8.2 Hz, 1H), 4.64-4.57 (m, 4H), 4.06 (s, 2H), 3.68-3.20 (br m, 2H), 2.09-1.90 (m, 4H). C$_{24}$H$_{23}$ClN$_2$O$_3$; MS (ESI) m/z 423 (MH)$^+$. |
| 13 | 1-(5-chloro-benzo[b]-furan-2-yl)carbonyl-5'-aminomethyl-spiro[piperidine-4,3'-(2H)-benzo[b]furan]<br>$^1$H NMR (CD$_3$OD) δ 7.75 (s, 1H), 7.57 (d, J = 8.8 Hz, 1H), 7.45 (d, J = 2.1 Hz, |

-continued

| Cpd | Name and Data |
|---|---|
| | 1H), 7.36 (s, 1H), 7.31 (s, 1H), 7.22 (m, 1H), 6.84 (d, J = 8.2 Hz, 1H), 4.61 (br s, 3H), 4.04 (s, 2H), 3.60-3.00 (br m, 3H), 2.03-1.84 (br m, 4H). $C_{22}H_{21}ClN_2O_3$; MS (ESI) m/z 397 (MH)+. |
| 14 | 1-(1-phenyl-2-methyl-benzoimidazol-5-yl)carbonyl-5'-aminomethyl-spiro[piperidine-4,3'-(2H)-benzo[b]furan]<br>$^1$H NMR (CD$_3$OD) δ 7.90 (s, 1H), 7.73 (m, 3H), 7.60 (m, 2H), 7.55 (m, 1H), 7.40 (d, J = 8.5 Hz, 1H), 7.34 (d, J = 1.7 Hz, 1H), 7.23 (dd, J = 1.9 Hz, J = 8.2 Hz, 1H) 6.82 (d, J = 8.2 Hz, 1H), 4.56 (br s, 3H), 4.04 (s, 2H), 3.85-3.70 (br m, 1H), 3.40-3.20 (m, 2H), 2.69 (s, 3H), 2.05-1.70 (m, 4H). $C_{28}H_{28}N_4O_2$; MS (ESI) m/z 453 (MH)+. |
| 15 | 1-[4-(3-trifluoromethyl-phenyl)-phenyl]carbonyl-5'-aminomethyl-spiro[piperidine-4,3'-(2H)-benzo[b]furan]<br>$^1$H NMR (CD$_3$OD) δ 7.94 (m, 2H), 7.80 (d, J = 8.3 Hz, 2H), 7.70 (m, 2H), 7.60 (d, J = 8.3 Hz, 2H), 7.34 (d, J = 1.8 Hz, 1H), 7.24 (dd, J = 1.9 Hz, J = 8.2 Hz, 1H) 6.83 (d, J = 8.2 Hz, 1H), 4.58 (br s, 3H), 4.05 (s, 2H), 3.90-3.85 (br m, 1H), 3.32-3.00 (m, 2H) 1.91-1.78 (m, 4H). $C_{27}H_{25}F_3N_2O_2$; MS (ESI) m/z 467 (MH)+. |
| 16 | 1-benzothiazol-6-ylcarbonyl-5'-aminomethyl-spiro[piperidine-4,3'-(2H)-benzo[b]furan]<br>$^1$H NMR (CD$_3$OD) δ 9.34 (s, 1H), 8.23 (s, 1H), 8.17 (d, J = 8.5 Hz, 1H), 7.65 (d, J = 8.4 Hz, 1H), 7.34 (s, 1H), 7.24 (d, J = 8.2 Hz, 1H) 6.83 (d, J = 8.2 Hz, 1H), 4.57 (br s, 3H), 4.05 (s, 2H), 3.90-3.75 (br m, 1H), 3.32-3.00 (m, 2H) 2.10-1.78 (m, 4H). $C_{21}H_{21}N_3O_2S$; MS (ESI) m/z 380 (MH)+. |
| 17 | 1-{4-[(4-benzoxazol-2-yl)-pyrazol-1-yl]-phenyl}carbonyl-5'-aminomethyl-spiro[piperidine-4,3'-(2H)-benzo[b]furan]<br>$^1$H NMR (CD$_3$OD) δ 9.12 (s, 1H), 8.41 (s, 1H), 8.05 (d, J = 8.7 Hz, 2H), 7.71-7.64 (m, 4H), 7.44-7.34 (m, 3H), 7.24 (dd, J = 1.9 Hz, J = 8.2 Hz, 1H) 6.83 (d, J = 8.2 Hz, 1H), 4.58 (br s, 3H), 4.06 (s, 2H), 3.90-3.75 (br m, 1H), 3.32-3.00 (m, 2H) 2.05-1.85 (br m, 4H). $C_{30}H_{27}N_5O_3$; MS (ESI) m/z 506 (MH)+. |
| 18 | 1-(3-phenylsulfonylamino-phenyl)carbonyl-5'-aminomethyl-spiro[piperidine-4,3'-(2H)-benzo[b]furan]<br>$^1$H NMR (CD$_3$OD) δ 7.76 (m, 2H), 7.57-7.12 (m, 9H), 6.82 (d, J = 8.2 Hz, 1H), 4.54 (br s, 3H), 4.06 (s, 2H), 3.60-3.45 (br m, 1H), 3.29-3.08 (m, 2H) 2.04-1.70 (m, 4H). $C_{26}H_{27}N_3O_4S$; MS (ESI) m/z 478 (MH)+. |
| 19 | 1-(3-thien-2-ylmethylcarbonylamino-phenyl)carbonyl-5'-aminomethyl-spiro[piperidine-4,3'-(2H)-benzo[b]furan]<br>$^1$H NMR (CD$_3$OD) δ 7.94 (d, J = 1.7 Hz, 1H), 7.51-7.17 (m, 6H), 7.01-6.95 (m, 2H), 6.81 (d, J = 8.2 Hz, 1H), 4.54 (br s, 3H), 4.04 (s, 2H), 3.91 (s, 2H), 3.80-3.70 (br m, 1H), 3.10 (m, 2H) 2.03-1.74 (br m, 4H). $C_{26}H_{27}N_3O_3S$; MS (ESI) m/z 462 (MH)+. |
| 20 | 1-(3-benzodioxol-5-yl-phenyl)carbonyl-5'-aminomethyl-spiro[piperidine-4,3'-(2H)-benzo[b]furan]<br>$^1$H NMR (CD$_3$OD) δ 7.68 (d, J = 8.0 Hz, 1H), 7.61 (s, 1H), 7.52 (t, J = 7.6 Hz, 1H), 7.38 (d, J = 7.6 Hz, 1H), 7.33 (d, J = 1.7 Hz, 1H), 7.23 (dd, J = 1.6 Hz, J = 6.8 Hz, 1H), 7.12 (m, 2H), 6.91 (d, J = 8.7 Hz, 1H), 6.82 (d, J = 8.2 Hz, 1H), 6.00 (s, 2H), 4.56 (br s, 3H), 4.04 (s, 2H), 3.85-3.75 (br m, 1H), 3.32-3.14 (m, 2H) 2.03-1.76 (br m, 4H). $C_{27}H_{26}N_2O_4$; MS (ESI) m/z 443 (MH)+. |
| 21 | 1-[3-(5-chloro-pyrimidin-2-yl)thiophenyl]carbonyl-5'-aminomethyl-spiro[piperidine-4,3'-(2H)-benzo[b]furan]<br>$^1$H NMR (CD$_3$OD) δ 8.54 (s, 2H), 7.23 (m, 2H), 7.58 (m, 2H), 7.30 (d, J = 1.7 Hz, 1H), 7.23 (d, J = 8.2 Hz, 1H), 6.82 (d, J = 8.2 Hz, 1H), 4.57 (br s, 3H), 4.03 (s, 2H), 3.90-3.75 (br m, 1H), 3.12 (m, 2H), 1.98-1.78 (br m, 4H). $C_{24}H_{23}ClN_4O_2S$; MS (ESI) m/z 467 (MH)+. |
| 22 | 1-(5-trifluoromethyl-furan-2-yl)carbonyl-5'-aminomethyl-spiro[piperidine-4, 3'-(2H)-benzo[b]furan]<br>$^1$H NMR (CD$_3$OD) δ 7.30 (d, J = 1.6 Hz, 1H), 7.24 (dd, J = 1.7 Hz, J = 8.2 Hz, 1H), 7.16 (m, 1H), 7.11 (m, 1H), 6.83 (d, J = 8.2 Hz, 1H), 4.59 (s, 2H), 4.52-4.08 (br m, 2H), 4.04 (s, 2H), 3.55-3.45 (br m, 1H), 3.20-3.10 (br m, 1H), 2.05-1.85 (m, 4H). $C_{19}H_{19}F_3N_2O_3$; MS (ESI) m/z 381 (MH)+. |
| 35 | 1-[5-(2-fluoro-phenylethynyl)-furan-2-yl]carbonyl-5'-aminomethyl-spiro[piperidine-4,3'-(2H)-benzo[b]furan]<br>$^1$H NMR (CD$_3$OD) δ 7.65-7.55 (m, 1H), 7.54-7.40 (m, 1H), 7.31 (d, J = 1.8 Hz, 1H), 7.11 (d, J = 3.7 Hz, 1H), 6.91 (d, J = 3.7 Hz, 1H), 6.83 (d, J = 1.8 Hz, 1H), 4.60 (s, 2H), 4.59-4.40 (m, 2H), 4.03 (s, 2H), 3.70-2.90 (br m, 4H), 2.08-1.80 (m, 4H). $C_{26}H_{23}FN_2O_3$; MS (ESI) m/z 431 (MH)+. |
| 109 | (E)-1-(phenylethenyl)carbonyl-5'-aminomethyl-spiro[piperidine-4,3'-(2H)-benzo[b]furan]<br>$^1$H NMR (CD$_3$OD) δ 7.65-7.59 (m, 3H), 7.44-7.35 (m, 3H), 7.28-7.19 (m, 3H), 6.83 (d, J = 8.2 Hz, 1H), 4.58 (br s, 3H), 4.31 (br d, J = 14.1 Hz, 1H), 4.03 (s, 2H), 3.40 (br t, J = 12.0 Hz, 1H), 3.02 (br t, J = 12.1 Hz, 1H), 2.03-1.75 (br m, 4H). $C_{22}H_{24}N_2O_2$; MS (ESI) m/z 349 (MH)+. |
| 110 | 1-benzothien-2-ylcarbonyl-5'-aminomethyl-spiro[piperidine-4,3'-(2H)-benzo[b]furan]<br>$^1$H NMR (CD$_3$OD) δ 7.95-7.87 (m, 2H), 7.66 (s, 1H), 7.58-7.41 (m, 2H), 7.33 (d, J = 1.9 Hz, 1H), 7.24 (dd, J = 1.9 Hz, J = 8.2 Hz, 1H), 6.83 (d, J = 8.2 Hz, |

| Cpd | Name and Data |
|---|---|
| | 1H), 4.59 (s, 2H), 4.50-4.40 (br m, 2H), 4.05 (s, 2H), 3.35-3.30 (br m, 2H), 2.06-1.49 (m, 4H). $C_{22}H_{22}N_2O_2S$; MS (ESI) m/z 379 (MH)+. |
| 160 | 1-benzo[b]furan-2-ylcarbonyl-5'-aminomethyl-spiro[piperidine-4,3'-(2H)-benzo[b]furan]<br>$^1$H NMR (CD$_3$OD) δ 7.72 (d, J = 7.8 Hz, 1H), 7.57 (d, J = 8.3 Hz, 1H), 7.45 (t, J = 7.3 Hz, 1H), 7.39-7.30 (m, 2H), 7.24 (dd, J = 1.7 Hz, J = 8.2 Hz, 1H), 6.83 (d, J = 8.2 Hz, 1H), 4.59 (s, 2H), 4.52 (br s, 2H), 4.05 (s, 2H), 3.55-3.40 (br m, 1H), 3.25-3.15 (br m, 1H), 2.09-1.86 (m, 4H). $C_{22}H_{22}N_2O_3$; MS (ESI) m/z 363 (MH)+. |
| 312 | (E)-1-(2,3-difluoro-phenylethenyl)carbonyl-5'-aminomethyl-spiro[piperidine-4,3'-(2H)-benzo[b]furan]<br>$^1$H NMR (CD$_3$OD) δ 7.63 (d, J = 15.6 Hz, 1H), 7.47 (d t, J = 1.5 Hz, J = 7.8 Hz, 1H), 7.25 (s, 1H), 7.22-7.09 (m, 4H), 6.73 (d, J = 8.2 Hz, 1H), 4.48 (s, 2H), 4.18 (br d, J = 14.2 Hz, 2H), 3.93 (s, 2H), 3.31 (br t, J = 11.4 Hz, 1H), 2.94 (br t, J = 11.0 hz, 1H), 1.98-1-78 (m, 4H). $C_{22}H_{22}F_2N_2O_2$; MS (ESI) m/z 385 (MH)+. |

Example 2

1-[(5-phenylthio)-furan-2-yl]carbonyl-5'-aminomethyl-spiro[piperidine-4,3'-benzo[b]furan] (Cpd 23)

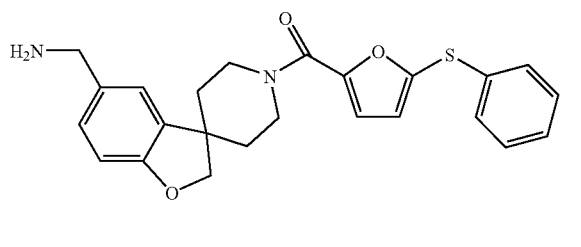

Cpd 23

Step A. 1-[2-(trimethylsilyl)ethoxy]carbonyl-5'-cyano-spiro[piperidine-4,3'-benzo[b]furan]

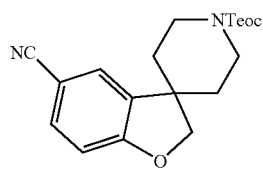

2a

Compound 1f, (4.79 g, 15.2 mmol; Example 1) was combined with trifluoroacetic acid (20 mL) in dry dichloromethane (50 mL) and stirred at room temperature for 15 minutes. The reaction mixture was concentrated in vacuo and the residue was dissolved in acetonitrile (70 ml) and treated with 4-dimethylaminopyridine (1.9 g, 15.2 mmol), triethylamine (6.2 g, 60.8 mmol) and 4-nitrophenyl-2-(trimethylsilyl)ethyl carbonate (4.3 g, 15.2 mmol). The resulting reaction mixture was refluxed for 16 hours under a nitrogen atmosphere and concentrated in vacuo. The residue was partitioned between dichloromethane (50 mL) and 1N aqueous hydrochloric acid (50 mL). The organic phase was separated and washed twice with 1N aqueous hydrochloric acid (50 mL) then with 1N aqueous sodium hydroxide (50 mL). The resulting suspension was and filtered through filter agent and the organic phase was separated and extracted sequentially with 1N aqueous sodium hydroxide (2×50 mL), water (50 mL), brine (50 mL), dried over sodium sulfate and concentrated in vacuo to give a thick pale yellow syrup. This syrup was recrystallized from dichloromethane/hexane to give 3.84 g (70%) of 2a as a pale yellow solid.

Step B. 1-[2-(trimethylsilyl)ethoxy]carbonyl-5'-aminomethyl-spiro[piperidine-4,3'-benzo[b]furan]

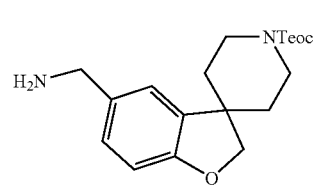

2b

Compound 2a (3.84 g, 10.7 mmol) was dissolved in absolute ethanol (82 mL), water (2.6 mL), concentrated hydrochloric acid (1 mL) and combined with 10% palladium on carbon (2.67 g) in a Parr reaction vessel and shaken with 55 psi of hydrogen at room temperature for 16 hours. The slurry was filtered through filter agent and the filtrate concentrated in vacuo to give 4.7 g (100%) of 2b as an off-white solid.

Step C. N-[(spiro[piperidine-4,3'-benzo[b]furan])-5'-methyl]carbamate Wang Resin

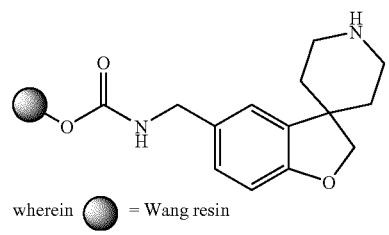

wherein ● = Wang resin

To a slurry of 4-nitrophenyl carbonate Wang resin (7.4 g, 1.3 mmol/g, 9.7 mmol) in N,N-dimethylformamide (82 mL) was added 2b (4.7 g, 10.7 mmol) in N,N-dimethylformamide (29 mL), N,N-diisopropylethylamine (3.19 g, 24.9 mmol) and 4-dimethylaminopyridine (424 mg, 3.5 mmol). The slurry was stirred overnight at room temperature under an argon atmosphere. After 16 hours, the resin was washed sequentially with N,N-dimethylformamide, methanol, N,N-dimethylformamide, methanol, dichloromethane, methanol, dichloromethane, methanol and tetrahydrofuran. The resin was added to tetrahydrofuran (62 mL) and treated with 1M tetrabutylammonium fluoride in tetrahydrofuran (45 mL). After 16 hours, the resin was washed sequentially with tetrahydrofuran, methanol, tetrahydrofuran, methanol, dichloromethane, methanol, dichloromethane, methanol and dried on high vacuum to give Wang resin-bound compound 2c.

Step D. 5-phenylsulfanyl-furan-2-carboxylic Acid Methyl Ester

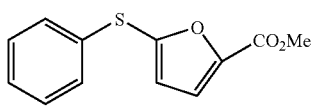

2d

To a solution of methyl 5-bromo-2-furoate (2.05 g, 10.0 mmol) in N,N-dimethylformamide (20 mL) was added benzenethiol sodium salt (1.58 g, 12 mmol). The reaction mixture was heated to 75° C. for 3 hours, then cooled and diluted with ethyl acetate (20 mL) and water (20 mL). The organic layer was separated, extracted with water (3×20 mL), brine (20 mL), dried over sodium sulfate and concentrated in vacuo to an amber syrup. This syrup was purified via column chromatography on silica gel eluting with hexane/ethyl acetate (7:3) to give 520 mg (22%) of 2d as a colorless liquid.

Step E. 5-phenylsulfanyl-furan-2-carboxylic Acid

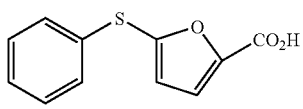

2e

To a slurry of 2d (520 mg, 2.2 mmol) in tetrahydrofuran (2 mL), ethanol (2 mL), and water (2 mL) was added lithium hydroxide (98 mg, 2.3 mmol). The reaction mixture was stirred 16 hours at room temperature and then diluted with ethyl acetate (5 mL) and water (5 mL). The organic layer was separated, dried over sodium sulfate, filtered, and the filtrate was concentrated in vacuo to give 2e as a white solid (466 mg, 95%).

Step F. 1-[(5-phenylthio)-furan-2-yl]carbonyl-5'-aminomethyl-spiro[piperidine-4,3'-benzo[b]furan] (Cpd 23)

Resin-bound compound 2c (585 mg, 0.45 mmol) in N,N-dimethylformamide (5 mL) was combined with 2e (466 mg, 2.1 mmol), 1,3-diisopropylcarbodiimide (265 mg, 2.1 mmol), and 1-hydroxybenzotriazole (284 mg, 2.1 mmol), and the mixture was shaken at room temperature for 16 hours. The resin was isolated by filtration and extracted sequentially with N,N-dimethylformamide, methanol, N,N-dimethyl-formamide, methanol, dichloromethane, methanol, dichloromethane, methanol and dichloromethane. The resulting resin was treated with trifluoroacetic acid (5 mL) in dichloromethane (20 mL), shaken for 15 minutes, extracted with dichloromethane (20 mL) and filtered. The filtrate was concentrated in vacuo and the residue was purified on a C18 reverse-phase column, eluting with water/acetonitrile (7:3) in the presence of 0.2% trifluoroacetic acid to give white powdered compound 23 (63 mg, 25%) as a trifluoroacetic acid salt: $H^1$ NMR (CD$_3$OD) δ 7.31-7.24 (m, 7H), 7.08 (d, J=3.4 Hz, 1H), 6.84 (d, J=3.4 Hz, 1H), 6.81 (d, J=8.2 Hz, 1H), 4.53 (s, 2H), 4.48-2.28 (br m, 2H), 4.03 (s, 2H), 3.32-3.08 (br m, 2H), 2.03-1.79 (m, 4H); MS (ESI) m/z 420.8 (MH)$^+$ for $C_{24}H_{24}N_2O_3S$.

Using the procedure of Example 2 and suitable reagents, starting materials and reaction conditions, other compounds representative of the present invention may be prepared:

| Cpd | Name |
|---|---|
| 24 | 1-(3,4-dimethyl-phenyl)carbonyl-5'-aminomethyl-spiro[piperidine-4,3'-(2H)-benzo[b]furan] <br> $^1$H NMR (CD$_3$OD) δ 7.32-7.15 (m, 5H), 6.82 (d, J = 8.2 Hz, 1H), 4.56 (s, 3H), 4.04 (s, 2H), 3.80 (br m, 1H), 3.11 (br m, 2H), 2.31 (s, 6H), 2.10-1.74 (m, 4H). $C_{22}H_{26}N_2O_2$; MS (ESI) m/z 350.9 (MH)$^+$. |
| 25 | 1-(3-methyl-4-chloro-phenyl)carbonyl-5'-aminomethyl-spiro[piperidine-4,3'-(2H)-benzo[b]furan] <br> $^1$H NMR (CD$_3$OD) δ 7.47 (d, J = 8.1 Hz, 1H), 7.39 (d, J = 1.5 Hz, 1H), 7.30 (dd, J = 1.8 Hz, J = 13.0 Hz, 1H), 7.25 (s, 1H), 7.22 (t, J = 6.3 Hz, 1H), 6.82 (d, J = 8.2 Hz, 1H), 4.56 (s, 3H), 4.04 (s, 2H), 3.74-3.71 (br m, 1H), 3.11-3.07 (br m, 2H), 2.42 (s, 3H), 2.03-1.75 (m, 4H). $C_{21}H_{23}ClN_2O_2$; MS (ESI) m/z 370.8 (MH)$^+$. |
| 26 | 1-(3,4-difluoro-phenyl)carbonyl-5'-aminomethyl-spiro[piperidine-4,3'-(2H)-benzo[b]furan] <br> $^1$H NMR (CD$_3$OD) δ 7.46-7.22 (m, 5H), 6.82 (d, J = 8.2 Hz, 1H), 4.56 (s, 3H), 4.04 (s, 2H), 3.88-3.55 (br m, 1H), 3.23-3.07 (br m, 2H), 1.93-1.88 (br m, 4H). $C_{20}H_{20}F_2N_2O_2$; MS (ESI) m/z 358.8 (MH)$^+$. |
| 27 | 1-(3-chloro-4-fluoro-phenyl)carbonyl-5'-aminomethyl-spiro[piperidine-4,3'-(2H)-benzo[b]furan] <br> $^1$H NMR (CD$_3$OD) δ 7.62 (dd, J = 2.0 Hz, J = 7.0 Hz, 1H), 7.48-7.43 (m, 1H), 7.38 (d, J = 8.8 Hz, 1H), 7.33 (t, J = 1.9 Hz, 1H), 7.24 (dd, J = 2.0 Hz, |

| Cpd | Name |
|---|---|
| | J = 8.2 Hz, 1H), 6.82 (d, J = 8.2 Hz, 1H), 4.56 (br s, 3H), 4.05 (s, 2H), 3.93-3.43 (br m, 1H), 3.30-3.13 (br m, 2H), 2.03-1.76 (br m, 4H). $C_{20}H_{20}ClFN_2O_2$; MS (ESI) m/z 374.9 (MH)$^+$. |
| 28 | 1-(3-chloro-4-methoxy-phenyl)carbonyl-5'-aminomethyl-spiro[piperidine-4,3'-(2H)-benzo[b]furan]<br>$^1$H NMR (CD$_3$OD) δ 7.51 (d, J = 2.0 Hz, 1H), 7.41 (dd, J = 2.0 Hz, J = 8.4 Hz, 1H), 7.32 (d, J = 1.9 Hz, 1H), 7.23 (dd, J = 2.0 Hz, J = 8.2 Hz, 1H), 7.16 (d, J = 8.6 Hz, 1H), 6.82 (d, J = 8.2 Hz, 1H), 4.56 (s, 3H), 4.05 (s, 2H), 3.94 (br s, 4H), 3.32-3.06 (br m, 2H), 2.03-1.82 (br m, 4H). $C_{21}H_{23}ClN_2O_3$; MS (ESI) m/z 386.9 (MH)$^+$. |
| 29 | 1-(3-bromo-phenyl)carbonyl-5'-aminomethyl-spiro[piperidine-4,3'-(2H)-benzo[b]furan]<br>$^1$H NMR (CD$_3$OD) δ 7.68-7.63 (m, 2H), 7.54-7.38 (m, 2H), 7.33 (d, J = 1.8 Hz, 1H), 7.23 (dd, J = 1.9 Hz, J = 8.2 Hz, 1H), 6.82 (d, J = 8.2 Hz, 1H), 4.56 (br s, 3H), 4.05 (s, 2H), 3.70-3.54 (br m, 1H), 3.12-3.07 (br m, 2H), 2.03-1.76 (br m, 4H). $C_{20}H_{21}BrN_2O_2$; MS (ESI) m/z 400.8/401.8 (MH)$^+$. |
| 30 | 1-(3-methyl-4-bromo-phenyl)carbonyl-5'-aminomethyl-spiro[piperidine-4,3'-(2H)-benzo[b]furan]<br>$^1$H NMR (CD$_3$OD) δ 7.66 (d, J = 8.1 Hz, 1H), 7.38 (d, J = 1.7 Hz, 1H), 7.32 (d, J = 1.9 Hz, 1H), 7.23 (dd, J = 1.9 Hz, J = 8.2 Hz, 1H), 7.18 (dd, J = 2.0 Hz, J = 8.2 Hz, 1H), 6.82 (d, J = 8.2 Hz, 1H), 4.56 (br s, 3H), 4.04 (s, 2H), 3.76 (br m, 1H), 3.12-3.07 (br m, 2H), 2.44 (s, 3H), 2.03-1.75 (br m, 4H). $C_{21}H_{23}BrN_2O_2$; MS (ESI) m/z 414.7/415.8 (MH)$^+$. |
| 31 | 1-(3-bromo-4-fluoro-phenyl)carbonyl-5'-aminomethyl-spiro[piperidine-4,3'-(2H)-benzo[b]furan]<br>$^1$H NMR (CD$_3$OD) δ 7.76 (dd, J = 2.0 Hz, J = 6.5 Hz, 1H), 7.52-7.47 (m, 1H), 7.40-7.31 (m, 2H), 7.24 (d, J = 2.0 Hz, J = 8.2 Hz, 1H), 6.82 (d, J = 8.2 Hz, 1H), 4.56 (br s, 3H), 4.05 (s, 2H), 3.73 (br m, 1H), 3.14 (br m, 2H), 2.03-1.88 (br m, 4H). $C_{20}H_{20}BrFN_2O_2$; MS (ESI) m/z 419.7/420.8 (MH)$^+$. |
| 32 | 1-(3-bromo-4-methoxy-phenyl)carbonyl-5'-aminomethyl-spiro[piperidine-4,3'-(2H)-benzo[b]furan]<br>$^1$H NMR (CD$_3$OD) δ 7.67 (d, J = 2.1 Hz, 1H), 7.46 (dd, J = 2.1 Hz, J = 8.5 Hz, 1H), 7.32 (d, J = 1.9 Hz, 1H), 7.23 (dd, J = 1.9 Hz, J = 8.2 Hz, 1H), 7.13 (d, J = 8.5 Hz, 1H), 6.82 (d, J = 8.2 Hz, 1H), 4.56 (br s, 3H), 4.05 (s, 2H), 3.93 (s, 4H), 3.29-3.14 (br m, 2H), 1.93-1.82 (br m, 4H). $C_{21}H_{23}BrN_2O_3$; MS (ESI) m/z 430.6/432.7 (MH)$^+$. |
| 33 | 1-(3-nitro-4-bromo-phenyl)carbonyl-5'-aminomethyl-spiro[piperidine-4,3'-(2H)-benzo[b]furan]<br>$^1$H NMR (CD$_3$OD) δ 8.02 (d, J = 2.0 Hz, 1H), 7.96 (d, J = 8.2 Hz, 1H), 7.63 (dd, J = 2.0 Hz, J = 8.2 Hz, 1H), 7.33 (d, J = 1.8 Hz, 1H), 7.24 (dd, J = 1.9 Hz, J = 8.2 Hz, 1H), 6.82 (d, J = 8.2 Hz, 1H), 4.56 (br s, 3H), 4.04 (s, 2H), 3.75-3.60 (br m, 1H), 3.25-3.05 (br m, 2H), 2.03-1.78 (br m, 4H). $C_{20}H_{20}BrN_3O_4$; MS (ESI) m/z 445.6/446.7 (MH)$^+$. |
| 34 | 1-(3-iodo-4-chloro-phenyl)carbonyl-5'-aminomethyl-spiro[piperidine-4,3'-(2H)-benzo[b]furan]<br>$^1$H NMR (CD$_3$OD) δ 8.00 (d, J = 1.9 Hz, 1H), 7.61 (d, J = 8.2 Hz, 1H), 7.46 (dd, J = 1.9 Hz, J = 8.2 Hz, 1H), 7.33 (d, J = 1.8 Hz, 1H), 7.24 (dd, J = 1.9 Hz, J = 8.2 Hz, 1H), 6.82 (d, J = 8.2 Hz, 1H), 4.55 (br s, 3H), 4.05 (s, 2H), 3.91-3.70 (br m, 1H), 3.25-3.05 (br m, 2H), 2.03-1.76 (br m, 4H). $C_{20}H_{20}ClIN_2O_2$; MS (ESI) m/z 482.7/484.6 (MH)$^+$. |
| 36 | 1-phenylcarbonyl-5'-aminomethyl-spiro[piperidine-4,3'-(2H)-benzo[b]furan]<br>$^1$H NMR (CD$_3$OD) δ 7.50-7.43 (m, 5H), 7.33 (d, J = 1.8 Hz, 1H), 7.23 (dd, J = 1.9 Hz, J = 8.2 Hz, 1H), 6.82 (d, J = 8.2 Hz, 1H), 4.55 (br s, 3H), 4.05 (s, 2H), 3.79-3.75 (br m, 1H), 3.25-3.05 (br m, 2H), 2.03-1.74 (br m, 4H). $C_{20}H_{22}N_2O_2$; MS (ESI) m/z 323.0 (MH)$^+$. |
| 37 | 1-cyclohexylcarbonyl-5'-aminomethyl-spiro[piperidine-4,3'-(2H)-benzo[b]furan]<br>$^1$H NMR (CD$_3$OD) δ 7.27 (d, J = 1.7 Hz, 1H), 7.22 (dd, J = 1.9 Hz, J = 8.2 Hz, 1H), 6.82 (d, J = 8.2 Hz, 1H), 4.57-4.46 (m, 3H), 4.08-4.03 (m, 3H), 2.90-2.81 (m, 1H), 2.73-2.66 (m, 1H), 1.88-1.74 (m, 8H), 1.56-1.24 (m, 7H). $C_{20}H_{28}N_2O_2$; MS (ESI) m/z 329.0 (MH)$^+$. |
| 38 | 1-(trans-4-methyl-cyclohexyl)carbonyl-5'-aminomethyl-spiro[piperidine-4,3'-(2H)-benzo[b]furan]<br>$^1$H NMR (CD$_3$OD) δ 7.26 (d, J = 1.7 Hz, 1H), 7.22 (dd, J = 1.9 Hz, J = 8.2 Hz, 1H), 6.82 (d, J = 8.2 Hz, 1H), 4.58-4.47 (m, 3H), 4.07-4.03 (m, 3H), 3.29 (m, 1H), 2.90-2.80 (m, 1H), 2.67-2.60 (m, 1H), 1.88-1.75 (m, 8H), 1.61-1.35 (m, 3H), 1.10-0.98 (m, 2H), 0.92 (d, J = 6.5 Hz, 3H). $C_{21}H_{30}N_2O_2$; MS (ESI) m/z 342.9 (MH)$^+$. |
| 39 | 1-(3-chloro-phenyl)carbonyl-5'-aminomethyl-spiro[piperidine-4,3'-(2H)-benzo[b]furan]<br>$^1$H NMR (CD$_3$OD) δ 7.53-7.45 (m, 3H), 7.40-7.37 (m, 1H), 7.33 (d, J = 1.9 Hz, 1H), 7.23 (dd, J = 1.9 Hz, J = 8.2 Hz, 1H), 6.82 (d, J = 8.2 Hz, 1H), 4.56 (br s, 3H), 4.05 (s, 2H), 3.80-3.65 (br m, 1H), 3.17-3.07 (br m, 2H), 2.03-1.76 (br m, 4H). $C_{20}H_{21}ClN_2O_2$; MS (ESI) m/z 356.9/358.8 (MH)$^+$. |

| Cpd | Name |
|---|---|
| 40 | 1-(3,4-dimethoxy-phenyl)carbonyl-5'-aminomethyl-spiro[piperidine-4,3'-(2H)-benzo[b]furan]<br>$^1$H NMR (CD$_3$OD) δ 7.32 (d, J = 1.7 Hz, 1H), 7.23 (dd, J = 1.9 Hz, J = 8.2 Hz, 1H), 7.08-7.01 (m, 3H), 6.82 (d, J = 8.2 Hz, 1H), 4.57 (s, 2H), 4.04 (s, 2H), 3.87 (s, 6H), 3.80-3.65 (br m, 2H), 3.17-3.07 (br m, 2H), 2.03-1.76 (br m, 4H). C$_{22}$H$_{26}$N$_2$O$_4$; MS (ESI) m/z 382.8 (MH)$^+$. |
| 41 | 1-(3-methyl-phenyl)carbonyl-5'-aminomethyl-spiro[piperidine-4,3'-(2H)-benzo[b]furan]<br>$^1$H NMR (CD$_3$OD) δ 7.38-7.30 (m, 4H), 7.26 (s, 1H), 7.23 (dd, J = 1.9 Hz, J = 8.2 Hz, 1H), 6.82 (d, J = 8.2 Hz, 1H), 4.56 (br s, 3H), 4.05 (s, 2H), 3.85-3.75 (br m, 1H), 3.17-3.07 (br m, 2H), 2.39 (s, 3H), 1.98-1.74 (br m, 4H). C$_{21}$H$_{24}$N$_2$O$_2$; MS (ESI) m/z 336.9 (MH)$^+$. |
| 42 | 1-(3-fluoro-phenyl)carbonyl-5'-aminomethyl-spiro[piperidine-4,3'-(2H)-benzo[b]furan]<br>$^1$H NMR (CD$_3$OD) δ 7.55-7.48 (m, 1H), 7.33-7.21 (m, 5H), 6.82 (d, J = 8.2 Hz, 1H), 4.56 (br s, 3H), 4.05 (s, 2H), 3.80-3.65 (br m, 1H), 3.17-3.07 (br m, 2H), 2.03-1.76 (br m, 4H). C$_{20}$H$_{21}$FN$_2$O$_2$; MS (ESI) m/z 340.8 (MH)$^+$. |
| 43 | 1-(4-fluoro-phenyl)carbonyl-5'-aminomethyl-spiro[piperidine-4,3'-(2H)-benzo[b]furan]<br>$^1$H NMR (CD$_3$OD) δ 7.54-7.49 (m, 2H), 7.31 (d, J = 1.8 Hz, 1H), 7.25-7.19 (m, 3H), 6.82 (d, J = 8.2 Hz, 1H), 4.56 (br s, 3H), 4.04 (s, 2H), 3.80-3.65 (br m, 1H), 3.17-3.07 (br m, 2H), 2.03-1.68 (br m, 4H). C$_{20}$H$_{21}$FN$_2$O$_2$; MS (ESI) m/z 340.8 (MH)$^+$. |
| 44 | 1-(4-chloro-phenyl)carbonyl-5'-aminomethyl-spiro[piperidine-4,3'-(2H)-benzo[b]furan]<br>$^1$H NMR (CD$_3$OD) δ 7.52-7.44 (m, 4H), 7.32 (d, J = 1.9 Hz, 1H), 7.23 (dd, J = 2.0 Hz, J = 8.2 Hz, 1H), 6.82 (d, J = 8.2 Hz, 1H), 4.56 (br s, 3H), 4.04 (s, 2H), 3.80-3.65 (br m, 1H), 3.17-3.07 (br m, 2H), 1.98-1.77 (br m, 4H). C$_{20}$H$_{21}$ClN$_2$O$_2$; MS (ESI) m/z 356.9/358.8 (MH)$^+$. |
| 45 | 1-(4-methylthio-phenyl)carbonyl-5'-aminomethyl-spiro[piperidine-4,3'-(2H)-benzo[b]furan]<br>$^1$H NMR (CD$_3$OD) δ 7.41-7.31 (m, 5H), 7.23 (dd, J = 2.0 Hz, J = 8.2 Hz, 1H), 6.82 (d, J = 8.2 Hz, 1H), 4.56 (br s, 3H), 4.04 (s, 2H), 3.95-3.75 (br m, 1H), 3.17-3.07 (br m, 2H), 2.51 (s, 3H), 2.03-1.86 (br m, 4H). C$_{21}$H$_{24}$N$_2$O$_2$S; MS (ESI) m/z 368.9 (MH)$^+$. |
| 46 | 1-(3-fluoro-4-chloro-phenyl)carbonyl-5'-aminomethyl-spiro[piperidine-4,3'-(2H)-benzo[b]furan]<br>$^1$H NMR (CD$_3$OD) δ 7.61 (t, J = 8.0 Hz, 1H), 7.40-7.22 (m, 4H), 6.82 (d, J = 8.2 Hz, 1H), 4.56 (br s, 3H), 4.04 (s, 2H), 3.85-3.65 (br m, 1H), 3.17-3.07 (br m, 2H), 2.03-1.86 (br m, 4H). C$_{20}$H$_{20}$ClFN$_2$O$_2$; MS (ESI) m/z 374.9/376.8 (MH)$^+$. |
| 47 | 1-(3-trifluoromethyl-phenyl)carbonyl-5'-aminomethyl-spiro[piperidine-4,3'-(2H)-benzo[b]furan]<br>$^1$H NMR (CD$_3$OD) δ 7.83-7.67 (m, 4H), 7.33 (d, J = 1.8 Hz, 1H), 7.23 (dd, J = 1.9 Hz, J = 8.2 Hz, 1H), 6.82 (d, J = 8.2 Hz, 1H), 4.56 (br s, 3H), 4.04 (s, 2H), 3.85-3.65 (br m, 1H), 3.17-3.07 (br m, 2H), 2.03-1.86 (br m, 4H). C$_{21}$H$_{21}$F$_3$N$_2$O$_2$; MS (ESI) m/z 390.8 (MH)$^+$. |
| 48 | 1-(3-iodo-phenyl)carbonyl-5'-aminomethyl-spiro[piperidine-4,3'-(2H)-benzo[b]furan]<br>$^1$H NMR (CD$_3$OD) δ 7.78-7.72 (m, 2H), 7.47-7.35 (m, 2H), ), 7.19-7.12 (m, 2H), 6.73 (d, J = 8.2 Hz, 1H), 4.46 (br s, 3H), 3.95 (s, 2H), 3.85-3.65 (br m, 1H), 3.17-3.07 (br m, 2H), 2.03-1.86 (br m, 4H). C$_{20}$H$_{21}$IN$_2$O$_2$; MS (ESI) m/z 448.6 (MH)$^+$. |
| 49 | 1-(4-iodo-phenyl)carbonyl-5'-aminomethyl-spiro[piperidine-4,3'-(2H)-benzo[b]furan]<br>$^1$H NMR (CD$_3$OD) δ 7.86 (dd, J = 1.7 Hz, J = 6.6 Hz, 2H), 7.31 (d, J = 1.9 Hz, 1H), 7.25-7.21 (m, 3H), 6.82 (d, J = 8.2 Hz, 1H), 4.56 (br s, 3H), 4.04 (s, 2H), 3.85-3.65 (br m, 1H), 3.17-3.07 (br m, 2H), 2.03-1.76 (br m, 4H). C$_{20}$H$_{21}$IN$_2$O$_2$; MS (ESI) m/z 448.6 (MH)$^+$. |
| 50 | 1-(3-iodo-4-methyl-phenyl)carbonyl-5'-aminomethyl-spiro[piperidine-4,3'-(2H)-benzo[b]furan]<br>$^1$H NMR (CD$_3$OD) δ 7.90 (d, J = 1.2 Hz, 1H), 7.41-7.35 (m, 2H), 7.32 (d, J = 1.9 Hz, 1H), 7.23 (dd, J = 1.9 Hz, J = 8.2 Hz, 1H), 6.82 (d, J = 8.2 Hz, 1H), 4.56 (br s, 3H), 4.04 (s, 2H), 3.85-3.65 (br m, 1H), 3.17-3.07 (br m, 2H), 2.47 (s, 3H), 2.03-1.77 (br m, 4H). C$_{21}$H$_{23}$IN$_2$O$_2$; MS (ESI) m/z 462.6 (MH)$^+$. |
| 51 | 1-(3-methyl-4-iodo-phenyl)carbonyl-5'-aminomethyl-spiro[piperidine-4,3'-(2H)-benzo[b]furan]<br>$^1$H NMR (CD$_3$OD) δ 7.94 (d, J = 8.0 Hz, 1H), 7.36 (d, J = 1.9 Hz, 1H), 7.32 (d, J = 1.9 Hz, 1H), 7.23 (dd, J = 1.9 Hz, J = 8.2 Hz, 1H), 6.99 (dd, J = 1.8 Hz, J = 8.0 Hz, 1H), 6.82 (d, J = 8.2 Hz, 1H), 4.55 (br s, 3H), 4.04 (s, 2H), 3.85-3.65 (br m, 1H), 3.17-3.07 (br m, 2H), 2.47 (s, 3H), 2.03-1.74 (br m, 4H). C$_{21}$H$_{23}$IN$_2$O$_2$; MS (ESI) m/z 462.6 (MH)$^+$. |
| 52 | 1-(3-iodo-4-methoxy-phenyl)carbonyl-5'-aminomethyl-spiro[piperidine-4,3'-(2H)-benzo[b]furan]<br>$^1$H NMR (CD$_3$OD) δ 7.89 (d, J = 2.1 Hz, 1H), 7.48 (dd, J = 2.1 Hz, J = 8.5 Hz, 1H), 7.32 (d, J = 1.8 Hz, 1H), 7.23 (dd, J = 1.9 Hz, J = 8.2 Hz, 1H), |

-continued

| Cpd | Name |
|---|---|
| | 7.03 (d, J = 8.5 Hz, 1H), 6.82 (d, J = 8.2 Hz, 1H), 4.56 (br s, 3H), 4.04 (s, 2H), 3.92 (s, 3H), 3.85-3.65 (br m, 1H), 3.17-3.07 (br m, 2H), 1.99-1.82 (br m, 4H). $C_{21}H_{23}IN_2O_3$; MS (ESI) m/z 478.6 (MH)$^+$. |
| 53 | 1-(3-methoxy-phenyl)carbonyl-5'-aminomethyl-spiro[piperidine-4,3'-(2H)-benzo[b]furan]<br>$^1$H NMR (CD$_3$OD) δ 7.42-7.34 (m, 2H), 7.23 (d, J = 8.2 Hz, 1H), 7.07-7.00 (m, 3H), 6.82 (d, J = 8.2 Hz, 1H), 4.56 (br s, 3H), 4.04 (s, 2H), 3.84 (s, 3H), 3.80-3.65 (br m, 1H), 3.17-3.07 (br m, 2H), 1.99-1.82 (br m, 4H). $C_{21}H_{24}N_2O_3$; MS (ESI) m/z 352.8 (MH)$^+$. |
| 54 | 1-(4-methoxy-phenyl)carbonyl-5'-aminomethyl-spiro[piperidine-4,3'-(2H)-benzo[b]furan]<br>$^1$H NMR (CD$_3$OD) δ 7.45-7.32 (m, 2H), 7.24 (d, J = 1.9 Hz, 1H), 7.21 (d, J = 1.9 Hz, 1H), 7.03-6.98 (m, 2H), 6.82 (d, J = 8.2 Hz, 1H), 4.56 (br s, 3H), 4.04 (s, 2H), 3.84 (s, 3H), 3.80-3.65 (br m, 1H), 3.17-3.07 (br m, 2H), 1.99-1.82 (br m, 4H). $C_{21}H_{24}N_2O_3$; MS (ESI) m/z 352.8 (MH)$^+$. |
| 55 | 1-(4-dimethylamino-phenyl)carbonyl-5'-aminomethyl-spiro[piperidine-4,3'-(2H)-benzo[b]furan]<br>$^1$H NMR (CD$_3$OD) δ 7.44-7.39 (m, 2H), 7.32 (d, J = 1.8 Hz, 1H), 7.23 (dd, J = 1.9 Hz, J = 8.2 Hz, 1H), 6.98-6.90 (m, 2H), 6.82 (d, J = 8.2 Hz, 1H), 4.56 (br s, 2H), 4.40-4.10 (br m, 1H), 4.04 (s, 2H), 3.17-3.07 (br m, 3H), 3.07 (s, 6H), 1.99-1.82 (br m, 4H).<br>$C_{22}H_{27}N_3O_2$; MS (ESI) m/z 365.9 (MH)$^+$. |
| 56 | 1-(3-dimethylamino-phenyl)carbonyl-5'-aminomethyl-spiro[piperidine-4,3'-(2H)-benzo[b]furan]<br>$^1$H NMR (CD$_3$OD) δ 7.51-7.11 (m, 6H), 6.82 (d, J = 8.2 Hz, 1H), 4.56 (br s, 3H), 4.04 (s, 2H), 3.80-3.70 (br m, 1H), 3.17-3.07 (br m, 2H), 3.13 (s, 6H), 1.99-1.82 (br m, 4H). $C_{22}H_{27}N_3O_2$; MS (ESI) m/z 365.9 (MH)$^+$. |
| 57 | 1-(3-methylthio-phenyl)carbonyl-5'-aminomethyl-spiro[piperidine-4,3'-(2H)-benzo[b]furan]<br>$^1$H NMR (CD$_3$OD) δ 7.43-7.36 (m, 2H), 7.33-7.31 (m, 2H), 7.25-7.18 (m, 2H), 6.82 (d, J = 8.2 Hz, 1H), 4.56 (br s, 3H), 4.04 (s, 2H), 3.85-3.75 (br m, 1H), 3.17-3.07 (br m, 2H), 2.51 (s, 3H), 2.00-1.75 (br m, 4H).<br>$C_{21}H_{24}N_2O_2S$; MS (ESI) m/z 368.9 (MH)$^+$. |
| 58 | 1-(4-methoxycarbonyl-phenyl)carbonyl-5'-aminomethyl-spiro[piperidine-4,3'-(2H)-benzo[b]furan]<br>$^1$H NMR (CD$_3$OD) δ 8.14-8.11 (m, 2H), 7.58-7.55 (m, 2H), 7.34 (d, J = 1.8 Hz, 1H), 7.23 (dd, J = 1.9 Hz, J = 8.2 Hz, 1H), 6.82 (d, J = 8.2 Hz, 1H), 4.55 (br s, 3H), 4.05 (s, 2H), 3.93 (s, 3H), 3.75-3.65 (br m, 1H), 3.17-3.07 (br m, 2H), 2.03-1.70 (br m, 4H). $C_{22}H_{24}N_2O_4$; MS (ESI) m/z 380.9 (MH)$^+$. |
| 59 | 1-(4-bromo-phenyl)carbonyl-5'-aminomethyl-spiro[piperidine-4,3'-(2H)-benzo[b]furan]<br>$^1$H NMR (CD$_3$OD) δ 7.70-7.66 (m, 2H), 7.43-7.40 (m, 2H), 7.35 (s, 1H), 7.26 (d, J = 8.2 Hz, 1H), 6.84 (dd, J = 1.3 Hz, J = 8.2 Hz, 1H), 4.55 (br s, 3H), 4.05 (s, 2H), 3.75-3.65 (br m, 1H), 3.17-3.07 (br m, 2H), 2.03-1.70 (br m, 4H). $C_{20}H_{21}BrN_2O_2$; MS (ESI) m/z 400.6/402.7 (MH)$^+$. |
| 60 | 1-(3-trifluoromethoxy-phenyl)carbonyl-5'-aminomethyl-spiro[piperidine-4,3'-(2H)-benzo[b]furan]<br>$^1$H NMR (CD$_3$OD) δ 7.60 (t, J = 7.9 Hz, 1H), 7.48-7.39 (m, 3H), 7.34 (d, J = 1.8 Hz, 1H), 7.23 (dd, J = 1.9 Hz, J = 8.2 Hz, 1H), 6.82 (d, J = 8.2 Hz, 1H), 4.56 (br s, 3H), 4.05 (s, 2H), 3.75-3.65 (br m, 1H), 3.17-3.07 (br m, 2H), 2.01-1.76 (br m, 4H). $C_{21}H_{21}F_3N_2O_3$; MS (ESI) m/z 406.8 (MH)$^+$. |
| 61 | 1-(4-trifluoromethoxy-phenyl)carbonyl-5'-aminomethyl-spiro[piperidine-4,3'-(2H)-benzo[b]furan]<br>$^1$H NMR (CD$_3$OD) δ 7.58 (d, J = 8.5 Hz, 2H), 7.40 (d, J = 8.6 Hz, 2H), 7.31 (s, 1H), 7.23 (d, J = 8.3 Hz, 1H), 6.82 (d, J = 8.3 Hz, 1H), 4.56 (br s, 3H), 4.05 (s, 2H), 3.75-3.65 (br m, 1H), 3.17-3.07 (br m, 2H), 2.01-1.76 (br m, 4H). $C_{21}H_{21}F_3N_2O_3$; MS (ESI) m/z 406.8 (MH)$^+$. |
| 62 | 1-(4-phenoxy-phenyl)carbonyl-5'-aminomethyl-spiro[piperidine-4,3'-(2H)-benzo[b]furan]<br>$^1$H NMR (CD$_3$OD) δ 7.49-7.37 (m, 4H), 7.32 (d, J = 1.9 Hz, 1H), 7.25-7.16 (m, 2H), 7.07-7.03 (m, 4H), 6.82 (d, J = 8.2 Hz, 1H), 4.56 (br s, 3H), 4.05 (s, 2H), 3.75-3.65 (br m, 1H), 3.17-3.07 (br m, 2H), 1.93-1.83 (br m, 4H). $C_{26}H_{26}N_2O_3$; MS (ESI) m/z 414.8 (MH)$^+$. |
| 63 | 1-(3-trifluoromethylthio-phenyl)carbonyl-5'-aminomethyl-spiro[piperidine-4,3'-(2H)-benzo[b]furan]<br>$^1$H NMR (CD$_3$OD) δ 7.83 (dd, J = 1.9 Hz, J = 6.8 Hz, 1H), 7.79 (s, 1H), 7.68-7.60 (m, 2H), 7.33 (d, J = 1.9 Hz, 1H), 7.23 (dd, J = 1.9 Hz, J = 8.2 Hz, 1H), 6.82 (d, J = 8.2 Hz, 1H), 4.56 (br s, 3H), 4.05 (s, 2H), 3.75-3.65 (br m, 1H), 3.17-3.07 (br m, 2H), 2.01-1.76 (br m, 4H).<br>$C_{21}H_{21}F_3N_2O_2S$; MS (ESI) m/z 422.7 (MH)$^+$. |
| 64 | 1-[3-(4-methoxy-phenyl)-phenyl]carbonyl-5'-aminomethyl-spiro[piperidine-4,3'-(2H)-benzo[b]furan]<br>$^1$H NMR (CD$_3$OD) δ 7.72 (m, 5H), 7.37 (dd, J = 1.3 Hz, J = 6.3 Hz, 1H), 7.33 (d, J = 1.8 Hz, 1H), 7.23 (dd, J = 1.9 Hz, J = 8.2 Hz, 1H), 7.05-7.00 (m, 2H), 6.82 (d, J = 8.2 Hz, 1H), 4.57 (br s, 3H), 4.04 (s, 2H), 3.84 (br s, 4H), 3.17-3.07 (br m, 2H), 2.02-1.76 (br m, 4H).<br>$C_{27}H_{28}N_2O_3$; MS (ESI) m/z 428.9 (MH)$^+$. |

-continued

| Cpd | Name |
|---|---|
| 66 | 1-(3-cyano-phenyl)carbonyl-5'-aminomethyl-spiro[piperidine-4,3'-(2H)-benzo[b]furan]<br>$^1$H NMR (CD$_3$OD) δ 7.88-7.85 (m, 2H), 7.78-7.75 (m, 1H), 7.70-7.65 (m, 1H), 7.33 (d, J = 1.8 Hz, 1H), 7.23 (dd, J = 2.0 Hz, J = 8.2 Hz, 1H), 6.82 (d, J = 8.2 Hz, 1H), 4.56 (br s, 3H), 4.05 (s, 2H), 3.75-3.60 (br m, 1H), 3.17-3.07 (br m, 2H), 2.09-1.76 (br m, 4H). C$_{21}$H$_{21}$N$_3$O$_2$; MS (ESI) m/z 347.9 (MH)$^+$. |
| 67 | 1-(4-methylcarbonyl-phenyl)carbonyl-5'-aminomethyl-spiro[piperidine-4,3'-(2H)-benzo[b]furan]<br>$^1$H NMR (CD$_3$OD) δ 8.09 (dd, J = 1.7 Hz, J = 6.8 Hz, 2H), 7.58 (dd, J = 1.7 Hz, J = 6.8 Hz, 2H), 7.34 (d, J = 1.7 Hz, 1H), 7.24 (dd, J = 1.9 Hz, J = 8.2 Hz, 1H), 6.82 (d, J = 8.2 Hz, 1H), 4.56 (br s, 3H), 4.05 (s, 2H), 3.80-3.65 (br m, 1H), 3.17-3.07 (br m, 2H), 2.64 (s, 3H), 2.06-1.70 (br m, 4H). C$_{22}$H$_{24}$N$_2$O$_3$; MS (ESI) m/z 364.8 (MH)$^+$. |
| 68 | 1-benzodioxol-5-ylcarbonyl-5'-aminomethyl-spiro[piperidine-4,3'-(2H)-benzo[b]furan]<br>$^1$H NMR (CD$_3$OD) δ 7.32 (d, J = 1.5 Hz, 1H), 7.22 (dd, J = 1.9 Hz, J = 8.2 Hz, 1H), 7.00-6.89 (m, 3H), 6.82 (d, J = 8.2 Hz, 1H), 6.02 (s, 2H), 4.56 (br s, 3H), 4.04 (s, 2H), 4.0-3.70 (br m, 1H), 3.40-3.15 (br m, 2H), 1.93-1.81 (br m, 4H). C$_{21}$H$_{22}$N$_2$O$_4$; MS (ESI) m/z 366.8 (MH)$^+$. |
| 69 | 1-(4-chloromethyl-phenyl)carbonyl-5'-aminomethyl-spiro[piperidine-4,3'-(2H)-benzo[b]furan]<br>$^1$H NMR (CD$_3$OD) δ 7.56-7.45 (m, 2H), 7.40-7.37 (m, 2H), 7.32 (d, J = 1.8 Hz, 1H), 7.23 (dd, J = 1.9 Hz, J = 8.2 Hz, 1H), 6.82 (d, J = 8.2 Hz, 1H), 4.69 (s, 2H), 4.56 (br s, 3H), 4.05 (s, 2H), 3.85-3.65 (br m, 1H), 3.20-3.05 (br m, 2H), 2.03-1.75 (br m, 4H). C$_{21}$H$_{23}$ClN$_2$O$_2$; MS (ESI) m/z 370.8/372.8 (MH)$^+$. |
| 70 | 1-naphthalen-2-ylcarbonyl-5'-aminomethyl-spiro[piperidine-4,3'-(2H)-benzo[b]furan]<br>$^1$H NMR (CD$_3$OD) δ 8.00-7.92 (m, 4H), 7.61-7.52 (m, 3H), 7.35 (d, J = 1.8 Hz, 1H), 7.23 (dd, J = 1.9 Hz, J = 8.2 Hz, 1H), 6.82 (d, J = 8.2 Hz, 1H), 4.70-4.60 (br m, 1H), 4.56 (s, 2H), 4.05 (s, 2H), 3.90-3.75 (br m, 1H), 3.25-3.10 (br m, 2H), 2.03-1.76 (br m, 4H). C$_{24}$H$_{24}$N$_2$O$_2$; MS (ESI) m/z 372.9 (MH)$^+$. |
| 71 | 1-(4-trifluoromethyl-phenyl)carbonyl-5'-aminomethyl-spiro[piperidine-4,3'-(2H)-benzo[b]furan]<br>$^1$H NMR (CD$_3$OD) δ 7.32 (d, J = 8.2 Hz, 2H), 7.65 (d, J = 8.1 Hz, 2H), 7.32 (d, J = 1.8 Hz, 1H), 7.23 (dd, J = 1.9 Hz, J = 8.2 Hz, 1H), 6.82 (d, J = 8.2 Hz, H), 4.57 (br s, 3H), 4.04 (s, 2H), 3.75-3.65 (br m, 1H), 3.20-3.05 (br m, 2H), 2.03-1.75 (br m, 4H). C$_{21}$H$_{21}$F$_3$N$_2$O$_2$; MS (ESI) m/z 390.9 (MH)$^+$. |
| 72 | 1-(3-methylsulfonyl-phenyl)carbonyl-5'-aminomethyl-spiro[piperidine-4,3'-(2H)-benzo[b]furan]<br>$^1$H NMR (CD$_3$OD) δ 8.11-8.07 (m, 1H), 8.04 (d, J = 1.5 Hz, 1H), 7.83-7.74 (m, 2H), 7.34 (d, J = 1.8 Hz, 1H), 7.23 (dd, J = 1.9 Hz, J = 8.2 Hz, 1H), 6.82 (d, J = 8.2 Hz, 1H), 4.57 (br s, 3H), 4.05 (s, 2H), 3.75-3.65 (br m, 1H), 3.17 (br s, 5H), 2.03-1.73 (br m, 4H). C$_{21}$H$_{24}$N$_2$O$_4$S; MS (ESI) m/z 400.8 (MH)$^+$. |
| 73 | 1-(4-cyclohexyl-phenyl)carbonyl-5'-aminomethyl-spiro[piperidine-4,3'-(2H)-benzo[b]furan]<br>$^1$H NMR (CD$_3$OD) δ 7.40-7.31 (m, 5H), 7.23 (dd, J = 1.9 Hz, J = 8.2 Hz, 1H), 6.81 (d, J = 8.2 Hz, 1H), 4.55 (br s, 3H), 4.04 (s, 2H), 3.95-3.75 (br m, 1H), 3.25-3.15 (br m, 2H), 2.65-2.50 (br m, 1H), 2.10-1.60 (br m, 9H), 1.50-1.20 (br m, 5H). C$_{26}$H$_{32}$N$_2$O$_2$; MS (ESI) m/z 404.9 (MH)$^+$. |
| 74 | 1-(3-trifluoromethyl-4-fluoro-phenyl)carbonyl-5'-aminomethyl-spiro[piperidine-4,3'-(2H)-benzo[b]furan]<br>$^1$H NMR (CD$_3$OD) δ 7.83-7.77 (m, 2H), 7.51-7.44 (m, 1H), 7.33 (d, J = 1.9 Hz, 1H), 7.23 (dd, J = 1.9 Hz, J = 8.2 Hz, 1H), 6.82 (d, J = 8.2 Hz, 1H), 4.56 (br s, 3H), 4.04 (s, 2H), 3.80-3.60 (br m, 1H), 3.25-3.05 (br m, 2H), 2.10-1.65 (br m, 4H). C$_{21}$H$_{20}$F$_4$N$_2$O$_2$; MS (ESI) m/z 408.8 (MH)$^+$. |
| 75 | 1-(4-benzyl-phenyl)carbonyl-5'-aminomethyl-spiro[piperidine-4,3'-(2H)-benzo[b]furan]<br>$^1$H NMR (CD$_3$OD) δ 7.41-7.15 (m, 11H), 6.82 (d, J = 8.2 Hz, 1H), 4.56 (br s, 3H), 4.06 (s, 2H), 4.04 (s, 2H), 3.85-3.70 (br m, 1H), 3.25-3.05 (br m, 2H), 2.10-1.65 (br m, 4H). C$_{27}$H$_{28}$N$_2$O$_2$; MS (ESI) m/z 413.2 (MH)$^+$. |
| 76 | 1-(4-benzyloxy-phenyl)carbonyl-5'-aminomethyl-spiro[piperidine-4,3'-(2H)-benzo[b]furan]<br>$^1$H NMR (CD$_3$OD) δ 7.46-7.31 (m, 8H), 7.23 (dd, J = 1.9 Hz, J = 8.2 Hz, 1H), 7.10-7.07 (m, 2H), 6.82 (d, J = 8.2 Hz, 1H), 5.15 (s, 2H), 4.56 (br s, 3H), 4.04 (s, 2H), 3.95-3.70 (br m, 1H), 3.25-3.10 (br m, 2H), 2.05-1.65 (br m, 4H). C$_{27}$H$_{28}$N$_2$O$_3$; MS (ESI) m/z 429.2 (MH)$^+$. |
| 78 | 1-benzylcarbonyl-5'-aminomethyl-spiro[piperidine-4,3'-(2H)-benzo[b]furan]<br>$^1$H NMR (CD$_3$OD) δ 7.28-7.10 (m, 5H), 7.06 (d, J = 1.8 Hz, 1H), 6.70 (d, J = 6.2 Hz, 1H), 4.50-4.42 (m, 1H), 4.39 (s, 2H), 4.00-3.95 (m, 1H), 3.92 (s, 2H), 3.74 (s, 2H), 3.18-3.09 (m, 1H), 2.86-2.76 (m, 1H), 3.25-3.10 (br m, 1H), 1.77-1.51 (m, 4H). C$_{21}$H$_{24}$N$_2$O$_2$; MS (ESI) m/z 337.2 (MH)$^+$. |

-continued

| Cpd | Name |
|---|---|
| 79 | 1-phenethylcarbonyl-5'-aminomethyl-spiro[piperidine-4,3'-(2H)-benzo[b]furan]<br>$^1$H NMR (CD$_3$OD) δ 7.35-7.21 (m, 7H), 6.83 (d, J = 8.0 Hz, 1H), 4.50 (br s, 3H), 4.05 (s, 2H), 3.92 (br d, J = 13.9 Hz, 1H), 3.34-3.14 (m, 1H), 3.00-2.73 (m, 5H), 1.80-1.62 (m, 4H). C$_{22}$H$_{26}$N$_2$O$_2$; MS (ESI) m/z 351.1 (MH)$^+$. |
| 80 | 1-(3-fluoro-benzyl)carbonyl-5'-aminomethyl-spiro[piperidine-4,3'-(2H)-benzo[b]furan]<br>$^1$H NMR (CD$_3$OD) δ 7.42-7.34 (m, 1H), 7.26-7.20 (m, 2H), 7.14-7.00 (m, 3H), 6.83 (d, J = 8.1 Hz, 1H), 4.52 (br s, 3H), 4.04 (br s, 3H), 3.87 (s, 2H), 3.34-3.24 (m, 1H), 2.99-2.89 (m, 1H), 2.05-1.70 (m, 4H). C$_{21}$H$_{23}$FN$_2$O$_2$; MS (ESI) m/z 355.2 (MH)$^+$. |
| 81 | 1-(3-chloro-benzyl)carbonyl-5'-aminomethyl-spiro[piperidine-4,3'-(2H)-benzo[b]furan]<br>$^1$H NMR (CD$_3$OD) δ 7.36-7.18 (m, 6H), 6.81 (d, J = 8.1 Hz, 1H), 4.51 (br s, 3H), 4.02 (br s, 3H), 3.84 (s, 2H), 3.00-2.87 (m, 1H), 2.76-2.03 (br m, 1H), 2.03-1.66 (m, 4H). C$_{21}$H$_{23}$ClN$_2$O$_2$; MS (ESI) m/z 371.2/373.2 (MH)$^+$. |
| 82 | 1-(3,4-difluoro-benzyl)carbonyl-5'-aminomethyl-spiro[piperidine-4,3'-(2H)-benzo[b]furan]<br>$^1$H NMR (CD$_3$OD) δ 7.18-7.11 (m, 4H), 7.09-6.97 (br m, 1H), 6.72 (d, J = 8.1 Hz, 1H), 4.42 (s, 2H), 4.41-4.37 (m, 1H), 3.99-3.95 (br m, 1H), 3.93 (s, 2H), 3.73 (s, 2H), 3.24-3.14 (m, 1H), 2.87-2.77 (m, 1H), 1.80-1.60 (m, 4H). C$_{21}$H$_{22}$F$_2$N$_2$O$_2$; MS (ESI) m/z 373.2 (MH)$^+$. |
| 83 | 1-(3-chloro-phenethyl)carbonyl-5'-aminomethyl-spiro[piperidine-4,3'-(2H)-benzo[b]furan]<br>$^1$H NMR (CD$_3$OD) δ 7.32-7.19 (m, 6H), 6.81 (d, J = 8.1 Hz, 1H), 4.49 (s, 2H), 4.48-4.44 (m, 1H), 4.04 (s, 2H), 3.92 (br d, J = 13.8 Hz, 1H), 3.24-3.15 (m, 1H), 2.98-2.70 (m, 5H), 1.78-1.62 (m, 4H). C$_{22}$H$_{25}$ClN$_2$O$_2$; MS (ESI) m/z 385.2 (MH)$^+$. |
| 84 | 1-naphthalen-2-ylmethylcarbonyl-5'-aminomethyl-spiro[piperidine-4,3'-(2H)-benzo[b]furan]<br>$^1$H NMR (CD$_3$OD) δ 7.81-7.68 (m, 4H), 7.42-7.34 (m, 3H), 7.09 (d, J = 8.1 Hz, 1H), 6.94 (s, 1H), 6.68 (d, J = 8.3 Hz, 1H), 4.50-4.41 (m, 1H), 4.39 (s, 2H), 4.01-3.97 (m, 1H), 3.91 (s, 2H), 3.86 (s, 2H), 3.21-3.12 (m, 1H), 2.89-2.78 (m, 1H), 1.77-1.63 (m, 2H), 1.57-1.42 (m, 2H). C$_{25}$H$_{26}$N$_2$O$_2$; MS (ESI) m/z 387.2 (MH)$^+$. |
| 85 | 1-(3-trifluoromethyl-benzyl)carbonyl-5'-aminomethyl-spiro[piperidine-4,3'-(2H)-benzo[b]furan]<br>$^1$H NMR (CD$_3$OD) δ 7.61-7.51 (m, 4H), 7.30-7.18 (m, 2H), 6.81 (d, J = 8.1 Hz, 1H), 4.52 (s, 2H), 4.51-4.47 (m, 1H), 4.15-4.07 (m, 1H), 4.02 (s, 2H), 3.94 (s, 2H), 3.34-3.25 (m, 1H), 3.07-2.72 (m, 1H), 1.85-1.71 (m, 4H). C$_{22}$H$_{23}$F$_3$N$_2$O$_2$; MS (ESI) m/z 405.1 (MH)$^+$. |
| 86 | 1-(3,4-dichloro-benzyl)carbonyl-5'-aminomethyl-spiro[piperidine-4,3'-(2H)-benzo[b]furan]<br>$^1$H NMR (CD$_3$OD) δ 7.41-7.38 (m, 2H), 7.14-7.11 (m, 3H), 6.71 (d, J = 8.0 Hz, 1H), 4.42 (s, 2H), 4.41-4.36 (m, 1H), 3.93 (br s, 3H), 3.74 (s, 2H), 3.24-3.14 (m, 1H), 2.87-2.77 (m, 1H), 1.84-1.64 (m, 4H). C$_{21}$H$_{22}$Cl$_2$N$_2$O$_2$; MS (ESI) m/z 405.1/407.1 (MH)$^+$. |
| 87 | 1-(3-bromo-benzyl)carbonyl-5'-aminomethyl-spiro[piperidine-4,3'-(2H)-benzo[b]furan]<br>$^1$H NMR (CD$_3$OD) δ 7.40 (s, 1H), 7.36-7.32 (m, 1H), 7.19-7.09 (m, 4H), 6.71 (d, J = 8.1 Hz, 1H), 4.41 (s, 2H), 4.40-4.38 (m, 1H), 3.93 (s, 2H), 3.92-3.89 (m, 1H), 3.74 (s, 2H), 3.22-3.12 (m, 1H), 2.86-2.65 (m, 1H), 1.79-1.56 (m, 4H). C$_{21}$H$_{23}$BrN$_2$O$_2$; MS (ESI) m/z 415.1/417.1 (MH)$^+$. |
| 88 | 1-(3-phenoxy-benzyl)carbonyl-5'-aminomethyl-spiro[piperidine-4,3'-(2H)-benzo[b]furan]<br>$^1$H NMR (CD$_3$OD) δ 7.28-7.26 (m, 3H), 7.25-6.86 (m, 6H), 6.85 (d, J = 1.9 Hz, 1H), 6.78 (dd, J = 2.0 Hz, J = 8.2 Hz, 1H), 6.71 (d, J = 8.1 Hz, 1H), 4.39 (s, 2H), 4.38-4.35 (m, 1H), 3.90 (br s, 3H), 3.72 (s, 2H), 3.20-3.10 (m, 1H), 2.85-2.76 (m, 1H), 1.78-1.57 (m, 4H). C$_{27}$H$_{28}$N$_2$O$_3$; MS (ESI) m/z 429.3 (MH)$^+$. |
| 89 | 1-(3-methyl-benzyl)carbonyl-5'-aminomethyl-spiro[piperidine-4,3'-(2H)-benzo[b]furan]<br>$^1$H NMR (CD$_3$OD) δ 7.15-6.97 (m, 6H), 6.70 (d, J = 8.2 Hz, 1H), 4.39 (br s, 3H), 3.92 (br s, 3H), 3.69 (s, 2H), 3.20-3.08 (m, 1H), 2.86-2.76 (m, 1H), 2.24 (s, 3H), 1.77-1.59 (m, 2H), 1.56-1.52 (m, 2H). C$_{22}$H$_{26}$N$_2$O$_2$; MS (ESI) m/z 351.3 (MH)$^+$. |
| 90 | 1-(4-fluoro-benzyl)carbonyl-5'-aminomethyl-spiro[piperidine-4,3'-(2H)-benzo[b]furan]<br>$^1$H NMR (CD$_3$OD) δ 7.23-7.18 (m, 2H), 7.14-7.08 (m, 2H), 7.02-6.95 (m, 2H), 6.71 (d, J = 8.2 Hz, 1H), 4.41 (br s, 3H), 3.92 (br s, 3H), 3.72 (s, 2H), 3.22-3.12 (m, 1H), 2.86-2.76 (m, 1H), 1.78-1.57 (m, 4H). C$_{21}$H$_{23}$FN$_2$O$_2$; MS (ESI) m/z 355.2 (MH)$^+$. |
| 91 | 1-(4-chloro-benzyl)carbonyl-5'-aminomethyl-spiro[piperidine-4,3'-(2H)-benzo[b]furan]<br>$^1$H NMR (CD$_3$OD) δ 7.27-7.08 (m, 6H), 6.71 (d, J = 8.1 Hz, 1H), 4.41 (br s, 3H), 3.93 (br s, 3H), 3.72 (s, 2H), 3.21-3.12 (m, 1H), 2.86-2.76 (m, 1H), 1.78-1.57 (m, 4H). C$_{21}$H$_{23}$ClN$_2$O$_2$; MS (ESI) m/z 371.2 (MH)$^+$. |

| Cpd | Name |
|---|---|
| 92 | 1-(4-phenyl-benzyl)carbonyl-5'-aminomethyl-spiro[piperidine-4,3'-(2H)-benzo[b]furan]<br>$^1$H NMR (CD$_3$OD) δ 7.64-7.60 (m, 4H), 7.46-7.30 (m, 5H), 7.19 (dd, J = 1.9 Hz, J = 8.1 Hz, 1H), 7.14 (d, J = 1.8 Hz, 1H), 6.80 (d, J = 8.2 Hz, 1H), 4.53-4.51 (m, 1H), 4.50 (s, 2H), 4.06 (br d, J = 14.5 Hz, 1H), 3.95 (d, J = 2.9 Hz, 2H), 3.88 (s, 2H), 3.31-3.22 (m, 1H), 2.97-2.87 (m, 1H), 1.87-1.58 (m, 4H). C$_{27}$H$_{28}$N$_2$O$_2$; MS (ESI) m/z 413.3 (MH)$^+$. |
| 93 | 1-(4-bromo-benzyl)carbonyl-5'-aminomethyl-spiro[piperidine-4,3'-(2H)-benzo[b]furan]<br>$^1$H NMR (CD$_3$OD) δ 7.52-7.48 (m, 2H), 7.24-7.17 (m, 4H), 6.80 (d, J = 8.2 Hz, 1H), 4.50 (s, 2H), 4.49-4.46 (m, 1H), 4.02 (s, 2H), 4.01-3.98 (m, 1H), 3.80 (s, 2H), 3.32-3.18 (m, 1H), 2.96-2.86 (m, 1H), 1.86-1.62 (m, 4H). C$_{21}$H$_{23}$BrN$_2$O$_2$; MS (ESI) m/z 415.2/417.1 (MH)$^+$. |
| 94 | 1-(4-methoxy-benzyl)carbonyl-5'-aminomethyl-spiro[piperidine-4,3'-(2H)-benzo[b]furan]<br>$^1$H NMR (CD$_3$OD) δ 7.34-7.07 (m, 7H), 7.00-6.94 (m, 4H), 6.80 (d, J = 8.2 Hz, 1H), 4.51 (br s, 3H), 4.10-4.06 (m, 1H), 3.99 (s, 2H), 3.82 (s, 2H), 3.32-3.22 (m, 1H), 2.96-2.86 (m, 1H), 1.89-1.60 (m, 4H). C$_{27}$H$_{28}$N$_2$O$_3$; MS (ESI) m/z 429.3 (MH)$^+$. |
| 95 | 1-(3-bromo-benzyl)carbonyl-5'-aminomethyl-spiro[piperidine-4,3'-(2H)-benzo[b]furan]<br>$^1$H NMR (CD$_3$OD) δ 7.46 (s, 1H), 7.40-7.36 (m, 1H), 7.27-7.20 (m, 4H), 6.80 (d, J = 8.2 Hz, 1H), 4.49 (s, 2H), 4.48-4.44 (m, 1H), 4.04 (s, 2H), 3.91 (br d, J = 14.2 Hz, 1H), 3.24-3.15 (m, 1H), 2.97-2.67 (m, 5H), 1.78-1.60 (m, 4H). C$_{22}$H$_{25}$BrN$_2$O$_2$; MS (ESI) m/z 429.1/431.2 (MH)$^+$. |
| 96 | 1-(4-iodo-benzyl)carbonyl-5'-aminomethyl-spiro[piperidine-4,3'-(2H)-benzo[b]furan]<br>$^1$H NMR (CD$_3$OD) δ 7.72-7.68 (m, 2H), 7.21 (dd, J = 2.0 Hz, J = 8.2 Hz, 1H), 7.16 (d, J = 1.8 Hz, 1H), 7.10 (s, 1H), 7.08 (s, 1H), 6.80 (d, J = 8.2 Hz, 1H), 4.50 (s, 2H), 4.49-4.46 (m, 1H), 4.03 (s, 2H), 4.02-3.97 (m, 1H), 3.79 (s, 2H), 3.32-3.20 (m, 1H), 2.95-2.86 (m, 1H), 1.82-1.64 (m, 4H). C$_{21}$H$_{23}$IN$_2$O$_2$; MS (ESI) m/z 463.2 (MH)$^+$. |
| 97 | 1-(3-iodo-phenethyl)carbonyl-5'-aminomethyl-spiro[piperidine-4,3'-(2H)-benzo[b]furan]<br>$^1$H NMR (CD$_3$OD) δ 7.65 (d, J = 1.5 Hz, 1H), 7.58 (d, J = 7.9 Hz, 1H), 7.30-7.22 (m, 3H), 7.08 (t, J = 7.8 Hz, 1H), 6.80 (d, J = 8.8 Hz, 1H), 4.49 (s, 2H), 4.48-4.43 (m, 1H), 4.05 (s, 2H), 3.90 (br d, J = 14.0 Hz, 1H), 3.23-3.13 (m, 1H), 2.94-2.68 (m, 5H), 1.78-1.60 (m, 4H). C$_{22}$H$_{25}$IN$_2$O$_2$; MS (ESI) m/z 477.1 (MH)$^+$. |
| 98 | 1-(3-methyl-phenethyl)carbonyl-5'-aminomethyl-spiro[piperidine-4,3'-(2H)-benzo[b]furan]<br>$^1$H NMR (CD$_3$OD) δ 7.24-7.16 (m, 3H), 7.08-7.02 (m, 3H), 6.81 (d, J = 8.1 Hz, 1H), 4.48 (s, 2H), 4.47-4.45 (m, 1H), 4.03 (s, 2H), 3.90 (br d, J = 14.5 Hz, 1H), 3.22-3.12 (m, 1H), 2.93-2.82 (m, 3H), 2.75-2.69 (m, 2H), 2.31 (m, 3H), 1.78-1.62 (m, 4H). C$_{23}$H$_{28}$N$_2$O$_2$; MS (ESI) m/z 365.2 (MH)$^+$. |
| 99 | 1-(3-methoxy-benzyl)carbonyl-5'-aminomethyl-spiro[piperidine-4,3'-(2H)-benzo[b]furan]<br>$^1$H NMR (CD$_3$OD) δ 7.32-7.23 (m, 2H), 7.18 (d, J = 1.6 Hz, 1H), 6.91-6.82 (m, 4H), 4.55-4.53 (m, 1H), 4.52 (s, 2H), 4.05 (s, 2H), 4.04-4.02 (m, 1H), 3.84 (s, 2H), 3.83 (s, 3H), 3.30-3.22 (m, 1H), 2.99-2.89 (m, 1H), 1.86-1.81 (m, 2H), 1.69-1.65 (m, 2H). C$_{22}$H$_{26}$N$_2$O$_3$; MS (ESI) m/z 367.2 (MH)$^+$. |
| 100 | 1-benzodioxol-5-ylmethylcarbonyl-5'-aminomethyl-spiro[piperidine-4,3'-(2H)-benzo[b]furan]<br>$^1$H NMR (CD$_3$OD) δ 7.23-7.18 (m, 2H), 6.82-6.73 (m, 4H), 5.93 (d, J = 1.7 Hz, 2H), 4.50 (s, 2H), 4.49-4.46 (m, 1H), 4.02 (br s, 3H), 3.74 (s, 2H), 3.30-3.20 (m, 1H), 2.95-2.85 (m, 1H), 1.90-1.65 (m, 4H). C$_{22}$H$_{24}$N$_2$O$_4$; MS (ESI) m/z 381.3 (MH)$^+$. |
| 101 | 1-(3-methoxy-phenethyl)carbonyl-5'-aminomethyl-spiro[piperidine-4,3'-(2H)-benzo[b]furan]<br>$^1$H NMR (CD$_3$OD) δ 7.24-7.18 (m, 3H), 6.85-6.76 (m, 4H), 4.48 (s, 2H), 4.47-4.44 (m, 1H), 4.04 (s, 2H), 3.90 (br d, J = 14.0 Hz, 1H), 3.79 (s, 3H), 3.22-3.12 (m, 1H), 2.95-2.68 (m, 5H), 1.77-1.51 (m, 4H). C$_{23}$H$_{28}$N$_2$O$_3$; MS (ESI) m/z 381.3 (MH)$^+$. |
| 102 | 1-(3-methyl-4-methoxy-benzyl)carbonyl-5'-aminomethyl-spiro[piperidine-4,3'-(2H)-benzo[b]furan]<br>$^1$H NMR (CD$_3$OD) δ 7.21 (dd, J = 1.9 Hz, J = 8.2 Hz, 1H), 7.15 (d, J = 1.8 Hz, 1H), 7.08-7.05 (m, 2H), 6.86 (d, J = 8.2 Hz, 1H), 6.80 (d, J = 8.2 Hz, 1H), 4.48 (br s, 3H), 4.01 (br s, 3H), 3.81 (s, 3H), 3.72 (s, 2H), 3.23-3.17 (m, 1H), 2.95-2.85 (m, 1H), 2.18 (s, 3H), 1.82-1.61 (m, 4H). C$_{23}$H$_{28}$N$_2$O$_3$; MS (ESI) m/z 381.3 (MH)$^+$. |
| 103 | 1-(3-methylthio-benzyl)carbonyl-5'-aminomethyl-spiro[piperidine-4,3'-(2H)-benzo[b]furan]<br>$^1$H NMR (CD$_3$OD) δ 7.28-7.20 (m, 5H), 7.14 (d, J = 1.8 Hz, 1H), 6.80 (d, J = 8.2 Hz, 1H), 4.49 (br s, 3H), 4.02 (s, 2H), 4.01-3.98 (m, 1H), 3.79 (s, 2H), 3.23-3.19 (m, 1H), 2.95-2.85 (m, 1H), 2.46 (s, 3H), 1.81-1.60 (m, 4H). C$_{22}$H$_{26}$N$_2$O$_2$S; MS (ESI) m/z 383.3 (MH)$^+$. |

-continued

| Cpd | Name |
|---|---|
| 104 | 1-(benzodioxol-5-ylethyl)carbonyl-5'-aminomethyl-spiro[piperidine-4,3'-(2H)-benzo[b]furan]<br>$^1$H NMR (CD$_3$OD) δ 7.22 (dd, J = 1.9 Hz, J = 8.2 Hz, 1H), 7.17 (d, J = 1.8 Hz, 1H), 6.82-6.69 (m, 4H), 5.90-5.87 (m, 2H), 4.49 (s, 2H), 4.48-4.46 (m, 1H), 4.04 (s, 2H), 3.91 (br d, J = 14.7 Hz, 1H), 3.23-3.14 (m, 1H), 2.90-2.60 (m, 5H), 1.76-1.51 (m, 4H). C$_{23}$H$_{26}$N$_2$O$_4$; MS (ESI) m/z 395.2 (MH)$^+$. |
| 105 | 1-(3,4-dimethoxy-benzyl)carbonyl-5'-aminomethyl-spiro[piperidine-4,3'-(2H)-benzo[b]furan]<br>$^1$H NMR (CD$_3$OD) δ 7.21 (dd, J = 1.9 Hz, J = 8.2 Hz, 1H), 7.10 (d, J = 1.8 Hz, 1H), 6.94-6.92 (m, 2H), 6.86-6.78 (m, 2H), 4.49 (br s, 3H), 4.02 (br s, 3H), 3.84 (s, 3H), 3.82 (s, 3H), 3.77 (s, 2H), 3.24-3.19 (m, 1H), 2.94-2.84 (m, 1H), 1.80-1.53 (m, 4H). C$_{23}$H$_{28}$N$_2$O$_4$; MS (ESI) m/z 397.2 (MH)$^+$. |
| 106 | 1-(3-methoxy-4-benzyloxy-benzyl)carbonyl-5'-aminomethyl-spiro[piperidine-4,3'-(2H)-benzo[b]furan]<br>$^1$H NMR (CD$_3$OD) δ 7.43-7.26 (m, 5H), 7.21 (dd, J = 1.9 Hz, J = 8.2 Hz, 1H), 7.11 (d, J = 1.8 Hz, 1H), 6.97-6.94 (m, 2H), 6.82-6.79 (m, 2H), 5.09 (s, 2H), 4.48 (br s, 3H), 4.00 (br s, 3H), 3.87 (s, 3H), 3.77 (s, 2H), 3.24-3.18 (m, 1H), 2.94-2.84 (m, 1H), 1.84-1.45 (m, 4H). C$_{29}$H$_{32}$N$_2$O$_4$; MS (ESI) m/z 473.2 (MH)$^+$. |
| 108 | 1-(phenylethynyl)carbonyl-5'-aminomethyl-spiro[piperidine-4,3'-(2H)-benzo[b]furan]<br>$^1$H NMR (CD$_3$OD) δ 7.61-7.58 (m, 2H), 7.52-7.41 (m, 3H), 7.29 (d, J = 1.8 Hz, 1H), 7.24 (dd, J = 1.9 Hz, J = 8.2 Hz, 1H), 6.84 (d, J = 8.2 Hz, 1H), 4.58 (s, 2H), 4.52 (br s, 1H), 4.47 (br s, 1H), 4.04 (s, 2H), 3.55-3.45 (m, 1H), 3.11-3.01 (m, 1H), 2.05-1.86 (m, 4H). C$_{22}$H$_{22}$N$_2$O$_2$; MS (ESI) m/z 347.2 (MH)$^+$. |
| 111 | (E)-1-(3,4-difluoro-phenylethenyl)carbonyl-5'-aminomethyl-spiro[piperidine-4,3'-(2H)-benzo[b]furan]<br>$^1$H NMR (CD$_3$OD) δ 7.71-7.63 (m, 1H), 7.54 (d, J = 15.3 Hz, 1H), 7.47-7.34 (m, 1H), 7.32-7.19 (m, 4H), 6.83 (d, J = 8.2 Hz, 1H), 4.58 (br s, 3H), 4.30 (br d, J = 14.3 Hz, 1H), 4.03 (s, 2H), 3.43-3.35 (m, 1H), 3.06-2.97 (m, 1H), 1.98-1.81 (m, 4H). C$_{22}$H$_{22}$F$_2$N$_2$O$_2$; MS (ESI) m/z 385.2 (MH)$^+$. |
| 112 | (E)-1-(phenylethenyl)carbonyl-5'-aminomethyl-spiro[piperidine-4,3'-(2H)-benzo[b]furan]<br>$^1$H NMR (CD$_3$OD) δ 7.30 (d, J = 1.8 Hz, 1H), 7.23 (dd, J = 1.9 Hz, J = 8.2 Hz, 1H), 7.04 (d, J = 3.6 Hz, 1H), 6.83 (d, J = 8.2 Hz, 1H), 6.62 (d, J = 3.6 Hz, 1H), 4.58 (s, 2H), 4.47 (br s, 1H), 4.43 (br s, 1H), 4.03 (s, 2H), 3.5-3.1 (br m, 2H), 2.03-1.84 (m, 4H). C$_{18}$H$_{19}$BrN$_2$O$_3$; MS (ESI) m/z 391.1/393.1 (MH)$^+$. |
| 113 | (E)-1-(naphthalene-2-ylethenyl)carbonyl-5'-aminomethyl-spiro[piperidine-4,3'-(2H)-benzo[b]furan]<br>$^1$H NMR (CD$_3$OD) δ 8.05 (s, 1H), 7.92-7.77 (m, 5H), 7.54-7.50 (m, 2H), 7.37-7.22 (m, 3H), 6.86-6.82 (m, 1H), 4.65-4.61 (m, 1H), 4.60 (s, 2H), 4.37 (br d, J = 13.6 Hz, 1H), 4.03 (s, 2H), 3.44 (br t, J = 12.5 Hz, 1H), 3.04 (br t, J = 12.4 Hz, 1H), 2.03-1.87 (m, 4H). C$_{26}$H$_{26}$N$_2$O$_2$; MS (ESI) m/z 399.3 (MH)$^+$. |
| 114 | 1-(5-phenyl-thien-2-yl)carbonyl-5'-aminomethyl-spiro[piperidine-4,3'-(2H)-benzo[b]furan]<br>$^1$H NMR (CD$_3$OD) δ 7.69-7.65 (m, 2H), 7.46-7.32 (m, 6H), 7.23 (dd, J = 1.9 Hz, J = 8.2 Hz, 1H), 6.83 (d, J = 8.2 Hz, 1H), 4.59 (s, 2H), 4.48 (br s, 1H), 4.44 (br s, 1H), 4.04 (s, 2H), 3.5-3.2 (br m, 2H), 2.05-1.84 (m, 4H). C$_{24}$H$_{24}$N$_2$O$_2$S; MS (ESI) m/z 405.1 (MH)$^+$. |
| 115 | 1-(3-phenoxy-phenyl)carbonyl-5'-aminomethyl-spiro[piperidine-4,3'-(2H)-benzo[b]furan]<br>$^1$H NMR (CD$_3$OD) δ 7.39-6.91 (m, 11H), 6.72 (d, J = 8.2 Hz, 1H), 4.44 (br s, 3H), 3.94 (s, 2H), 3.68 (br d, J = 12.1 Hz, 1H), 3.35-2.9 (br m, 2H), 1.87-1.64 (m, 4H). C$_{26}$H$_{26}$N$_2$O$_3$; MS (ESI) m/z 415.2 (MH)$^+$. |
| 116 | (E)-1-(3,4-dichloro-phenylethenyl)carbonyl-5'-aminomethyl-spiro[piperidine-4,3'-(2H)-benzo[b]furan]<br>$^1$H NMR (CD$_3$OD) δ 7.87 (d, J = 1.1 Hz, 1H), 7.60-7.50 (m, 3H), 7.31-7.22 (m, 3H), 6.83 (d, J = 8.1 Hz, 1H), 4.58 (br s, 3H), 4.30 (br d, J = 12.8 Hz, 1H), 4.03 (s, 2H), 3.40 (br t, J = 11.4 Hz, 1H), 3.02 (br t, J = 14.2 Hz, 1H), 1.98-1.85 (m, 4H). C$_{22}$H$_{22}$Cl$_2$N$_2$O$_2$; MS (ESI) m/z 417.1/419.1 (MH)$^+$. |
| 117 | (E)-1-(4-phenyl-phenylethenyl)carbonyl-5'-aminomethyl-spiro[piperidine-4,3'-(2H)-benzo[b]furan]<br>$^1$H NMR (CD$_3$OD) δ 7.74-7.64 (m, 7H), 7.47-7.22 (m, 6H), 6.83 (d, J = 8.2 Hz, 1H), 4.59 (br s, 3H), 4.34 (br d, J = 14.2 Hz, 1H), 4.03 (s, 2H), 3.42 (br t, J = 10.7 Hz, 1H), 3.03 (br t, J = 11.8 Hz, 1H), 1.95-1.86 (m, 4H). C$_{28}$H$_{28}$N$_2$O$_2$; MS (ESI) m/z 425.2 (MH)$^+$. |
| 118 | 1-(2,4-dimethyl-thiazol-5-yl)carbonyl-5'-aminomethyl-spiro[piperidine-4,3'-(2H)-benzo[b]furan]<br>$^1$H NMR (CD$_3$OD) δ 7.31 (d, J = 1.8 Hz, 1H), 7.23 (dd, J = 1.9 Hz, J = 8.2 Hz, 1H), 6.82 (d, J = 8.2 Hz, 1H), 4.56 (br s, 3H), 4.04 (br s, 3H), 3.32-3.22 (br m, 2H), 2.69 (s, 3H), 2.40 (s, 3H), 1.96-1.80 (m, 4H). C$_{19}$H$_{23}$N$_3$O$_2$S; MS (ESI) m/z 358.2 (MH)$^+$. |

-continued

| Cpd | Name |
|---|---|
| 119 | 1-(6-methyl-imidazo[1,2-a]pyridin-2-yl)carbonyl-5'-aminomethyl-spiro[piperidine-4,3'-(2H)-benzo[b]furan]<br>$^1$H NMR (CD$_3$OD) δ 8.73 (s, 1H), 8.26 (s, 1H), 7.64 (d, J = 9.6 Hz, 1H), 7.50 (dd, J = 2.0 Hz, J = 9.7 Hz, 1H), 7.31 (d, J = 1.8 Hz, 1H), 7.24 (dd, J = 1.9 Hz, J = 8.2 Hz, 1H), 6.83 (d, J = 8.2 Hz, 1H), 4.65-4.60 (m, 2H), 4.59 (s, 2H), 4.04 (s, 2H), 3.54-3.37 (br m, 1H), 3.23-3.07 (br m, 1H), 2.08-1.84 (m, 4H). C$_{21}$H$_{21}$ClN$_4$O$_2$; MS (ESI) m/z 397.2 (MH)$^+$. |
| 120 | 1-(5-pyridin-2-yl-thien-2-yl)carbonyl-5'-aminomethyl-spiro[piperidine-4,3'-(2H)-benzo[b]furan]<br>$^1$H NMR (CD$_3$OD) δ 8.54-8.52 (m, 1H), 7.93-7.85 (m, 2H), 7.70 (d, J = 3.8 Hz, 1H), 7.44 (d, J = 3.9 Hz, 1H), 7.37-7.33 (m, 2H), 7.24 (dd, J = 1.9 Hz, J = 8.2 Hz, 1H), 6.83 (d, J = 8.2 Hz, 1H), 4.59 (s, 2H), 4.43 (br d, J = 12.2 Hz, 2H), 4.05 (s, 2H), 3.45-3.20 (br m, 2H), 2.05-1.84 (m, 4H). C$_{23}$H$_{23}$N$_3$O$_2$S; MS (ESI) m/z 406.2 (MH)$^+$. |
| 121 | 1-(2-pyridin-3-yl-thiazol-4-yl)carbonyl-5'-aminomethyl-spiro[piperidine-4,3'-(2H)-benzo[b]furan]<br>$^1$H NMR (CD$_3$OD) δ 9.11 (d, J = 1.6 Hz, 1H), 8.59 (d, J = 4.9 Hz, 1H), 8.40-8.36 (m, 1H), 8.08 (s, 1H), 7.57-7.53 (m, 1H), 7.24 (d, J = 1.8 Hz, 1H), 7.14 (dd, J = 1.9 Hz, J = 8.2 Hz, 1H), 6.74 (d, J = 8.2 Hz, 1H), 4.56-4.50 (m, 1H), 4.51 (s, 2H), 4.36 (br d, J = 15.4 Hz, 1H), 3.95 (s, 2H), 3.34 (br t, J = 13.2 Hz, 1H), 3.06 (br t, J = 13.3 Hz, 1H), 1.99-1.74 (m, 4H). C$_{22}$H$_{22}$N$_4$O$_2$S; MS (ESI) m/z 407.3 (MH)$^+$. |
| 122 | 1-(2-pyridin-4-yl-thiazol-4-yl)carbonyl-5'-aminomethyl-spiro[piperidine-4,3'-(2H)-benzo[b]furan]<br>$^1$H NMR (CD$_3$OD) δ 8.80 (d, J = 4.8 Hz, 2H), 8.35 (s, 1H), 8.25 (d, J = 6.4 Hz, 2H), 7.34 (d, J = 1.8 Hz, 1H), 7.24 (dd, J = 1.8 Hz, J = 8.2 Hz, 1H), 6.84 (d, J = 8.2 Hz, 1H), 4.65-4.61 (m, 1H), 4.60 (s, 2H), 4.44 (br d, J = 14.0 Hz, 1H), 4.05 (s, 2H), 3.46 (br t, J = 13.0 Hz, 1H), 3.18 (br t, J = 15.1 Hz, 1H), 2.15-1.84 (m, 4H). C$_{22}$H$_{22}$N$_4$O$_2$S; MS (ESI) m/z 407.1 (MH)$^+$. |
| 123 | 1-(2-phenyl-4-methyl-thiazol-5-yl)carbonyl-5'-aminomethyl-spiro[piperidine-4,3'-(2H)-benzo[b]furan]<br>$^1$H NMR (CD$_3$OD) δ 7.96 (m, 2H), 7.52-7.47 (m, 3H), 7.33 (d, J = 1.8 Hz, 1H), 7.24 (dd, J = 1.8 Hz, J = 8.2 Hz, 1H), 6.83 (d, J = 8.2 Hz, 1H), 4.58 (s, 2H), 4.45-4.04 (br m, 2H), 4.05 (s, 2H), 3.40-3.20 (br m, 2H), 2.50 (s, 3H), 2.03-1.83 (m, 4H). C$_{24}$H$_{25}$N$_3$O$_2$S; MS (ESI) m/z 420.1 (MH)$^+$. |
| 124 | 1-(2-pyridin-3-yl-4-methyl-thiazol-5-yl)carbonyl-5'-aminomethyl-spiro[piperidine-4,3'-(2H)-benzo[b]furan]<br>$^1$H NMR (CD$_3$OD) δ 9.13 (s, 1H), 8.65 (d, J = 4.3 Hz, 1H), 8.51-8.48 (m, 1H), 7.67 (dd, J = 5.1 Hz, J = 8.1 Hz, 1H), 7.25 (d, J = 1.8 Hz, 1H), 7.16 (dd, J = 1.9 Hz, J = 8.2 Hz, 1H), 6.74 (d, J = 8.2 Hz, 1H), 4.49 (s, 2H), 4.40-4.00 (br m, 2H), 3.97 (s, 2H), 3.35-3.15 (br m, 2H), 2.45 (s, 3H), 1.92-1.75 (m, 4H). C$_{23}$H$_{24}$N$_4$O$_2$S; MS (ESI) m/z 421.2 (MH)$^+$. |
| 125 | 1-[2-(4-methyl-phenyl)-4-methyl-thiazol-5-yl]carbonyl-5'-aminomethyl-spiro[piperidine-4,3'-(2H)-benzo[b]furan]<br>$^1$H NMR (CD$_3$OD) δ 7.82 (d, J = 8.2 Hz, 2H), 7.32-7.30 (m, 3H), 7.23 (dd, J = 1.9 Hz, J = 8.2 Hz, 1H), 6.83 (d, J = 8.2 Hz, 1H), 4.59 (s, 2H), 4.50-4.04 (br m, 2H), 4.05 (s, 2H), 3.40-3.20 (br m, 2H), 2.49 (s, 3H), 2.40 (s, 3H), 2.00-1.83 (m, 4H). C$_{25}$H$_{27}$N$_3$O$_2$S; MS (ESI) m/z 434.2 (MH)$^+$. |
| 126 | 1-(6-bromo-naphthalen-2-yl)carbonyl-5'-aminomethyl-spiro[piperidine-4,3'-(2H)-benzo[b]furan]<br>$^1$H NMR (CD$_3$OD) δ 8.16 (s, 1H), 7.99 (s, 1H), 7.95 (d, J = 8.5 Hz, 1H), 7.89 (d, J = 8.8 Hz, 1H), 7.68 (dd, J = 1.9 Hz, J = 8.8 Hz, 1H), 7.59 (dd, J = 1.5 Hz, J = 8.5 Hz, 1H), 7.35 (d, J = 1.8 Hz, 1H), 7.23 (dd, J = 1.9 Hz, J = 8.2 Hz, 1H), 6.82 (d, J = 8.2 Hz, 1H), 4.58 (br s, 3H), 4.05 (s, 2H), 3.90-3.75 (br m, 1H), 3.50-3.10 (m, 2H), 2.03-1.76 (m, 4H). C$_{24}$H$_{23}$BrN$_2$O$_2$; MS (ESI) m/z 451.0/453.1 (MH)$^+$. |
| 127 | 1-[5-(1-methyl-3-trifluoromethyl-pyrazol-5-yl)-thien-2-yl]carbonyl-5'-aminomethyl-spiro[piperidine-4,3'-(2H)-benzo[b]furan]<br>$^1$H NMR (CD$_3$OD) δ 7.33 (d, J = 3.8 Hz, 1H), 7.29 (d, J = 3.8 Hz, 1H), 7.22 (d, J = 1.8 Hz, 1H), 7.14 (dd, J = 1.9 Hz, J = 8.2 Hz, 1H), 7.03 (s, 1H), 6.74 (d, J = 8.2 Hz, 1H), 4.49 (s, 2H), 4.34 (br d, J = 15.3 Hz, 2H), 3.93 (s, 2H), 3.92 (s, 3H), 3.35-3.15 (m, 2H), 1.95-1.74 (m, 4H). C$_{23}$H$_{23}$F$_3$N$_4$O$_2$S; MS (ESI) m/z 477.1 (MH)$^+$. |
| 128 | 1-[2-(4-trifluoromethyl-phenyl)-4-methyl-thiazol-5-yl]carbonyl-5'-aminomethyl-spiro[piperidine-4,3'-(2H)-benzo[b]furan]<br>$^1$H NMR (CD$_3$OD) δ 8.15 (d, J = 8.3 Hz, 2H), 7.80 (d, J = 8.4 Hz, 2H), 7.32 (d, J = 1.9 Hz, 1H), 7.24 (dd, J = 1.7 Hz, J = 8.1 Hz, 1H), 6.83 (d, J = 8.2 Hz, 1H), 4.58 (s, 2H), 4.41-4.11 (br, 1H), 4.05 (br s, 3H), 3.41-3.21 (br m, 2H), 2.52 (s, 3H), 2.00-1.83 (m, 4H). C$_{25}$H$_{24}$F$_3$N$_3$O$_2$S; MS (ESI) m/z 488.1 (MH)$^+$. |
| 129 | 1-[5-(2-chloro-5-trifluoromethyl-phenyl)-furan-2-yl]carbonyl-5'-aminomethyl-spiro[piperidine-4,3'-(2H)-benzo[b]furan]<br>$^1$H NMR (CD$_3$OD) δ 8.11 (s, 1H), 7.65 (d, J = 8.4 Hz, 1H), 7.55 (d, J = 8.4 Hz, 1H), 7.28-7.09 (m, 4H), 6.74 (d, J = 8.2 Hz, 1H), 4.51 (s, 2H), 4.45 (br d, J = 14.2 Hz, 2H), 3.94 (s, 2H), 3.60-2.90 (br m, 2H), 1.98-1.77 (m, 4H). C$_{25}$H$_{22}$ClF$_3$N$_2$O$_3$; MS (ESI) m/z 491.1 (MH)$^+$. |

-continued

| Cpd | Name |
|---|---|

130 1-(5-phenyl-furan-2-yl)carbonyl-5'-aminomethyl-spiro[piperidine-4,3'-(2H)-benzo[b]furan]
$^1$H NMR (CD$_3$OD) δ 7.69-7.66 (m, 2H), 7.36-7.21 (m, 4H), 7.14 (dd, J = 2.0 Hz, J = 8.2 Hz, 1H), 7.06 (d, J = 3.6 Hz, 1H), 6.85 (d, J = 3.6 Hz, 1H), 6.74 (d, J = 8.2 Hz, 1H), 4.52 (s, 2H), 4.51-4.48 (br m, 2H), 3.94 (s, 2H), 3.50-3.10 (br m, 2H), 2.00-1.79 (m, 4H).
C$_{24}$H$_{24}$N$_2$O$_3$; MS (ESI) m/z 389.2 (MH)$^+$.

131 1-[5-(4-methyl-phenyl)-furan-2-yl]carbonyl-5'-aminomethyl-spiro[piperidine-4,3'-(2H)-benzo[b]furan]
$^1$H NMR (CD$_3$OD) δ 7.56 (d, J = 8.0 Hz, 2H), 7.21 (s, 1H), 7.17-7.13 (m, 3H), 7.05 (d, J = 3.5 Hz, 1H), 6.78-6.73 (m, 2H), 4.52 (s, 2H), 4.51-4.48 (br m, 2H), 3.94 (s, 2H), 3.59-3.09 (br m, 2H), 2.27 (s, 3H), 1.94-1.79 (m, 4H). C$_{25}$H$_{26}$N$_2$O$_3$; MS (ESI) m/z 403.2 (MH)$^+$.

132 1-[5-(4-methoxy-phenyl)-furan-2-yl]carbonyl-5'-aminomethyl-spiro[piperidine-4,3'-(2H)-benzo[b]furan]
$^1$H NMR (CD$_3$OD) δ 7.63-7.58 (m, 2H), 7.22 (d, J = 1.8 Hz, 1H), 7.14 (dd, J = 1.9 Hz, J = 8.2 Hz, 1H), 7.04 (d, J = 3.5 Hz, 1H), 6.92-6.87 (m, 2H), 6.74 (d, J = 8.2 Hz, 1H), 6.70 (d, J = 3.5 Hz, 1H), 4.52 (s, 2H), 4.51-4.48 (br m, 2H), 3.94 (s, 2H), 3.73 (s, 3H), 3.35-3.10 (br m, 2H), 1.99-1.78 (m, 4H). C$_{25}$H$_{26}$N$_2$O$_4$; MS (ESI) m/z 419.2 (MH)$^+$.

133 1-(3,5-di-tert-butyl-phenyl)carbonyl-5'-aminomethyl-spiro[piperidine-4,3'-(2H)-benzo[b]furan]
$^1$H NMR (CD$_3$OD) δ 7.49 (d, J = 1.7 Hz, 1H), 7.24 (d, J = 1.8 Hz, 1H), 7.20 (d, J = 1.8 Hz, 2H), 7.14 (d, J = 8.2 Hz, 1H), 6.73 (d, J = 8.2 Hz, 1H), 4.47 (br s, 3H), 3.95 (s, 2H), 3.71-3.67 (br m, 1H), 3.21-3.04 (br m, 2H), 1.93-1.67 (m, 4H), 1.25 (s, 18H). C$_{28}$H$_{38}$N$_2$O$_2$; MS (ESI) m/z 435.3 (MH)$^+$.

134 1-[5-(3-chloro-phenoxymethyl)-furan-2-yl]carbonyl-5'-aminomethyl-spiro[piperidine-4,3'-(2H)-benzo[b]furan]
$^1$H NMR (CD$_3$OD) δ 7.18-7.12 (m, 3H), 6.96-6.93 (m, 2H), 6.88-6.83 (m, 2H), 6.73 (d, J = 8.1 Hz, 1H), 6.57 (d, J = 3.4 Hz, 1H), 5.03 (s, 2H), 4.48 (s, 2H), 4.40-4.25 (m, 2H), 3.93 (s, 2H), 3.30-3.00 (br m, 2H), 1.91-1.71 (m, 4H). C$_{25}$H$_{25}$ClN$_2$O$_4$; MS (ESI) m/z 453.1 (MH)$^+$.

135 1-[5-(3-trifluoromethyl-phenyl)-furan-2-yl]carbonyl-5'-aminomethyl-spiro[piperidine-4,3'-(2H)-benzo[b]furan]
$^1$H NMR (CD$_3$OD) δ 7.98-7.93 (m, 2H), 7.56 (dd, J = 1.1 Hz, J = 3.6 Hz, 2H), 7.22 (d, J = 1.8 Hz, 1H), 7.14 (dd, J = 1.9 Hz, J = 8.2 Hz, 1H), 7.07 (d, J = 3.7 Hz, 1H), 7.03 (d, J = 3.7 Hz, 1H), 6.75 (d, J = 8.2 Hz, 1H), 4.52 (s, 2H), 4.47 (d, J = 13.9 Hz, 2H), 3.94 (s, 2H), 3.50-3.00 (br m, 2H), 1.99-1.79 (m, 4H). C$_{25}$H$_{23}$F$_3$N$_2$O$_3$; MS (ESI) m/z 457.1 (MH)$^+$.

136 1-[5-(2,4-dichloro-phenyl)-furan-2-yl]carbonyl-5'-aminomethyl-spiro[piperidine-4,3'-(2H)-benzo[b]furan]
$^1$H NMR (CD$_3$OD) δ 7.78 (d, J = 8.6 Hz, 1H), 7.52 (d, J = 2.1 Hz, 1H), 7.36 (dd, J = 2.2 Hz, J = 8.6 Hz, 1H), 7.21 (d, J = 1.8 Hz, 1H), 7.14 (dd, J = 3.8 Hz, J = 7.5 Hz, 2H), 7.09 (d, J = 3.7 Hz, 1H), 6.74 (d, J = 8.2 Hz, 1H), 4.51 (s, 2H), 4.47 (d, J = 14.0 Hz, 2H), 3.94 (s, 2H), 3.50-3.00 (br m, 2H), 1.98-1.78 (m, 4H). C$_{24}$H$_{22}$Cl$_2$N$_2$O$_3$; MS (ESI) m/z 457.2 (MH)$^+$.

137 1-[5-(2,5-dichloro-phenyl)-furan-2-yl]carbonyl-5'-aminomethyl-spiro[piperidine-4,3'-(2H)-benzo[b]furan]
$^1$H NMR (CD$_3$OD) δ 7.83 (d, J = 2.5 Hz, 1H), 7.44 (d, J = 8.6 Hz, 1H), 7.28 (dd, J = 2.5 Hz, J = 8.6 Hz, 1H), 7.21 (d, J = 3.4 Hz, 2H), 7.14 (d, J = 1.9 Hz, J = 8.2 Hz, 1H), 7.09 (d, J = 3.7 Hz, 1H), 6.74 (d, J = 8.2 Hz, 1H), 4.52 (s, 2H), 4.47 (d, J = 14.1 Hz, 2H), 3.94 (s, 2H), 3.50-3.00 (br m, 2H), 1.98-1.78 (m, 4H). C$_{24}$H$_{22}$Cl$_2$N$_2$O$_3$; MS (ESI) m/z 457.2 (MH)$^+$.

138 1-[5-(3,4-dichloro-phenyl)-furan-2-yl]carbonyl-5'-aminomethyl-spiro[piperidine-4,3'-(2H)-benzo[b]furan]
$^1$H NMR (CD$_3$OD) δ 7.86 (d, J = 2.0 Hz, 1H), 7.61 (dd, J = 2.1 Hz, J = 8.5 Hz, 1H), 7.50 (d, J = 8.4 Hz, 1H), 7.21 (d, J = 1.8 Hz, 1H), 7.14 (dd, J = 1.9 Hz, J = 8.2 Hz, 1H), 7.06 (d, J = 3.6 Hz, 1H), 6.97 (d, J = 3.6 Hz, 1H), 6.74 (d, J = 8.2 Hz, 1H), 4.52 (s, 2H), 4.46 (d, J = 14.2 Hz, 2H), 3.94 (s, 2H), 3.50-3.00 (br m, 2H), 1.98-1.78 (m, 4H). C$_{24}$H$_{22}$Cl$_2$N$_2$O$_3$; MS (ESI) m/z 457.2 (MH)$^+$.

139 1-[5-(3-methyl-4-chloro-phenoxymethyl)-furan-2-yl]carbonyl-5'-aminomethyl-spiro[piperidine-4,3'-(2H)-benzo[b]furan]
$^1$H NMR (CD$_3$OD) δ 7.18-7.11 (m, 3H), 6.93 (d, J = 3.4 Hz, 1H), 6.84 (d, J = 2.9 Hz, 1H), 6.74 (d, J = 3.0 Hz, 1H), 6.71 (d, J = 3.5 Hz, 1H), 6.55 (d, J = 3.4 Hz, 1H), 4.99 (s, 2H), 4.48 (s, 2H), 4.45-4.25 (br m, 2H), 3.93 (s, 2H), 3.40-2.90 (br m, 2H), 2.21 (s, 3H), 1.91-1.71 (m, 4H). C$_{26}$H$_{27}$ClN$_2$O$_4$; MS (ESI) m/z 467.3 (MH)$^+$.

140 1-[5-(4-bromo-phenyl)-furan-2-yl]carbonyl-5'-aminomethyl-spiro[piperidine-4,3'-(2H)-benzo[b]furan]
$^1$H NMR (CD$_3$OD) δ 7.62-7.48 (m, 4H), 7.22 (d, J = 1.8 Hz, 1H), 7.14 (dd, J = 1.9 Hz, J = 8.2 Hz, 1H), 7.06 (d, J = 3.6 Hz, 1H), 6.90 (d, J = 3.56 Hz, 1H), 6.74 (d, J = 8.2 Hz, 1H), 4.52 (s, 2H), 4.47 (d, J = 14.3 Hz, 2H), 3.94 (s, 2H), 3.50-3.10 (br m, 2H), 1.98-1.78 (m, 4H). C$_{24}$H$_{23}$BrN$_2$O$_3$; MS (ESI) m/z 467.1 (MH)$^+$.

141 1-(trans-2-phenyl-cyclopropyl)carbonyl-5'-aminomethyl-spiro[piperidine-4,3'-(2H)-benzo[b]furan]

| Cpd | Name |
|---|---|
| | $^1$H NMR (CD$_3$OD) δ 7.17-7.05 (m, 7H), 6.72 (d, J = 8.5 Hz, 1H), 4.45 (s, 2H), 4.44-4.37 (m, 1H), 4.14 (d, J = 13.1 Hz, 1H), 3.92 (s, 2H), 3.28-3.25 (m, 1H), 2.84 (t, J = 13.8 Hz, 1H), 2.34-2.24 (m, 1H), 2.20-2.10 (m, 1H), 1.87-1.73 (m, 4H), 1.50-1.44 (m, 1H), 1.28-1.18 (m, 1H). C$_{23}$H$_{26}$N$_2$O$_2$; MS (ESI) m/z 363.3 (MH)$^+$. |
| 142 | 1-(5-phenyl-pyridin-3-yl)carbonyl-5'-aminomethyl-spiro[piperidine-4,3'-(2H)-benzo[b]furan] <br> $^1$H NMR (CD$_3$OD) δ 8.86 (s, 1H), 8.57 (s, 1H), 8.12 (t, J = 2.0 Hz, 1H), 7.65-7.62 (m, 2H), 7.48-7.35 (m, 3H), 7.25 (d, J = 1.8 Hz, 1H), 7.14 (dd, J = 1.9 Hz, J = 8.2 Hz, 1H), 6.74 (d, J = 8.2 Hz, 1H), 4.56-4.53 (m, 1H), 4.52 (s, 2H), 3.95 (s, 2H), 3.80-3.60 (m, 1H), 3.45-3.30 (m, 1H), 3.18-3.02 (m, 1H), 1.90-1.71 (m, 4H). C$_{25}$H$_{25}$N$_3$O$_2$; MS (ESI) m/z 400.2 (MH)$^+$. |
| 143 | 1-(5-thien-2-yl-pyridin-3-yl)carbonyl-5'-aminomethyl-spiro[piperidine-4,3'-(2H)-benzo[b]furan] <br> $^1$H NMR (CD$_3$OD) δ 8.86 (s, 1H), 8.46 (s, 1H), 8.06 (d, J = 2.0 Hz, 1H), 7.53 (d, J = 3.6 Hz, 1H), 7.48 (d, J = 5.0 Hz, 1H), 7.24 (s, 1H), 7.16-7.09 (m, 2H), 6.73 (d, J = 8.2 Hz, 1H), 4.52-4.49 (m, 1H), 4.48 (s, 2H), 3.95 (s, 2H), 3.80-3.60 (m, 1H), 3.45-3.30 (m, 1H), 3.18-3.02 (m, 1H), 1.93-1.70 (m, 4H). C$_{23}$H$_{23}$N$_3$O$_2$S; MS (ESI) m/z 406.2 (MH)$^+$. |
| 144 | 1-[5-(3-methoxy-phenyl)-furan-2-yl]carbonyl-5'-aminomethyl-spiro[piperidine-4,3'-(2H)-benzo[b]furan] <br> $^1$H NMR (CD$_3$OD) δ 7.26-7.22 (m, 4H), 7.14 (dd, J = 1.9 Hz, J = 8.2 Hz, 1H), 7.05 (d, J = 3.6 Hz, 1H), 6.86-6.81 (m, 2H), 6.74 (d, J = 8.2 Hz, 1H), 4.52 (s, 2H), 4.51-4.46 (m, 2H), 3.94 (s, 2H), 3.74 (s, 3H), 3.40-3.10 (br m, 2H), 1.99-1.79 (m, 4H). C$_{25}$H$_{26}$N$_2$O$_4$; MS (ESI) m/z 419.2 (MH)$^+$. |
| 145 | 1-[5-(4-chloro-pyrazol-1-ylmethyl)-furan-2-yl]carbonyl-5'-aminomethyl-spiro[piperidine-4,3'-(2H)-benzo[b]furan] <br> $^1$H NMR (DMSO$_{d6}$) δ 8.87 (s, 1H), 8.86 (br s, 2H), 8.39 (s, 1H), 8.20 (d, J = 1.5 Hz, 1H), 8.04 (dd, J = 1.7 Hz, J = 8.2 Hz, 1H), 7.77 (d, J = 3.4 Hz, 1H), 7.66 (d, J = 8.2 Hz, 1H), 7.41 (d, J = 3.4 Hz, 1H), 6.22 (s, 2H), 5.33 (s, 2H), 5.01 (br d, J = 13.7 Hz, 2H), 4.78-4.73 (m, 2H), 4.20-3.90 (br m, 2H), 2.65-2.50 (m, 4H). C$_{22}$H$_{23}$ClN$_4$O$_3$; MS (ESI) m/z 427.2 (MH)$^+$. |
| 146 | 1-[5-(2-chloro-phenylethynyl)-furan-2-yl]carbonyl-5'-aminomethyl-spiro[piperidine-4,3'-(2H)-benzo[b]furan] <br> $^1$H NMR (CD$_3$OD) δ 7.53 (d, J = 1.9 Hz, 1H), 7.50 (d, J = 1.9 Hz, 1H), 7.43-7.23 (m, 2H), 7.21 (d, J = 1.8 Hz, 1H), 7.14 (dd, J = 1.9 Hz, J = 8.2 Hz, 1H), 7.02 (d, J = 3.6 Hz, 1H), 6.83 (d, J = 3.5 Hz, 1H), 6.73 (d, J = 8.2 Hz, 1H), 4.50 (s, 2H), 4.40 (br d, J = 13.6 Hz, 2H), 3.94 (s, 2H), 3.50-3.00 (m, 2H), 1.97-1.76 (m, 4H). C$_{26}$H$_{23}$ClN$_2$O$_3$; MS (ESI) m/z 447.1 (MH)$^+$. |
| 147 | 1-[5-(benzylthiomethyl)-furan-2-yl]carbonyl-5'-aminomethyl-spiro[piperidine-4,3'-(2H)-benzo[b]furan] <br> $^1$H NMR (CD$_3$OD) δ 7.20-7.12 (m, 7H), 6.88-6.87 (m, 1H), 6.74-6.72 (m, 1H), 6.27-6.26 (m, 1H), 4.48 (s, 2H), 4.40 (br d, J = 12.1 Hz, 2H), 3.94 (s, 2H), 3.64 (d, J = 3.1 Hz, 2H), 3.57 (d, J = 2.7 Hz, 2H), 3.35-2.95 (br m, 2H), 1.92-1.72 (m, 4H). C$_{26}$H$_{28}$N$_2$O$_3$S; MS (ESI) m/z 449.2 (MH)$^+$. |
| 148 | 1-[5-(4,6-dimethyl-pyrimidin-2-ylthiomethyl)-furan-2-yl]carbonyl-5'-aminomethyl-spiro[piperidine-4,3'-(2H)-benzo[b]furan] <br> $^1$H NMR (CD$_3$OD) δ 7.17-7.12 (m, 2H), 6.87 (d, J = 3.4 Hz, 1H), 6.81 (s, 1H), 6.73 (d, J = 8.1 Hz, 1H), 6.38 (d, J = 3.3 Hz, 1H), 4.46 (s, 2H), 4.43 (s, 2H), 4.42-4.34 (br m, 2H), 3.94 (s, 2H), 3.25-2.9 (br m, 2H), 2.29 (s, 6H), 1.87-1.70 (m, 4H). C$_{25}$H$_{28}$N$_4$O$_3$S; MS (ESI) m/z 465.2 (MH)$^+$. |
| 149 | 1-[5-(3,5-dichloro-phenoxy)-furan-2-yl]carbonyl-5'-aminomethyl-spiro[piperidine-4,3'-(2H)-benzo[b]furan] <br> $^1$H NMR (CD$_3$OD) δ 7.23-7.00 (m, 6H), 6.74-6.71 (m, 1H), 5.86-5.84 (m, 1H), 4.47 (s, 2H), 4.34 (br d, J = 12.5 Hz, 2H), 3.93 (s, 2H), 3.30-3.00 (br m, 2H), 1.90-1.71 (m, 4H). C$_{24}$H$_{22}$Cl$_2$N$_2$O$_4$; MS (ESI) m/z 473.1 (MH)$^+$. |
| 150 | 1-[5-(3,5-dimethyl-4-bromo-pyrazol-1-yl)-furan-2-yl]carbonyl-5'-aminomethyl-spiro[piperidine-4,3'-(2H)-benzo[b]furan] <br> $^1$H NMR (CD$_3$OD) δ 7.17-7.12 (m, 2H), 6.89 (d, J = 3.4 Hz, 1H), 6.74 (d, J = 8.1 Hz, 1H), 6.41 (d, J = 3.4 Hz, 1H), 5.23 (s, 2H), 4.46 (s, 2H), 4.40-4.10 (br m, 2H), 3.94 (s, 2H), 3.25-2.90 (br m, 2H), 2.22 (s, 3H), 2.01 (s, 3H), 1.86-1.68 (m, 4H). C$_{24}$H$_{27}$BrN$_4$O$_3$; MS (ESI) m/z 499.2 (MH)$^+$. |
| 151 | 1-[5-(5-trifluoromethyl-pyridin-2-ylthiomethyl)-furan-2-yl]carbonyl-5'-aminomethyl-spiro[piperidine-4,3'-(2H)-benzo[b]furan] <br> $^1$H NMR (CD$_3$OD) δ 8.64 (s, 1H), 7.76 (d, J = 8.4 Hz, 1H), 7.36 (d, J = 8.3 Hz, 1H), 7.15-7.12 (m, 2H), 6.87 (d, J = 3.4 Hz, 1H), 6.73 (d, J = 7.9 Hz, 1H), 6.39 (s, 1H), 4.52 (s, 2H), 4.45 (s, 2H), 4.35 (br d, J = 12.6 Hz, 2H), 3.93 (s, 2H), 3.25-2.80 (br m, 2H), 1.86-1.70 (m, 4H). C$_{25}$H$_{24}$F$_3$N$_3$O$_3$S; MS (ESI) m/z 504.1 (MH)$^+$. |
| 152 | 1-[4-phenylethynyl-pyridin-2-yl]carbonyl-5'-aminomethyl-spiro[piperidine-4,3'-(2H)-benzo[b]furan] <br> C$_{27}$H$_{25}$N$_3$O$_2$; MS (ESI) m/z 424.2 (MH)$^+$. |
| 153 | 1-[5-(2-methyl-phenylethynyl)-furan-2-yl]carbonyl-5'-aminomethyl-spiro[piperidine-4,3'-(2H)-benzo[b]furan] <br> C$_{27}$H$_{26}$N$_2$O$_3$; MS (ESI) m/z 427.2 (MH)$^+$. |

| Cpd | Name |
|---|---|
| 154 | 1-[5-(4-fluoro-phenoxymethyl)-furan-2-yl]carbonyl-5'-aminomethyl-spiro[piperidine-4,3'-(2H)-benzo[b]furan]<br>$C_{25}H_{25}FN_2O_4$; MS (ESI) m/z 437.3 (MH)$^+$. |
| 155 | 1-(3-methylthio-4-oxo-5,6,7-trihydro-4H-benzo[c]thien-1-yl)carbonyl-5'-aminomethyl-spiro[piperidine-4,3'-(2H)-benzo[b]furan]<br>$C_{23}H_{26}N_2O_3S_2$; MS (ESI) m/z 443.2 (MH)$^+$. |
| 156 | 1-[5-(2,5-dimethyl-furan-3-yl-carbonylaminomethyl)-furan-2-yl]carbonyl-5'-aminomethyl-spiro[piperidine-4,3'-(2H)-benzo[b]furan]<br>$C_{26}H_{29}N_3O_5$; MS (ESI) m/z 464.4 (MH)$^+$. |
| 157 | 1-(3-chloro-4-isopropylsulfonyl-5-methylthio-thien-2-yl)carbonyl-5'-aminomethyl-spiro[piperidine-4,3'-(2H)-benzo[b]furan]<br>$C_{22}H_{27}ClN_2O_4S_3$; MS (ESI) m/z 515.1 (MH)$^+$. |
| 159 | 1-thien-2-ylcarbonyl-5'-aminomethyl-spiro[piperidine-4,3'-(2H)-benzo[b]furan]<br>$C_{18}H_{20}N_2O_2S$; MS (ESI) m/z 329.1 (MH)$^+$. |
| 161 | (E)-1-(3-fluoro-phenylethenyl)carbonyl-5'-aminomethyl-spiro[piperidine-4,3'-(2H)-benzo[b]furan]<br>$C_{22}H_{23}FN_2O_2$; MS (ESI) m/z 367.2 (MH)$^+$. |
| 162 | (Z)-1-(1-fluoro-2-phenylethenyl)carbonyl-5'-aminomethyl-spiro[piperidine-4,3'-(2H)-benzo[b]furan]<br>$C_{22}H_{23}FN_2O_2$; MS (ESI) m/z 367.2 (MH)$^+$. |
| 163 | 1-(5,6,7-trihydro-4H-benzo[b]thien-2-yl)carbonyl-5'-aminomethyl-spiro[piperidine-4,3'-(2H)-benzo[b]furan]<br>$C_{22}H_{26}N_2O_2S$; MS (ESI) m/z 383.3 (MH)$^+$. |
| 164 | (E)-1-(3-chloro-phenylethenyl)carbonyl-5'-aminomethyl-spiro[piperidine-4,3'-(2H)-benzo[b]furan], ; MS (ESI) m/z 467.1 (MH)$^+$.<br>$C_{22}H_{23}ClN_2O_2$; MS (ESI) m/z 383.1 (MH)$^+$. |
| 165 | (E)-1-(4-chloro-phenylethenyl)carbonyl-5'-aminomethyl-spiro[piperidine-4,3'-(2H)-benzo[b]furan],<br>$C_{22}H_{23}ClN_2O_2$; MS (ESI) m/z 383.1 (MH)$^+$. |
| 166 | 1-(3-chloro-benzo[b]thien-2-yl)carbonyl-5'-aminomethyl-spiro[piperidine-4,3'-(2H)-benzo[b]furan]<br>$C_{22}H_{21}ClN_2O_2S$; MS (ESI) m/z 413.1 (MH)$^+$. |
| 167 | (E)-1-(3-trifluoromethoxy-phenylethenyl)carbonyl-5'-aminomethyl-spiro[piperidine-4,3'-(2H)-benzo[b]furan]<br>$C_{23}H_{23}F_3N_2O_3$; MS (ESI) m/z 433.2 (MH)$^+$. |
| 168 | 1-(4-fluoro-benzo[b]thien-2-yl)carbonyl-5'-aminomethyl-spiro[piperidine-4,3'-(2H)-benzo[b]furan]<br>$C_{22}H_{21}FN_2O_2S$; MS (ESI) m/z 397.2 (MH)$^+$. |
| 169 | 1-(5-methylsulfonyl-thien-2-yl)carbonyl-5'-aminomethyl-spiro[piperidine-4,3'-(2H)-benzo[b]furan]<br>$C_{19}H_{22}N_2O_4S_2$; MS (ESI) m/z 407.1 (MH)$^+$. |
| 170 | 1-[5-(4-methyl-phenylethynyl)-furan-2-yl]carbonyl-5'-aminomethyl-spiro[piperidine-4,3'-(2H)-benzo[b]furan]<br>$C_{27}H_{26}N_2O_3$; MS (ESI) m/z 427.2 (MH)$^+$. |
| 171 | 1-(3-chloro-6-fluoro-benzo[b]thien-2-yl)carbonyl-5'-aminomethyl-spiro[piperidine-4,3'-(2H)-benzo[b]furan]<br>$C_{22}H_{20}ClFN_2O_2S$; MS (ESI) m/z 431.1 (MH)$^+$. |
| 172 | 1-[5-(2,5-dimethyl-phenylethynyl)-furan-2-yl]carbonyl-5'-aminomethyl-spiro[piperidine-4,3'-(2H)-benzo[b]furan]<br>$C_{28}H_{28}N_2O_3$; MS (ESI) m/z 441.3 (MH)$^+$. |
| 173 | 1-[5-(2-methoxy-phenylethynyl)-furan-2-yl]carbonyl-5'-aminomethyl-spiro[piperidine-4,3'-(2H)-benzo[b]furan]<br>$C_{27}H_{26}N_2O_4$; MS (ESI) m/z 443.2 (MH)$^+$. |
| 174 | 1-[5-(2,5-dimethyl-phenoxymethyl)-furan-2-yl]carbonyl-5'-aminomethyl-spiro[piperidine-4,3'-(2H)-benzo[b]furan]<br>$C_{27}H_{30}N_2O_4$; MS (ESI) m/z 447.3 (MH)$^+$. |
| 175 | 1-(3,4-dichloro-benzo[b]thien-2-yl)carbonyl-5'-aminomethyl-spiro[piperidine-4,3'-(2H)-benzo[b]furan]<br>$C_{22}H_{20}Cl_2N_2O_2S$; MS (ESI) m/z 447.1 (MH)$^+$. |
| 176 | 1-[5-(3,5-difluoro-phenylethynyl)-furan-2-yl]carbonyl-5'-aminomethyl-spiro[piperidine-4,3'-(2H)-benzo[b]furan]<br>$C_{26}H_{22}F_2N_2O_3$; MS (ESI) m/z 449.2 (MH)$^+$. |
| 177 | 1-(5-naphthalen-1-ylethynyl-furan-2-yl)carbonyl-5'-aminomethyl-spiro[piperidine-4,3'-(2H)-benzo[b]furan]<br>$C_{30}H_{26}N_2O_3$; MS (ESI) m/z 463.2 (MH)$^+$. |
| 178 | 1-[5-(4-tert-butyl-phenoxymethyl)-furan-2-yl]carbonyl-5'-aminomethyl-spiro[piperidine-4,3'-(2H)-benzo[b]furan]<br>$C_{29}H_{34}N_2O_4$; MS (ESI) m/z 475.4 (MH)$^+$. |
| 179 | (E)-1-(3-methyl-phenylethenyl)carbonyl-5'-aminomethyl-spiro[piperidine-4,3'-(2H)-benzo[b]furan]<br>$C_{23}H_{26}N_2O_2$; MS (ESI) m/z 363.3 (MH)$^+$. |
| 180 | (E)-1-(4-methyl-phenylethenyl)carbonyl-5'-aminomethyl-spiro[piperidine-4,3'-(2H)-benzo[b]furan]<br>$C_{23}H_{26}N_2O_2$; MS (ESI) m/z 363.3 (MH)$^+$. |
| 181 | (Z)-1-(1-methyl-2-phenylethenyl)carbonyl-5'-aminomethyl-spiro[piperidine-4,3'-(2H)-benzo[b]furan]<br>$C_{23}H_{26}N_2O_2$; MS (ESI) m/z 363.3 (MH)$^+$. |

| Cpd | Name |
|---|---|
| 182 | (E)-1-(4-fluoro-phenylethenyl)carbonyl-5'-aminomethyl-spiro[piperidine-4,3'-(2H)-benzo[b]furan]<br>$C_{22}H_{23}FN_2O_2$; MS (ESI) m/z 367.2 (MH)$^+$. |
| 183 | (Z)-1-(2-methoxy-phenylethenyl)carbonyl-5'-aminomethyl-spiro[piperidine-4,3'-(2H)-benzo[b]furan]<br>$C_{23}H_{26}N_2O_3$; MS (ESI) m/z 379.2 (MH)$^+$. |
| 184 | (E)-1-(3-methoxy-phenylethenyl)carbonyl-5'-aminomethyl-spiro[piperidine-4,3'-(2H)-benzo[b]furan]<br>$C_{23}H_{26}N_2O_3$; MS (ESI) m/z 379.2 (MH)$^+$. |
| 185 | (E)-1-(4-methoxy-phenylethenyl)carbonyl-5'-aminomethyl-spiro[piperidine-4,3'-(2H)-benzo[b]furan]<br>$C_{23}H_{26}N_2O_3$; MS (ESI) m/z 379.2 (MH)$^+$. |
| 186 | (E)-1-(2-chloro-phenylethenyl)carbonyl-5'-aminomethyl-spiro[piperidine-4,3'-(2H)-benzo[b]furan]<br>$C_{22}H_{23}ClN_2O_2$; MS (ESI) m/z 383.2 (MH)$^+$. |
| 187 | (E)-1-(benzodioxol-5-ylethenyl)carbonyl-5'-aminomethyl-spiro[piperidine-4,3'-(2H)-benzo[b]furan]<br>$C_{23}H_{24}N_2O_4$; MS (ESI) m/z 392.9 (MH)$^+$. |
| 187 | (E)-1-(benzodioxol-5-ylethenyl)carbonyl-5'-aminomethyl-spiro[piperidine-4,3'-(2H)-benzo[b]furan]<br>$C_{23}H_{24}N_2O_4$; MS (ESI) m/z 392.9 (MH)$^+$. |
| 188 | (E)-1-(naphthalen-1-ylethenyl)carbonyl-5'-aminomethyl-spiro[piperidine-4,3'-(2H)-benzo[b]furan]<br>$C_{26}H_{26}N_2O_2$; MS (ESI) m/z 399.1 (MH)$^+$. |
| 189 | 1-(1-oxo-2-fluoren-9-ylidene-ethyl)-5'-aminomethyl-spiro[piperidine-4,3'-(2H)-benzo[b]furan]<br>$C_{28}H_{26}N_2O_2$; MS (ESI) m/z 423.3 (MH)$^+$. |
| 190 | (E)-1-(1-phenyl-2-phenylethenyl)carbonyl-5'-aminomethyl-spiro[piperidine-4,3'-(2H)-benzo[b]furan]<br>$C_{28}H_{28}N_2O_2$; MS (ESI) m/z 425.2 (MH)$^+$. |
| 191 | (E)-1-(2-methyl-phenylethenyl)carbonyl-5'-aminomethyl-spiro[piperidine-4,3'-(2H)-benzo[b]furan]<br>$C_{23}H_{26}N_2O_2$; MS (ESI) m/z 363.3 (MH)$^+$. |
| 192 | 1-(1-methyl-3H-inden-2-yl)carbonyl-5'-aminomethyl-spiro[piperidine-4,3'-(2H)-benzo[b]furan]<br>$C_{24}H_{26}N_2O_2$; MS (ESI) m/z 375.3 (MH)$^+$. |
| 193 | 1-(1-methyl-indol-2-yl)carbonyl-5'-aminomethyl-spiro[piperidine-4,3'-(2H)-benzo[b]furan]<br>$C_{23}H_{25}N_3O_2$; MS (ESI) m/z 376.2 (MH)$^+$. |
| 194 | (E)-1-(2-methoxy-phenylethenyl)carbonyl-5'-aminomethyl-spiro[piperidine-4,3'-(2H)-benzo[b]furan]<br>$C_{23}H_{26}N_2O_3$; MS (ESI) m/z 379.2 (MH)$^+$. |
| 195 | (E)-1-(2,6-difluoro-phenylethenyl)carbonyl-5'-aminomethyl-spiro[piperidine-4,3'-(2H)-benzo[b]furan]<br>$C_{22}H_{22}F_2N_2O_2$; MS (ESI) m/z 385.2 (MH)$^+$. |
| 196 | 1-(2-oxo-(2H)-chromen-3-yl)carbonyl-5'-aminomethyl-spiro[piperidine-4,3'-(2H)-benzo[b]furan]<br>$C_{23}H_{22}N_2O_4$; MS (ESI) m/z 391.2 (MH)$^+$. |
| 197 | 1-(8-methoxy-(2H)-chromen-3-yl)carbonyl-5'-aminomethyl-spiro[piperidine-4,3'-(2H)-benzo[b]furan]<br>$C_{24}H_{26}N_2O_4$; MS (ESI) m/z 407.3 (MH)$^+$. |
| 198 | 1-(5-bromo-thien-2-yl)carbonyl-5'-aminomethyl-spiro[piperidine-4,3'-(2H)-benzo[b]furan]<br>$C_{18}H_{19}BrN_2O_2S$; MS (ESI) m/z 407.0 (MH)$^+$. |
| 199 | (E)-1-(2-bromo-phenylethenyl)carbonyl-5'-aminomethyl-spiro[piperidine-4,3'-(2H)-benzo[b]furan]<br>$C_{22}H_{23}BrN_2O_2$; MS (ESI) m/z 427.1 (MH)$^+$. |
| 200 | 1-(5-trifluoromethyl-benzo[b]thien-2-yl)carbonyl-5'-aminomethyl-spiro[piperidine-4,3'-(2H)-benzo[b]furan]<br>$C_{23}H_{21}F_3N_2O_2S$; MS (ESI) m/z 447.1 (MH)$^+$. |
| 201 | 1-[3-(4-methoxy-phenyl)-4-cyano-5-methylthio-thien-2-yl]carbonyl-5'-aminomethyl-spiro[piperidine-4,3'-(2H)-benzo[b]furan]<br>$C_{27}H_{27}N_3O_3S_2$; MS (ESI) m/z 506.1 (MH)$^+$. |
| 202 | 1-[3-(4-chloro-phenyl)-4-cyano-5-methylthio-thien-2-yl]carbonyl-5'-aminomethyl-spiro[piperidine-4,3'-(2H)-benzo[b]furan]<br>$C_{26}H_{24}ClN_3O_2S_2$; MS (ESI) m/z 510.1 (MH)$^+$. |
| 203 | 1-(5,6,7-trihydro-4H-benzo[c]thien-1-yl)carbonyl-5'-aminomethyl-spiro[piperidine-4,3'-(2H)-benzo[b]furan]<br>$C_{22}H_{26}N_2O_2S$; MS (ESI) m/z 383.0 (MH)$^+$. |
| 204 | 1-thieno[3,2-b]thien-2-ylcarbonyl-5'-aminomethyl-spiro[piperidine-4,3'-(2H)-benzo[b]furan]<br>$C_{20}H_{20}N_2O_2S_2$; MS (ESI) m/z 384.9 (MH)$^+$. |
| 205 | (Z)-1-(1-methylcarbonylamino-2-phenylethenyl)carbonyl-5'-aminomethyl-spiro[piperidine-4,3'-(2H)-benzo[b]furan]<br>$C_{24}H_{27}N_3O_3$; MS (ESI) m/z 405.9 (MH)$^+$. |
| 206 | 1-[5-(2-methyl-thiazol-4-yl)-thien-2-yl]carbonyl-5'-aminomethyl-spiro[piperidine-4,3'-(2H)-benzo[b]furan]<br>$C_{22}H_{23}N_3O_2S_2$; MS (ESI) m/z 425.9 (MH)$^+$. |

| Cpd | Name |
|---|---|
| 207 | 1-(3-chloro-6-methyl-benzo[b]thien-2-yl)carbonyl-5'-aminomethyl-spiro[piperidine-4,3'-(2H)-benzo[b]furan]<br>$C_{23}H_{23}ClN_2O_2S$; MS (ESI) m/z 426.9 (MH)+. |
| 207 | 1-(3-chloro-6-methyl-benzo[b]thien-2-yl)carbonyl-5'-aminomethyl-spiro[piperidine-4,3'-(2H)-benzo[b]furan]<br>$C_{23}H_{23}ClN_2O_2S$; MS (ESI) m/z 428.9 (MH)+. |
| 208 | 1-[3-(2-methyl-phenoxy)-benzyl]carbonyl-5'-aminomethyl-spiro[piperidine-4,3'-(2H)-benzo[b]furan]<br>$C_{28}H_{30}N_2O_3$; MS (ESI) m/z 443.0 (MH)+. |
| 209 | 1-(3-chloro-6-methoxy-benzo[b]thien-2-yl)carbonyl-5'-aminomethyl-spiro[piperidine-4,3'-(2H)-benzo[b]furan]<br>$C_{23}H_{23}ClN_2O_3S$; MS (ESI) m/z 442.8 (MH)+. |
| 210 | 1-[3-(2-fluoro-phenoxy)-benzyl]carbonyl-5'-aminomethyl-spiro[piperidine-4,3'-(2H)-benzo[b]furan]<br>$C_{27}H_{27}FN_2O_3$; MS (ESI) m/z 446.9 (MH)+. |
| 211 | 1-(3-propylthio-4-oxo-5,6,7-trihydro-4H-benzo[c]thien-1-yl)carbonyl-5'-aminomethyl-spiro[piperidine-4,3'-(2H)-benzo[b]furan]<br>$C_{25}H_{30}N_2O_3S_2$; MS (ESI) m/z 470.9 (MH)+. |
| 212 | 1-[5-(2-methoxy-4-propyl-phenoxymethyl)-furan-2-yl]carbonyl-5'-aminomethyl-spiro[piperidine-4,3'-(2H)-benzo[b]furan]<br>$C_{29}H_{34}N_2O_5$; MS (ESI) m/z 491.0 (MH)+. |
| 213 | 1-[5-(2-bromo-phenoxymethyl)-furan-2-yl]carbonyl-5'-aminomethyl-spiro[piperidine-4,3'-(2H)-benzo[b]furan]<br>$C_{25}H_{25}BrN_2O_4$; MS (ESI) m/z 496.8 (MH)+. |
| 214 | 1-(3-benzylthio-4-oxo-5,6,7-trihydro-4H-benzo[c]thien-1-yl)carbonyl-5'-aminomethyl-spiro[piperidine-4,3'-(2H)-benzo[b]furan]<br>$C_{29}H_{30}N_2O_3S_2$; MS (ESI) m/z 518.8 (MH)+. |
| 215 | 1-[1-oxo-2-(3-oxo-3H-isobenzofuran-1-ylidene)-ethyl]-5'-aminomethyl-spiro[piperidine-4,3'-(2H)-benzo[b]furan]<br>$C_{23}H_{22}N_2O_4$; MS (ESI) m/z 390.9 (MH)+. |
| 216 | 1-(5-morpholin-4-ylmethyl-furan-2-yl)carbonyl-5'-aminomethyl-spiro[piperidine-4,3'-(2H)-benzo[b]furan]<br>$C_{23}H_{29}N_3O_4$; MS (ESI) m/z 411.9 (MH)+. |
| 217 | 1-(4-phenyl-[1,2,3]thiadiazol-5-yl)carbonyl-5'-aminomethyl-spiro[piperidine-4,3'-(2H)-benzo[b]furan]<br>$C_{22}H_{22}N_4O_2S$; MS (ESI) m/z 407.0 (MH)+. |
| 218 | 1-(3-methylthio-5,6,7-trihydro-4H-benzo[c]thien-1-yl)carbonyl-5'-aminomethyl-spiro[piperidine-4,3'-(2H)-benzo[b]furan]<br>$^1$H NMR (CD$_3$OD) δ 7.23 (d, J = 1.9 Hz, 1H), 7.25 (dd, J = 1.9 Hz, J = 8.2 Hz, 1H), 6.84 (d, J = 8.2 Hz, 1H), 4.58 (s, 2H), 4.23 (br d, J = 13.6 Hz, 2H), 4.06 (s, 2H), 3.25 (br t, J = 11.7 Hz, 2H), 2.76-2.67 (m, 4H), 2.43 (s, 3H), 1.99-1.78 (m, 8H).<br>$C_{23}H_{28}N_2O_2S_2$; MS (ESI) m/z 429.0 (MH)+. |
| 219 | 1-(3-methylthio-7-hydro-6H-benzo[c]thien-1-yl)carbonyl-5'-aminomethyl-spiro[piperidine-4,3'-(2H)-benzo[b]furan]<br>$C_{23}H_{26}N_2O_2S_2$; MS (ESI) m/z 426.9 (MH)+. |
| 220 | 1-[5-(2-methyl-furan-3-yl-carbonylaminomethyl)-furan-2-yl]carbonyl-5'-aminomethyl-spiro[piperidine-4,3'-(2H)-benzo[b]furan]<br>$C_{25}H_{27}N_3O_5$; MS (ESI) m/z 449.9 (MH)+. |
| 221 | 1-[5-(3,5-dimethyl-4-chloro-pyrazol-1-yl)-furan-2-yl]carbonyl-5'-aminomethyl-spiro[piperidine-4,3'-(2H)-benzo[b]furan]<br>$C_{24}H_{27}ClN_4O_3$ MS (ESI) m/z 455.0 (MH)+. |
| 222 | 1-(3-methyl-4-oxo-6-phenyl-5,6,7-trihydro-4H-benzo[b]furan-2-yl)carbonyl-5'-aminomethyl-spiro[piperidine-4,3'-(2H)-benzo[b]furan]<br>$C_{29}H_{30}N_2O_4$; MS (ESI) m/z 470.9 (MH)+. |
| 223 | 1-(3-ethylthio-4-oxo-6,6-dimethyl-6,7-dihydro-5H-benzo[c]thien-1-yl)carbonyl-5'-aminomethyl-spiro[piperidine-4,3'-(2H)-benzo[b]furan]<br>$C_{26}H_{32}N_2O_3S_2$; MS (ESI) m/z 485.0 (MH)+. |
| 224 | 1-[5-(2-methoxy-4-allyl-phenoxymethyl)-furan-2-yl]carbonyl-5'-aminomethyl-spiro[piperidine-4,3'-(2H)-benzo[b]furan]<br>$C_{29}H_{32}N_2O_5$; MS (ESI) m/z 489.0 (MH)+. |
| 225 | 1-(3-isopropylthio-4-oxo-6,6-dimethyl-6,7-dihydro-5H-benzo[c]thien-1-yl)carbonyl-5'-aminomethyl-spiro[piperidine-4,3'-(2H)-benzo[b]furan]<br>$C_{27}H_{34}N_2O_3S_2$; MS (ESI) m/z 498.9 (MH)+. |
| 226 | 1-(3,4-dimethyl-5-cyano-thieno[2,3-b]thien-2-yl)carbonyl-5'-aminomethyl-spiro[piperidine-4,3'-(2H)-benzo[b]furan]<br>$C_{23}H_{23}N_3O_2S_2$; MS (ESI) m/z 437.9 (MH)+. |
| 227 | 1-[5-(3-methoxy-phenoxymethyl)-furan-2-yl]carbonyl-5'-aminomethyl-spiro[piperidine-4,3'-(2H)-benzo[b]furan]<br>$C_{26}H_{25}N_2O_5$; MS (ESI) m/z 449.0 (MH)+. |
| 228 | 1-(3-methyl-6-phenyl-benzo[b]furan-2-yl)carbonyl-5'-aminomethyl-spiro[piperidine-4,3'-(2H)-benzo[b]furan]<br>$C_{29}H_{28}N_2O_3$; MS (ESI) m/z 452.9 (MH)+. |
| 229 | 1-(3-butylthio-4-oxo-5,6,7-trihydro-4H-benzo[c]thien-1-yl)carbonyl-5'-aminomethyl-spiro[piperidine-4,3'-(2H)-benzo[b]furan]<br>$C_{26}H_{32}N_2O_3S_2$; MS (ESI) m/z 484.8 (MH)+. |

-continued

| Cpd | Name |
|---|---|
| 230 | 1-(3-chloro-6-bromo-benzo[b]thien-2-yl)carbonyl-5'-aminomethyl-spiro[piperidine-4,3'-(2H)-benzo[b]furan] $C_{22}H_{20}BrClN_2O_2S$; MS (ESI) m/z 491.0 (MH)$^+$. |
| 231 | 1-(3-sec-butylthio-4-oxo-6,6-dimethyl-6,7-dihydro-5H-benzo[c]thien-1-yl)carbonyl-5'-aminomethyl-spiro[piperidine-4,3'-(2H)-benzo[b]furan] $C_{28}H_{36}N_2O_3S_2$; MS (ESI) m/z 512.8 (MH)$^+$. |
| 232 | 1-(3-benzylthio-4-oxo-6,6-dimethyl-6,7-dihydro-5H-benzo[c]thien-1-yl)carbonyl-5'-aminomethyl-spiro[piperidine-4,3'-(2H)-benzo[b]furan] $C_{31}H_{34}N_2O_3S_2$; MS (ESI) m/z 546.9 (MH)$^+$. |
| 233 | 1-thieno[2,3-b]thien-2-ylcarbonyl-5'-aminomethyl-spiro[piperidine-4,3'-(2H)-benzo[b]furan] $C_{20}H_{20}N_2O_2S_2$; MS (ESI) m/z 384.9 (MH)$^+$. |
| 234 | 1-(3-methylthio-benzo[c]thien-1-yl)carbonyl-5'-aminomethyl-spiro[piperidine-4,3'-(2H)-benzo[b]furan] $C_{23}H_{24}N_2O_2S_2$; MS (ESI) m/z 424.8 (MH)$^+$. |
| 235 | 1-(3-Methylthio-4-methoxy-benzo[c]thien-1-yl)carbonyl-5'-aminomethyl-spiro[piperidine-4,3'-(2H)-benzo[b]furan] $C_{24}H_{26}N_2O_3S_2$; MS (ESI) m/z 454.8 (MH)$^+$. |
| 236 | 1-indol-3-ylcarbonyl-5'-aminomethyl-spiro[piperidine-4,3'-(2H)-benzo[b]furan] $C_{22}H_{23}N_3O_2$; MS (ESI) m/z 362.0 (MH)$^+$. |
| 237 | 1-(1-methyl-indol-3-yl)carbonyl-5'-aminomethyl-spiro[piperidine-4,3'-(2H)-benzo[b]furan] $C_{23}H_{25}N_3O_2$; MS (ESI) m/z 375.9 (MH)$^+$. |
| 238 | 1-(5-methoxy-indol-3-yl)carbonyl-5'-aminomethyl-spiro[piperidine-4,3'-(2H)-benzo[b]furan] $C_{23}H_{25}N_3O_3$; MS (ESI) m/z 392.0 (MH)$^+$. |
| 239 | 1-(1-benzyl-indol-3-yl)carbonyl-5'-aminomethyl-spiro[piperidine-4,3'-(2H)-benzo[b]furan] $C_{29}H_{29}N_3O_2$; MS (ESI) m/z 452.0 (MH)$^+$. |
| 240 | 1-(3-benzylthio-benzo[c]thien-1-yl)carbonyl-5'-aminomethyl-spiro[piperidine-4,3'-(2H)-benzo[b]furan] $C_{29}H_{28}N_2O_2S_2$; MS (ESI) m/z 500.9 (MH)$^+$. |
| 241 | 1-(3-benzylthio-7-hydro-6H-benzo[c]thien-1-yl)carbonyl-5'-aminomethyl-spiro[piperidine-4,3'-(2H)-benzo[b]furan] $C_{29}H_{30}N_2O_2S_2$; MS (ESI) m/z 502.8 (MH)$^+$. |
| 242 | (Z)-1-(furan-2-ylethenyl)carbonyl-5'-aminomethyl-spiro[piperidine-4,3'-(2H)-benzo[b]furan] $C_{20}H_{22}N_2O_3$; MS (ESI) m/z 338.9 (MH)$^+$. |
| 243 | (Z)-1-(imidazol-4-ylethenyl)carbonyl-5'-aminomethyl-spiro[piperidine-4,3'-(2H)-benzo[b]furan] $C_{19}H_{22}N_4O_2$; MS (ESI) m/z 339.0 (MH)$^+$. |
| 244 | (E)-1-(pyridin-4-ylethenyl)carbonyl-5'-aminomethyl-spiro[piperidine-4,3'-(2H)-benzo[b]furan] $C_{21}H_{23}N_3O_2$; MS (ESI) m/z 350.0 (MH)$^+$. |
| 245 | 1-(5-formyl-thien-2-yl)carbonyl-5'-aminomethyl-spiro[piperidine-4,3'-(2H)-benzo[b]furan] $C_{19}H_{20}N_2O_3S$; MS (ESI) m/z 356.9 (MH)$^+$. |
| 246 | 1-(5,6-dihydro-4H-cyclopenta[b]thien-2-yl)carbonyl-5'-aminomethyl-spiro[piperidine-4,3'-(2H)-benzo[b]furan] $C_{21}H_{24}N_2O_2S$; MS (ESI) m/z 368.9 (MH)$^+$. |
| 247 | 1-(5-methylthio-thien-2-yl)carbonyl-5'-aminomethyl-spiro[piperidine-4,3'-(2H)-benzo[b]furan] $C_{19}H_{22}N_2O_2S_2$; MS (ESI) m/z 374.9 (MH)$^+$. |
| 248 | (E)-1-(1-cyano-2-phenylethenyl)carbonyl-5'-aminomethyl-spiro[piperidine-4,3'-(2H)-benzo[b]furan] $C_{23}H_{23}N_3O_2$; MS (ESI) m/z 374.0 (MH)$^+$. |
| 249 | 1-(7-methyl-indol-3-yl)carbonyl-5'-aminomethyl-spiro[piperidine-4,3'-(2H)-benzo[b]furan] $C_{23}H_{25}N_3O_2$; MS (ESI) m/z 375.9 (MH)$^+$. |
| 250 | 1-(1-ethyl-7-methyl-indol-3-yl)carbonyl-5'-aminomethyl-spiro[piperidine-4,3'-(2H)-benzo[b]furan] $C_{25}H_{29}N_3O_2$; MS (ESI) m/z 404.0 (MH)$^+$. |
| 251 | (E)-1-(furan-3-ylethenyl)carbonyl-5'-aminomethyl-spiro[piperidine-4,3'-(2H)-benzo[b]furan] $C_{20}H_{22}N_2O_3$; MS (ESI) m/z 339.0 (MH)$^+$. |
| 252 | (E)-1-(pyridin-2-ylethenyl)carbonyl-5'-aminomethyl-spiro[piperidine-4,3'-(2H)-benzo[b]furan] $C_{21}H_{23}N_3O_2$; MS (ESI) m/z 350.0 (MH)$^+$. |
| 253 | (E)-1-(pyridin-3-ylethenyl)carbonyl-5'-aminomethyl-spiro[piperidine-4,3'-(2H)-benzo[b]furan] $C_{21}H_{23}N_3O_2$; MS (ESI) m/z 350.0 (MH)$^+$. |
| 254 | (E)-1-(thien-2-ylethenyl)carbonyl-5'-aminomethyl-spiro[piperidine-4,3'-(2H)-benzo[b]furan] $C_{20}H_{22}N_2O_2S$; MS (ESI) m/z 354.9 (MH)$^+$. |
| 255 | (E)-1-(thien-3-ylethenyl)carbonyl-5'-aminomethyl-spiro[piperidine-4,3'-(2H)-benzo[b]furan] $C_{20}H_{22}N_2O_2S$; MS (ESI) m/z 354.9 (MH)$^+$. |

-continued

| Cpd | Name |
|---|---|
| 256 | 1-(5-dihydroxymethyl-4-methyl-thien-2-yl)carbonyl-5'-aminomethyl-spiro[piperidine-4,3'-(2H)-benzo[b]furan]<br>$^1$H NMR (CD$_3$OD) δ 7.32 (d, J = 1.7 Hz, 1H), 7.23 (dd, J = 1.8 Hz, J = 8.2 Hz, 1H), 7.17 (s, 1H), 6.82 (d, J = 8.2 Hz, 1H), 5.66 (s, 1H), 4.57 (s, 2H), 4.39 (br d, J = 11.7 Hz, 2H), 4.04 (s, 2H), 3.35-3.15 (br m, 2H), 2.24 (s, 3H), 2.03-1.81 (m, 4H). $C_{20}H_{24}N_2O_4S$ |
| 257 | 1-(5,6,7,8-tetrahydro-4H-cyclohepta[b]thien-2-yl)carbonyl-5'-aminomethyl-spiro[piperidine-4,3'-(2H)-benzo[b]furan]<br>$C_{23}H_{28}N_2O_2S$; MS (ESI) m/z 396.9 (MH)$^+$. |
| 258 | 1-(4-cyano-5-methylthio-thien-2-yl)carbonyl-5'-aminomethyl-spiro[piperidine-4,3'-(2H)-benzo[b]furan]<br>$C_{20}H_{21}N_3O_2S_2$; MS (ESI) m/z 399.9 (MH)$^+$. |
| 259 | 1-(4-methyl-5-bromo-thien-2-yl)carbonyl-5'-aminomethyl-spiro[piperidine-4,3'-(2H)-benzo[b]furan]<br>$C_{19}H_{21}BrN_2O_2S$; MS (ESI) m/z 420.8 (MH)$^+$. |
| 260 | spiro[cyclohexane-1,6'-5,7-dihydro-4H-benzo[b]thiophene]-2'-carbonyl-5'-aminomethyl-spiro[piperidine-4,3'-(2H)-benzo[b]furan]<br>$C_{27}H_{34}N_2O_2S$; MS (ESI) m/z 450.9 (MH)$^+$. |
| 261 | 1-(3-ethoxy-4-oxo-5,6,7-trihydro-4H-benzo[c]thien-1-yl)carbonyl-5'-aminomethyl-spiro[piperidine-4,3'-(2H)-benzo[b]furan]<br>$C_{24}H_{28}N_2O_4S$; MS (ESI) m/z 440.9 (MH)$^+$. |
| 264 | 1-(4-hydroxy-phenylethynyl)carbonyl-5'-aminomethyl-spiro[piperidine-4,3'-(2H)-benzo[b]furan]<br>$C_{22}H_{22}N_2O_3$; MS (ESI) m/z 362.9 (MH)$^+$. |
| 265 | (E)-1-(3-hydroxy-phenylethenyl)carbonyl-5'-aminomethyl-spiro[piperidine-4,3'-(2H)-benzo[b]furan]<br>$C_{22}H_{24}N_2O_3$; MS (ESI) m/z 365.0 (MH)$^+$. |
| 266 | 1-(5-tert-butyl-thien-2-yl)carbonyl-5'-aminomethyl-spiro[piperidine-4,3'-(2H)-benzo[b]furan]<br>$C_{22}H_{28}N_2O_2S$; MS (ESI) m/z 384.9 (MH)$^+$. |
| 267 | 1-(5-methoxycarbonyl-thien-2-yl)carbonyl-5'-aminomethyl-spiro[piperidine-4,3'-(2H)-benzo[b]furan]<br>$C_{20}H_{22}N_2O_4S$; MS (ESI) m/z 386.9 (MH)$^+$. |
| 268 | (E)-1-(4-tert-butyl-phenylethenyl)carbonyl-5'-aminomethyl-spiro[piperidine-4,3'-(2H)-benzo[b]furan]<br>$C_{26}H_{32}N_2O_2$; MS (ESI) m/z 405.0 (MH)$^+$. |
| 269 | 1-fluoren-1-ylcarbonyl-5'-aminomethyl-spiro[piperidine-4,3'-(2H)-benzo[b]furan]<br>$C_{27}H_{26}N_2O_2$; MS (ESI) m/z (MH)$^+$. |
| 270 | 1-(9-oxo-fluoren-1-yl)carbonyl-5'-aminomethyl-spiro[piperidine-4,3'-(2H)-benzo[b]furan]<br>$C_{27}H_{24}N_2O_3$; MS (ESI) m/z 410.9 (MH)$^+$. |
| 271 | 1-(3-chloro-6-ethyl-benzo[b]thien-2-yl)carbonyl-5'-aminomethyl-spiro[piperidine-4,3'-(2H)-benzo[b]furan]<br>$C_{24}H_{25}ClN_2O_2S$; MS (ESI) m/z 440.9 (MH)$^+$. |
| 272 | (E)-1-(2-hydroxy-phenylethenyl)carbonyl-5'-aminomethyl-spiro[piperidine-4,3'-(2H)-benzo[b]furan]<br>$C_{22}H_{24}N_2O_3$; MS (ESI) m/z 365.0 (MH)$^+$. |
| 273 | 1-(3-aminocarbonyl-phenyl)carbonyl-5'-aminomethyl-spiro[piperidine-4,3'-(2H)-benzo[b]furan]<br>$C_{21}H_{23}N_3O_3$; MS (ESI) m/z 365.9 (MH)$^+$. |
| 274 | 1-(3-tert-butyl-phenyl)carbonyl-5'-aminomethyl-spiro[piperidine-4,3'-(2H)-benzo[b]furan]<br>$C_{24}H_{30}N_2O_2$; MS (ESI) m/z 378.9 (MH)$^+$. |
| 275 | 1-(3,4,5-trichloro-thien-2-yl)carbonyl-5'-aminomethyl-spiro[piperidine-4,3'-(2H)-benzo[b]furan]<br>$C_{18}H_{17}Cl_3N_2O_2S$; MS (ESI) m/z 430.6 (MH)$^+$. |
| 276 | 1-(4-trifluoromethyl-6-methyl-1H-thieno[2,3-c]pyrazol-2-yl)carbonyl-5'-aminomethyl-spiro[piperidine-4,3'-(2H)-benzo[b]furan]<br>$C_{21}H_{21}F_3N_4O_2S$; MS (ESI) m/z 450.8 (MH)$^+$. |
| 277 | 1-(3-thien-2-yl-[1,2,4]oxadiazol-5-yl)carbonyl-5'-aminomethyl-spiro[piperidine-4,3'-(2H)-benzo[b]furan]<br>$C_{26}H_{24}N_4O_3S$; MS (ESI) m/z 472.8 (MH)$^+$. |
| 278 | 1-(4,5-dibromo-thien-2-yl)carbonyl-5'-aminomethyl-spiro[piperidine-4,3'-(2H)-benzo[b]furan]<br>$C_{18}H_{18}Br_2N_2O_2S$; MS (ESI) m/z 486.6 (MH)$^+$. |
| 279 | 1-[4-(3,5-bis-trifluoromethyl-phenoxy)-phenyl]carbonyl-5'-aminomethyl-spiro[piperidine-4,3'-(2H)-benzo[b]furan]<br>$C_{28}H_{24}F_6N_2O_3$; MS (ESI) m/z 550.8 (MH)$^+$. |
| 280 | 1-(3,4-dichlorophenyl)sulfonyl-5'-aminomethyl-spiro[piperidine-4,3'-(2H)-benzo[b]furan]<br>$C_{19}H_{20}Cl_2N_2O_3S$; MS (ESI) m/z 426.7 (MH)$^+$. |
| 281 | (E)-1-(3-benzyloxy-phenylethenyl)carbonyl-5'-aminomethyl-spiro[piperidine-4,3'-(2H)-benzo[b]furan]<br>$C_{29}H_{30}N_2O_3$; MS (ESI) m/z 455.0 (MH)$^+$. |
| 282 | 1-[5-(4-tert-butyl-phenylethynyl)-furan-2-yl]carbonyl-5'-aminomethyl-spiro[piperidine-4,3'-(2H)-benzo[b]furan]<br>$C_{30}H_{32}N_2O_3$; MS (ESI) m/z 468.9 (MH)$^+$. |

-continued

| Cpd | Name |
|---|---|
| 283 | 1-(1-phenylsulfonyl-1H-indol-2-yl)carbonyl-5'-aminomethyl-spiro[piperidine-4,3'-(2H)-benzo[b]furan]<br>$C_{28}H_{27}N_3O_4S$; MS (ESI) m/z 501.9 (MH)$^+$. |
| 284 | 1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan]<br>$C_{27}H_{25}N_5O_4S$; MS (ESI) m/z 515.8 (MH)$^+$. |
| 286 | 1-3H-inden-1-ylcarbonyl-5'-aminomethyl-spiro[piperidine-4,3'-(2H)-benzo[b]furan]<br>$C_{23}H_{24}N_2O_2$; MS (ESI) m/z 360.1 (MH)$^+$. |
| 287 | 1-(3-oxo-indan-1-yl)carbonyl-5'-aminomethyl-spiro[piperidine-4,3'-(2H)-benzo[b]furan]<br>$C_{23}H_{24}N_2O_3$; MS (ESI) m/z 377.1 (MH)$^+$. |
| 288 | 1-(4-phenyl-thien-2-yl)carbonyl-5'-aminomethyl-spiro[piperidine-4,3'-(2H)-benzo[b]furan]<br>$C_{24}H_{24}N_2O_2S$; MS (ESI) m/z 405.1 (MH)$^+$. |
| 289 | 1-fluoren-9-ylcarbonyl-5'-aminomethyl-spiro[piperidine-4,3'-(2H)-benzo[b]furan]<br>$C_{27}H_{26}N_2O_2$; MS (ESI) m/z 411.1 (MH)$^+$. |
| 290 | 1-(1-oxo-2,2-diphenyl-ethyl)-5'-aminomethyl-spiro[piperidine-4,3'-(2H)-benzo[b]furan]<br>$C_{27}H_{28}N_2O_2$; MS (ESI) m/z 413.0 (MH)$^+$. |
| 291 | (E)-1-[3-(2-methoxy-ethoxy)-phenylethenyl]carbonyl-5'-aminomethyl-spiro[piperidine-4,3'-(2H)-benzo[b]furan]<br>$C_{25}H_{30}N_2O_4$; MS (ESI) m/z 423.2 (MH)$^+$. |
| 292 | 1-9H-xanthen-9-ylcarbonyl-5'-aminomethyl-spiro[piperidine-4,3'-(2H)-benzo[b]furan]<br>$C_{27}H_{26}N_2O_3$; MS (ESI) m/z 427.1 (MH)$^+$. |
| 293 | 1-9H-xanthen-9-ylmethylcarbonyl-5'-aminomethyl-spiro[piperidine-4,3'-(2H)-benzo[b]furan]<br>$C_{28}H_{28}N_2O_3$; MS (ESI) m/z 440.9 (MH)$^+$. |
| 294 | (E)-1-(3-phenethoxy-phenylethenyl)carbonyl-5'-aminomethyl-spiro[piperidine-4,3'-(2H)-benzo[b]furan]<br>$C_{30}H_{32}N_2O_3$; MS (ESI) m/z 469.1 (MH)$^+$. |
| 295 | 1-(4-phenyl-5-trifluoromethyl-thien-2-yl)carbonyl-5'-aminomethyl-spiro[piperidine-4,3'-(2H)-benzo[b]furan]<br>$C_{25}H_{23}F_3N_2O_2S$; MS (ESI) m/z 473.0 (MH)$^+$. |
| 298 | 1-(1-chloro-naphtho[2,1-b]thien-2-yl)carbonyl-5'-aminomethyl-spiro[piperidine-4,3'-(2H)-benzo[b]furan]<br>$C_{26}H_{23}ClN_2O_2S$; MS (ESI) m/z 462.7 (MH)$^+$. |
| 299 | 1-[3-(4-chloro-phenyl)-5-methylthio-thien-2-yl]carbonyl-5'-aminomethyl-spiro[piperidine-4,3'-(2H)-benzo[b]furan]<br>$C_{25}H_{25}ClN_2O_2S_2$; MS (ESI) m/z 484.8 (MH)$^+$. |
| 300 | (E)-1-(4-benzyloxy-phenylethenyl)carbonyl-5'-aminomethyl-spiro[piperidine-4,3'-(2H)-benzo[b]furan]<br>$C_{29}H_{30}N_2O_3$; MS (ESI) m/z 455.0 (MH)$^+$. |
| 301 | (E)-1-[3-(3-methoxy-propoxy)-phenylethenyl]carbonyl-5'-aminomethyl-spiro[piperidine-4,3'-(2H)-benzo[b]furan]<br>$C_{26}H_{32}N_2O_4$; MS (ESI) m/z 437.1 (MH)$^+$. |
| 302 | (E)-1-[3-(2-ethoxy-ethoxy)-phenylethenyl]carbonyl-5'-aminomethyl-spiro[piperidine-4,3'-(2H)-benzo[b]furan]<br>$C_{26}H_{32}N_2O_4$; MS (ESI) m/z 437.1 (MH)$^+$. |
| 303 | 1-(3-methyl-4-bromo-5-propoxy-thien-2-yl)carbonyl-5'-aminomethyl-spiro[piperidine-4,3'-(2H)-benzo[b]furan]<br>$C_{22}H_{27}BrN_2O_3S$; MS (ESI) m/z 479.2 (MH)$^+$. |
| 309 | (E)-1-(2-fluoro-phenylethenyl)carbonyl-5'-aminomethyl-spiro[piperidine-4,3'-(2H)-benzo[b]furan]<br>$C_{22}H_{23}FN_2O_2$; MS (ESI) m/z 367.2 (MH)$^+$. |
| 354 | 1-(2,2-diphenylethyl)carbonyl-5'-aminomethyl-spiro[piperidine-4,3'-(2H)-benzo[b]furan]<br>$C_{28}H_{30}N_2O_2$; MS (ESI) m/z 426.9 (MH)$^+$. |
| 355 | 1-(9H-fluoren-9-ylmethyl)carbonyl-5'-aminomethyl-spiro[piperidine-4,3'-(2H)-benzo[b]furan]<br>$C_{28}H_{28}N_2O_2$; MS (ESI) m/z 425.0 (MH)$^+$. |
| 356 | (E)-1-(3-methyl-thien-2-ylethenyl)carbonyl-5'-aminomethyl-spiro[piperidine-4,3'-(2H)-benzo[b]furan]<br>$C_{21}H_{24}N_2O_2S$; MS (ESI) m/z 368.5 (MH)$^+$. |
| 357 | 1-[4-(4-chloro-phenyl)-thien-2-yl]carbonyl-5'-aminomethyl-spiro[piperidine-4,3'-(2H)-benzo[b]furan]<br>$C_{24}H_{23}ClN_2O_2S$; MS (ESI) m/z 438.7 (MH)$^+$. |

Example 3

5'-(3,4-dichlorophenylcarbonylaminomethyl)-spiro[piperidine-4,3'-(2H)-benzo[b]furan] (Cpd 2)

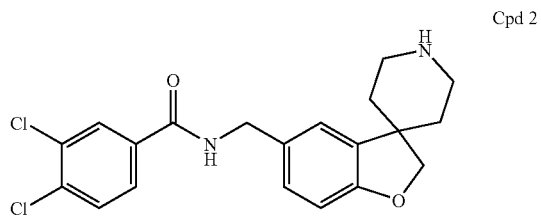
Cpd 2

Step A. 1-(tert-butyloxy)carbonyl-5'-(3,4-dichlorophenylcarbonyl-aminomethyl)-spiro[piperidine-4,3'-benzo[b]furan]

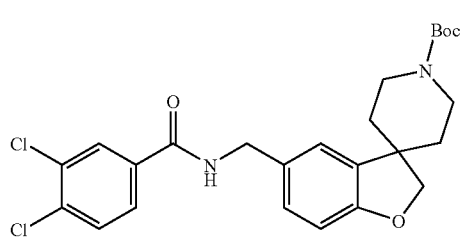
3a

A mixture of intermediate 1f (9 mg, 0.028 mmol; Example 1), 3,4-dichlorobenzoic acid (8 mg, 0.042 mmol), EDC (8 mg, 0.042 mmol), HOBt (6 mg, 0.042 mmol), and DIPEA (0.1 mL) in CH$_2$Cl$_2$ (2 mL) was stirred at room temperature for 36 h. The reaction mixture was concentrated and the residue was purified by chromatography on silica gel eluting with CH$_2$Cl$_2$/MeOH (200:1) to give 3a (14 mg, 100%).

Step B. 5'-(3,4-dichlorophenylcarbonylaminomethyl)-spiro[piperidine-4,3'-(2H)-benzo[b]furan] (Cpd 2)

Compound 3a (14 mg, 0.028 mmol) was treated with a mixture of TFA/CH$_2$Cl$_2$ (1:2) containing thioanisole (0.2 mL) at room temperature for 1 h. The reaction was concentration in vacuo and the residue was purified by chromatography on silica gel eluting with CH$_2$Cl$_2$/MeOH/concd NH$_4$OH (100:10:1) to give the free base of Compound 2 (12.3 mg, 88%), which was converted to TFA salt by treatment of with a solution of TFA in CH$_2$Cl$_2$ (5%) followed by concentration in vacuo. $^1$H NMR (CDCl$_3$, 400 MHz) 7.90 (s, 1H), 7.63 (d, 1H, J=8.3 Hz), 7.51 (d, 1H, J=8.4 Hz), 7.18-7.16 (m, 2H), 6.80 (d, 1H, J=8.7 Hz), 6.50 (br s, 1H), 4.56 (d, 2H, J=5.7 Hz), 4.43 (s, 2H), 3.36 (br s, 2H), 3.25 (d, 2H, J=12.2 Hz), 2.82 (t, 2H, J=12.2 Hz), 2.00 (dt, 2H, J=14.1, 3.9 Hz), 1.81 (d, 2H, J=13.1 Hz); MS (ES) m/z 390.9 (MH)$^+$ for C$_{20}$H$_{20}$Cl$_2$N$_2$O$_2$.

Example 4

1-(5-phenylethynyl-furan-2-yl)carbonyl-5'-aminomethyl-spiro[piperidine-4,3'-indane] (Cpd 318)

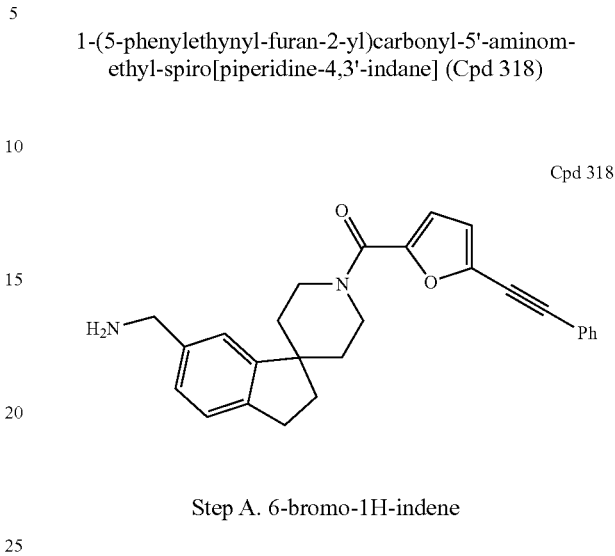
Cpd 318

Step A. 6-bromo-1H-indene

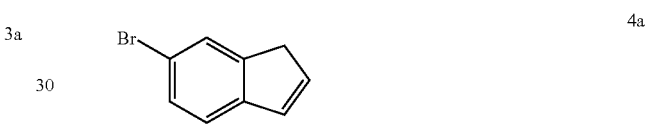
4a

Sodium borohydride (1.1 g, 0.029 mol) was added, in 3 portions, to a solution of 5-bromo-indan-1-one (3.09 g, 0.0136 mol; CAS# 3459849-7) in methanol (25 mL) at 0° C. under an atmosphere of argon. After 2 h, the reaction mixture was partitioned between EtOAc and water. The organic layer was separated, extracted with water, brine, dried (Na$_2$SO$_4$) and concentrated in vacuo to give an amber solid (3.16 g). This solid (1.58 g) was dissolved in ethylene glycol (63 mL) and treated with 20% vol. aq. sulfuric acid (63 mL). The reaction mixture was heated to 75° C. for 2 hours then cooled to room temperature and extracted with DCM (2×). The combined organic layers were extracted with saturated aq. NaHCO$_3$, dried (Na$_2$SO$_4$) and concentrated in vacuo. The resulting residue was purified by silica gel column eluted with hexanes to afford 4a (0.76 g, 52%) as a clear liquid.

Step B. 1-(tert-butyloxy)carbonyl-spiro[piperidine-4,3'-indane]

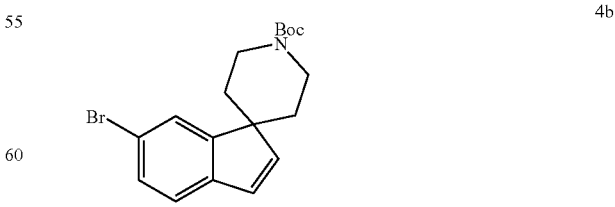
4b

To a solution of bis(2-chloroethyl)amine hydrochloride (2.0 g, 11 mmol; CAS# 821-48-7), TEA (1.9 mL, 13 mmol) in DCM (50 mL) was added di-tert-butyl dicarbonate (2.9 g, 13 mmol) and allowed to stir 16 h at room temperature under an atmosphere of argon. The reaction mixture was diluted with water and the organic layer separated. The organic layer was extracted with 1 N aq. HCl, saturated aq. NaHCO₃, dried (Na₂SO₄), and concentrated in vacuo. The resulting residue was purified on silica gel column eluted with 3:2 hexanes/ EtOAc to yield bis(2-chloroethyl)carbamic acid tert-butyl ester (1.5 g, 55%).

A solution of lithium hexamethyldisilazide in THF (7.8 mL, 1 M, 7.8 mmol) was added dropwise to a solution of 4a (759 mg, 3.89 mmol) in THF (5 mL) at 0° C. under an atmosphere of argon. After stirring for 45 minutes, a solution of bis(2-chloroethyl)carbamic acid tert-butyl ester (0.94 g, 3.9 mmol) in THF (5 mL) was added dropwise. After stirring for 2 h at 0° C., the reaction mixture was quenched with saturated aq. NH₄Cl. The resulting mixture was extracted with EtOAc. The organic layer was separated, dried (Na₂SO₄), and concentrated in vacuo. The resulting residue was purified on silica gel column eluted with 4:1 hexanes/ EtOAc to yield 4b as a clear syrup (467 mg, 33%).

Step C. 1-(tert-butyloxy)carbonyl-spiro[piperidine-4, 3'-indane]-5'-carboxaldehyde

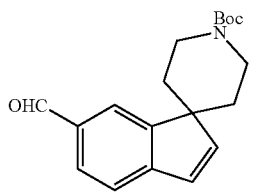

4c

A slurry of 4b (600 mg, 1.65 mmol), tris(3-chlorophenyl) phosphine (11 mg, 0.03 mmol), bis(triphenylphosphine)palladium(II) bromide (24 mg, 0.03 mmol), sodium formate (166 mg, 2.44 mmol) in DMF (1.7 mL) was heated to 110° C. under an atmosphere of carbon monoxide. After 3 h, the reaction was cooled to room temperature and filtered through a nylon filter. The filtrate was diluted with 0.5 N aq. NaOH and DCM. The organic layer was separated, extracted with water, dried (Na₂SO₄) and concentrated in vacuo. The resulting residue was purified on a silica gel column eluted with 4:1 hexanes/EtOAc to give 4c as a yellow syrup (296 mg, 51%).

Step D. 1-(tert-butyloxy)carbonyl-5'-aminomethyl-spiro[piperidine-4,3'-indane]

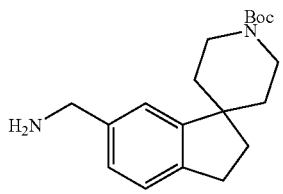

4d

To a solution of 4c (104 mg, 0.330 mmol) in absolute ethanol (1 mL) was added anhydrous hydrazine (0.052 mL, 1.65 mmol) at room temperature. After stirring for 2 h, the reaction mixture was concentrated in vacuo. The residue was dissolved in methanol (5 mL) and PtO₂ (0.06 mmol., 14 mg) added. The slurry was shaken under 50 psi H₂ at room temperature. After 16 h, the reaction mixture was filter through a nylon filter, concentrated in vacuo and purified by reverse-phase HPLC eluting on a C18 column with a gradient of 1:4 to 9:1 ACN/water containing 0.1% TFA to furnish 4d as a white powder (42 mg, 29%).

Step E. 1-(tert-butyloxy)carbonyl-spiro[piperidine-4, 3'-indane]

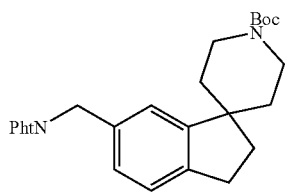

4e

A solution of 4d (42 mg, 0.10 mmol), phthalic anhydride (15 mg, 0.1 mmol) and DIPEA (0.042 mL, 0.24 mmol) in toluene (1 mL) was refluxed with a Dean-Stark trap. After 16 hrs, the reaction mixture was cooled to RT and extracted with 10% wt. aq. citric acid, brine, dried (Na₂SO₄), concentrated in vacuo. The residue was purified on silica gel column eluting with hexanes/EtOAc (4:1) to give 4e as a colorless liquid (28 mg, 63%).

Step F. 1-(5-phenylethynyl-furan-2-yl)carbonyl-5'-(1, 3-dioxo-1,3-dihydro-isoindol-2-ylmethyl)-spiro[piperidine-4,3'-indane]

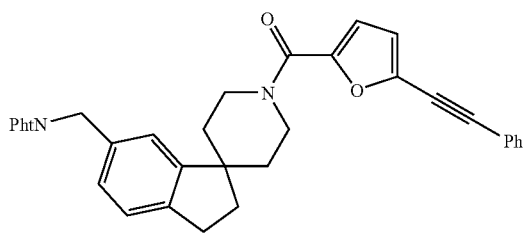

4f

To a solution of 4e (28 mg, 0.063 mmol) in DCM (5 mL) was added TFA (1 mL) at RT. After 15 minutes, the reaction mixture was concentrated in vacuo and the residue was dissolved in DCM. The DCM solution was extracted with 10% wt. aq. Na₂CO₃, dried (Na₂SO₄), and concentrated in vacuo. To the resulting residue was added 5-phenylethynylfuran-2-carboxylic acid (34 mg, 0.16 mmol), EDC (30 mg, 0.16 mmol) and DMF (1 mL). This mixture was stirred 16 hrs at RT under an argon atmosphere. The reaction mixture was diluted with EtOAc and extracted with water (3×), saturated aq. NaHCO₃ (3×), dried (Na₂SO₄) and concentrated in vacuo. The resulting residue was purified on silica gel eluted with 1:1 EtOAc/hexanes to give 4f as a colorless film (18 mg, 53%).

Step G. 1-(5-phenylethynyl-furan-2-yl)carbonyl-5'-aminomethyl-spiro[piperidine-4,3'-indane] (Cpd 318)

To a solution of 4f (18 mg, 0.033 mmol) in ethanol (5 mL) was added anhydrous hydrazine (1 mL) at RT. After 3 hrs, the reaction mixture was concentrated in vacuo and purified by C18 reverse-phase HPLC eluting with a gradient of 3:17 to 9:1 ACN/water containing 0.1% TFA to give the TFA salt of Compound 318 as a white powder (6.3 mg, 34%): $^1$H NMR (CD$_3$OD) δ 7.53 (m, 2H), 7.42 (m, 3H), 7.29 (m, 3H), 7.08 (d, J=3.6 Hz, 1H), 6.85 (d, J=3.5 z, 1H), 4.54 (m, 2H), 4.07 (s, 2H), 3.54 (m, 1H), 2.98 (t, J=7.4 Hz, 2H), 2.73 (m, 1H), 2.25 (t, J=7.3 Hz, 2H), 1.95 (m, 2H), 1.72 (m, 2H); MS (ES) m/z 410.9 (MH)$^+$.

Example 5

1-(3,4-dichlorophenyl)carbonyl-5'-aminomethyl-spiro[piperidine-4,3'-(2H)-benzo[b]thiophene] (Cpd 353)

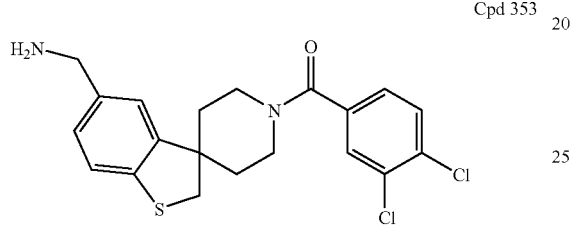

Cpd 353

Step A. 4-(2-bromo-phenylsulfanylmethyl)-3,6-dihydro-2H-pyridine-1-carboxylic Acid Tert-Butyl Ester

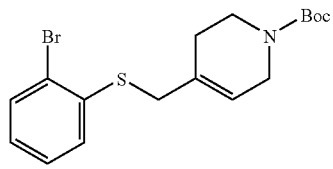

5a

Finely ground K$_2$CO$_3$ (3.58 g, 25.9 mmol) was added to a solution of 2-bromothiophenol (1.14 mL, 9.49 mmol) and 1c (2.00 g, 8.63 mmol; 1c, Example 1) in dry acetone (48 mL). The reaction mixture was heated at reflux for 18 h while stirring under argon. The reaction mixture was filtered and the filtrate was concentrated in vacuo and partitioned between EtOAc and 5% aqueous K$_2$CO$_3$. The organic layer was extracted 5% aqueous K$_2$CO$_3$ (2×), brine (2×), dried (MgSO$_4$), filtered through filter agent and concentrated in vacuo to furnish 5a (3.09 g, 93%) as a brown oil.

Step B. 1-(tert-butyloxy)carbonyl-spiro[piperidine-4,3'-(2H)-benzo[b]thiophene]

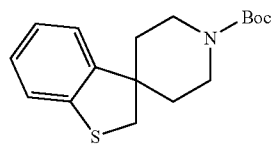

5b

A solution of 5a (3.08 g, 8.01 mmol) and Bu$_3$SnH (5.43 mL, 20.2 mmol) in toluene (401 mL) was treated with AIBN (0.066 g, 0.402 mmol). The reaction mixture was heated at 80° C. under argon for 18 h, cooled to room temperature, and concentrated in vacuo. The residue was dissolved in EtOAc, cooled to 5° C. and treated with DBU (5.5 mL, 37.2 mmol). Bromine was added dropwise until a brown endpoint was reached. The resulting precipitate was removed by filtration through a bed of silica gel. The filtrate was extracted with 1 N aqueous Na$_2$S$_2$O$_4$ (2×), brine (2×), dried (MgSO$_4$), filtered through filter agent and concentrated in vacuo. The residue was purified by chromatography on silica gel eluting with 0-20% EtOAc in hexane to give 5b (0.77 g, 32%) as a clear oil.

Step C. spiro[piperidine-4,3'-(2H)-benzo[b]thiophene]

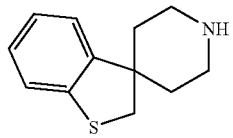

5c

A solution of 5b (0.076 g, 0.249 mmol) was dissolved in a 4:1 mixture of DCM/TFA and stirred for 1 h at room temperature under an argon atmosphere. The reaction mixture was concentrated in vacuo and the residue was partitioned between 1.0 N aq. NaOH and diethylether. The basic aqueous layer was extracted 2 more times with diethylether and the combined diethylether extracts were washed twice with brine, dried overy anhydrous K$_2$CO$_3$, and filtered. The filtrate was concentrated in vacuo to afford 5c as a clear waxy solid (37 mg, 72%).

Step D. 1-(3,4-dichlorophenyl)carbonyl-spiro[piperidine-4,3'-(2H)-benzo[b]thiophene]

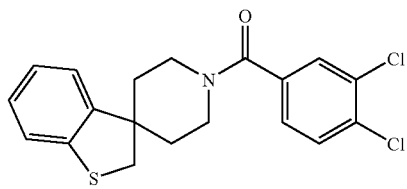

5d

A solution of 5c (0.200 g, 0.974 mmol), 3,4-dichlorobenzoic acid (0.205 g, 1.07 mmol) and DIPEA (0.51 mL, 2.92 mmol) in dry dichloromethane (6 mL) was treated with BOP-Cl (0.298 g, 1.17 mmol) and stirred at room temperature for 1 h under an argon atmosphere. The reaction mixture was concentrated in vacuo and the residue was partitioned between EtOAc and 10% aq. citric acid. The EtOAc layer was extracted twice with 10% aq. citric acid, saturated aq. NaHCO$_3$, and brine, then dried over anhydrous MgSO$_4$ and filtered. The filtrate was concentrated in vacuo and the residue was purified by chromatography on silica gel eluting with hexane/EtOAc (4:1) to furnish 5d (0.200 g, 54%) as a white sold.

Step E. 1-(3,4-dichlorophenyl)carbonyl 5'-(1,3-di-oxo-1,3-dihydro-isoindol-2-ylmethyl)-spiro[piperidine-4,3'-(2H)-benzo[b]thiophene]

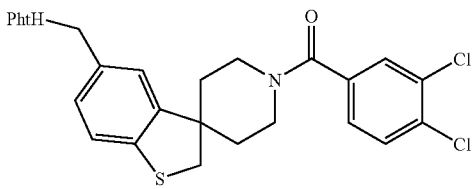

5e

A solution of 5d (0.144 g, 0.382 mmol) in 8 mL of a mixture of glacial acetic acid and concentrated $H_2SO_4$ (9:1) was warmed to 60° C. and treated with (N-hydroxymethyl) phthalimide (0.068 g, 0.382 mmol) while stirring under an argon atmosphere. After 16 h, the reaction mixture was poured onto ice and extracted three times with EtOAc. The combined EtOAc layers were extracted twice with saturated aq. $NaHCO_3$ and brine, dried over anhydrous $MgSO_4$ and filtered. The filtrate was purified by chromatography on silica gel eluting with hexane/EtOAc (1:1) to give 5e (0.041 g, 20%) as white solid.

Step F. 1-(3,4-dichlorophenyl)carbonyl-5'-aminom-ethyl-spiro[piperidine-4,3'-(2H)-benzo[b]thiophene] (Cpd 353)

A solution of 5e (0.014 g, 0.026 mmol) in 5.5 mL of a mixture of absolute ethanol and methylhydrazine (10:1) was heated at 40° C. for 6 h under nitrogen. The reaction mixture was concentrated in vacuo and the residue was purified by reverse-phase HPLC eluting on a C18 column with a gradient of 20-80% acetonitrile in water containing 0.1% TFA to give the TFA salt of Compound 353 (0.012 g, 81%) as a white solid: $^1H$ NMR ($CD_3OD$) δ 7.75-7.60 (m, 2H), 7.45-7.30 (m, 1H), 7.35-7.20 (m, 3H), 4.80-4.50 (br m, 1H), 4.07 (s, 2H), 3.80-3.60 (m, 1H), 3.52 (s, 1H), 3.51-3.10 (ov m, 2H), 2.10-175 (br m, 4H); MS (ES) m/z 407.1 $(MH)^+$ for $C_{20}H_{20}Cl_2N_2OS$.

Example 6

1-(5-phenylethynyl-furan-2-yl)carbonyl-5'-aminom-ethyl-spiro[piperidine-4,3'-(2H)-indole] (Cpd 319)

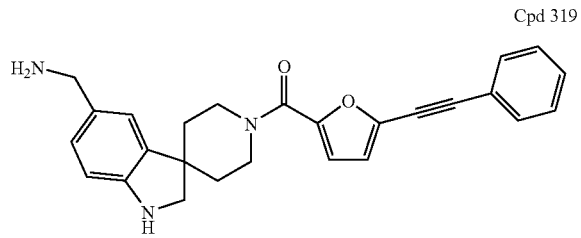

Cpd 319

Step A. 1-methyl-1'-formyl-spiro[piperidine-4,3'-(2H)-indole]

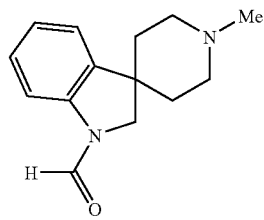

6a

A solution of 1,2-dihydro-1'-methyl-spiro[3H-indole-3,4'-piperidine] (29.8 g, 0.148 mol; CAS# 69584-91-4; *J. Med. Chem.* 1983, 26, 981-986) in toluene (737 mL) was treated with formic acid (27.8 mL, 0.737 mol). The reaction vessel was fitted with a Dean-Stark trap and the reaction mixture, which appears as two layers, was heated at reflux under nitrogen with azeotropic removal of water for 16 h. The reaction mixture was coole to room temperature and concentrated invacuo. The residue was partitioned between chloroform (500 mL) and 3N aq. NaOH (300 mL). The organic layer was extracted three more times with N aq. NaOH (300 mL), dried over anhydrous $K_2CO_3$, and filtered. The filtrate was concentrated in vacuo to furnish 6a (33.5 g, 99%) as a beige solid.

Step B. 5'-(1,3-dioxo-1,3-dihydro-isoindol-2-ylm-ethyl)-1'-formyl-1-methyl-spiro[piperidine-4,3'-(2H)-indole]

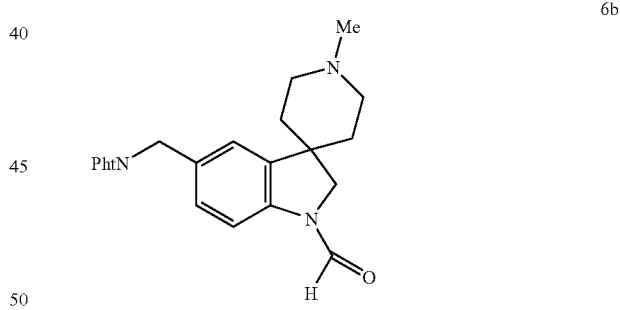

6b

Compound 6a (32.1 g, 0.139 mol) was dissolved in concentrated $H_2SO_4$ (140 mL) at 5° C. while stirring under a nitrogen atmosphere. The resulting brown solution was treated with N-(hydroxymethyl)phthalimide (24.7 g, 0.139 mol) and the mixture was slowly warmed to room temperature over 18 h. The reaction mixture was slowly poured onto ice (500 g) and the resulting precipitate was isolated by filtration; 200 mL of water was used to assist the transfer. The filter cake was added to a beaker and suspended in 1 liter of water and 800 mL of chloroform. The mixture was stirred while the pH was cautiously adjusted to pH 10 by the addition of solid $Na_2CO_3$ and then transferred to a separatory funnel. The layers were separated and the basic aqueous layer was extracted twice with chloroform. The combined chloroform extracts were washed twice with brine, dried over anhydrous K₂CO₃ and filtered. The filtrate was concentrated in vacuo to give 6b (50.5 g, 93%) as a yellow foam.

Step C. 5'-(1,3-dioxo-1,3-dihydro-isoindol-2-ylmethyl)-spiro[piperidine-4,3'-(2H)-indole]

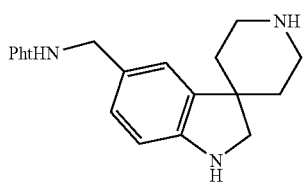

Compound 6b (25.0 g, 0.0642 mol) was combined with 1,8-bis-(dimethylamino)naphthalene (27.5 g, 0.128 mol; CAS# 20734-58-1) and dissolved in dichloroethane (320 mL) while stirring under an argon atmosphere. 1-Chloroethyl chloroformate (27.7 mL, 0.257 mol; CAS# 50893-53-3) was added and the resulting black solution was heated at reflux for 2 h. The reaction mixture was cooled to room temperature and esxtracted with 3 times with 10% aq. citric acid, 3 times with saturated aq. NaHCO₃, dried over anhydrous MgSO₄, and filtered. The filtrate was concentrated in vacuo to yield a reddish-brown foam.

This foam was dissolved in dry methanol (300 mL), treated with 33 mL of 5.5 M HCl in isopropanol and heated at reflux while stirring under a nitrogen atmosphere. After 1 h, the reaction mixture was concentrated in vacuo. The resulting solid recrystallized from methanol to give the dihydrochloride salt of 6c as a brown solid. The material was slowly partitioned between chloroform (200 mL) and 10% aq. Na₂CO₃ (150 mL). The basic aqueous layer was extracted twice with chloroform and the combined organic layers were extracted twice with 10% aq. Na₂CO₃, dried over anhydrous K₂CO₃, and filtered. The filtrate was concentrated in vacuo to afford 6c (15.0 g, 68%) s a brown solid.

Step D. 5-phenylethynyl-furan-2-carboxylic acid 2,5-dioxo-pyrrolidin-1-yl Ester

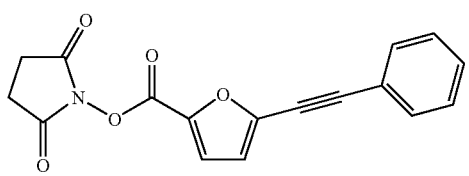

A solution of 5-(phenylethynyl)-2-furoic acid (10.1 g, 0.048 mmol; CAS# 130423-83-5) and pyridine (26.9 mL, 0.333 mol) in acetonitrile (475 mL) was treated with N,N'-disuccinimidyl carbonate (36.5 g, 0.142 mol; CAS# 74124-79-1) while stirring at room temperature under a nitrogen atmosphere and the resulting slurry was stirred for 18 h. The reaction mixture was concentrated in vacuo and the residue was partitioned between water and DCM. The aqueous layer was extracted twice with DCM and the combined organic layers were extracted twice with 10% aq. citric acid, twice with saturated aq. NaHCO₃, dried over MgSO₄ and filtered. The filtrate was concentrated in vacuo and the residue was purified by chromatography on silica gel eluting with DCM to give 6d (13.5 g, 92%) as a white solid.

Step E. 5'-(1,3-dioxo-1,3-dihydro-isoindol-2-ylmethyl)-1-(5-phenylethynyl-furan-2-yl)carbonyl-spiro[piperidine-4,3'-(2H)-indole]

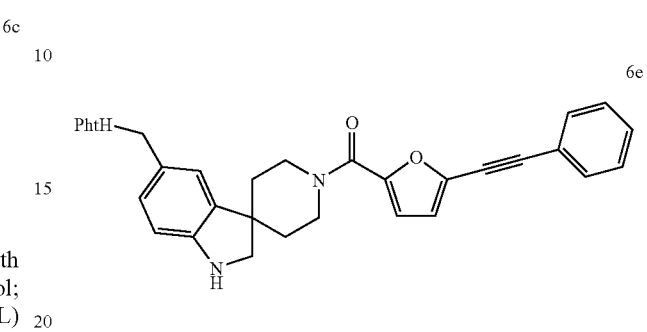

Compound 6c (6.74 g, 0.0194 mol) was dissolved in THF (194 mL; warming required) and treated at room temperature with 6d (8.10 g, 0.0262 mol). After 6 h, the reaction mixture was concentrated in vacuo and the residue was portioned between EtOAc and water. The organic layer was extracted twice with water, twice with brine, dried over anhydrous Na₂SO₄ and filtered. The filtrate was concentrated in vacuo and the residue was purified by chromatography on silica gel eluting with heptane/EtOAc (7:3) to give 6e (8.11; 77%) as a yellow foam.

Step F. 1-(5-phenylethynyl-furan-2-yl)carbonyl-5'-aminomethyl-spiro[piperidine-4,3'-(2H)-indole] (Cpd 319)

A solution of 6e (0.115 g, 0.212 mmol) and methylhydrazine (0.6 mL) in anhydrous ethanol (6 mL) was heated at 40° C. for 3 h while stirring under argon. The reaction mixture was concentrated in vacuo and purified by reverse-phase HPLC eluting on a C18 column with a gradient of 10-90% acetonitrile in water containing 0.1% TFA to furnish Compound 319 (15 mg, 11%) as a tan solid: MS (ES) m/z 412.2 (MH)⁺ for $C_{26}H_{25}N_3O_2$.

Example 7

1-(5-phenylethynyl-furan-2-yl)carbonyl-1'-hydroxysulfonyl-5'-aminomethyl-spiro[piperidine-4,3'-(2H)-indole] (Cpd 327)

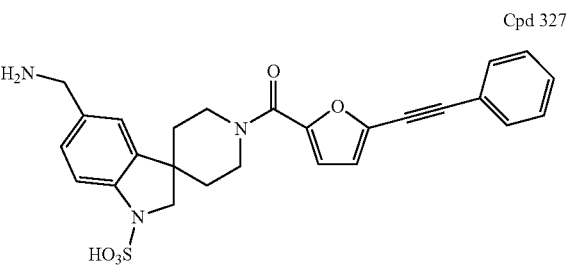

Step A. 5'-(1,3-dioxo-1,3-dihydro-isoindol-2-ylm-ethyl)-1-(5-phenylethynyl-furan-2-yl)carbonyl-1'-hydroxysulfonyl-spiro[piperidine-4,3'-(2H)-indole] (Cpd 327)

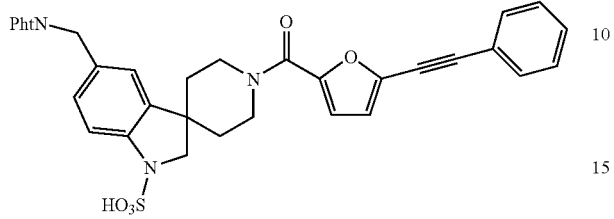

A solution of 6e (16.9 g, 0.031 mol) and triethylamine (26.1 mL, 0.187 mol) in THF (312 mL) was cooled to 0° C. and treated dropwise over 30 minutes with chlorosulfonic acid (3.11 mL, 0.047 mol). After 2 h at 0° C., the reaction was quenched by the addition of methanol (100 mL) and concentrated in vacuo to give crude 7a as a brown oil.

Step B. 1-(5-phenylethynyl-furan-2-yl)carbonyl-1'-hydroxysulfonyl-5'-aminomethyl-spiro[piperidine-4,3'-(2H)-indole] (Cpd 327)

A solution of crude 7a (0.031 mol) and methylhydrazine in anhydrous ethanol (310 mL) was heated at 40° C. for 6 h while stirring under a nitrogen atmosphere. The reaction mixture was concentrated in vacuo and the residue was triturated with several portions of diethyl ether to give a yellow solid. This material was purified by reverse-phase HPLC eluting on a C18 column with a gradient of 20-50% acetonitrile in water containing 0.1% TFA. The fractions containing the desired product were immediately basified to pH 9 with concentrated NH$_4$OH and placed on a lyophilzer. The resulting solid was triturated 4 times with hot EtOAc (250 mL) and then slurried in 1 L of methanol. Anhydrous NH$_3$ gas was bubbled into the slurry over 45 minutes until a solution was achieved. The solution was filtered through a Nylon-66 (0.45µ) filter. The filtrate was boiled down to 250 mL and cooled to room temperature. The resulting solid was washed with methanol and diethyl ether and then dried overnight in vacuo at 60° C. to furnish Compound 319 (10.9 g, 65%) as a beige solid: MS (ES) m/z 492.1 (MH)$^+$ for C$_{26}$H$_{25}$N$_3$O$_5$S.

Example 8

1-(3,4-dichlorophenyl)carbonyl-2'-oxo-5'-aminomethyl-spiro[piperidine-4,3'-(2H)-indole] (Cpd 315)

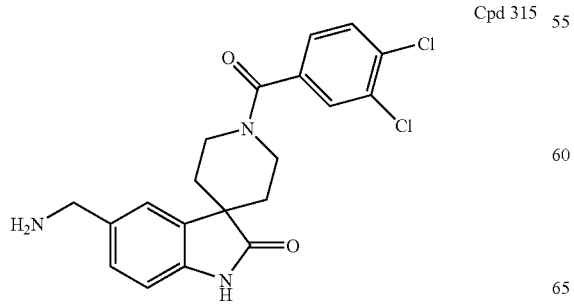

Step A. 4-(2-bromo-4-cyano-phenylcarbamoyl)-piperidine-1-carboxylic Acid Tert-Butyl Ester

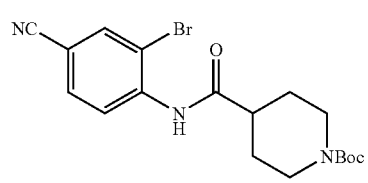

Thionyl chloride (0.028 mol, 2.0 mL) was added to a solution of 1-(tert-butoxycarbonyl)piperidine-4-carboxylic acid (0.024 mol, 5.6 g; CAS# 84358-13-4), pyridine (0.060 mol, 4.9 mL), in DCM (32 mL) at 0° C. under an atmosphere of argon. After 5 min., a solution of 4-amino-3-bromo-benzonitrile (0.027 mol, 5.3 g; CAS# 50397-74-5), DMAP (0.037 mol, 4.5 g) in DCM (44 mL) was added to the reaction mixture and allowed to slowly warm to room temperature over 16 hrs. Triethylamine (0.047 mol, 6.6 mL) was added and the reaction mixture was refluxed for 4 hours, stirred at room temperature for 16 hrs, and concentrated in vacuo. The residue was dissolved in Et$_2$O and extracted with water (2×), 1N aq. HCl (2×), saturated aq. NaHCO$_3$, brine, dried over Na$_2$SO$_4$, filtered and concentrated in vacuo. The resulting material was purified on a silica gel column eluting with heptane/EtOAc (3:2) to afford 8a as a white solid (3.2 g, 32%).

Step B. 4-[(2-bromo-4-cyano-phenyl)-(4-methoxy-benzyl)-carbamoyl]-piperidine-1-carboxylic Acid Tert-Butyl Ester

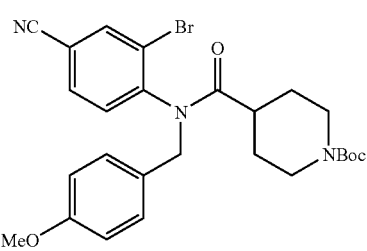

A slurry of 8a (7.7 mmol, 3.2 g), 1-chloromethyl-4-methoxy-benzene (14 mmol, 2.19 g, 1.9 mL) and 40 wt. % potassium fluoride on alumina (30 mmol, 4.4 g) in acetonitrile (32 mL) was refluxed 6 hrs, then cooled and stirred at room temperature for 48 hrs. The reaction material was filtered through filter agent and the filtrate was concentrated in vacuo. The resulting residue was purified by chromatography on a silica gel column eluting with heptane/EtOAc (3:2) to give 8b as a colorless wax (3.4 g, 83%).

Step C. 1-(tert-butyloxy)carbonyl-5'-cyano-2'-oxo-1'-(4-methoxybenzyl)-spiro[piperidine-4,3'-(2H)-indole]

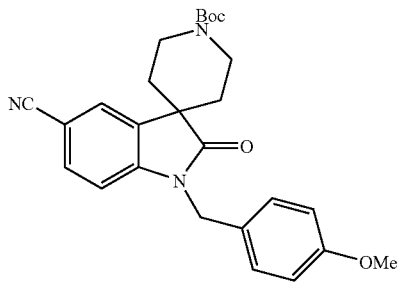

8c

To a solution of 8b (6.4 mmol, 3.4 g), tris(dibenzylideneacetone)dipalladium (0.64 mmol, 590 mg), racemic-2,2'-bis(diphenylphosphino)-1,1'-binaphthyl (0.94 mmol, 590 mg) in dioxane (200 mL) was added sodium tert-butoxide (9.6 mmol, 930 mg). After heating at 110° C. under argon for 16 hrs, the reaction mixture was cooled to room temperature filtered through filter agent. The filter pad was washed with DCM and the combined filtrate concentrated in vacuo. The resulting residue was taken up in DCM and extracted with 10 wt. % aq. citric acid (2×), water, saturated aq. NaHCO$_3$, brine, dried over Na$_2$SO$_4$, and concentrated in vacuo. The resulting residue was purified on a silica gel column eluted with 7:3 heptane/EtOAc to give 8c as a solid (1.0 g, 35%).

Step D. 1-(tert-butyloxy)carbonyl-5'-cyano-2'-oxo-spiro[piperidine-4,3'-(2H)-indole]

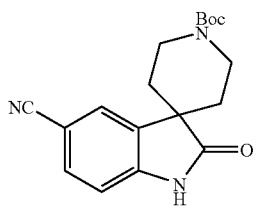

8d

To a solution of 8c (2.2 mmol, 1.0 g), in acetonitrile (28 mL) and water (8 mL) was added ammonium cerium(IV) nitrate (8.9 mmol, 4.9 g). After stirring at room temperature for 2 hrs, the reaction mixture was diluted with DCM, extracted with water (2×), saturated aq. NaHCO$_3$ (2×), brine, dried over Na$_2$SO$_4$, and concentrated in vacuo. The resulting residue was purified on a silica gel column eluted with 3:2 EtOAc/heptane to give 8d as a white solid (113 mg, 15%).

Step E. 5'-cyano-1-(3,4-dichlorophenyl)carbonyl-2'-oxo-spiro[piperidine-4,3'-(2H)-indole]

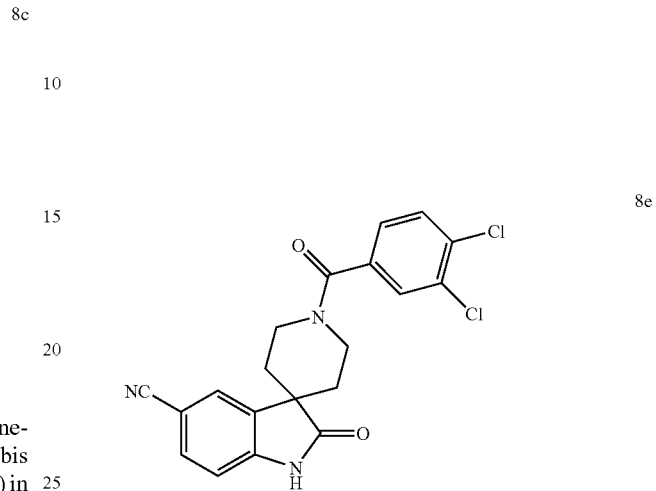

8e

To a slurry of 8d (0.39 mmol, 130 mg) in isopropyl alcohol (10 mL) was added 5N HCl in isopropyl alcohol (0.78 mmol, 160 µL). After 16 hrs at 50° C., the reaction mixture was concentrated in vacuo. To this residue was added 3,4-dichlorobenzoic acid (0.78 mmol, 150 mg), EDC.HCl (0.78 mmol, 150 mg) and DMF (5 mL). The resulting solution was stirred at room temperature under argon 16 hrs then quenched with water and diluted with DCM. The organic layer was separated, extracted with water, 1N aq. HCl, saturated aq. NaHCO$_3$ (2×), ammonium cerium(IV) nitrate (8.9 mmol, 4.9 g). After stirring at room temperature for 2 hrs, the reaction mixture was diluted with DCM, extracted with water (2×), saturated aq. NaHCO$_3$ (2×), dried over Na$_2$SO$_4$, and concentrated in vacuo. The resulting residue was purified on a silica gel column eluted with 1:1 EtOAc/heptane to give 8e as a solid (74 mg, 47%).

Step F. 1-(3,4-dichlorophenyl)carbonyl-2'-oxo-5'-aminomethyl-spiro[piperidine-4,3'-(2H)-indole] (Cpd 315)

A slurry of 8e (0.18 mmol, 74 mg), Raney Nickel® (14 mg) in ethyl alcohol (2.5 mL) and 3N aq. NaOH (0.87 mL) was shaken under 50 psi H$_2$ at room temperature for 16 hrs. The reaction mixture was filtered through a nylon filter and concentrated under a stream of nitrogen. The residue was purified on a C18 reverse-phase column eluted with acetonitrile/water/trifluoroacetic acid to and freeze-dried give the trifluoroacetate salt of Compound 315 as a white powder (33 mg, 32%): $^1$H NMR (CD$_3$OD) δ 7.69 (d, J=1.9 Hz, 1H), 7.66 (d, J=8.2 Hz, 1H), 7.52 (d, J=1.4 Hz, 1H), 7.43 (dd, J=1.9 Hz, J=8.2 Hz, 1H), 7.34 (dd, J=1.6 Hz, J=8.0 Hz, 1H), 6.98 (d, J=8.0 Hz, 1H), 4.32-3.9 (m, 5H), 3.70 (bm, 1H), 1.95-1.85 (m, 4H); MS (ES) m/z 403.8/405.7 (MH)+.

Example 9

1-(5-phenylethynyl-furan-2-yl)carbonyl-1'-oxo-5'-aminomethyl-spiro[piperidine-4,3'-1H-isoindole]
(Cpd 317)

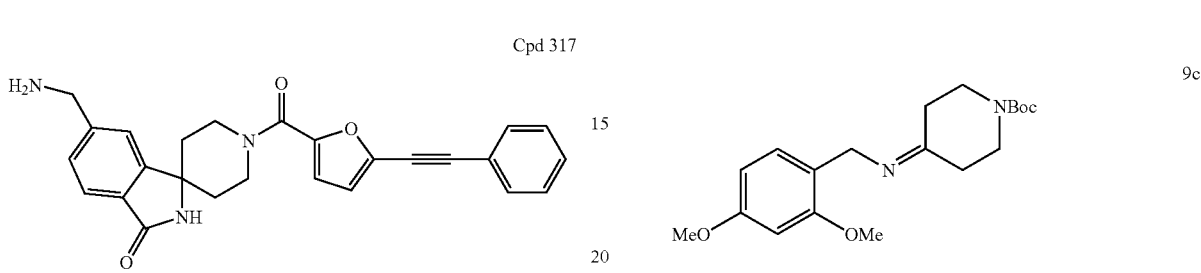

Step A. 2-bromo-4-(1,3-dioxo-1,3-dihydro-isoindol-2-ylmethyl)-benzoic Acid Methyl Ester

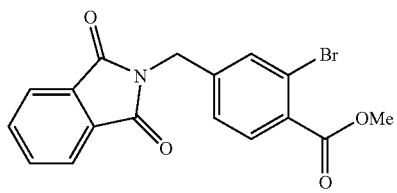

A solution of methyl 2-bromo-4-(bromomethyl)benzoate (2.00 g, 6.49 mmol; CAS# 128577-48-0) in DMF (65 mL) was treated with potassium phthalimide (1.32 g, 7.14 mmol) and stirred at room temperature under a nitrogen atmosphere. After 18 h, the reaction mixture was concentrated in vacuo and partitioned between EtOAc and water. The aqueous layer was extracted twice with EtOAc and the combined organic layers were washed twice with brine, dried over anhydrous MgSO$_4$ and filtered. The filtrate was concentrated in vacuo to give 9a (2.38 g, 98%) as a beige solid.

Step B. 2-bromo-4-(1,3-dioxo-1,3-dihydro-isoindol-2-ylmethyl)-benzoic Acid

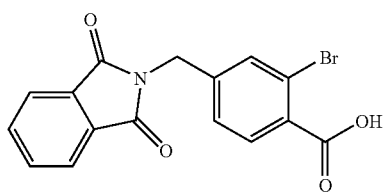

Compound 9a (1.86 g, 4.97 mmol) was combined with lithium iodide (6.65 g, 49.7 mmol) in 50 mL of dry pyridine and heated at reflux while stirring under a nitrogen atmosphere. After 2.5 days, the reaction mixture was concentrated in vacuo and the residue was suspended in water. The pH was adjusted to pH 2 with 1N HCl and the resulting slurry was extracted 3 times with EtOAc. The combined EtOAc extracts were washed twice with brine, dried over anhydrous MgSO$_4$ and filtered. The filtrate was concentrated in vacuo to afford 9b (1.45 g, 81%) as beige solid.

Step C. 4-(2,4-dimethoxy-benzylimino)-piperidine-1-carboxylic Acid Tert-Butyl Ester

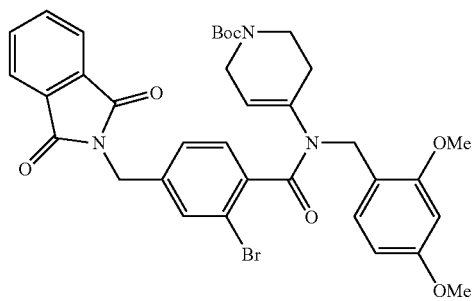

A solution of 1-Boc-4-piperidone (1.05 g, 5.29 mmol; CAS# 79099-07-3) and 2,4-dimethoxybenzylamine (0.885 g, 5.29 mmol) in 50 mL of toluene were heated at reflux under a nitrogen atmosphere with azeotropic removal of water with a Dean-Stark trap. After 16 h, the reaction mixture was cooled to room temperature and concentrated in vacuo to afford 9c (1.84 g, 100%) as a light yellow oil.

Step D. 4-[[2-bromo-4-(1,3-dioxo-1,3-dihydro-isoindol-2-ylmethyl)-benzoyl]-(2,4-dimethoxy-benzyl)-amino]-3,6-dihydro-2H-pyridine-1-carboxylic Acid Tert-Butyl Ester Compound 9b (1.35 g, 3.75 mmol) was added to thionyl chloride (38 mL) and the resulting slurry was heated at reflux for 2 h while stirring under a nitrogen atmosphere. The reaction mixture was concentrated in vacuo and the residue was triturated with heptane to furnish the corresponding acid chloride as a white solid.

The acid chloride was treated with triethylamine (2.6 mL, 18.8 mmol) and combined with 9c (1.71 g, 4.91 mmol) in 38 mL of dry toluene. The reaction mixture was heated at 80° C. over 18.5 h while stirring under a nitrogen atmosphere. After cooling to room temperature, the reaction mixture was partitioned between water and EtOAc. The aqueous layer was extracted twice with EtOAc and the combined organic extracts were washed twice with brine, dried over anhydrous MgSO$_4$ and filtered. The filtrate was concentrated in vacuo and the residue was purified by chromatography on silica gel eluting with 30-70% EtOAc in heptane to give 9d (2.11 g, 82%) as a white foam.

Step E

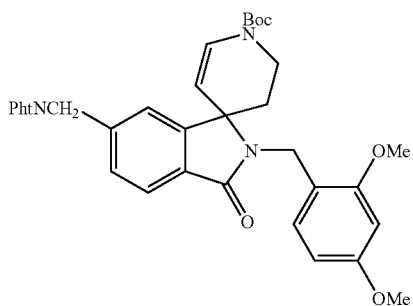

9e

Compound 9d (1.50 g, 2.17 mmol, triicyclopentylphosphine (1.46 g, 5.21 mmol; CAS# 7650-88-6), and dicyclohexylamine (6.90 mL, 32.5 mmol) and palladium(II) acetate (585 mg, 2.61 mmol) were dissolved in N,N-dimethylacetamide (22 mL) and heated at 100° C. in a sealed tube for 7 days. The reaction mixture was cooled to room temperature, diluted with methanol (22 mL) and filtered through filter agent. The filtrate was concentrated in vacuo and partitioned between EtOAc and 10% aq. citric acid. The organic layer was extracted twice with 10% aq. citric acid, twice with brine, dried over anhydrous MgSO₄ and filtered. The filtrate was concentrated in vacuo and the residue was purified by chromatography on silica gel eluting with 60-80% EtOAc in hexane to give 9e (0.65 g, 49%) was a white foam.

Step G. 5'-(1,3-dioxo-1,3-dihydro-isoindol-2-ylmethyl)-1'-oxo-spiro[piperidine-4,3'-1H-isoindole]

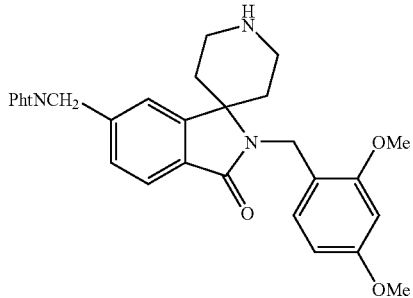

9g

A solution of 9f (0.64 g, 1.05 mmol) in 20 mL of a 4:1 mixture of DCM and TFA was stirred at room temperature for 45 minutes. The reaction mixture was concentrated in vacuo and the residue was triturated 3 times with diethyl ether to provide a white solid. This material was dissolved in anhydrous ethanol (20 mL) and combined with 10% palladium on carbon (0.51 g) and placed on Parr hydrogenator under 50 psig of hydrogen. After 36 h, the reaction mixture was filtered first through filter agent and then through a Nylon-66 (0.45µ) filter. The filtrate was concentrated in vacuo and the residue was partitioned between EtOAc and 10% aq. Na₂CO₃. The organic layer was extracted twice with 10% aq. Na₂CO₃, twice with brine, dried over anhydrous K₂CO₃ and filtered. The filtrate was concentrated in vacuo to give 9g as a white foam.

Step H. 5'-(1,3-dioxo-1,3-dihydro-isoindol-2-ylmethyl)-1-(5-Phenylethynyl-furan-2-yl)carbonyl-1'-oxo-spiro[piperidine-4,3'-1H-isoindole]

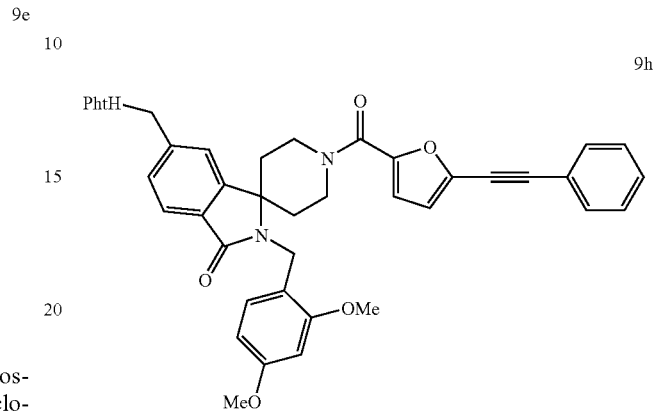

9h

A solution of 9g (0.200 g, 0.391 mmol), 5-(2-phenyleth-1-ynyl-2-furoic acid, 0.091 g, 0.430 mmol) and DIPEA (0.204 mL, 1.17 mmol) in dry DCM (5 mL) was treated with BOP-Cl (0.119 g, 0.469 mmol) while stirring at room temperature under a nitrogen atmosphere. After 1.5 h, the reaction mixture was extraxcted 3 times with 10% aq. citric acid, 3 times with saturated aq. NaHCO₃, 3 times with brine, dried over anhydrous MgSO₄ and filtered. The filtrate was concentrated in vacuo to afford 9h (0.282 g, 100%) as a white solid.

Step I. 5'-(1,3-dioxo-1,3-dihydro-isoindol-2-ylmethyl)-1-(5-Phenylethynyl-furan-2-yl)carbonyl-1'-oxo-spiro[piperidine-4,3'-1H-isoindole]

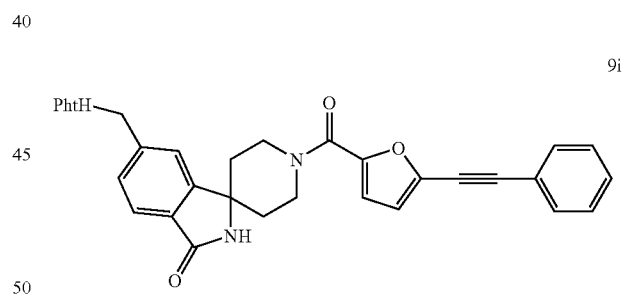

9i

Compound 9h (0.268 g, 0.380 mmol) was slurried in TFA (10 mL) and stirred at room temperature under a nitrogen atmosphere for 22 h. The reaction mixture was concentrated in vacuo. The residue was partitioned between saturated aq. NaHCO₃ and DCM. The organic layer was extracted twice with saturated aq. NaHCO₃, twice with brine, dried over anhydrous MgSO₄ and filtered. The filtrate was concentrated in vacuo to furnish 9i (0.094 g, 45%) as a tan solid.

Step I. 1-(5-phenylethynyl-furan-2-yl)carbonyl-1'-oxo-5'-aminomethyl-spiro[piperidine-4,3'-1H-isoindole] (Cpd 317)

Compound 9i (47 mg, 0.0856 mmol) was dissolved in 10:1 mixture of ethanol and methylhydrazine at heated at 40° C. for 3 h. The reaction mixture was concentrated in vacuo and purified by reverse-phase HPLC eluting on a C18 column with a gradient of 20-80% acetonitrile in water containing 0.1% TFA to furnish Compound 317(34 mg, 71%) as a tan solid: MS (ES) m/z 426.3 (MH)$^+$ for $C_{26}H_{23}N_3O_3$.

Biological Examples

β-Tryptase In-Vitro Enzyme Assay

The β-tryptase assay was conducted with human lung tryptase (Cortex Biochem #CP3033) in an aqueous buffer (10 mM Tris, 10 mM Hepes, 150 mM NaCl, 0.1% PEG 8000, pH 7.4) using the chromogenic substrate H-D-HHT-Ala-Arg-pNa. 2AcOH (American Diagnostica #238)/Km 580 μM) and a microplate reader (Molecular Devices). IC$_{50}$ experiments were conducted by fixing the enzyme and substrate concentrations (1 nM [E]/500 μM [S]) and varying the inhibitor concentration. Changes in absorbance at 405 nm were monitored using the software program Softmax Pro (Molecular Devices), upon addition of enzyme without inhibition at room temperature for 15 min. Percent inhibition was calculated by comparing the initial reaction velocity of samples without inhibitor to those with inhibitor. The initial reaction velocities were analyzed using Microsoft Excel.

TABLE 1

| Tryptase IC$_{50}$, (μM) <0.01 μM; <0.05 μM; <1.0 μM; <5.0 μM | |
|---|---|
| Cpd | IC$_{50}$ |
| 1 | 0.031 |
| 2 | 1.4 |
| 3 | 0.0035 |
| 4 | 0.75 |
| 5 | 0.45 |
| 6 | 5.8 |
| 7 | 0.78 |
| 8 | 3.4 |
| 9 | 3.3 |
| 10 | 3.0 |
| 11 | 4.7 |
| 12 | 0.066 |
| 13 | 1.1 |
| 14 | 3.7 |
| 15 | 5.5 |
| 16 | 0.43 |
| 17 | 0.29 |
| 18 | 3.3 |
| 19 | 0.56 |
| 20 | 0.14 |
| 21 | 0.51 |
| 22 | 2.1 |
| 23 | 0.090 |
| 24 | 0.15 |
| 25 | 0.14 |
| 26 | 0.23 |
| 27 | 0.034 |
| 28 | 0.12 |
| 29 | 0.13 |
| 30 | 0.14 |
| 31 | 0.055 |
| 32 | 0.041 |
| 33 | 0.43 |
| 34 | 0.020 |
| 35 | 0.0043 |
| 36 | 0.82 |
| 37 | 0.73 |
| 38 | 0.65 |
| 39 | 3.7 |
| 40 | 0.25 |
| 41 | 0.47 |
| 42 | 0.36 |
| 43 | 0.25 |
| 44 | 0.23 |
| 45 | 0.22 |
| 46 | 0.11 |
| 47 | 0.82 |
| 48 | 0.016 |
| 49 | 0.13 |
| 50 | 0.036 |
| 51 | 0.19 |
| 52 | 0.022 |
| 53 | 0.87 |
| 54 | 0.75 |
| 55 | 1.0 |
| 56 | 0.19 |
| 57 | 0.18 |
| 58 | 0.71 |
| 59 | 0.36 |
| 60 | 2.1 |
| 61 | 7.5 |
| 62 | 0.80 |
| 63 | 0.041 |
| 64 | 0.095 |
| 65 | 0.0045 |
| 66 | 1.9 |
| 67 | 4.8 |
| 68 | 0.19 |
| 69 | 1.6 |
| 70 | 0.15 |
| 71 | 0.91 |
| 72 | 0.52 |
| 73 | 2.5 |
| 74 | 0.16 |
| 75 | 0.47 |
| 76 | 0.42 |
| 77 | 0.10 |
| 78 | 1.4 |
| 79 | 1.4 |
| 80 | 2.7 |
| 81 | 2.3 |
| 82 | 1.3 |
| 83 | 4.3 |
| 84 | 1.4 |
| 85 | 2.7 |
| 86 | 0.62 |
| 87 | 1.7 |
| 88 | 0.026 |
| 89 | 1.4 |
| 90 | 0.98 |
| 91 | 0.48 |
| 92 | 0.49 |
| 93 | 0.35 |
| 94 | 0.24 |
| 95 | 3.2 |
| 96 | 0.45 |
| 97 | 1.5 |
| 98 | 1.7 |
| 99 | 0.58 |
| 100 | 0.68 |
| 101 | 2.4 |
| 102 | 0.60 |
| 103 | 0.96 |
| 104 | 4.5 |
| 105 | 0.77 |
| 106 | 0.61 |
| 107 | 0.082 |
| 108 | 0.25 |
| 109 | 0.21 |
| 110 | 0.037 |
| 111 | 0.19 |
| 112 | 0.18 |
| 113 | 0.13 |
| 114 | 0.24 |
| 115 | 0.24 |
| 116 | 0.29 |
| 117 | 0.60 |
| 118 | 0.11 |
| 119 | 1.4 |
| 120 | 0.13 |

TABLE 1-continued

Tryptase IC$_{50}$, (μM)
<0.01 μM; <0.05 μM; <1.0 μM; <5.0 μM

| Cpd | IC$_{50}$ |
| --- | --- |
| 121 | 0.51 |
| 122 | 0.76 |
| 123 | 0.69 |
| 124 | 1.1 |
| 125 | 7.5 |
| 126 | 0.15 |
| 127 | 3.7 |
| 128 | 0.17 |
| 129 | 0.099 |
| 130 | 0.028 |
| 131 | 0.072 |
| 132 | 0.026 |
| 133 | 0.081 |
| 134 | 0.076 |
| 135 | 0.33 |
| 136 | 0.025 |
| 137 | 0.053 |
| 138 | 0.14 |
| 139 | 0.087 |
| 140 | 0.040 |
| 141 | 0.48 |
| 142 | 0.65 |
| 143 | 0.056 |
| 144 | 0.030 |
| 145 | 0.34 |
| 146 | 0.0052 |
| 147 | 0.066 |
| 148 | 0.33 |
| 149 | 0.11 |
| 150 | 0.18 |
| 151 | 0.18 |
| 152 | 0.0023 |
| 153 | 0.0012 |
| 154 | 0.26 |
| 155 | 0.012 |
| 156 | 0.13 |
| 157 | 0.017 |
| 158 | 4.5 |
| 159 | 0.21 |
| 160 | 0.21 |
| 161 | 0.053 |
| 162 | 0.079 |
| 163 | 0.054 |
| 164 | 0.14 |
| 165 | 0.38 |
| 166 | 0.071 |
| 167 | 0.60 |
| 168 | 0.048 |
| 169 | 1.6 |
| 170 | 0.0083 |
| 171 | 0.17 |
| 172 | 0.0072 |
| 173 | 0.013 |
| 174 | 0.017 |
| 175 | 0.058 |
| 176 | 0.041 |
| 177 | 0.026 |
| 178 | 0.44 |
| 179 | 0.26 |
| 180 | 0.78 |
| 181 | 1.7 |
| 182 | 0.74 |
| 183 | 5.8 |
| 184 | 0.21 |
| 185 | 1.5 |
| 186 | 0.053 |
| 187 | 0.79 |
| 188 | 0.13 |
| 189 | 0.38 |
| 190 | 0.59 |
| 191 | 0.25 |
| 192 | 0.15 |
| 193 | 0.36 |
| 194 | 0.15 |
| 195 | 0.12 |
| 196 | 0.68 |
| 197 | 0.23 |
| 198 | 0.073 |
| 199 | 0.18 |
| 200 | 4.1 |
| 201 | 0.045 |
| 202 | 0.051 |
| 203 | 0.28 |
| 204 | 0.089 |
| 205 | 0.74 |
| 206 | 0.26 |
| 207 | 1.5 |
| 208 | 0.012 |
| 209 | 0.33 |
| 210 | 0.026 |
| 211 | 0.017 |
| 212 | 0.37 |
| 213 | 0.24 |
| 214 | 0.0065 |
| 215 | 0.76 |
| 216 | 1.7 |
| 217 | 0.65 |
| 218 | 0.008 |
| 219 | 0.0029 |
| 220 | 0.69 |
| 221 | 0.55 |
| 222 | 0.26 |
| 223 | 0.021 |
| 224 | 0.28 |
| 225 | 0.047 |
| 226 | 3.2 |
| 227 | 0.044 |
| 228 | 0.037 |
| 229 | 0.0053 |
| 230 | 0.14 |
| 231 | 0.091 |
| 232 | 0.015 |
| 233 | 0.082 |
| 234 | 0.0095 |
| 235 | 0.0092 |
| 236 | 0.75 |
| 237 | 0.27 |
| 238 | 0.21 |
| 239 | 0.27 |
| 240 | 0.0018 |
| 241 | 0.0051 |
| 242 | 0.65 |
| 243 | 3.1 |
| 244 | 2.5 |
| 245 | 0.51 |
| 246 | 0.20 |
| 247 | 0.036 |
| 248 | 0.33 |
| 249 | 0.83 |
| 250 | 0.44 |
| 251 | 1.5 |
| 252 | 1.6 |
| 253 | 2.4 |
| 254 | 0.37 |
| 255 | 0.58 |
| 256 | 0.82 |
| 257 | 0.44 |
| 258 | 0.028 |
| 259 | 0.055 |
| 260 | 1.2 |
| 261 | 0.073 |
| 262 | 4.5 |
| 263 | 5.1 |
| 264 | 3.2 |
| 265 | 0.87 |
| 266 | 0.20 |
| 267 | 0.34 |
| 268 | 2.9 |
| 269 | 1.0 |
| 270 | 6.4 |

TABLE 1-continued

Tryptase IC$_{50}$, (μM)
<0.01 μM; <0.05 μM; <1.0 μM; <5.0 μM

| Cpd | IC$_{50}$ |
|---|---|
| 271 | 2.8 |
| 272 | 0.19 |
| 273 | 1.2 |
| 274 | 6.4 |
| 275 | 0.022 |
| 276 | 0.15 |
| 277 | 0.0060 |
| 278 | 0.012 |
| 279 | 8.0 |
| 280 | 0.22 |
| 281 | 0.024 |
| 282 | 0.70 |
| 283 | 0.91 |
| 284 | 0.0046 |
| 285 | 0.36 |
| 286 | 0.92 |
| 287 | 4.3 |
| 288 | 0.28 |
| 289 | 1.4 |
| 290 | 0.16 |
| 291 | 0.40 |
| 292 | 6.1 |
| 293 | 1.2 |
| 294 | 0.097 |
| 295 | 0.042 |
| 296 | 0.21 |
| 297 | 9.6 |
| 298 | 0.21 |
| 299 | 0.017 |
| 300 | 1.5 |
| 301 | 1.5 |
| 302 | 0.75 |
| 303 | 0.0037 |
| 304 | 0.030 |
| 305 | 6.3 |
| 306 | 0.071 |
| 307 | 0.060 |
| 308 | 7.3 |
| 309 | 0.10 |
| 310 | 0.78 |
| 311 | 0.039 |
| 312 | 0.59 |
| 313 | 0.14 |
| 314 | 1.3 |
| 315 | 0.48 |
| 316 | 0.074 |
| 317 | 0.0073 |
| 318 | 0.0031 |
| 319 | 0.026 |
| 320 | 0.28 |
| 321 | 0.16 |
| 322 | 0.45 |
| 323 | 0.11 |
| 324 | 0.20 |
| 325 | 0.025 |
| 326 | 0.47 |
| 327 | 0.018 |
| 328 | 0.29 |
| 329 | 0.044 |
| 330 | 0.025 |
| 331 | 0.041 |
| 332 | 0.028 |
| 333 | 0.065 |
| 334 | 0.047 |
| 335 | 0.020 |
| 336 | 0.028 |
| 337 | 0.036 |
| 338 | 0.073 |
| 339 | 0.015 |
| 340 | 0.0018 |
| 341 | 0.0057 |
| 342 | 0.0052 |
| 343 | 0.023 |
| 344 | 0.023 |
| 345 | 0.013 |
| 346 | 0.040 |
| 347 | 0.024 |
| 348 | 0.024 |
| 349 | 0.016 |
| 350 | 0.025 |
| 351 | 0.068 |
| 352 | 5.3 |
| 353 | 0.037 |
| 354 | 0.43 |
| 355 | 0.29 |
| 356 | 0.18 |
| 357 | 0.28 |
| 358 | 0.026 |
| 359 | 0.015 |

Sheep Efficacy Model In-Vivo Efficacy Assays

Figure 2:
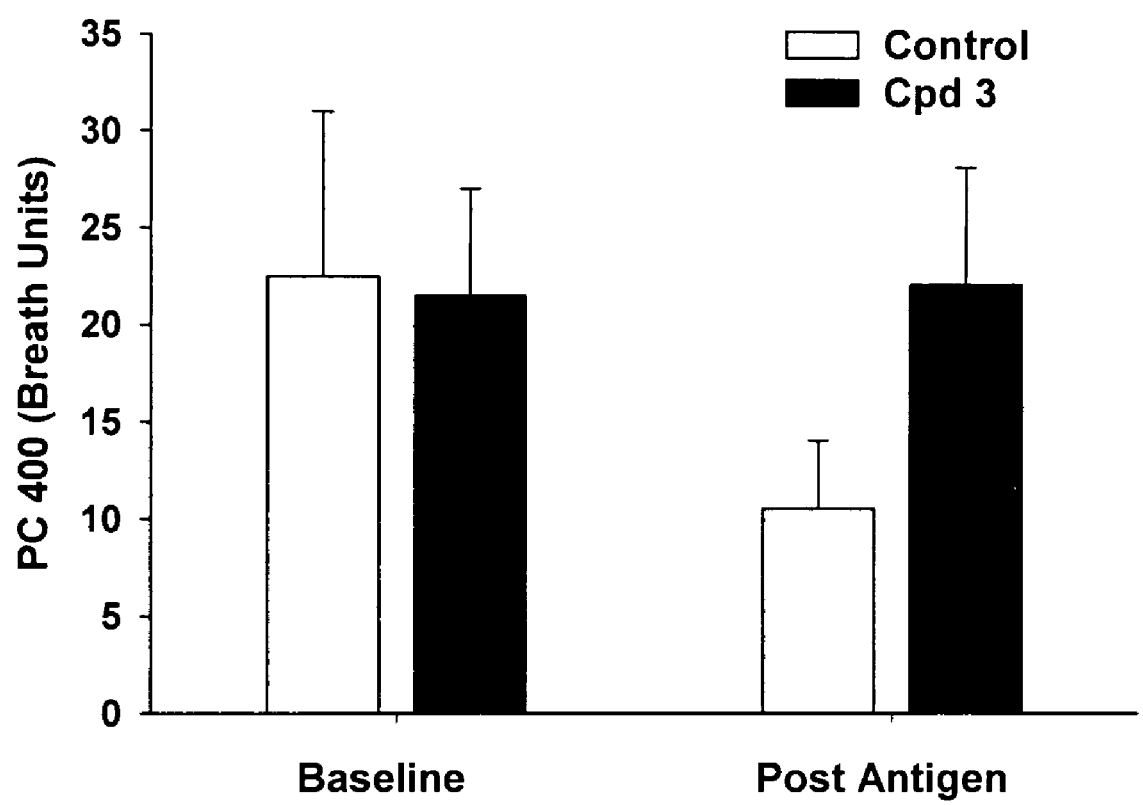
FIG. 2 shows late phase response and airway hyperreactivity to antigen challenge.

The in vivo efficacy of Compound 3 was evaluated in antigen-induced allergic sheep, which is a well-characterized asthma model (Abraham, W. M. *Pulmonary Pharmacol.* 1989, 2, 33-40). Compound 3 was administered via oral gavage to two sheep previously shown to be allergic responders to inhaled *Ascaris suum* antigen (FIG. 1). The compound was given at a dose of 30 mg/kg, BID, on day 1, and again on day 2 at 2 h prior to antigen challenge and then 4 h after antigen challenge. Airway resistance (SR$_L$) was monitored for 8 h post antigen challenge and airway hyper-reactivity to carbachol (PC$_{400}$) was measured 24 h post antigen challenge. The changes in specific airway resistance (SRL) during the early phase (EP) is shown in FIG. 1. The late phase (LP) responses and airway hyperreactivity in response to antigen challenge is shown in FIG. 2. The results demonstrate that Compound 3 completely blocked the late response (LP; 4-8 h post antigen) and the increase in airway hyper-reactivity at 24 h, but did not effect a change in acute early phase response (EP; 0-4 h) post antigen.

Guinea Pig Efficacy Model.

The in vivo efficacy of Compound 3 was evaluated in a guinea pig model of allergic asthma. In this model, guinea pigs were sensitized and challenged with chicken egg ovalbumin (OVA) according to the protocol of N. Smith and F. J. Johnson (*Clin. Exp. Allergy* 2005, 35, 522-530), with some slight modifications. Guinea pigs were sensitized with 80 mg of OVA and 80 mg of aluminum hydroxide administered intraperitoneally on day 0, then challenged with 0.03% OVA aerosol for 10 minutes on day 14. In the experiment measuring early phase pulmonary response (EAR), guinea pigs were challenged for an additional three minutes with 0.06% OVA aerosol. EAR was measured as enhanced pause (PenH) using BUXCO whole body plethysmography for 10 minutes immediately following the OVA aerosol challenge. The animals were then euthanized and assessed for bronchoalveolar lavage (BAL) immune cell counts 24 hours after aerosol challenge on day 15. Either Compound 3 in doses of 3, 10, and/or 30 mg/kg or vehicle were administered subcutaneously, 1-2 hours before and 4-6 hours after OVA aerosol challenge.

Figure 3:
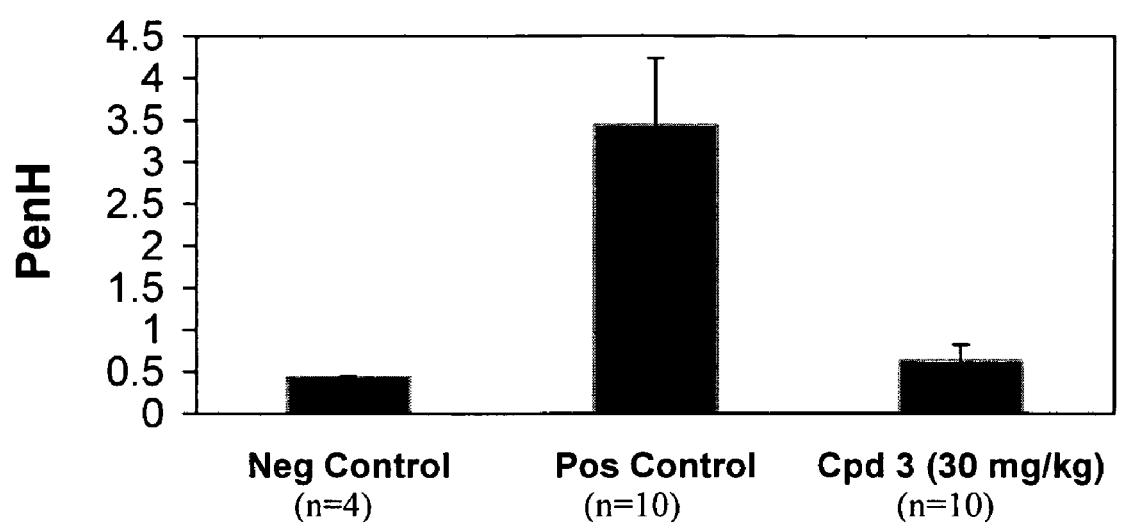
FIG. 3 shows changes in early phase pulmonary responses as measured in PenH with whole body plethysmography following OVA challenge.
Figure 4:
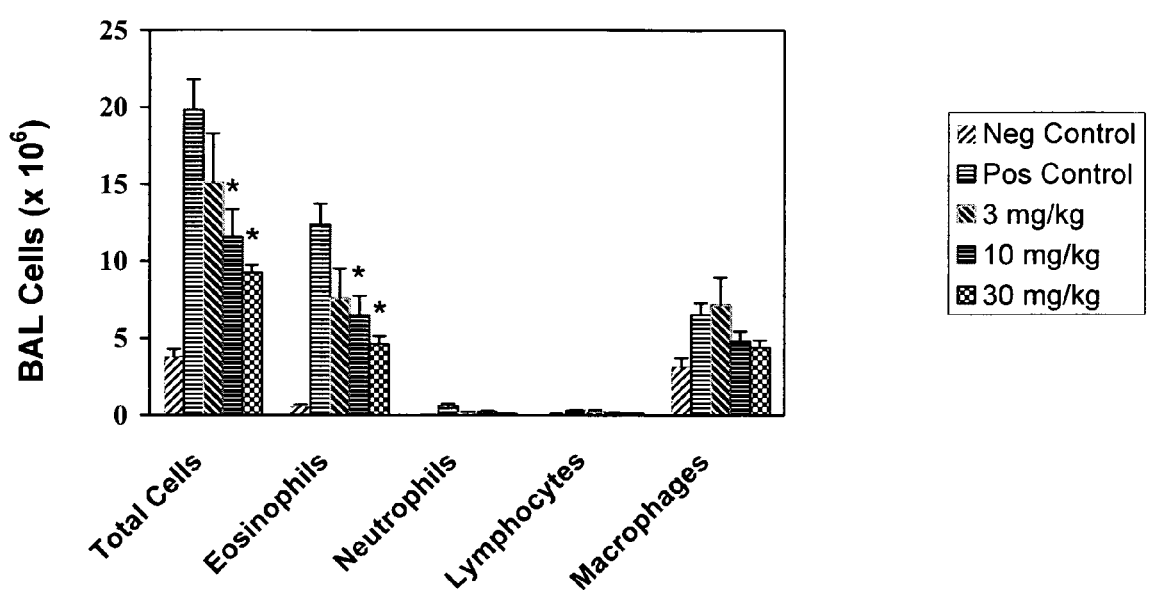
FIG. 4 shows changes in BAL immune cells following OVA challenge at various dose levels.

As shown in FIG. 3, when Compound 3 was administered at 30 mg/kg, it produced a greater than 93% reduction in EAR as measured with whole body plethysmography (in PenH) relative to sensitized and challenged guinea pigs treated with vehicle (positive control group). As shown in FIG. 4, when administered at dose levels of 3, 10 and 30 mg/kg, Compound 3 also produced a dose-dependent reduction in the total and eosinophilic BAL cell counts with the highest dose (30 mg/kg) producing a 66% reduction in BAL eosinophils (EAR and BAL samples per group ranged from 5 to 18; values represent the mean±SEM; *represents p value of ≦0.005).

Throughout this application, various publications are cited. The disclosure of these publications is hereby incorporated by reference into this application to describe more fully the state of the art to which this invention pertains.

While the foregoing specification teaches the principles of the present invention, with examples provided for the purpose of illustration, it will be understood that the practice of the invention encompasses all of the usual variations, adaptations and modifications as come within the scope of the following claims and their equivalents.

What is claimed is:
1. A compound of Formula (I):

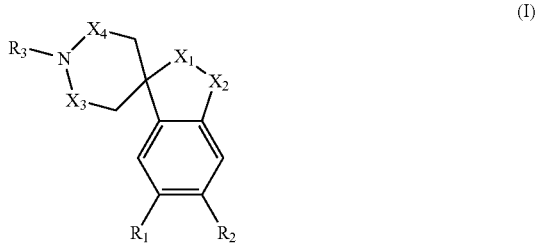

(I)

wherein
X$_1$ and X$_2$, respectively, are —CH$_2$— and —O—;
X$_3$ and X$_4$, respectively, are —CH$_2$— and —CH$_2$—;
R$_1$ is selected from the group consisting of aminoC$_{1-4}$alkyl, (C$_{1-4}$alkyl)aminoC$_{1-4}$alkyl, formylaminoC$_{1-4}$alkyl, phenylcarbonylaminoC$_{1-4}$alkyl, aminoimino, hydroxyaminoimino, (C$_{1-4}$alkyl)aminoimino, (C$_{1-4}$alkyl)$_2$aminoimino and aminoaminoimino,
wherein each instance of phenyl is optionally substituted with one or two halogen substituents;
R$_2$ is absent or is one halogen substituent;
R$_3$ is hydrogen or is selected from the group consisting of R$^5$-phenylC$_{1-4}$alkyl, carbonyl and sulfonyl,
wherein carbonyl and sulfonyl are each substituted with a substituent selected from the group consisting of R$^5$-phenyl, R$^5$-naphthalenyl, R$^5$-phenyl-C$_{1-4}$alkyl, R$^5$-naphthalenyl-C$_{1-4}$alkyl, R$^6$-fluorenyl-C$_{1-4}$alkyl, R$^5$-phenyl-C$_{1-4}$alkylamino, (R$^5$-phenyl)$_{1-2}$ C$_{1-4}$alkyl, R$^5$-phenyl-C$_{2-4}$alkenyl, R$^5$-naphthalenyl-C$_{2-4}$alkenyl, R$^5$-phenylC$_{2-4}$alkynyl, R$^6$-cyclopropyl, R$^6$-indanyl, R$^6$-1H-indenyl, R$^6$-9H-fluorenyl, R$^6$-C$_{3-14}$cycloalkylC$_{1-4}$alkyl, R$^6$-9H-fluorenyl-C$_{1-4}$alkenyl, R$^7$-benzo[1,3]dioxolyl, R$^7$-4,5-dihydro-benzo[c]thiophenyl, R$^7$-4,5,6,7-tetrahydro-benzo[c]thiophenyl, R$^7$-4,5,6,7-tetrahydro-benzo[b]thiophenyl, R$^7$-chromenyl, R$^7$-9H-xanthenyl, R$^7$-9H-thioxanthenyl, R$^7$-5,6-dihydro-4H-cyclopenta[b]thiophenyl, R$^7$-4,5,6,7-tetrahydro-benzofuranyl, R$^7$-5,6,7,8-tetrahydro-4H-cyclohepta[b]thiophenyl, R$^7$-spiro[cyclohexane-1,6'-5,7-dihydro-4H-benzo[b]thiophene], R$^7$-benzo[1,3]dioxolyl-C$_{1-4}$alkyl, R$^7$-benzo[1,3]dioxolyl-C$_{1-4}$alkenyl, R$^7$-3H-isobenzofuranyl-C$_{1-4}$alkenyl, R$^8$-furanyl, R$^8$-thienyl, R$^8$-thiazolyl, R$^8$-[1,2,3]thiadiazolyl, R$^8$-pyridinyl, R$^8$-1H-indolyl, R$^8$-benzo[b]furanyl, R$^8$-benzo[b]thiophenyl, R$^8$-benzo[c]thiophenyl, R$^8$-1H-benzoimidazolyl, R$^8$-benzothiazolyl, R$^8$-thieno[3,2-b]thiophenyl, R$^8$-thieno[2,3-b]thiophenyl, R$^8$-naphtho[2,1-b]thiophenyl, R$^8$-1H-thieno[2,3-c]pyrazolyl, R$^8$-imidazo[1,2-a]pyridinyl, R$^8$-1H-imidazolyl-C$_{2-4}$alkenyl, R$^8$-furanyl-C$_{2-4}$alkenyl, R$^8$-thienyl-C$_{2-4}$alkenyl and R$^8$-pyridinyl-C$_{2-4}$alkenyl, wherein each instance of C$_{2-4}$alkenyl is optionally substituted with one substituent selected from the group consisting of halogen, cyano, C$_{1-4}$alkylcarbonylamino and aryl;
R$^5$ is one optional substituent selected from the group consisting of R$^{5a}$-phenyl, R$^{5a}$-phenylC$_{1-4}$alkyl, R$^{5a}$-phenylC$_{1-4}$alkoxy, R$^{5a}$-phenoxy, R$^{5a}$-phenylcarbonyl, R$^{5a}$-phenylsulfonylamino, R$^{5b}$-1H-benzoimidazolyl-C$_{1-4}$alkyl, R$^{5b}$-1H-benzoimidazolyl-C$_{1-4}$ alkylcarbonylamino, R$^{5b}$-thienyl-C$_{1-4}$alkylcarbonylamino, R$^{5b}$-pyrimidinylthio, R$^{5b}$-benzoxazolyl-(R$^{5b}$)-pyrazolyl, R$^{5b}$-thienyl-(R$^{5b}$)-[1,2,4]oxadiazolyl, R$^{5b}$-benzo[1,3]dioxolyl and cyclohexyl, and
one or two optional substituents each selected from the group consisting of halogen, hydroxy, cyano, nitro, C$_{1-4}$alkyl, C$_{2-4}$alkenyl, haloC$_{1-4}$alkyl, C$_{1-4}$alkoxy, C$_{1-4}$alkoxyC$_{1-4}$alkoxy, haloC$_{1-4}$alkoxy, C$_{1-4}$alkylthio, haloC$_{1-4}$alkylthio, C$_{1-4}$alkylcarbonyl, C$_{1-4}$alkoxycarbonyl, aminothiocarbonylamino, (C$_{1-4}$alkyl)$_2$amino, aminocarbonyl, C$_{1-4}$alkylsulfonyl and aminosulfonyl;
R$^{5a}$ is one or two optional substituents each selected from the group consisting of halogen, C$_{1-4}$alkyl, haloC$_{1-4}$alkyl and C$_{1-4}$alkoxy;
R$^{5b}$ is one or two optional halogen substituents;
R$^6$ is one optional substituent selected from the group consisting of C$_{1-4}$alkyl, oxo and phenyl;
R$^7$ is an optional substituent on one, two or three carbon atoms each selected from the group consisting of halogen, C$_{1-4}$alkyl, C$_{1-4}$alkoxy, C$_{1-4}$alkylthio, arylC$_{1-4}$alkylthio, oxo and phenyl, and
two optional C$_{1-4}$alkyl substituents on one carbon atom, and
two optional oxo substituents on a sulfur atom, when said sulfur atom is present;
R$^8$ is an optional substituent on one carbon atom or an available nitrogen atom selected from the group consisting of R$^{8a}$-phenyl, R$^{8a}$-phenylC$_{1-4}$alkyl, R$^{8a}$-phenylC$_{2-4}$ alkenyl, R$^{8a}$-phenylC$_{2-4}$alkynyl, R$^{8a}$-naphthalenylC$_{2-4}$ alkynyl, R$^{8a}$-phenoxy, R$^{8a}$-phenoxyC$_{1-4}$alkyl, R$^{8a}$-phenylthio, R$^{8a}$-arylC$_{1-4}$alkylthio, R$^{8a}$-phenylC$_{1-4}$alkylthioC$_{1-4}$alkyl, R$^{8a}$-phenylsulfonyl, R$^{8b}$-pyridinyl, R$^{8b}$-pyrazolyl, R$^{8b}$-thienyl, R$^{8b}$-thiazolyl, R$^{8b}$-pyrazolylC$_{1-4}$alkyl, R$^{8b}$-pyrimidinylthioC$_{1-4}$alkyl, R$^{8b}$-furanylcarbonylaminoC$_{1-4}$alkyl and R$^{8c}$-morpholinylC$_{1-4}$ alkyl, and
an optional C$_{1-4}$alkyl substituent on an available nitrogen atom, and
an optional substituent on one, two or three carbon atoms each selected from the group consisting of halogen, cyano, C$_{1-4}$alkyl, haloC$_{1-4}$alkyl, hydroxyC$_{1-4}$alkyl, C$_{1-4}$alkoxy, formyl, C$_{1-4}$alkoxycarbonyl, C$_{1-4}$alkylthio and C$_{1-4}$alkylsulfonyl;
R$^{8a}$ is one or two optional substituents each selected from the group consisting of halogen, C$_{1-4}$alkyl, C$_{2-4}$alkenyl, haloC$_{1-4}$alkyl and C$_{1-4}$alkoxy;
R$^{8b}$ is one, two or three optional substituents each selected from the group consisting of halogen, C$_{1-4}$alkyl and haloC$_{1-4}$alkyl;
R$^9$ is one or two optional substituents each selected from the group consisting of C$_{1-4}$alkoxy, carboxy and C$_{1-4}$alkoxycarbonyl;
R$^{10}$ is an optional (C$_{1-4}$alkyl)aminoamino substituent on one carbon atom, and
two oxo substituents on a sulfur atom, when said sulfur atom is present; and $R^{11}$ is an optional $C_{1-4}$alkyl substituent on an available nitrogen atom, and an optional substituent on one carbon atom selected from the group consisting of carboxy and $C_{1-4}$alkoxycarbonyl.

2. The compound of claim 1 wherein
$R_1$ is selected from the group consisting of amino$C_{1-4}$alkyl and aminoimino,
$R_2$ is absent;
$R^3$ is carbonyl substituted with a substituent selected from the group consisting of $R^5$-aryl, $R^7$-heterocyclyl and $R^8$-heteroaryl;
$R^5$ is heteroaryl-heteroaryl, and
an optional aminocarbonyl substituent;
$R^7$ is an optional substituent on one or two carbon atoms each selected from the group consisting of $C_{1-4}$alkylthio, aryl$C_{1-4}$alkylthio and oxo;
$R^8$ is an optional substituent on one carbon atom selected from the group consisting of $R^{8a}$-aryl, $R^{8a}$-aryl$C_{2-4}$alkynyl and $R^{8a}$-aryl$C_{1-4}$alkylthio, and
an optional substituent on one, two or three carbon atoms each selected from the group consisting of halogen, $C_{1-4}$alkyl, $C_{1-4}$alkoxy and $C_{1-4}$alkylthio;
$R^{8a}$ is one or two optional substituents each selected from the group consisting of halogen and $C_{1-4}$alkyl.

3. The compound of claim 2, wherein
$R_1$ is selected from the group consisting of amino$C_{1-4}$alkyl and aminoimino,
$R_2$ is absent;
$R^3$ is carbonyl substituted with a substituent selected from the group consisting of $R^5$-phenyl, $R^7$-4,5-dihydrobenzo[c]thiophenyl, $R^7$-4,5,6,7-tetrahydro-benzo[c]thiophenyl, $R^8$-furanyl, $R^8$-thienyl, $R^8$-pyridinyl and $R^8$-benzo[c]thiophenyl;
$R^5$ is thienyl-[1,2,4]oxadiazolyl, and
an optional aminocarbonyl substituent;
$R^7$ is an optional substituent on one or two carbon atoms each selected from the group consisting of $C_{1-4}$alkylthio, phenyl$C_{1-4}$alkylthio and oxo;
$R^8$ is an optional substituent on one carbon atom selected from the group consisting of $R^{8a}$-phenyl, $R^{8a}$-phenyl$C_{2-4}$ alkynyl and $R^{8a}$-phenyl$C_{1-4}$alkylthio, and
an optional substituent on one, two or three carbon atoms each selected from the group consisting of halogen, $C_{1-4}$alkyl, $C_{1-4}$alkoxy and $C_{1-4}$alkylthio;
$R^{8a}$ is one or two optional substituents each selected from the group consisting of halogen and $C_{1-4}$alkyl.

4. The compound of claim 3, wherein
$R_1$ is selected from the group consisting of aminomethyl and aminoimino,
$R_2$ is absent;
$R^3$ is carbonyl substituted with a substituent selected from the group consisting of $R^5$-phenyl, $R^7$-4,5-dihydrobenzo[c]thiophenyl, $R^7$-4,5,6,7-tetrahydro-benzo[c]thiophenyl, $R^8$-furanyl, $R^8$-thienyl, $R^8$-pyridinyl and $R^8$-benzo[c]thiophenyl;
$R^5$ is thienyl-[1,2,4]oxadiazolyl, and
an optional aminocarbonyl substituent;
$R^7$ is an optional substituent on one or two carbon atoms each selected from the group consisting of methylthio, butylthio, phenylmethylthio and oxo;
$R^8$ is an optional substituent on one carbon atom selected from the group consisting of $R^{8a}$-phenyl, $R^{8a}$-phenylethynyl and $R^{8a}$-phenylmethylthio, and
an optional substituent on one, two or three carbon atoms each selected from the group consisting of bromo, methyl, methoxy, propoxy and methylthio;

$R^{8a}$ is one or two optional substituents each selected from the group consisting of chloro, fluoro and methyl.

5. The compound of claim 1, wherein
$R_1$ is selected from the group consisting of aminomethyl and aminoimino;
$R_2$ is absent;
$R^3$ is selected from the group consisting of (5-phenylethynyl-furan-2-yl)carbonyl, [5-(2-fluoro-phenylethynyl)-furan-2-yl]carbonyl, [5-(2-chloro-phenylethynyl)-furan-2-yl]carbonyl, [4-phenylethynyl-pyridin-2-yl]carbonyl, [5-(2-methyl-phenylethynyl)-furan-2-yl]carbonyl, [5-(4-methyl-phenylethynyl)-furan-2-yl]carbonyl, [5-(2,5-dimethyl-phenylethynyl)-furan-2-yl]carbonyl, (3-benzylthio-4-oxo-5,6,7-trihydro-4H-benzo[c]thien-1-yl)carbonyl, (3-butylthio-4-oxo-5,6,7-trihydro-4H-benzo[c]thien-1-yl)carbonyl, (3-methylthio-5,6,7-trihydro-4H-benzo[c]thien-1-yl)carbonyl, (3-methylthio-7-hydro-6H-benzo[c]thien-1-yl)carbonyl, (3-methylthio-benzo[c]thien-1-yl)carbonyl, (3-methylthio-4-methoxy-benzo[c]thien-1-yl)carbonyl, (3-benzylthio-benzo[c]thien-1-yl)carbonyl, (3-benzylthio-7-hydro-6H-benzo[c]thien-1-yl)carbonyl, (3-thien-2-yl-[1,2,4]oxadiazol-5-yl)carbonyl, [3-(3-thien-2-yl-[1,2,4]oxadiazol-5-yl)-5-aminocarbonyl-phenyl]carbonyl and (3-methyl-4-bromo-5-propoxy-thien-2-yl) carbonyl.

6. A compound of claim 1 selected from the group consisting of
1-(3,4-dichlorophenyl)carbonyl-5'-aminomethyl-spiro[piperidine-4,3'-(2H)-benzo [b]furan],
5'-(3,4-dichlorophenylcarbonylaminomethyl)-spiro[piperidine-4,3'-(2H)-benzo [b]furan],
1-(5-phenylethynyl-furan-2-yl)carbonyl-5'-aminomethyl-spiro[piperidine-4,3'-(2H)-benzo[b]furan],
1-(3-benzoyl-phenyl)carbonyl-5'-aminomethyl-spiro[piperidine-4,3'-(2H)-benzo[b]furan],
1-(3-aminothiocarbonylamino-phenyl)carbonyl-5'-aminomethyl-spiro[piperidine-4,3'-(2H)-benzo[b]furan],
1-(4-benzoyl-phenyl)carbonyl-5'-aminomethyl-spiro[piperidine-4,3'-(2H)-benzo[b]furan],
1-(9-oxo-10,10-dioxo-thioxanthen-3-yl)carbonyl-5'-aminomethyl-spiro[piperidine-4,3'-(2H)-benzo[b]furan],
1-(9-oxo-fluoren-2-yl)carbonyl-5'-aminomethyl-spiro[piperidine-4,3'-(2H)-benzo[b]furan],
1-(4-benzoimidazol-1-ylmethylcarbonylamino-phenyl)carbonyl-5'-aminomethyl-spiro[piperidine-4,3'-(2H)-benzo[b]furan],
1-(4-benzoimidazol-1-ylmethyl-phenyl)carbonyl-5'-aminomethyl-spiro[piperidine-4,3'-(2H)-benzo[b]furan],
1-(4-aminosulfonyl-phenyl)carbonyl-5'-aminomethyl-spiro[piperidine-4,3'-(2H)-benzo[b]furan],
1-[5-(4-chloro-phenyl)-furan-2-yl]carbonyl-5'-aminomethyl-spiro[piperidine-4,3'-(2H)-benzo[b]furan],
1-(5-chloro-benzo[b]-furan-2-yl)carbonyl-5'-aminomethyl-spiro[piperidine-4,3'-(2H)-benzo[b]furan],
1-(1-phenyl-2-methyl-benzoimidazol-5-yl)carbonyl-5'-aminomethyl-spiro[piperidine-4,3'-(2H)-benzo[b]furan],
1-[4-(3-trifluoromethyl-phenyl)-phenyl]carbonyl-5'-aminomethyl-spiro[piperidine-4,3'-(2H)-benzo[b]furan],
1-benzothiazol-6-ylcarbonyl-5'-aminomethyl-spiro[piperidine-4,3'-(2H)-benzo[b]furan],
1-{4-[(4-benzoxazol-2-yl)-pyrazol-1-yl]-phenyl}carbonyl-5'-aminomethyl-spiro[piperidine-4, 3'-(2H)-benzo[b]furan],
1-(3-phenylsulfonylamino-phenyl)carbonyl-5'-aminomethyl-spiro[piperidine-4,3'-(2H)-benzo[b]furan], 1-(3-thien-2-ylmethylcarbonylamino-phenyl)carbonyl-5'-aminomethyl-spiro[piperidine-4,3'-(2H)-benzo[b]furan],
1-benzodioxol-5-yl-phenyl)carbonyl-5'-aminomethyl-spiro[piperidine-4,3'-(2H)-benzo[b]furan],
1-[3-(5-chloro-pyrimidin-2-yl)thiophenyl]carbonyl-5'-aminomethyl-spiro[piperidine-4,3'-(2H)-benzo[b]furan],
1-(5-trifluoromethyl-furan-2-yl)carbonyl-5'-aminomethyl-spiro[piperidine-4,3'-(2H)-benzo[b]furan],
1-[(5-phenylthio)-furan-2-yl]carbonyl-5'-aminomethyl-spiro[piperidine-4,3'-(2H)-benzo[b]furan],
1-(3,4-dimethyl-phenyl)carbonyl-5'-aminomethyl-spiro[piperidine-4,3'-(2H)-benzo[b]furan],
1-(3-methyl-4-chloro-phenyl)carbonyl-5'-aminomethyl-spiro[piperidine-4,3'-(2H)-benzo[b]furan],
1-(3,4-difluoro-phenyl)carbonyl-5'-aminomethyl-spiro[piperidine-4,3'-(2H)-benzo[b]furan],
1-(3-chloro-4-fluoro-phenyl)carbonyl-5'-aminomethyl-spiro[piperidine-4,3'-(2H)-benzo[b]furan],
1-(3-chloro-4-methoxy-phenyl)carbonyl-5'-aminomethyl-spiro[piperidine-4,3'-(2H)-benzo[b]furan],
1-(3-bromo-phenyl)carbonyl-5'-aminomethyl-spiro[piperidine-4,3'-(2H)-benzo[b]furan],
1-(3-methyl-4-bromo-phenyl)carbonyl-5'-aminomethyl-spiro[piperidine-4,3'-(2H)-benzo[b]furan],
1-(3-bromo-4-fluoro-phenyl)carbonyl-5'-aminomethyl-spiro[piperidine-4,3'-(2H)-benzo[b]furan],
1-(3-bromo-4-methoxy-phenyl)carbonyl-5'-aminomethyl-spiro[piperidine-4,3'-(2H)-benzo[b]furan],
1-(3-nitro-4-bromo-phenyl)carbonyl-5'-aminomethyl-spiro[piperidine-4,3'-(2H)-benzo[b]furan],
1-(3-iodo-4-chloro-phenyl)carbonyl-5'-aminomethyl-spiro[piperidine-4,3'-(2H)-benzo[b]furan],
1-[5-(2-fluoro-phenylethynyl)-furan-2-yl]carbonyl-5'-aminomethyl-spiro[piperidine-4,3'-(2H)-benzo[b]furan],
1-phenylcarbonyl-5'-aminomethyl-spiro[piperidine-4,3'-(2H)-benzo[b]furan],
1-cyclohexylcarbonyl-5'-aminomethyl-spiro[piperidine-4,3'-(2H)-benzo[b]furan],
1-(trans-4-methyl-cyclohexyl)carbonyl-5'-aminomethyl-spiro[piperidine-4,3'-(2H)-benzo[b]furan],
1-(3-chloro-phenyl)carbonyl-5'-aminomethyl-spiro[piperidine-4,3'-(2H)-benzo[b]furan],
1-(3,4-dimethoxy-phenyl)carbonyl-5'-aminomethyl-spiro[piperidine-4,3'-(2H)-benzo[b]furan],
1-(3-methyl-phenyl)carbonyl-5'-aminomethyl-spiro[piperidine-4,3'-(2H)-benzo[b]furan],
1-(3-fluoro-phenyl)carbonyl-5'-aminomethyl-spiro[piperidine-4,3'-(2H)-benzo[b]furan],
1-(4-fluoro-phenyl)carbonyl-5'-aminomethyl-spiro[piperidine-4,3'-(2H)-benzo[b]furan],
1-(4-chloro-phenyl)carbonyl-5'-aminomethyl-spiro[piperidine-4,3'-(2H)-benzo[b]furan],
1-(4-methylthio-phenyl)carbonyl-5'-aminomethyl-spiro[piperidine-4,3'-(2H)-benzo[b]furan],
1-(3-fluoro-4-chloro-phenyl)carbonyl-5'-aminomethyl-spiro[piperidine-4,3'-(2H)-benzo[b]furan],
1-(3-trifluoromethyl-phenyl)carbonyl-5'-aminomethyl-spiro[piperidine-4,3'-(2H)-benzo[b]furan],
1-(3-iodo-phenyl)carbonyl-5'-aminomethyl-spiro[piperidine-4,3'-(2H)-benzo[b]furan],
1-(4-iodo-phenyl)carbonyl-5'-aminomethyl-spiro[piperidine-4,3'-(2H)-benzo[b]furan],
1-(3-iodo-4-methyl-phenyl)carbonyl-5'-aminomethyl-spiro[piperidine-4,3'-(2H)-benzo[b]furan],
1-(3-methyl-4-iodo-phenyl)carbonyl-5'-aminomethyl-spiro[piperidine-4,3'-(2H)-benzo[b]furan],
1-(3-iodo-4-methoxy-phenyl)carbonyl-5'-aminomethyl-spiro[piperidine-4,3'-(2H)-benzo[b]furan],
1-(3-methoxy-phenyl)carbonyl-5'-aminomethyl-spiro[piperidine-4,3'-(2H)-benzo[b]furan],
1-(4-methoxy-phenyl)carbonyl-5'-aminomethyl-spiro[piperidine-4,3'-(2H)-benzo[b]furan],
1-(4-dimethylamino-phenyl)carbonyl-5'-aminomethyl-spiro[piperidine-4,3'-(2H)-benzo[b]furan],
1-(3-dimethylamino-phenyl)carbonyl-5'-aminomethyl-spiro[piperidine-4,3'-(2H)-benzo[b]furan],
1-(3-methylthio-phenyl)carbonyl-5'-aminomethyl-spiro[piperidine-4,3'-(2H)-benzo[b]furan],
1-(4-methoxycarbonyl-phenyl)carbonyl-5'-aminomethyl-spiro[piperidine-4,3'-(2H)-benzo[b]furan],
1-(4-bromo-phenyl)carbonyl-5'-aminomethyl-spiro[piperidine-4,3'-(2H)-benzo[b]furan],
1-(3-trifluoromethoxy-phenyl)carbonyl-5'-aminomethyl-spiro[piperidine-4,3'-(2H)-benzo[b]furan],
1-(4-trifluoromethoxy-phenyl)carbonyl-5'-aminomethyl-spiro[piperidine-4,3'-(2H)-benzo[b]furan],
1-(4-phenoxy-phenyl)carbonyl-5'-aminomethyl-spiro[piperidine-4,3'-(2H)-benzo[b]furan],
1-(3-trifluoromethylthio-phenyl)carbonyl-5'-aminomethyl-spiro[piperidine-4,3'-(2H)-benzo[b]furan],
1-[3-(4-methoxy-phenyl)-phenyl]carbonyl-5'-aminomethyl-spiro[piperidine-4,3'-(2H)-benzo[b]furan],
1-(5-phenylethynyl-furan-2-yl)carbonyl-5'-aminoiminomethyl-spiro[piperidine-4,3'-(2H)-benzo[b]furan],
1-(3-cyano-phenyl)carbonyl-5'-aminomethyl-spiro[piperidine-4,3'-(2H)-benzo[b]furan],
1-(4-methylcarbonyl-phenyl)carbonyl-5'-aminomethyl-spiro[piperidine-4,3'-(2H)-benzo[b]furan],
1-benzodioxol-5-ylcarbonyl-5'-aminomethyl-spiro[piperidine-4,3'-(2H)-benzo[b]furan],
1-(4-chloromethyl-phenyl)carbonyl-5'-aminomethyl-spiro[piperidine-4,3'-(2H)-benzo[b]furan],
1-naphthalen-2-ylcarbonyl-5'-aminomethyl-spiro[piperidine-4,3'-(2H)-benzo[b]furan],
1-(4-trifluoromethyl-phenyl)carbonyl-5'-aminomethyl-spiro[piperidine-4,3'-(2H)-benzo[b]furan],
1-(3-methylsulfonyl-phenyl)carbonyl-5'-aminomethyl-spiro[piperidine-4,3'-(2H)-benzo[b]furan],
1-(4-cyclohexyl-phenyl)carbonyl-5'-aminomethyl-spiro[piperidine-4,3'-(2H)-benzo[b]furan],
1-(3-trifluoromethyl-4-fluoro-phenyl)carbonyl-5'-aminomethyl-spiro[piperidine-4,3'-(2H)-benzo[b]furan],
1-(4-benzyl-phenyl)carbonyl-5'-aminomethyl-spiro[piperidine-4,3'-(2H)-benzo[b]furan],
1-(4-benzyloxy-phenyl)carbonyl-5'-aminomethyl-spiro[piperidine-4,3'-(2H)-benzo[b]furan],
(Z)-1-(5-phenylethenyl-furan-2-yl)carbonyl-5'-aminomethyl-spiro[piperidine-4,3'-(2H)-benzo[b]furan],
1-benzylcarbonyl-5'-aminomethyl-spiro[piperidine-4,3'-(2H)-benzo[b]furan],
1-phenethylcarbonyl-5'-aminomethyl-spiro[piperidine-4,3'-(2H)-benzo[b]furan],
1-(3-fluoro-benzyl)carbonyl-5'-aminomethyl-spiro[piperidine-4,3'-(2H)-benzo[b]furan],
1-(3-chloro-benzyl)carbonyl-5'-aminomethyl-spiro[piperidine-4,3'-(2H)-benzo[b]furan],
1-(3,4-difluoro-benzyl)carbonyl-5'-aminomethyl-spiro[piperidine-4,3'-(2H)-benzo[b]furan],
1-(3-chloro-phenethyl)carbonyl-5'-aminomethyl-spiro[piperidine-4,3'-(2H)-benzo[b]furan], 1-naphthalen-2-ylmethylcarbonyl-5'-aminomethyl-spiro[piperidine-4,3'-(2H)-benzo[b]furan],
1-(3-trifluoromethyl-benzyl)carbonyl-5'-aminomethyl-spiro[piperidine-4,3'-(2H)-benzo[b]furan],
1-(3,4-dichloro-benzyl)carbonyl-5'-aminomethyl-spiro[piperidine-4,3'-(2H)-benzo[b]furan],
1-(3-bromo-benzyl)carbonyl-5'-aminomethyl-spiro[piperidine-4,3'-(2H)-benzo[b]furan],
1-(3-phenoxy-benzyl)carbonyl-5'-aminomethyl-spiro[piperidine-4,3'-(2H)-benzo[b]furan],
1-(3-methyl-benzyl)carbonyl-5'-aminomethyl-spiro[piperidine-4,3'-(2H)-benzo[b]furan],
1-(4-fluoro-benzyl)carbonyl-5'-aminomethyl-spiro[piperidine-4,3'-(2H)-benzo[b]furan],
1-(4-chloro-benzyl)carbonyl-5'-aminomethyl-spiro[piperidine-4,3'-(2H)-benzo[b]furan],
1-(4-phenyl-benzyl)carbonyl-5'-aminomethyl-spiro[piperidine-4,3'-(2H)-benzo[b]furan],
1-(4-bromo-benzyl)carbonyl-5'-aminomethyl-spiro[piperidine-4,3'-(2H)-benzo[b]furan],
1-(4-methoxy-benzyl)carbonyl-5'-aminomethyl-spiro[piperidine-4,3'-(2H)-benzo[b]furan],
1-(3-bromo-benzyl)carbonyl-5'-aminomethyl-spiro[piperidine-4,3'-(2H)-benzo[b]furan],
1-(4-iodo-benzyl)carbonyl-5'-aminomethyl-spiro[piperidine-4,3'-(2H)-benzo[b]furan],
1-(3-iodo-phenethyl)carbonyl-5'-aminomethyl-spiro[piperidine-4,3'-(2H)-benzo[b]furan],
1-(3-methyl-phenethyl)carbonyl-5'-aminomethyl-spiro[piperidine-4,3'-(2H)-benzo[b]furan],
1-(3-methoxy-benzyl)carbonyl-5'-aminomethyl-spiro[piperidine-4,3'-(2H)-benzo[b]furan],
1-benzodioxol-5-ylmethylcarbonyl-5'-aminomethyl-spiro[piperidine-4,3'-(2H)-benzo[b]furan],
1-(3-methoxy-phenethyl)carbonyl-5'-aminomethyl-spiro[piperidine-4,3'-(2H)-benzo[b]furan],
1-(3-methyl-4-methoxy-benzyl)carbonyl-5'-aminomethyl-spiro[piperidine-4,3'-(2H)-benzo[b]furan],
1-(3-methylthio-benzyl)carbonyl-5'-aminomethyl-spiro[piperidine-4,3'-(2H)-benzo[b]furan],
1-(benzodioxol-5-ylethyl)carbonyl-5'-aminomethyl-spiro[piperidine-4,3'-(2H)-benzo[b]furan],
1-(3,4-dimethoxy-benzyl)carbonyl-5'-aminomethyl-spiro[piperidine-4,3'-(2H)-benzo[b]furan],
1-(3-methoxy-4-benzyloxy-benzyl)carbonyl-5'-aminomethyl-spiro[piperidine-4,3'-(2H)-benzo[b]furan],
1-(5-phenethyl-furan-2-yl)carbonyl-5'-aminomethyl-spiro[piperidine-4,3'-(2H)-benzo[b]furan],
1-(phenylethynyl)carbonyl-5'-aminomethyl-spiro[piperidine-4,3'-(2H)-benzo[b]furan],
(E)-1-(phenylethenyl)carbonyl-5'-aminomethyl-spiro[piperidine-4,3'-(2H)-benzo[b]furan],
1-benzothien-2-ylcarbonyl-5'-aminomethyl-spiro[piperidine-4,3'-(2H)-benzo[b]furan],
(E)-1-(3,4-difluoro-phenylethenyl)carbonyl-5'-aminomethyl-spiro[piperidine-4,3'-(2H)-benzo[b]furan],
(E)-1-(phenylethenyl)carbonyl-5'-aminomethyl-spiro[piperidine-4,3'-(2H)-benzo[b]furan],
(E)-1-(naphthalene-2-ylethenyl)carbonyl-5'-aminomethyl-spiro[piperidine-4,3'-(2H)-benzo[b]furan],
1-(5-phenyl-thien-2-yl)carbonyl-5'-aminomethyl-spiro[piperidine-4,3'-(2H)-benzo[b]furan],
1-(3-phenoxy-phenyl)carbonyl-5'-aminomethyl-spiro[piperidine-4,3'-(2H)-benzo[b]furan],
(E)-1-(3,4-dichloro-phenylethenyl)carbonyl-5'-aminomethyl-spiro[piperidine-4,3'-(2H)-benzo[b]furan],
(E)-1-(4-phenyl-phenylethenyl)carbonyl-5'-aminomethyl-spiro[piperidine-4,3'-(2H)-benzo[b]furan],
1-(2,4-dimethyl-thiazol-5-yl)carbonyl-5'-aminomethyl-spiro[piperidine-4,3'-(2H)-benzo[b]furan],
1-(6-methyl-imidazo[1,2-a]pyridin-2-yl)carbonyl-5'-aminomethyl-spiro[piperidine-4,3'-(2H)-benzo[b]furan],
1-(5-pyridin-2-yl-thien-2-yl)carbonyl-5'-aminomethyl-spiro[piperidine-4,3'-(2H)-benzo[b]furan],
1-(2-pyridin-3-yl-thiazol-4-yl)carbonyl-5'-aminomethyl-spiro[piperidine-4,3'-(2H)-benzo[b]furan],
1-(2-pyridin-4-yl-thiazol-4-yl)carbonyl-5'-aminomethyl-spiro[piperidine-4,3'-(2H)-benzo[b]furan],
1-(2-phenyl-4-methyl-thiazol-5-yl)carbonyl-5'-aminomethyl-spiro[piperidine-4,3'-(2H)-benzo[b]furan],
1-(2-pyridin-3-yl-4-methyl-thiazol-5-yl)carbonyl-5'-aminomethyl-spiro[piperidine-4,3'-(2H)-benzo[b]furan],
1-[2-(4-methyl-phenyl)-4-methyl-thiazol-5-yl]carbonyl-5'-aminomethyl-spiro[piperidine-4,3'-(2H)-benzo[b]furan],
1-(6-bromo-naphthalen-2-yl)carbonyl-5'-aminomethyl-spiro[piperidine-4,3'-(2H)-benzo[b]furan],
1-[5-(1-methyl-3-trifluoromethyl-pyrazol-5-yl)-thien-2-yl]carbonyl-5'-aminomethyl-spiro[piperidine-4,3'-(2H)-benzo[b]furan],
1-[2-(4-trifluoromethyl-phenyl)-4-methyl-thiazol-5-yl]carbonyl-5'-aminomethyl-spiro[piperidine-4,3'-(2H)-benzo[b]furan],
1-[5-(2-chloro-5-trifluoromethyl-phenyl)-furan-2-yl]carbonyl-5'-aminomethyl-spiro[piperidine-4,3'-(2H)-benzo[b]furan],
1-(5-phenyl-furan-2-yl)carbonyl-5'-aminomethyl-spiro[piperidine-4,3'-(2H)-benzo[b]furan],
1-[5-(4-methyl-phenyl)-furan-2-yl]carbonyl-5'-aminomethyl-spiro[piperidine-4,3'-(2H)-benzo[b]furan],
1-[5-(4-methoxy-phenyl)-furan-2-yl]carbonyl-5'-aminomethyl-spiro[piperidine-4,3'-(2H)-benzo[b]furan],
1-(3,5-di-tert-butyl-phenyl)carbonyl-5'-aminomethyl-spiro[piperidine-4,3'-(2H)-benzo[b]furan],
1-[5-(3-chloro-phenoxymethyl)-furan-2-yl]carbonyl-5'-aminomethyl-spiro[piperidine-4,3'-(2H)-benzo[b]furan],
1-[5-(3-trifluoromethyl-phenyl)-furan-2-yl]carbonyl-5'-aminomethyl-spiro[piperidine-4,3'-(2H)-benzo[b]furan],
1-[5-(2,4-dichloro-phenyl)-furan-2-yl]carbonyl-5'-aminomethyl-spiro[piperidine-4,3'-(2H)-benzo[b]furan],
1-[5-(2,5-dichloro-phenyl)-furan-2-yl]carbonyl-5'-aminomethyl-spiro[piperidine-4,3'-(2H)-benzo[b]furan],
1-[5-(3,4-dichloro-phenyl)-furan-2-yl]carbonyl-5'-aminomethyl-spiro[piperidine-4,3'-(2H)-benzo[b]furan],
1-[5-(3-methyl-4-chloro-phenoxymethyl)-furan-2-yl]carbonyl-5'-aminomethyl-spiro[piperidine-4,3'-(2H)-benzo[b]furan],
1-[5-(4-bromo-phenyl)-furan-2-yl]carbonyl-5'-aminomethyl-spiro[piperidine-4,3'-(2H)-benzo[b]furan],
1-(trans-2-phenyl-cyclopropyl)carbonyl-5'-aminomethyl-spiro[piperidine-4,3'-(2H)-benzo[b]furan],
1-(5-phenyl-pyridin-3-yl)carbonyl-5'-aminomethyl-spiro[piperidine-4,3'-(2H)-benzo[b]furan],
1-(5-thien-2-yl-pyridin-3-yl)carbonyl-5'-aminomethyl-spiro[piperidine-4,3'-(2H)-benzo[b]furan],
1-[5-(3-methoxy-phenyl)-furan-2-yl]carbonyl-5'-aminomethyl-spiro[piperidine-4,3'-(2H)-benzo[b]furan],
1-[5-(4-chloro-pyrazol-1-ylmethyl)-furan-2-yl]carbonyl-5'-aminomethyl-spiro[piperidine-4,3'-(2H)-benzo[b]furan], 1-[5-(2-chloro-phenylethynyl)-furan-2-yl]carbonyl-5'-aminomethyl-spiro[piperidine-4,3'-(2H)-benzo[b]furan],
1-[5-(benzylthiomethyl)-furan-2-yl]carbonyl-5'-aminomethyl-spiro[piperidine-4,3'-(2H)-benzo[b]furan],
1-[5-(4,6-dimethyl-pyrimidin-2-ylthiomethyl)-furan-2-yl]carbonyl-5'-aminomethyl-spiro[piperidine-4,3'-(2H)-benzo[b]furan],
1-[5-(3,5-dichloro-phenoxy)-furan-2-yl]carbonyl-5'-aminomethyl-spiro[piperidine-4,3'-(2H)-benzo[b]furan],
1-[5-(3,5-dimethyl-4-bromo-pyrazol-1-yl)-furan-2-yl]carbonyl-5'-aminomethyl-spiro[piperidine-4,3'-(2H)-benzo[b]furan],
1-[5-(5-trifluoromethyl-pyridin-2-ylthiomethyl)-furan-2-yl]carbonyl-5'-aminomethyl-spiro[piperidine-4,3'-(2H)-benzo[b]furan],
1-[4-phenylethynyl-pyridin-2-yl]carbonyl-5'-aminomethyl-spiro[piperidine-4,3'-(2H)-benzo[b]furan],
1-[5-(2-methyl-phenylethynyl)-furan-2-yl]carbonyl-5'-aminomethyl-spiro[piperidine-4,3'-(2H)-benzo[b]furan],
1-[5-(4-fluoro-phenoxymethyl)-furan-2-yl]carbonyl-5'-aminomethyl-spiro[piperidine-4,3'-(2H)-benzo[b]furan],
1-(3-methylthio-4-oxo-5,6,7-trihydro-4H-benzo[c]thien-1-yl)carbonyl-5'-aminomethyl-spiro[piperidine-4,3'-(2H)-benzo[b]furan],
1-[5-(2,5-dimethyl-furan-3-yl-carbonylaminomethyl)-furan-2-yl]carbonyl-5'-aminomethyl-spiro[piperidine-4,3'-(2H)-benzo[b]furan],
1-(3-chloro-4-isopropylsulfonyl-5-methylthio-thien-2-yl)carbonyl-5'-aminomethyl-spiro[piperidine-4,3'-(2H)-benzo[b]furan],
1-(3,4-dichloro-benzyl)-5'-aminomethyl-spiro[piperidine-4,3'-(2H)-benzo[b]furan],
1-thien-2-ylcarbonyl-5'-aminomethyl-spiro[piperidine-4,3'-(2H)-benzo[b]furan],
1-benzo[b]furan-2-ylcarbonyl-5'-aminomethyl-spiro[piperidine-4,3'-(2H)-benzo[b]furan],
(E)-1-(3-fluoro-phenylethenyl)carbonyl-5'-aminomethyl-spiro[piperidine-4,3'-(2H)-benzo[b]furan],
(Z)-1-(1-fluoro-2-phenylethenyl)carbonyl-5'-aminomethyl-spiro[piperidine-4,3'-(2H)-benzo[b]furan],
1-(5,6,7-trihydro-4H-benzo[b]thien-2-yl)carbonyl-5'-aminomethyl-spiro[piperidine-4,3'-(2H)-benzo[b]furan],
(E)-1-(3-chloro-phenylethenyl)carbonyl-5'-aminomethyl-spiro[piperidine-4,3'-(2H)-benzo[b]furan],
(E)-1-(4-chloro-phenylethenyl)carbonyl-5'-aminomethyl-spiro[piperidine-4,3'-(2H)-benzo[b]furan],
1-(3-chloro-benzo[b]thien-2-yl)carbonyl-5'-aminomethyl-spiro[piperidine-4,3'-(2H)-benzo[b]furan],
(E)-1-(3-trifluoromethoxy-phenylethenyl)carbonyl-5'-aminomethyl-spiro[piperidine-4,3'-(2H)-benzo[b]furan],
1-(4-fluoro-benzo[b]thien-2-yl)carbonyl-5'-aminomethyl-spiro[piperidine-4,3'-(2H)-benzo[b]furan],
1-(5-methylsulfonyl-thien-2-yl)carbonyl-5'-aminomethyl-spiro[piperidine-4,3'-(2H)-benzo[b]furan],
1-[5-(4-methyl-phenylethynyl)-furan-2-yl]carbonyl-5'-aminomethyl-spiro[piperidine-4,3'-(2H)-benzo[b]furan],
1-(3-chloro-6-fluoro-benzo[b]thien-2-yl)carbonyl-5'-aminomethyl-spiro[piperidine-4,3'-(2H)-benzo[b]furan],
1-[5-(2,5-dimethyl-phenylethynyl)-furan-2-yl]carbonyl-5'-aminomethyl-spiro[piperidine-4,3'-(2H)-benzo[b]furan],
1-[5-(2-methoxy-phenylethynyl)-furan-2-yl]carbonyl-5'-aminomethyl-spiro[piperidine-4,3'-(2H)-benzo[b]furan],
1-[5-(2,5-dimethyl-phenoxymethyl)-furan-2-yl]carbonyl-5'-aminomethyl-spiro[piperidine-4,3'-(2H)-benzo[b]furan],
1-(3,4-dichloro-benzo[b]thien-2-yl)carbonyl-5'-aminomethyl-spiro[piperidine-4,3'-(2H)-benzo[b]furan],
1-[5-(3,5-difluoro-phenylethynyl)-furan-2-yl]carbonyl-5'-aminomethyl-spiro[piperidine-4,3'-(2H)-benzo[b]furan],
1-(5-naphthalen-1-ylethenyl-furan-2-yl)carbonyl-5'-aminomethyl-spiro[piperidine-4,3'-(2H)-benzo[b]furan],
1-[5-(4-tert-butyl-phenoxymethyl)-furan-2-yl]carbonyl-5'-aminomethyl-spiro[piperidine-4,3'-(2H)-benzo[b]furan],
(E)-1-(3-methyl-phenylethenyl)carbonyl-5'-aminomethyl-spiro[piperidine-4,3'-(2H)-benzo[b]furan],
(E)-1-(4-methyl-phenylethenyl)carbonyl-5'-aminomethyl-spiro[piperidine-4,3'-(2H)-benzo[b]furan],
(Z)-1-(1-methyl-2-phenylethenyl)carbonyl-5'-aminomethyl-spiro[piperidine-4,3'-(2H)-benzo[b]furan],
(E)-1-(4-fluoro-phenylethenyl)carbonyl-5'-aminomethyl-spiro[piperidine-4,3'-(2H)-benzo[b]furan],
(Z)-1-(2-methoxy-phenylethenyl)carbonyl-5'-aminomethyl-spiro[piperidine-4,3'-(2H)-benzo[b]furan],
(E)-1-(3-methoxy-phenylethenyl)carbonyl-5'-aminomethyl-spiro[piperidine-4,3'-(2H)-benzo[b]furan],
(E)-1-(4-methoxy-phenylethenyl)carbonyl-5'-aminomethyl-spiro[piperidine-4,3'-(2H)-benzo[b]furan],
(E)-1-(2-chloro-phenylethenyl)carbonyl-5'-aminomethyl-spiro[piperidine-4,3'-(2H)-benzo[b]furan],
(E)-1-(benzodioxol-5-ylethenyl)carbonyl-5'-aminomethyl-spiro[piperidine-4,3'-(2H)-benzo[b]furan],
(E)-1-(naphthalen-1-ylethenyl)carbonyl-5'-aminomethyl-spiro[piperidine-4,3'-(2H)-benzo[b]furan],
1-(1-oxo-2-fluoren-9-ylidene-ethyl)-5'-aminomethyl-spiro[piperidine-4,3'-(2H)-benzo[b]furan],
(E)-1-(1-phenyl-2-phenylethenyl)carbonyl-5'-aminomethyl-spiro[piperidine-4,3'-(2H)-benzo[b]furan],
(E)-1-(2-methyl-phenylethenyl)carbonyl-5'-aminomethyl-spiro[piperidine-4,3'-(2H)-benzo[b]furan],
1-(1-methyl-3H-inden-2-yl)carbonyl-5'-aminomethyl-spiro[piperidine-4,3'-(2H)-benzo[b]furan],
1-(1-methyl-indol-2-yl)carbonyl-5'-aminomethyl-spiro[piperidine-4,3'-(2H)-benzo[b]furan],
(E)-1-(2-methoxy-phenylethenyl)carbonyl-5'-aminomethyl-spiro[piperidine-4,3'-(2H)-benzo[b]furan],
(E)-1-(2,6-difluoro-phenylethenyl)carbonyl-5'-aminomethyl-spiro[piperidine-4,3'-(2H)-benzo[b]furan],
1-(2-oxo-(2H)-chromen-3-yl)carbonyl-5'-aminomethyl-spiro[piperidine-4,3'-(2H)-benzo[b]furan],
1-(8-methoxy-(2H)-chromen-3-yl)carbonyl-5'-aminomethyl-spiro[piperidine-4,3'-(2H)-benzo[b]furan],
1-(5-bromo-thien-2-yl)carbonyl-5'-aminomethyl-spiro[piperidine-4,3'-(2H)-benzo[b]furan],
(E)-1-(2-bromo-phenylethenyl)carbonyl-5'-aminomethyl-spiro[piperidine-4,3'-(2H)-benzo[b]furan],
1-(5-trifluoromethyl-benzo[b]thien-2-yl)carbonyl-5'-aminomethyl-spiro[piperidine-4,3'-(2H)-benzo[b]furan],
1-[3-(4-methoxy-phenyl)-4-cyano-5-methylthio-thien-2-yl]carbonyl-5'-aminomethyl-spiro[piperidine-4,3'-(2H)-benzo[b]furan],
1-[3-(4-chloro-phenyl)-4-cyano-5-methylthio-thien-2-yl]carbonyl-5'-aminomethyl-spiro[piperidine-4,3'-(2H)-benzo[b]furan], 1-(5,6,7-trihydro-4H-benzo[c]thien-1-yl)carbonyl-5'-aminomethyl-spiro[piperidine-4,3'-(2H)-benzo[b]furan], 1-thieno[3,2-b]thien-2-ylcarbonyl-5'-aminomethyl-spiro[piperidine-4,3'-(2H)-benzo[b]furan], (Z)-1-(1-methylcarbonylamino-2-phenylethenyl)carbonyl-5'-aminomethyl-spiro[piperidine-4,3'-(2H)-benzo[b]furan], 1-[5-(2-methyl-thiazol-4-yl)-thien-2-yl]carbonyl-5'-aminomethyl-spiro[piperidine-4,3'-(2H)-benzo[b]furan], 1-(3-chloro-6-methyl-benzo[b]thien-2-yl)carbonyl-5'-aminomethyl-spiro[piperidine-4,3'-(2H)-benzo[b]furan], 1-[3-(2-methyl-phenoxy)-benzyl]carbonyl-5'-aminomethyl-spiro[piperidine-4,3'-(2H)-benzo[b]furan], 1-(3-chloro-6-methoxy-benzo[b]thien-2-yl)carbonyl-5'-aminomethyl-spiro[piperidine-4,3'-(2H)-benzo[b]furan], 1-[3-(2-fluoro-phenoxy)-benzyl]carbonyl-5'-aminomethyl-spiro[piperidine-4,3'-(2H)-benzo[b]furan], 1-(3-propylthio-4-oxo-5,6,7-trihydro-4H-benzo[c]thien-1-yl)carbonyl-5'-aminomethyl-spiro[piperidine-4,3'-(2H)-benzo[b]furan], 1-[5-(2-methoxy-4-propyl-phenoxymethyl)-furan-2-yl]carbonyl-5'-aminomethyl-spiro[piperidine-4,3'-(2H)-benzo[b]furan], 1-[5-(2-bromo-phenoxymethyl)-furan-2-yl]carbonyl-5'-aminomethyl-spiro[piperidine-4,3'-(2H)-benzo[b]furan], 1-(3-benzylthio-4-oxo-5,6,7-trihydro-4H-benzo[c]thien-1-yl)carbonyl-5'-aminomethyl-spiro[piperidine-4,3'-(2H)-benzo[b]furan], 1-[1-oxo-2-(3-oxo-3H-isobenzofuran-1-ylidene)-ethyl]-5'-aminomethyl-spiro[piperidine-4,3'-(2H)-benzo[b]furan], 1-(5-morpholin-4-ylmethyl-furan-2-yl)carbonyl-5'-aminomethyl-spiro[piperidine-4,3'-(2H)-benzo[b]furan], 1-(4-phenyl-[1,2,3]thiadiazol-5-yl)carbonyl-5'-aminomethyl-spiro[piperidine-4,3'-(2H)-benzo[b]furan], 1-(3-methylthio-5,6,7-trihydro-4H-benzo[c]thien-1-yl)carbonyl-5'-aminomethyl-spiro[piperidine-4,3'-(2H)-benzo[b]furan], 1-(3-methylthio-7-hydro-6H-benzo[c]thien-1-yl)carbonyl-5'-aminomethyl-spiro[piperidine-4,3'-(2H)-benzo[b]furan], 1-[5-(2-methyl-furan-3-yl-carbonylaminomethyl)-furan-2-yl]carbonyl-5'-aminomethyl-spiro[piperidine-4,3'-(2H)-benzo[b]furan], 1-[5-(3,5-dimethyl-4-chloro-pyrazol-1-yl)-furan-2-yl]carbonyl-5'-aminomethyl-spiro[piperidine-4,3'-(2H)-benzo[b]furan], 1-(3-methyl-4-oxo-6-phenyl-5,6,7-trihydro-4H-benzo[b]furan-2-yl)carbonyl-5'-aminomethyl-spiro[piperidine-4,3'-(2H)-benzo[b]furan], 1-(3-ethylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], 1-[5-(2-methoxy-4-alkyl-phenoxymethyl)-furan-2-yl]carbonyl-5'-aminomethyl-spiro[piperidine-4,3'-(2H)-benzo[b]furan], 1-(3-isopropylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], 1-(3,4-dimethyl-5-cyano-thieno[2,3-b]thien-2-yl)carbonyl-5'-aminomethyl-spiro[piperidine-4,3'-(2H)-benzo[b]furan], 1-[5-(3-methoxy-phenoxymethyl)-furan-2-yl]carbonyl-5'-aminomethyl-spiro[piperidine-4,3'-(2H)-benzo[b]furan], 1-(3-methyl-6-phenyl-benzo[b]furan-2-yl)carbonyl-5'-aminomethyl-spiro[piperidine-4,3'-(2H)-benzo[b]furan], 1-(3-butylthio-4-oxo-5,6,7-trihydro-4H-benzo[c]thien-1-yl)carbonyl-5'-aminomethyl-spiro[piperidine-4,3'-(2H)-benzo[b]furan], 1-(3-chloro-6-bromo-benzo[b]thien-2-yl)carbonyl-5'-aminomethyl-spiro[piperidine-4,3'-(2H)-benzo[b]furan], 1-(3-sec-butylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], 1-(3-benzylthio-4-oxo-6,6-dimethyl-6,7-dihydro-5H-benzo[c]thien-1-yl)carbonyl-5'-aminomethyl-spiro[piperidine-4,3'-(2H)-benzo[b]furan], 1-thieno[2,3-b]thien-2-ylcarbonyl-5'-aminomethyl-spiro[piperidine-4,3'-(2H)-benzo[b]furan], 1-(3-methylthio-benzo[c]thien-1-yl)carbonyl-5'-aminomethyl-spiro[piperidine-4,3'-(2H)-benzo[b]furan], 1-(3-methylthio-4-methoxy-benzo[c]thien-1-yl)carbonyl-5'-aminomethyl-spiro[piperidine-4,3'-(2H)-benzo[b]furan], 1-indol-3-ylcarbonyl-5'-aminomethyl-spiro[piperidine-4,3'-(2H)-benzo[b]furan], 1-(1-methyl-indol-3-yl)carbonyl-5'-aminomethyl-spiro[piperidine-4,3'-(2H)-benzo[b]furan], 1-(5-methoxy-indol-3-yl)carbonyl-5'-aminomethyl-spiro[piperidine-4,3'-(2H)-benzo[b]furan], 1-(1-benzyl-indol-3-yl)carbonyl-5'-aminomethyl-spiro[piperidine-4,3'-(2H)-benzo[b]furan], 1-(3-benzylthio-benzo[c]thien-1-yl)carbonyl-5'-aminomethyl-spiro[piperidine-4,3'-(2H)-benzo[b]furan], 1-(3-benzylthio-7-hydro-6H-benzo[c]thien-1-yl)carbonyl-5'-aminomethyl-spiro[piperidine-4,3'-(2H)-benzo[b]furan], (Z)-1-(furan-2-ylethenyl)carbonyl-5'-aminomethyl-spiro[piperidine-4,3'-(2H)-benzo[b]furan], (Z)-1-(imidazol-4-ylethenyl)carbonyl-5'-aminomethyl-spiro[piperidine-4,3'-(2H)-benzo[b]furan], (E)-1-(pyridin-4-ylethenyl)carbonyl-5'-aminomethyl-spiro[piperidine-4,3'-(2H)-benzo[b]furan], 1-(5-formyl-thien-2-yl)carbonyl-5'-aminomethyl-spiro[piperidine-4,3'-(2H)-benzo[b]furan], 1-(5,6-dihydro-4H-cyclopenta[b]thien-2-yl)carbonyl-5'-aminomethyl-spiro[piperidine-4,3'-(2H)-benzo[b]furan], 1-(5-methylthio-thien-2-yl)carbonyl-5'-aminomethyl-spiro[piperidine-4,3'-(2H)-benzo[b]furan], (E)-1-(1-cyano-2-phenylethenyl)carbonyl-5'-aminomethyl-spiro[piperidine-4,3'-(2H)-benzo[b]furan], 1-(7-methyl-indol-3-yl)carbonyl-5'-aminomethyl-spiro[piperidine-4,3'-(2H)-benzo[b]furan], 1-(1-ethyl-7-methyl-indol-3-yl)carbonyl-5'-aminomethyl-spiro[piperidine-4,3'-(2H)-benzo[b]furan], (E)-1-(furan-3-ylethenyl)carbonyl-5'-aminomethyl-spiro[piperidine-4,3'-(2H)-benzo[b]furan], (E)-1-(pyridin-2-ylethenyl)carbonyl-5'-aminomethyl-spiro[piperidine-4,3'-(2H)-benzo[b]furan], (E)-1-(pyridin-3-ylethenyl)carbonyl-5'-aminomethyl-spiro[piperidine-4,3'-(2H)-benzo[b]furan], (E)-1-(thien-2-ylethenyl)carbonyl-5'-aminomethyl-spiro[piperidine-4,3'-(2H)-benzo[b]furan], (E)-1-(thien-3-ylethenyl)carbonyl-5'-aminomethyl-spiro[piperidine-4,3'-(2H)-benzo[b]furan], 1-(5-dihydroxymethyl-4-methyl-thien-2-yl)carbonyl-5'-aminomethyl-spiro[piperidine-4,3'-(2H)-benzo[b]furan],
1-(5,6,7,8-tetrahydro-4H-cyclohepta[b]thien-2-yl)carbonyl-5'-aminomethyl-spiro[piperidine-4,3'-(2H)-benzo[b]furan],
1-(4-cyano-5-methylthio-thien-2-yl)carbonyl-5'-aminomethyl-spiro[piperidine-4,3'-(2H)-benzo[b]furan],
1-(4-methyl-5-bromo-thien-2-yl)carbonyl-5'-aminomethyl-spiro[piperidine-4,3'-(2H)-benzo[b]furan],
spiro[cyclohexane-1,6'-5,7-dihydro-4H-benzo[b]thiophene]-2'-carbonyl-5'-aminomethyl-spiro[piperidine-4,3'-(2H)-benzo[b]furan],
1-(3-ethoxy-4-oxo-5,6,7-trihydro-4H-benzo[c]thien-1-yl)carbonyl-5'-aminomethyl-spiro[piperidine-4,3'-(2H)-benzo[b]furan],
1-(3,4-dichlorophenyl)carbonyl-2-oxo-5'-aminomethyl-spiro[piperidine-4,3'-(2H)-benzo[b]furan],
1-benzylaminocarbonyl-5'-aminomethyl-spiro[piperidine-4,3'-(2H)-benzo[b]furan],
1-(4-hydroxy-phenylethynyl)carbonyl-5'-aminomethyl-spiro[piperidine-4,3'-(2H)-benzo[b]furan],
(E)-1-(3-hydroxy-phenylethenyl)carbonyl-5'-aminomethyl-spiro[piperidine-4,3'-(2H)-benzo[b]furan],
1-(5-tert-butyl-thien-2-yl)carbonyl-5'-aminomethyl-spiro[piperidine-4,3'-(2H)-benzo[b]furan],
1-(5-methoxycarbonyl-thien-2-yl)carbonyl-5'-aminomethyl-spiro[piperidine-4,3'-(2H)-benzo[b]furan],
(E)-1-(4-tert-butyl-phenylethenyl)carbonyl-5'-aminomethyl-spiro[piperidine-4,3'-(2H)-benzo[b]furan],
1-fluoren-1-ylcarbonyl-5'-aminomethyl-spiro[piperidine-4,3'-(2H)-benzo[b]furan],
1-(9-oxo-fluoren-1-yl)carbonyl-5'-aminomethyl-spiro[piperidine-4,3'-(2H)-benzo[b]furan],
1-(3-chloro-6-ethyl-benzo[b]thien-2-yl)carbonyl-5'-aminomethyl-spiro[piperidine-4,3'-(2H)-benzo[b]furan],
(E)-1-(2-hydroxy-phenylethenyl)carbonyl-5'-aminomethyl-spiro[piperidine-4,3'-(2H)-benzo[b]furan],
1-(3-aminocarbonyl-phenyl)carbonyl-5'-aminomethyl-spiro[piperidine-4,3'-(2H)-benzo[b]furan],
1-(3-tert-butyl-phenyl)carbonyl-5'-aminomethyl-spiro[piperidine-4,3'-(2H)-benzo[b]furan],
1-(3,4,5-trichloro-thien-2-yl)carbonyl-5'-aminomethyl-spiro[piperidine-4,3'-(2H)-benzo[b]furan],
1-(4-trifluoromethyl-6-methyl-1H-thieno[2,3-c]pyrazol-2-yl)carbonyl-5'-aminomethyl-spiro[piperidine-4,3'-(2H)-benzo[b]furan],
1-(3-thien-2-yl-[1,2,4]oxadiazol-5-yl)carbonyl-5'-aminomethyl-spiro[piperidine-4,3'-(2H)-benzo[b]furan],
1-(4,5-dibromo-thien-2-yl)carbonyl-5'-aminomethyl-spiro[piperidine-4,3'-(2H)-benzo[b]furan],
1-[4-(3,5-bis-trifluoromethyl-phenoxy)-phenyl]carbonyl-5'-aminomethyl-spiro[piperidine-4,3'-(2H)-benzo[b]furan],
1-(3,4-dichlorophenyl)sulfonyl-5'-aminomethyl-spiro[piperidine-4,3'-(2H)-benzo[b]furan],
(E)-1-(3-benzyloxy-phenylethenyl)carbonyl-5'-aminomethyl-spiro[piperidine-4,3'-(2H)-benzo[b]furan],
1-[5-(4-tert-butyl-phenylethynyl)-furan-2-yl]carbonyl-5'-aminomethyl-spiro[piperidine-4,3'-(2H)-benzo[b]furan],
1-(1-phenylsulfonyl-1H-indol-2-yl)carbonyl-5'-aminomethyl-spiro[piperidine-4,3'-(2H)-benzo[b]furan],
1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan],
1-1H-indol-2-ylcarbonyl-5'-aminomethyl-spiro[piperidine-4,3'-(2H)-benzo[b]furan],
1-3H-inden-1-ylcarbonyl-5'-aminomethyl-spiro[piperidine-4,3'-(2H)-benzo[b]furan],
1-(3-oxo-indan-1-yl)carbonyl-5'-aminomethyl-spiro[piperidine-4,3'-(2H)-benzo[b]furan],
1-(4-phenyl-thien-2-yl)carbonyl-5'-aminomethyl-spiro[piperidine-4,3'-(2H)-benzo[b]furan],
1-fluoren-9-ylcarbonyl-5'-aminomethyl-spiro[piperidine-4,3'-(2H)-benzo[b]furan],
1-(1-oxo-2,2-diphenyl-ethyl)-5'-aminomethyl-spiro[piperidine-4,3'-(2H)-benzo[b]furan],
(E)-1-[3-(2-methoxy-ethoxy)-phenylethenyl]carbonyl-5'-aminomethyl-spiro[piperidine-4,3'-(2H)-benzo[b]furan],
1-9H-xanthen-9-ylcarbonyl-5'-aminomethyl-spiro[piperidine-4,3'-(2H)-benzo[b]furan],
1-9H-xanthen-9-ylmethylcarbonyl-5'-aminomethyl-spiro[piperidine-4,3'-(2H)-benzo[b]furan],
(E)-1-(3-phenethoxy-phenylethenyl)carbonyl-5'-aminomethyl-spiro[piperidine-4,3'-(2H)-benzo[b]furan],
1-(4-phenyl-5-trifluoromethyl-thien-2-yl)carbonyl-5'-aminomethyl-spiro[piperidine-4,3'-(2H)-benzo[b]furan],
1-phenylethynylcarbonyl-5'-aminomethyl-spiro[piperidine-4,3'-(2H)-benzo[b]furan],
1-(1-chloro-naphtho[2,1-b]thien-2-yl)carbonyl-5'-aminomethyl-spiro[piperidine-4,3'-(2H)-benzo[b]furan],
1-[3-(4-chloro-phenyl)-5-methylthio-thien-2-yl]carbonyl-5'-aminomethyl-spiro[piperidine-4,3'-(2H)-benzo[b]furan],
(E)-1-(4-benzyloxy-phenylethenyl)carbonyl-5'-aminomethyl-spiro[piperidine-4,3'-(2H)-benzo[b]furan],
(E)-1-[3-(3-methoxy-propoxy)-phenylethenyl]carbonyl-5'-aminomethyl-spiro[piperidine-4,3'-(2H)-benzo[b]furan],
(E)-1-[3-(2-ethoxy-ethoxy)-phenylethenyl]carbonyl-5'-aminomethyl-spiro[piperidine-4,3'-(2H)-benzo[b]furan],
1-(3-methyl-4-bromo-5-propoxy-thien-2-yl)carbonyl-5'-aminomethyl-spiro[piperidine-4,3'-(2H)-benzo[b]furan],
1-(5-phenylethynyl-furan-2-yl)carbonyl-5'-formylaminomethyl-spiro[piperidine-4,3'-(2H)-benzo[b]furan],
1-(5-phenylethynyl-furan-2-yl)carbonyl-5'-[hydroxyamino(imino)methyl]-spiro[piperidine-4,3'-(2H)-benzo[b]furan],
1-(5-phenylethynyl-furan-2-yl)carbonyl-5'-[hydrazino(imino)methyl]-spiro[piperidine-4,3'-(2H)-benzo[b]furan],
1-(3,4-dichlorophenyl)carbonyl-5'-aminomethyl-6'-fluoro-spiro[piperidine-4,3'-(2H)-benzo[b]furan],
(E)-1-(2-fluoro-phenylethenyl)carbonyl-5'-aminomethyl-spiro[piperidine-4,3'-(2H)-benzo[b]furan],
1-(5-phenylethynyl-furan-2-yl)carbonyl-5'-[methylamino(imino)methyl]-spiro[piperidine-4,3'-(2H)-benzo[b]furan],
1-(5-phenylethynyl-furan-2-yl)carbonyl-5'-aminomethyl-6'-fluoro-spiro[piperidine-4,3'-(2H)-benzo[b]furan],
(E)-1 (2,3-difluoro-phenylethenyl)carbonyl-5'-aminomethyl-spiro[piperidine-4,3'-(2H)-benzo[b]furan],
1-(5-phenylethynyl-furan-2-yl)carbonyl-5'-[dimethylamino(imino)methyl]-spiro[piperidine-4,3'-(2H)-benzo[b]furan],
1-(5-phenylethynyl-furan-2-yl)carbonyl-5'-aminoethyl-spiro[piperidine-4,3'-(2H)-benzo[b]furan].

7. The compound of claim 6, wherein
1-(3,4-dichlorophenyl)carbonyl-5'-aminomethyl-spiro[piperidine-4,3'-(2H)-benzo[b]furan],
1-(5-phenylethynyl-furan-2-yl)carbonyl-5'-aminomethyl-spiro[piperidine-4,3'-(2H)-benzo[b]furan],
1-(3-benzoyl-phenyl)carbonyl-5'-aminomethyl-spiro[piperidine-4,3'-(2H)-benzo[b]furan],
1-(3-aminothiocarbonylamino-phenyl)carbonyl-5'-aminomethyl-spiro[piperidine-4,3'-(2H)-benzo[b]furan],
1-(9-oxo-10,10-dioxo-thioxanthen-3-yl)carbonyl-5'-aminomethyl-spiro[piperidine-4,3'-(2H)-benzo[b]furan],
1-[5-(4-chloro-phenyl)-furan-2-yl]carbonyl-5'-aminomethyl-spiro[piperidine-4,3'-(2H)-benzo[b]furan],
1-benzothiazol-6-ylcarbonyl-5'-aminomethyl-spiro[piperidine-4,3'-(2H)-benzo[b]furan],
1-{4-[(4-benzoxazol-2-yl)-pyrazol-1-yl]-phenyl}carbonyl-5'-aminomethyl-spiro[piperidine-4,3'-(2H)-benzo[b]furan],
1-(3-thien-2-ylmethylcarbonylamino-phenyl)carbonyl-5'-aminomethyl-spiro[piperidine-4,3'-(2H)-benzo[b]furan],
1-(3-benzodioxol-5-yl-phenyl)carbonyl-5'-aminomethyl-spiro[piperidine-4,3'-(2H)-benzo[b]furan],
1-[3-(5-chloro-pyrimidin-2-yl)thiophenyl]carbonyl-5'-aminomethyl-spiro[piperidine-4,3'-(2H)-benzo[b]furan],
1-[(5-phenylthio)-furan-2-yl]carbonyl-5'-aminomethyl-spiro[piperidine-4,3'-(2H)-benzo[b]furan],
1-(3,4-dimethyl-phenyl)carbonyl-5'-aminomethyl-spiro[piperidine-4,3'-(2H)-benzo[b]furan],
1-(3-methyl-4-chloro-phenyl)carbonyl-5'-aminomethyl-spiro[piperidine-4,3'-(2H)-benzo[b]furan],
1-(3,4-difluoro-phenyl)carbonyl-5'-aminomethyl-spiro[piperidine-4,3'-(2H)-benzo[b]furan],
1-(3-chloro-4-fluoro-phenyl)carbonyl-5'-aminomethyl-spiro[piperidine-4,3'-(2H)-benzo[b]furan],
1-(3-chloro-4-methoxy-phenyl)carbonyl-5'-aminomethyl-spiro[piperidine-4,3'-(2H)-benzo[b]furan],
1-(3-bromo-phenyl)carbonyl-5'-aminomethyl-spiro[piperidine-4,3'-(2H)-benzo[b]furan],
1-(3-methyl-4-bromo-phenyl)carbonyl-5'-aminomethyl-spiro[piperidine-4,3'-(2H)-benzo[b]furan],
1-(3-bromo-4-fluoro-phenyl)carbonyl-5'-aminomethyl-spiro[piperidine-4,3'-(2H)-benzo[b]furan],
1-(3-bromo-4-methoxy-phenyl)carbonyl-5'-aminomethyl-spiro[piperidine-4,3'-(2H)-benzo[b]furan],
1-(3-nitro-4-bromo-phenyl)carbonyl-5'-aminomethyl-spiro[piperidine-4,3'-(2H)-benzo[b]furan],
1-(3-iodo-4-chloro-phenyl)carbonyl-5'-aminomethyl-spiro[piperidine-4,3'-(2H)-benzo[b]furan],
1-[5-(2-fluoro-phenylethynyl)-furan-2-yl]carbonyl-5'-aminomethyl-spiro[piperidine-4,3'-(2H)-benzo[b]furan],
1-phenylcarbonyl-5'-aminomethyl-spiro[piperidine-4,3'-(2H)-benzo[b]furan],
1-cyclohexylcarbonyl-5'-aminomethyl-spiro[piperidine-4,3'-(2H)-benzo[b]furan],
1-(trans-4-methyl-cyclohexyl)carbonyl-5'-aminomethyl-spiro[piperidine-4,3'-(2H)-benzo[b]furan],
1-(3,4-dimethoxy-phenyl)carbonyl-5'-aminomethyl-spiro[piperidine-4,3'-(2H)-benzo[b]furan],
1-(3-methyl-phenyl)carbonyl-5'-aminomethyl-spiro[piperidine-4,3'-(2H)-benzo[b]furan],
1-(3-fluoro-phenyl)carbonyl-5'-aminomethyl-spiro[piperidine-4,3'-(2H)-benzo[b]furan],
1-(4-fluoro-phenyl)carbonyl-5'-aminomethyl-spiro[piperidine-4,3'-(2H)-benzo[b]furan],
1-(4-chloro-phenyl)carbonyl-5'-aminomethyl-spiro[piperidine-4,3'-(2H)-benzo[b]furan],
1-(4-methylthio-phenyl)carbonyl-5'-aminomethyl-spiro[piperidine-4,3'-(2H)-benzo[b]furan],
1-(3-fluoro-4-chloro-phenyl)carbonyl-5'-aminomethyl-spiro[piperidine-4,3'-(2H)-benzo[b]furan],
1-(3-trifluoromethyl-phenyl)carbonyl-5'-aminomethyl-spiro[piperidine-4,3'-(2H)-benzo[b]furan],
1-(3-iodo-phenyl)carbonyl-5'-aminomethyl-spiro[piperidine-4,3'-(2H)-benzo[b]furan],
1-(4-iodo-phenyl)carbonyl-5'-aminomethyl-spiro[piperidine-4,3'-(2H)-benzo[b]furan],
1-(3-iodo-4-methyl-phenyl)carbonyl-5'-aminomethyl-spiro[piperidine-4,3'-(2H)-benzo[b]furan],
1-(3-methyl-4-iodo-phenyl)carbonyl-5'-aminomethyl-spiro[piperidine-4,3'-(2H)-benzo[b]furan],
1-(3-iodo-4-methoxy-phenyl)carbonyl-5'-aminomethyl-spiro[piperidine-4,3'-(2H)-benzo[b]furan],
1-(3-methoxy-phenyl)carbonyl-5'-aminomethyl-spiro[piperidine-4,3'-(2H)-benzo[b]furan],
1-(4-methoxy-phenyl)carbonyl-5'-aminomethyl-spiro[piperidine-4,3'-(2H)-benzo[b]furan],
1-(3-dimethylamino-phenyl)carbonyl-5'-aminomethyl-spiro[piperidine-4,3'-(2H)-benzo[b]furan],
1-(3-methylthio-phenyl)carbonyl-5'-aminomethyl-spiro[piperidine-4,3'-(2H)-benzo[b]furan],
1-(4-methoxycarbonyl-phenyl)carbonyl-5'-aminomethyl-spiro[piperidine-4,3'-(2H)-benzo[b]furan],
1-(4-bromo-phenyl)carbonyl-5'-aminomethyl-spiro[piperidine-4,3'-(2H)-benzo[b]furan],
1-(4-phenoxy-phenyl)carbonyl-5'-aminomethyl-spiro[piperidine-4,3'-(2H)-benzo[b]furan],
1-(3-trifluoromethylthio-phenyl)carbonyl-5'-aminomethyl-spiro[piperidine-4,3'-(2H)-benzo[b]furan],
1-[3-(4-methoxy-phenyl)-phenyl]carbonyl-5'-aminomethyl-spiro[piperidine-4,3'-(2H)-benzo[b]furan],
1-(5-phenylethynyl-furan-2-yl)carbonyl-5'-aminoiminomethyl-spiro[piperidine-4,3'-(2H)-benzo[b]furan],
1-benzodioxol-5-ylcarbonyl-5'-aminomethyl-spiro[piperidine-4,3'-(2H)-benzo[b]furan],
1-naphthalen-2-ylcarbonyl-5'-aminomethyl-spiro[piperidine-4,3'-(2H)-benzo[b]furan],
1-(4-trifluoromethyl-phenyl)carbonyl-5'-aminomethyl-spiro[piperidine-4,3'-(2H)-benzo[b]furan],
1-(3-methylsulfonyl-phenyl)carbonyl-5'-aminomethyl-spiro[piperidine-4,3'-(2H)-benzo[b]furan],
1-(3-trifluoromethyl-4-fluoro-phenyl)carbonyl-5'-aminomethyl-spiro[piperidine-4,3'-(2H)-benzo[b]furan],
1-(4-benzyl-phenyl)carbonyl-5'-aminomethyl-spiro[piperidine-4,3'-(2H)-benzo[b]furan],
1-(4-benzyloxy-phenyl)carbonyl-5'-aminomethyl-spiro[piperidine-4,3'-(2H)-benzo[b]furan],
(Z)-1-(5-phenylethenyl-furan-2-yl)carbonyl-5'-aminomethyl-spiro[piperidine-4,3'-(2H)-benzo[b]furan],
1-(3,4-dichloro-benzyl)carbonyl-5'-aminomethyl-spiro[piperidine-4,3'-(2H)-benzo[b]furan],
1-(3-phenoxy-benzyl)carbonyl-5'-aminomethyl-spiro[piperidine-4,3'-(2H)-benzo[b]furan],
1-(4-fluoro-benzyl)carbonyl-5'-aminomethyl-spiro[piperidine-4,3'-(2H)-benzo[b]furan],
1-(4-chloro-benzyl)carbonyl-5'-aminomethyl-spiro[piperidine-4,3'-(2H)-benzo[b]furan],
1-(4-phenyl-benzyl)carbonyl-5'-aminomethyl-spiro[piperidine-4,3'-(2H)-benzo[b]furan],
1-(4-bromo-benzyl)carbonyl-5'-aminomethyl-spiro[piperidine-4,3'-(2H)-benzo[b]furan], 1-(4-methoxy-benzyl)carbonyl-5'-aminomethyl-spiro[piperidine-4,3'-(2H)-benzo[b]furan],
1-(4-iodo-benzyl)carbonyl-5'-aminomethyl-spiro[piperidine-4,3'-(2H)-benzo[b]furan],
1-(3-methoxy-benzyl)carbonyl-5'-aminomethyl-spiro[piperidine-4,3'-(2H)-benzo[b]furan],
1-benzodioxol-5-ylmethylcarbonyl-5'-aminomethyl-spiro[piperidine-4,3'-(2H)-benzo[b]furan],
1-(3-methyl-4-methoxy-benzyl)carbonyl-5'-aminomethyl-spiro[piperidine-4,3'-(2H)-benzo[b]furan],
1-(3-methylthio-benzyl)carbonyl-5'-aminomethyl-spiro[piperidine-4,3'-(2H)-benzo[b]furan],
1-(3,4-dimethoxy-benzyl)carbonyl-5'-aminomethyl-spiro[piperidine-4,3'-(2H)-benzo[b]furan],
1-(3-methoxy-4-benzyloxy-benzyl)carbonyl-5'-aminomethyl-spiro[piperidine-4,3'-(2H)-benzo[b]furan],
1-(5-phenethyl-furan-2-yl)carbonyl-5'-aminomethyl-spiro[piperidine-4,3'-(2H)-benzo[b]furan],
1-(phenylethynyl)carbonyl-5'-aminomethyl-spiro[piperidine-4,3'-(2H)-benzo[b]furan],
(E)-1-(phenylethenyl)carbonyl-5'-aminomethyl-spiro[piperidine-4,3'-(2H)-benzo[b]furan],
1-benzothien-2-ylcarbonyl-5'-aminomethyl-spiro[piperidine-4,3'-(2H)-benzo[b]furan],
(E)-1-(3,4-difluoro-phenylethenyl)carbonyl-5'-aminomethyl-spiro[piperidine-4,3'-(2H)-benzo[b]furan],
(E)-1-(phenylethenyl)carbonyl-5'-aminomethyl-spiro[piperidine-4,3'-(2H)-benzo[b]furan],
(E)-1-(naphthalene-2-ylethenyl)carbonyl-5'-aminomethyl-spiro[piperidine-4,3'-(2H)-benzo[b]furan],
1-(5-phenyl-thien-2-yl)carbonyl-5'-aminomethyl-spiro[piperidine-4,3'-(2H)-benzo[b]furan],
1-(3-phenoxy-phenyl)carbonyl-5'-aminomethyl-spiro[piperidine-4,3'-(2H)-benzo[b]furan],
(E)-1-(3,4-dichloro-phenylethenyl)carbonyl-5'-aminomethyl-spiro[piperidine-4,3'-(2H)-benzo[b]furan],
(E)-1-(4-phenyl-phenylethenyl)carbonyl-5'-aminomethyl-spiro[piperidine-4,3'-(2H)-benzo[b]furan],
1-(2,4-dimethyl-thiazol-5-yl)carbonyl-5'-aminomethyl-spiro[piperidine-4,3'-(2H)-benzo[b]furan],
1-(5-pyridin-2-yl-thien-2-yl)carbonyl-5'-aminomethyl-spiro[piperidine-4,3'-(2H)-benzo[b]furan],
1-(2-pyridin-3-yl-thiazol-4-yl)carbonyl-5'-aminomethyl-spiro[piperidine-4,3'-(2H)-benzo[b]furan],
1-(2-pyridin-4-yl-thiazol-4-yl)carbonyl-5'-aminomethyl-spiro[piperidine-4,3'-(2H)-benzo[b]furan],
1-(2-phenyl-4-methyl-thiazol-5-yl)carbonyl-5'-aminomethyl-spiro[piperidine-4,3'-(2H)-benzo[b]furan],
1-(6-bromo-naphthalen-2-yl)carbonyl-5'-aminomethyl-spiro[piperidine-4,3'-(2H)-benzo[b]furan],
1-[2-(4-trifluoromethyl-phenyl)-4-methyl-thiazol-5-yl]carbonyl-5'-aminomethyl-spiro[piperidine-4,3'-(2H)-benzo[b]furan],
1-[5-(2-chloro-5-trifluoromethyl-phenyl)-furan-2-yl]carbonyl-5'-aminomethyl-spiro[piperidine-4,3'-(2H)-benzo[b]furan],
1-(5-phenyl-furan-2-yl)carbonyl-5'-aminomethyl-spiro[piperidine-4,3'-(2H)-benzo[b]furan],
1-[5-(4-methyl-phenyl)-furan-2-yl]carbonyl-5'-aminomethyl-spiro[piperidine-4,3'-(2H)-benzo[b]furan],
1-[5-(4-methoxy-phenyl)-furan-2-yl]carbonyl-5'-aminomethyl-spiro[piperidine-4,3'-(2H)-benzo[b]furan],
1-(3,5-di-tert-butyl-phenyl)carbonyl-5'-aminomethyl-spiro[piperidine-4,3'-(2H)-benzo[b]furan],
1-[5-(3-chloro-phenoxymethyl)-furan-2-yl]carbonyl-5'-aminomethyl-spiro[piperidine-4,3'-(2H)-benzo[b]furan],
1-[5-(3-trifluoromethyl-phenyl)-furan-2-yl]carbonyl-5'-aminomethyl-spiro[piperidine-4,3'-(2H)-benzo[b]furan],
1-[5-(2,4-dichloro-phenyl)-furan-2-yl]carbonyl-5'-aminomethyl-spiro[piperidine-4,3'-(2H)-benzo[b]furan],
1-[5-(2,5-dichloro-phenyl)-furan-2-yl]carbonyl-5'-aminomethyl-spiro[piperidine-4,3'-(2H)-benzo[b]furan],
1-[5-(3,4-dichloro-phenyl)-furan-2-yl]carbonyl-5'-aminomethyl-spiro[piperidine-4,3'-(2H)-benzo[b]furan],
1-[5-(3-methyl-4-chloro-phenoxymethyl)-furan-2-yl]carbonyl-5'-aminomethyl-spiro[piperidine-4,3'-(2H)-benzo[b]furan],
1-[5-(4-bromo-phenyl)-furan-2-yl]carbonyl-5'-aminomethyl-spiro[piperidine-4,3'-(2H)-benzo[b]furan],
1-(trans-2-phenyl-cyclopropyl)carbonyl-5'-aminomethyl-spiro[piperidine-4,3'-(2H)-benzo[b]furan],
1-(5-phenyl-pyridin-3-yl)carbonyl-5'-aminomethyl-spiro[piperidine-4,3'-(2H)-benzo[b]furan],
1-(5-thien-2-yl-pyridin-3-yl)carbonyl-5'-aminomethyl-spiro[piperidine-4,3'-(2H)-benzo[b]furan],
1-[5-(3-methoxy-phenyl)-furan-2-yl]carbonyl-5'-aminomethyl-spiro[piperidine-4,3'-(2H)-benzo[b]furan],
1-[5-(4-chloro-pyrazol-1-ylmethyl)-furan-2-yl]carbonyl-5'-aminomethyl-spiro[piperidine-4,3'-(2H)-benzo[b]furan],
1-[5-(2-chloro-phenylethynyl)-furan-2-yl]carbonyl-5'-aminomethyl-spiro[piperidine-4,3'-(2H)-benzo[b]furan],
1-[5-(benzylthiomethyl)-furan-2-yl]carbonyl-5'-aminomethyl-spiro[piperidine-4,3'-(2H)-benzo[b]furan],
1-[5-(4,6-dimethyl-pyrimidin-2-ylthiomethyl)-furan-2-yl]carbonyl-5'-aminomethyl-spiro[piperidine-4,3'-(2H)-benzo[b]furan],
1-[5-(3,5-dichloro-phenoxy)-furan-2-yl]carbonyl-5'-aminomethyl-spiro[piperidine-4,3'-(2H)-benzo[b]furan],
1-[5-(3,5-dimethyl-4-bromo-pyrazol-1-yl)-furan-2-yl]carbonyl-5'-aminomethyl-spiro[piperidine-4,3'-(2H)-benzo[b]furan],
1-[5-(5-trifluoromethyl-pyridin-2-ylthiomethyl)-furan-2-yl]carbonyl-5'-aminomethyl-spiro[piperidine-4,3'-(2H)-benzo[b]furan],
1-[4-phenylethynyl-pyridin-2-yl]carbonyl-5'-aminomethyl-spiro[piperidine-4,3'-(2H)-benzo[b]furan],
1-[5-(2-methyl-phenylethynyl)-furan-2-yl]carbonyl-5'-aminomethyl-spiro[piperidine-4,3'-(2H)-benzo[b]furan],
1-[5-(4-fluoro-phenoxymethyl)-furan-2-yl]carbonyl-5'-aminomethyl-spiro[piperidine-4,3'-(2H)-benzo[b]furan],
1-(3-methylthio-4-oxo-5,6,7-trihydro-4H-benzo[c]thien-1-yl)carbonyl-5'-aminomethyl-spiro[piperidine-4,3'-(2H)-benzo[b]furan],
1-[5-(2,5-dimethyl-furan-3-yl-carbonylaminomethyl)-furan-2-yl]carbonyl-5'-aminomethyl-spiro[piperidine-4,3'-(2H)-benzo[b]furan],
1-(3-chloro-4-isopropylsulfonyl-5-methylthio-thien-2-yl)carbonyl-5'-aminomethyl-spiro[piperidine-4,3'-(2H)-benzo[b]furan],
1-thien-2-ylcarbonyl-5'-aminomethyl-spiro[piperidine-4,3'-(2H)-benzo[b]furan],
1-benzo[b]furan-2-ylcarbonyl-5'-aminomethyl-spiro[piperidine-4,3'-(2H)-benzo[b]furan],
(E)-1-(3-fluoro-phenylethenyl)carbonyl-5'-aminomethyl-spiro[piperidine-4,3'-(2H)-benzo[b]furan],
(Z)-1-(1-fluoro-2-phenylethenyl)carbonyl-5'-aminomethyl-spiro[piperidine-4,3'-(2H)-benzo[b]furan], 1-(5,6,7-trihydro-4H-benzo[b]thien-2-yl)carbonyl-5'-aminomethyl-spiro[piperidine-4,3'-(2H)-benzo[b]furan],
(E)-1-(3-chloro-phenylethenyl)carbonyl-5'-aminomethyl-spiro[piperidine-4,3'-(2H)-benzo[b]furan],
(E)-1-(4-chloro-phenylethenyl)carbonyl-5'-aminomethyl-spiro[piperidine-4,3'-(2H)-benzo[b]furan],
1-(3-chloro-benzo[b]thien-2-yl)carbonyl-5'-aminomethyl-spiro[piperidine-4,3'-(2H)-benzo[b]furan],
(E)-1-(3-trifluoromethoxy-phenylethenyl)carbonyl-5'-aminomethyl-spiro[piperidine-4,3'-(2H)-benzo[b]furan],
1-(4-fluoro-benzo[b]thien-2-yl)carbonyl-5'-aminomethyl-spiro[piperidine-4,3'-(2H)-benzo[b]furan],
1-[5-(4-methyl-phenylethynyl)-furan-2-yl]carbonyl-5'-aminomethyl-spiro[piperidine-4,3'-(2H)-benzo[b]furan],
1-(3-chloro-6-fluoro-benzo[b]thien-2-yl)carbonyl-5'-aminomethyl-spiro[piperidine-4,3'-(2H)-benzo[b]furan],
1-[5-(2,5-dimethyl-phenylethynyl)-furan-2-yl]carbonyl-5'-aminomethyl-spiro[piperidine-4,3'-(2H)-benzo[b]furan],
1-[5-(2-methoxy-phenylethynyl)-furan-2-yl]carbonyl-5'-aminomethyl-spiro[piperidine-4,3'-(2H)-benzo[b]furan],
1-[5-(2,5-dimethyl-phenoxymethyl)-furan-2-yl]carbonyl-5'-aminomethyl-spiro[piperidine-4,3'-(2H)-benzo[b]furan],
1-(3,4-dichloro-benzo[b]thien-2-yl)carbonyl-5'-aminomethyl-spiro[piperidine-4,3'-(2H)-benzo[b]furan],
1-[5-(3,5-difluoro-phenylethynyl)-furan-2-yl]carbonyl-5'-aminomethyl-spiro[piperidine-4,3'-(2H)-benzo[b]furan],
1-(5-naphthalen-1-ylethenyl-furan-2-yl)carbonyl-5'-aminomethyl-spiro[piperidine-4,3'-(2H)-benzo[b]furan],
1-[5-(4-tert-butyl-phenoxymethyl)-furan-2-yl]carbonyl-5'-aminomethyl-spiro[piperidine-4,3'-(2H)-benzo[b]furan],
(E)-1-(3-methyl-phenylethenyl)carbonyl-5'-aminomethyl-spiro[piperidine-4,3'-(2H)-benzo[b]furan],
(E)-1-(4-methyl-phenylethenyl)carbonyl-5'-aminomethyl-spiro[piperidine-4,3'-(2H)-benzo[b]furan],
(E)-1-(4-fluoro-phenylethenyl)carbonyl-5'-aminomethyl-spiro[piperidine-4,3'-(2H)-benzo[b]furan],
(E)-1-(3-methoxy-phenylethenyl)carbonyl-5'-aminomethyl-spiro[piperidine-4,3'-(2H)-benzo[b]furan],
(E)-1-(2-chloro-phenylethenyl)carbonyl-5'-aminomethyl-spiro[piperidine-4,3'-(2H)-benzo[b]furan],
(E)-1-(benzodioxol-5-ylethenyl)carbonyl-5'-aminomethyl-spiro[piperidine-4,3'-(2H)-benzo[b]furan],
(E)-1-(naphthalen-1-ylethenyl)carbonyl-5'-aminomethyl-spiro[piperidine-4,3'-(2H)-benzo[b]furan],
1-(1-oxo-2-fluoren-9-ylidene-ethyl)-5'-aminomethyl-spiro[piperidine-4,3'-(2H)-benzo[b]furan],
(E)-1-(1-phenyl-2-phenylethenyl)carbonyl-5'-aminomethyl-spiro[piperidine-4,3'-(2H)-benzo[b]furan],
(E)-1-(2-methyl-phenylethenyl)carbonyl-5'-aminomethyl-spiro[piperidine-4,3'-(2H)-benzo[b]furan],
1-(1-methyl-3H-inden-2-yl)carbonyl-5'-aminomethyl-spiro[piperidine-4,3'-(2H)-benzo[b]furan],
1-(1-methyl-indol-2-yl)carbonyl-5'-aminomethyl-spiro[piperidine-4,3'-(2H)-benzo[b]furan],
(E)-1-(2-methoxy-phenylethenyl)carbonyl-5'-aminomethyl-spiro[piperidine-4,3'-(2H)-benzo[b]furan],
(E)-1-(2,6-difluoro-phenylethenyl)carbonyl-5'-aminomethyl-spiro[piperidine-4,3'-(2H)-benzo[b]furan],
1-(2-oxo-(2H)-chromen-3-yl)carbonyl-5'-aminomethyl-spiro[piperidine-4,3'-(2H)-benzo[b]furan],
1-(8-methoxy-(2H)-chromen-3-yl)carbonyl-5'-aminomethyl-spiro[piperidine-4,3'-(2H)-benzo[b]furan],
1-(5-bromo-thien-2-yl)carbonyl-5'-aminomethyl-spiro[piperidine-4,3'-(2H)-benzo[b]furan],
(E)-1-(2-bromo-phenylethenyl)carbonyl-5'-aminomethyl-spiro[piperidine-4,3'-(2H)-benzo[b]furan],
1-[3-(4-methoxy-phenyl)-4-cyano-5-methylthio-thien-2-yl]carbonyl-5'-aminomethyl-spiro[piperidine-4,3'-(2H)-benzo[b]furan],
1-[3-(4-chloro-phenyl)-4-cyano-5-methylthio-thien-2-yl]carbonyl-5'-aminomethyl-spiro[piperidine-4,3'-(2H)-benzo[b]furan],
1-(5,6,7-trihydro-4H-benzo[c]thien-1-yl)carbonyl-5'-aminomethyl-spiro[piperidine-4,3'-(2H)-benzo[b]furan],
1-thieno[3,2-b]thien-2-ylcarbonyl-5'-aminomethyl-spiro[piperidine-4,3'-(2H)-benzo[b]furan],
(Z)-1-(1-methylcarbonylamino-2-phenylethenyl)carbonyl-5'-aminomethyl-spiro[piperidine-4,3'-(2H)-benzo[b]furan],
1-[5-(2-methyl-thiazol-4-yl)-thien-2-yl]carbonyl-5'-aminomethyl-spiro[piperidine-4,3'-(2H)-benzo[b]furan],
1-[3-(2-methyl-phenoxy)-benzyl]carbonyl-5'-aminomethyl-spiro[piperidine-4,3'-(2H)-benzo[b]furan],
1-[3-(2-fluoro-phenoxy)-benzyl]carbonyl-5'-aminomethyl-spiro[piperidine-4,3'-(2H)-benzo[b]furan],
1-(3-propylthio-4-oxo-5,6,7-trihydro-4H-benzo[c]thien-1-yl)carbonyl-5'-aminomethyl-spiro[piperidine-4,3'-(2H)-benzo[b]furan],
1-[5-(2-methoxy-4-propyl-phenoxymethyl)-furan-2-yl]carbonyl-5'-aminomethyl-spiro[piperidine-4,3'-(2H)-benzo[b]furan],
1-[5-(2-bromo-phenoxymethyl)-furan-2-yl]carbonyl-5'-aminomethyl-spiro[piperidine-4,3'-(2H)-benzo[b]furan],
1-(3-benzylthio-4-oxo-5,6,7-trihydro-4H-benzo[c]thien-1-yl)carbonyl-5'-aminomethyl-spiro[piperidine-4,3'-(2H)-benzo[b]furan],
1-[1-oxo-2-(3-oxo-3H-isobenzofuran-1-ylidene)-ethyl]-5'-aminomethyl-spiro[piperidine-4,3'-(2H)-benzo[b]furan],
1-(4-phenyl-[1,2,3]thiadiazol-5-yl)carbonyl-5'-aminomethyl-spiro[piperidine-4,3'-(2H)-benzo[b]furan],
1-(3-methylthio-5,6,7-trihydro-4H-benzo[c]thien-1-yl)carbonyl-5'-aminomethyl-spiro[piperidine-4,3'-(2H)-benzo[b]furan],
1-(3-methylthio-7-hydro-6H-benzo[c]thien-1-yl)carbonyl-5'-aminomethyl-spiro[piperidine-4,3'-(2H)-benzo[b]furan],
1-[5-(2-methyl-furan-3-yl-carbonylaminomethyl)-furan-2-yl]carbonyl-5'-aminomethyl-spiro[piperidine-4,3'-(2H)-benzo[b]furan],
1-[5-(3,5-dimethyl-4-chloro-pyrazol-1-yl)-furan-2-yl]carbonyl-5'-aminomethyl-spiro[piperidine-4,3'-(2H)-benzo[b]furan],
1-(3-methyl-4-oxo-6-phenyl-5,6,7-trihydro-4H-benzo[b]furan-2-yl)carbonyl-5'-aminomethyl-spiro[piperidine-4,3'-(2H)-benzo[b]furan],
1-(3-ethylthio-4-oxo-6,6-dimethyl-6,7-dihydro-5H-benzo[c]thien-1-yl)carbonyl-5'-aminomethyl-spiro[piperidine-4,3'-(2H)-benzo[b]furan],
1-[5-(2-methoxy-4-allyl-phenoxymethyl)-furan-2-yl]carbonyl-5'-aminomethyl-spiro[piperidine-4,3'-(2H)-benzo[b]furan], 1-(3-isopropylthio-4-oxo-6,6-dimethyl-6,7-dihydro-5H-benzo[c]thien-1-yl)carbonyl-5'-aminomethyl-spiro[piperidine-4,3'-(2H)-benzo[b]furan],
1-[5-(3-methoxy-phenoxymethyl)-furan-2-yl]carbonyl-5'-aminomethyl-spiro[piperidine-4,3'-(2H)-benzo[b]furan],
1-(3-methyl-6-phenyl-benzo[b]furan-2-yl)carbonyl-5'-aminomethyl-spiro[piperidine-4,3'-(2H)-benzo[b]furan],
1-(3-butylthio-4-oxo-5,6,7-tri hydro-4H-benzo[c]thien-1-yl)carbonyl-5'-aminomethyl-spiro[piperidine-4,3'-(2H)-benzo[b]furan],
1-(3-chloro-6-bromo-benzo[b]thien-2-yl)carbonyl-5'-aminomethyl-spiro[piperidine-4,3'-(2H)-benzo[b]furan],
1-(3-sec-butylthio-4-oxo-6,6-dimethyl-6,7-dihydro-5H-benzo[c]thien-1-yl)carbonyl-5'-aminomethyl-spiro[piperidine-4,3'-(2H)-benzo[b]furan],
1-(3-benzylthio-4-oxo-6,6-dimethyl-6,7-dihydro-5H-benzo[c]thien-1-yl)carbonyl-5'-aminomethyl-spiro[piperidine-4,3'-(2H)-benzo[b]furan],
1-thieno[2,3-b]thien-2-ylcarbonyl-5'-aminomethyl-spiro[piperidine-4,3'-(2H)-benzo[b]furan],
1-(3-methylthio-benzo[c]thien-1-yl)carbonyl-5'-aminomethyl-spiro[piperidine-4,3'-(2H)-benzo[b]furan],
1-(3-methylthio-4-methoxy-benzo[c]thien-1-yl)carbonyl-5'-aminomethyl-spiro[piperidine-4,3'-(2H)-benzo[b]furan],
1-indol-3-ylcarbonyl-5'-aminomethyl-spiro[piperidine-4,3'-(2H)-benzo[b]furan],
1-(1-methyl-indol-3-yl)carbonyl-5'-aminomethyl-spiro[piperidine-4,3'-(2H)-benzo[b]furan],
1-(5-methoxy-indol-3-yl)carbonyl-5'-aminomethyl-spiro[piperidine-4,3'-(2H)-benzo[b]furan],
1-(1-benzyl-indol-3-yl)carbonyl-5'-aminomethyl-spiro[piperidine-4,3'-(2H)-benzo[b]furan],
1-(3-benzylthio-benzo[c]thien-1-yl)carbonyl-5'-aminomethyl-spiro[piperidine-4,3'-(2H)-benzo[b]furan],
1-(3-benzylthio-7-hydro-6H-benzo[c]thien-1-yl)carbonyl-5'-aminomethyl-spiro[piperidine-4,3'-(2H)-benzo[b]furan],
(Z)-1-(furan-2-ylethenyl)carbonyl-5'-aminomethyl-spiro[piperidine-4,3'-(2H)-benzo[b]furan],
1-(5-formyl-thien-2-yl)carbonyl-5'-aminomethyl-spiro[piperidine-4,3'-(2H)-benzo[b]furan],
1-(5,6-dihydro-4H-cyclopenta[b]thien-2-yl)carbonyl-5'-aminomethyl-spiro[piperidine-4,3'-(2H)-benzo[b]furan],
1-(5-methylthio-thien-2-yl)carbonyl-5'-aminomethyl-spiro[piperidine-4,3'-(2H)-benzo[b]furan],
(E)-1-(1-cyano-2-phenylethenyl)carbonyl-5'-aminomethyl-spiro[piperidine-4,3'-(2H)-benzo[b]furan],
1-(7-methyl-indol-3-yl)carbonyl-5'-aminomethyl-spiro[piperidine-4,3'-(2H)-benzo[b]furan],
1-(1-ethyl-7-methyl-indol-3-yl)carbonyl-5'-aminomethyl-spiro[piperidine-4,3'-(2H)-benzo[b]furan],
(E)-1-(thien-2-ylethenyl)carbonyl-5'-aminomethyl-spiro[piperidine-4,3'-(2H)-benzo[b]furan],
(E)-1-(thien-3-ylethenyl)carbonyl-5'-aminomethyl-spiro[piperidine-4,3'-(2H)-benzo[b]furan],
1-(5-dihydroxymethyl-4-methyl-thien-2-yl)carbonyl-5'-aminomethyl-spiro[piperidine-4,3'-(2H)-benzo[b]furan],
1-(5,6,7,8-tetrahydro-4H-cyclohepta[b]thien-2-yl)carbonyl-5'-aminomethyl-spiro[piperidine-4,3'-(2H)-benzo[b]furan],
1-(4-cyano-5-methylthio-thien-2-yl)carbonyl-5'-aminomethyl-spiro[piperidine-4,3'-(2H)-benzo[b]furan],
1-(4-methyl-5-bromo-thien-2-yl)carbonyl-5'-aminomethyl-spiro[piperidine-4,3'-(2H)-benzo[b]furan],
1-(3-ethoxy-4-oxo-5,6,7-trihydro-4H-benzo[c]thien-1-yl)carbonyl-5'-aminomethyl-spiro[piperidine-4,3'-(2H)-benzo[b]furan],
(E)-1-(3-hydroxy-phenylethenyl)carbonyl-5'-aminomethyl-spiro[piperidine-4,3'-(2H)-benzo[b]furan],
1-(5-tert-butyl-thien-2-yl)carbonyl-5'-aminomethyl-spiro[piperidine-4,3'-(2H)-benzo[b]furan],
1-(5-methoxycarbonyl-thien-2-yl)carbonyl-5'-aminomethyl-spiro[piperidine-4,3'-(2H)-benzo[b]furan],
(E)-1-(2-hydroxy-phenylethenyl)carbonyl-5'-aminomethyl-spiro[piperidine-4,3'-(2H)-benzo[b]furan],
1-(3,4,5-trichloro-thien-2-yl)carbonyl-5'-aminomethyl-spiro[piperidine-4,3'-(2H)-benzo[b]furan],
1-(4-trifluoromethyl-6-methyl-1H-thieno[2,3-c]pyrazol-2-yl)carbonyl-5'-aminomethyl-spiro[piperidine-4,3'-(2H)-benzo[b]furan],
1-(3-thien-2-yl-[1,2,4]oxadiazol-5-yl)carbonyl-5'-aminomethyl-spiro[piperidine-4,3'-(2H)-benzo[b]furan],
1-(4,5-dibromo-thien-2-yl)carbonyl-5'-aminomethyl-spiro[piperidine-4,3'-(2H)-benzo[b]furan],
1-(3,4-dichlorophenyl)sulfonyl-5'-aminomethyl-spiro[piperidine-4,3'-(2H)-benzo[b]furan],
(E)-1-(3-benzyloxy-phenylethenyl)carbonyl-5'-aminomethyl-spiro[piperidine-4,3'-(2H)-benzo[b]furan],
1-[5-(4-tert-butyl-phenylethynyl)-furan-2-yl]carbonyl-5'-aminomethyl-spiro[piperidine-4,3'-(2H)-benzo[b]furan],
1-(1-phenylsulfonyl-1H-indol-2-yl)carbonyl-5'-aminomethyl-spiro[piperidine-4,3'-(2H)-benzo[b]furan],
1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan],
1-1H-indol-2-ylcarbonyl-5'-aminomethyl-spiro[piperidine-4,3'-(2H)-benzo[b]furan],
1-3H-inden-1-ylcarbonyl-5'-aminomethyl-spiro[piperidine-4,3'-(2H)-benzo[b]furan],
1-(4-phenyl-thien-2-yl)carbonyl-5'-aminomethyl-spiro[piperidine-4,3'-(2H)-benzo[b]furan],
1-(1-oxo-2,2-diphenyl-ethyl)-5'-aminomethyl-spiro[piperidine-4,3'-(2H)-benzo[b]furan],
(E)-1-[3-(2-methoxy-ethoxy)-phenylethenyl]carbonyl-5'-aminomethyl-spiro[piperidine-4,3'-(2H)-benzo[b]furan],
(E)-1-(3-phenethoxy-phenylethenyl)carbonyl-5'-aminomethyl-spiro[piperidine-4,3'-(2H)-benzo[b]furan],
1-(4-phenyl-5-trifluoromethyl-thien-2-yl)carbonyl-5'-aminomethyl-spiro[piperidine-4,3'-(2H)-benzo[b]furan],
1-(1-chloro-naphtho[2,1-b]thien-2-yl)carbonyl-5'-aminomethyl-spiro[piperidine-4,3'-(2H)-benzo[b]furan],
1-[3-(4-chloro-phenyl)-5-methylthio-thien-2-yl]carbonyl-5'-aminomethyl-spiro[piperidine-4,3'-(2H)-benzo[b]furan],
(E)-1-[3-(2-ethoxy-ethoxy)-phenylethenyl]carbonyl-5'-aminomethyl-spiro[piperidine-4,3'-(2H)-benzo[b]furan],
1-(3-methyl-4-bromo-5-propoxy-thien-2-yl)carbonyl-5'-aminomethyl-spiro[piperidine-4,3'-(2H)-benzo[b]furan],
1-(5-phenylethynyl-furan-2-yl)carbonyl-5'-formylaminomethyl-spiro[piperidine-4,3'-(2H)-benzo[b]furan], 1-(5-phenylethynyl-furan-2-yl)carbonyl-5'-[hydroxyamino(imino)methyl]-spiro[piperidine-4,3'-(2H)-benzo[b]furan], 1-(5-phenylethynyl-furan-2-yl)carbonyl-5'-[hydrazino(imino)methyl]-spiro[piperidine-4,3'-(2H)-benzo[b]furan], (E)-1-(2-fluoro-phenylethenyl)carbonyl-5'-aminomethyl-spiro[piperidine-4,3'-(2H)-benzo[b]furan], 1-(5-phenylethynyl-furan-2-yl)carbonyl-5'-[methylamino(imino)methyl]-spiro[piperidine-4,3'-(2H)-benzo[b]furan], 1-(5-phenylethynyl-furan-2-yl)carbonyl-5'-aminomethyl-6'-fluoro-spiro[piperidine-4,3'-(2H)-benzo[b]furan], and (E)-1-(2,3-difluoro-phenylethenyl)carbonyl-5'-aminomethyl-spiro[piperidine-4,3'-(2H)-benzo[b]furan].

8. The compound of claim 6, wherein 1-(5-phenylethynyl-furan-2-yl)carbonyl-5'-aminomethyl-spiro[piperidine-4,3'-(2H)-benzo[b]furan], 1-[5-(2-fluoro-phenylethynyl)-furan-2-yl]carbonyl-5'-aminomethyl-spiro[piperidine-4,3'-(2H)-benzo[b]furan], 1-(5-phenylethynyl-furan-2-yl)carbonyl-5'-aminoiminomethyl-spiro[piperidine-4,3'-(2H)-benzo[b]furan], 1-[5-(2-chloro-phenylethynyl)-furan-2-yl]carbonyl-5'-aminomethyl-spiro[piperidine-4,3'-(2H)-benzo[b]furan], 1-[4-phenylethynyl-pyridin-2-yl]carbonyl-5'-aminomethyl-spiro[piperidine-4,3'-(2H)-benzo[b]furan], 1-[5-(2-methyl-phenylethynyl)-furan-2-yl]carbonyl-5'-aminomethyl-spiro[piperidine-4,3'-(2H)-benzo[b]furan], 1-[5-(4-methyl-phenylethynyl)-furan-2-yl]carbonyl-5'-aminomethyl-spiro[piperidine-4,3'-(2H)-benzo[b]furan], 1-[5-(2,5-dimethyl-phenylethynyl)-furan-2-yl]carbonyl-5'-aminomethyl-spiro[piperidine-4,3'-(2H)-benzo[b]furan], 1-(3-benzylthio-4-oxo-5,6,7-trihydro-4H-benzo[c]thien-1-yl)carbonyl-5'-aminomethyl-spiro[piperidine-4,3'-(2H)-benzo[b]furan], 1-(3-methylthio-5,6,7-trihydro-4H-benzo[c]thien-1-yl)carbonyl-5'-aminomethyl-spiro[piperidine-4,3'-(2H)-benzo[b]furan], 1-(3-methylthio-7-hydro-6H-benzo[c]thien-1-yl)carbonyl-5'-aminomethyl-spiro[piperidine-4,3'-(2H)-benzo[b]furan], 1-(3-butylthio-4-oxo-5,6,7-trihydro-4H-benzo[c]thien-1-yl)carbonyl-5'-aminomethyl-spiro[piperidine-4,3'-(2H)-benzo[b]furan], 1-(3-methylthio-benzo[c]thien-1-yl)carbonyl-5'-aminomethyl-spiro[piperidine-4,3'-(2H)-benzo[b]furan], 1-(3-methylthio-4-methoxy-benzo[c]thien-1-yl)carbonyl-5'-aminomethyl-spiro[piperidine-4,3'-(2H)-benzo[b]furan], 1-(3-benzylthio-benzo[c]thien-1-yl)carbonyl-5'-aminomethyl-spiro[piperidine-4,3'-(2H)-benzo[b]furan], 1-(3-benzylthio-7-hydro-6H-benzo[c]thien-1-yl)carbonyl-5'-aminomethyl-spiro[piperidine-4,3'-(2H)-benzo[b]furan], 1-(3-thien-2-yl-[1,2,4]oxadiazol-5-yl)carbonyl-5'-aminomethyl-spiro[piperidine-4,3'-(2H)-benzo[b]furan], 1-[3-(3-thien-2-yl-[1,2,4]oxadiazol-5-yl)-5-aminocarbonyl-phenyl]carbonyl-5'-aminomethyl-spiro[piperidine-4,3'-(2H)-benzo[b]furan], 1-(3-methyl-4-bromo-5-propoxy-thien-2-yl)carbonyl-5'-aminomethyl-spiro[piperidine-4,3'-(2H)-benzo[b]furan].

* * * * *